US011730769B2

(12) United States Patent
Feng et al.

(10) Patent No.: US 11,730,769 B2
(45) Date of Patent: Aug. 22, 2023

(54) COMPOSITIONS AND METHODS FOR WILLIAMS SYNDROME (WS) THERAPY

(71) Applicants: MASSACHUSETTS INSTITUTE OF TECHNOLOGY, Cambridge, MA (US); CHILDREN'S MEDICAL CENTER CORPORATION, Boston, MA (US)

(72) Inventors: Guoping Feng, Cambridge, MA (US); Boaz Barak, Cambridge, MA (US); Zhigang He, Boston, MA (US)

(73) Assignees: Children's Medical Center Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 311 days.

(21) Appl. No.: 16/955,958

(22) PCT Filed: Dec. 21, 2018

(86) PCT No.: PCT/US2018/067092
§ 371 (c)(1),
(2) Date: Jun. 19, 2020

(87) PCT Pub. No.: WO2019/126643
PCT Pub. Date: Jun. 27, 2019

(65) Prior Publication Data
US 2020/0316132 A1    Oct. 8, 2020

Related U.S. Application Data

(60) Provisional application No. 62/610,063, filed on Dec. 22, 2017.

(51) Int. Cl.
*A61K 35/30* (2015.01)
*A61K 31/14* (2006.01)
*A61K 31/40* (2006.01)
*A61K 31/4409* (2006.01)
*C07K 16/28* (2006.01)
*A61K 45/06* (2006.01)

(52) U.S. Cl.
CPC ............. *A61K 35/30* (2013.01); *A61K 31/14* (2013.01); *A61K 31/40* (2013.01); *A61K 31/4409* (2013.01); *C07K 16/2803* (2013.01); *A61K 45/06* (2013.01)

(58) Field of Classification Search
CPC ........ A61K 35/30; A61K 31/14; A61K 31/40; A61K 31/4409
See application file for complete search history.

(56) References Cited

U.S. PATENT DOCUMENTS

| 2006/0025452 A1 | 2/2006 | Smith et al. |
| 2009/0324572 A1 | 12/2009 | Fallon |
| 2011/0023143 A1 | 1/2011 | Weinstein et al. |
| 2013/0030025 A1* | 1/2013 | Wessel ............... A61K 31/44 514/352 |
| 2017/0166903 A1 | 6/2017 | Zhang et al. |

FOREIGN PATENT DOCUMENTS

| WO | 2008/058536 A1 | 5/2008 |
| WO | 2008/058537 A1 | 5/2008 |
| WO | 2008/067965 A1 | 6/2008 |
| WO | 2010/020585 A1 | 2/2010 |
| WO | 2013/001412 A1 | 1/2013 |
| WO | 2017075222 A1 | 5/2017 |
| WO | 2017/120298 A1 | 7/2017 |

OTHER PUBLICATIONS

Avery; NeuroImage 2012, 59, 887-894. http://dx.doi.org/10.1016/j.neuroimage.2011.09.065 (Year: 2012).*
Barak; Nat Neurosci 2019, 22, 700-708. https://doi.org/10.1038/s41593-019-0380-9 (Year: 2019).*
Barak; Nat Neurosci 2016, 19, 647-655. https://doi.org/10.1038/nn.4276 (Year: 2016).*
Blight; Ann. N.Y. Acad. Sci. 2014, 1329, 33-44. https://doi.org/10.1111/nyas.12512 (Year: 2014).*
Borralleras; Mol. Ther. 2015, 23, 1691-1699. https://doi.org/10.1038/mt.2015.130 (Year: 2015).*
Hayes; CNS Drug Reviews 2004, 10, 295-316. https://doi.org/10.1111/j.1527-3458.2004.tb00029.x (Year: 2004).*
Liu; ACS Chem Neurosci. 2014, 5, 477-483. https://doi.org/10.1021%2Fcn500077p (Year: 2014).*
Liu; Journal of Neuroscience 2016, 36, 957-962. https://doi.org/10.1523/JNEUROSCI.3608-15.2016 (Year: 2016).*
Zada; Disease Models & Mechanisms 2016, 9, 1339-1348. https://doi.org/10.1242/dmm.027227 (Year: 2016).*
Prescribing information for dalfampridine, 7 pages. 2010. (Year: 2010).*
Pober; N Engl J Med 2010, 362, 239-252. DOI: 10.1056/NEJMra0903074 (Year: 2010).*
Extended European Search Report in corresponding EP application No. 18893304.8 dated Jan. 24, 2022.
Kaczmarek, L. Development of pharmacological activators of FMRP-regulated potassium channels, Feb. 4, 2010.
Partial Supplementary European Search Report in corresponding EP application No. 18893304.8 dated Oct. 20, 2021.
Guglielmi, L. Update on the implication of potassium channels in autism K+ channelautism spectrum disorder, Frontiers in Cellular Neuroscience, vol. 9, 1, Jan. 1, 2015.

(Continued)

*Primary Examiner* — Daniel R Carcanague
(74) *Attorney, Agent, or Firm* — Withers Bergman LLP; Christopher R. Cowles

(57) ABSTRACT

The present disclosure relates to compositions and methods for treating Williams syndrome (WS), herein identified as a neurodevelopmental oligodendrocyte hypomyelination-associated disease, and to compositions and methods for treatment of other neurodevelopmental myelination abnormality diseases or disorders.

8 Claims, 163 Drawing Sheets

(56) References Cited

OTHER PUBLICATIONS

Erickson, C. et al. Brief Report: Acamprosate in Fragile X Syndrome. Journal of Autism and Development Disorders, Kluwer Academic Publishers-Plenum Publishers, NE, vol. 40, No. 11, Mar. 6, 2010.
International Search Report dated Jul. 2, 2020 for related Application No. PCT/US2018/067092.
Jurevics et al. "Alterations in metabolism and gene expression in brain regions during cuprizone-induced demyelination and remyelination" Journal of Neurochemistry, 2002, 82, 126-136; abstract, Fig. 5, p. 131, col. 2, last para.
Lee et al. "Major Determinants and Long-Term Outcomes of Successful Balloon Dilatation for the Pediatric Patients with Isolated Native Valvular Pulmonary Stenosis: A 10-Year Institutional Experience". Yonsei Med J, vol. 49, No. 3, pp. 416-421, 2008; p. 416, col. 2, para 2, to p. 417, col. 1, para 1.
International Search Report dated May 1, 2019 for related Application No. PCT/US2018/067092.

* cited by examiner

| Gene ID | Gene description |
|---|---|
| Dlk1 | Protein delta homolog 1 |
| Neurod6 | Neurogenic differentiation factor 6 |
| Myl4 | Myosin light chain 4 |
| Gtf2i | General transcription factor II-I |
| Fibcd1 | Fibrinogen C domain-containing protein 1 |
| Krt80 | Keratin 80, Type II |
| Mobp | #Myelin-associated oligodendrocyte basic protein |
| Herc6 | Hect domain and RLD 5 |
| Mbp | #Myelin basic protein |
| Trf | #Serotransferrin precursor |
| Prr18 | #Proline rich 18 |
| Mog | #Myelin-oligodendrocyte glycoprotein |
| Sstr2 | Somatostatin receptor 2 |
| Cnp | #2',3'-cyclic-nucleotide 3'-phosphodiesterase |
| Mag | #Myelin-associated glycoprotein |
| Enpp6 | #Ectonucleotide pyrophosphatase/phosphodiesterase 6 |
| Mal | #Myelin and lymphocyte protein |
| Gjc2 | #Gap junction gamma-2 protein |
| Cldn11 | #Claudin-11 |
| Gsn | #Gelsolin |
| Adamts4 | #ADAM metallopeptidase with thrombospondin motif, 4 |
| Rspo2 | #R-Spondin 2 |
| Plp1 | #Proteolipid protein |
| Wnt7b | #Wingless-type MMTV integration site, member 7B |
| Tspan2 | #Tetraspanin 2 |
| Gltp | #Glycolipid Transfer Protein |

FIG. 2A

| Subject | Group | Age (Years) | Sex | PMI (Hours) | Cause of death |
|---|---|---|---|---|---|
| PM1 | WS | 17 | Male | 24 | Complication of Disorder |
| PM2 | WS | 34 | Male | 23 | Multiple Injuries |
| PM3 | WS | 42 | Female | 18 | Complication of Disorder |
| PM4 | Control | 34 | Male | 28 | Atherosclerotic Cardiovascular Disease |
| PM5 | Control | 42 | Female | 12 | Cardiac Arrhythmia |
| PM6 | Control | 17 | Female | 14 | Cardiac Arrhythmia |

FIG. 31

Amiodarone
Aminopyridines
    4-Aminopyridine (4-AP)
    3,4-Diaminopyridine (3,4-DAP)
    2,3-Diaminopyridine (2,3-DAP)
    3-Hydroxypyridine (3-HP)
    4-Aminopyridine methiodide (4-APMI)
Anandamide
Arachidonic acid
Astemizole
Azimilide
Bepridil
BRL32872
Bupivacaine
Capsaicin
8-(4-chlorophenylthio)-adenosine (cpt-cAMP)
Calcium/calmodulin
Chromakalim
Chromanol-293B
Cisapride
Clofilium
Cocaine
Correolide
CP339818
CT haloperidol
D-NONOate
Dichlorophenyl
Diltiazem
Dofetilide
E-4031
Flecainide
H37
Halofantrine
Halothane
HMR-1556

SCORPION:
    AaI [α-KTx15.1]
    Agitoxins:
        Agitoxin-1 (AgTx1) / [α-KTx3.4]
        Agitoxin-2 (AgTx2) / [α-KTx3.2]
        Agitoxin-3 (AgTx3) / [α-KTx3.3]
    Aminetoxin [α-KTx6.12]
    BeKm [γ-KTx2.1]
    BmKK2 [α-KTx14]
    BmTx3:
        BmTx3-Y36F37del (deletion construct)
    Ce (C. elegans) toxins:
        Ce toxin 1 (Ce1) / [α-KTx 2.8]
        Ce toxin 2 (Ce2) / [α-KTx 2.9]
        Ce toxin 4 (Ce4) / [α-KTx 2.11]
    Charybdotoxin (ChTx or CTX) / [α-KTx1.1];
    Lqh 2
    Lqh 18-2
    Cobatoxins:
        Cobatoxin 1 (CoTX1) / [α-KTx9.1]
            ACoTX1 (synthetic derivative)
        Cobatoxin 2 (CoTX2) / [α-KTx9.2]
    Discrepin [α-KTx15.6]
    Ergtoxins:
        Ergtoxin-1 (CnErg1) / [γ-KTx1.1]
        Ergtoxin-2 (CnErg2) / [γ-KTx3.1]
    α-Hefutoxin 1
    Hongotoxins:
        Hongotoxin 1 (HgTx1) / [α-KTx1.9]
        Hongotoxin 2 (HgTx2) / [α-KTx2.5]
    HsTx1 [α-KTx6.3]
    Iberiotoxin (IbTX) / [α-KTx1.3]
    KAaH1
    KAaH2
    Kaliotoxins.

Barium ($Ba^{2+}$)
Cadmium ($Cd^{2+}$)
Calcium ($Ca^{2+}$)
Cesium ($Cs^+$)
Cobalt ($Co^{2+}$)
Gadolinium ($Gd^{3+}$)
Hydrogen ($H^+$)
Lanthanum ($La^{3+}$)
Lead ($Pb^{2+}$)
Lithium ($Li^+$)
Magnesium ($Mg^{2+}$)
Manganese ($Mn^{2+}$)
Mercury ($Hg^{2+}$)
Nickel ($Ni^{2+}$)
Sodium ($Na^+$)
Strontium ($Sr^{2+}$)
Zinc ($Zn^{2+}$)

FIG. 32

Imipramine
Isobutyl-methylxanthine (IBMX)
Ketoconazole
L735821
Linopirdine
Loratadine
LY97241
Mefloquine
Nicotine
Nifedipine
Nitric oxide-activated phosphatase (8-Br-cGMP)
OsK2
Quaternary ammonium ions (QA)
Quinine
Quinidine
Perhexiline
Phencyclidine
Pimozide
Propafenone
Riluzole
S9947
Sertindole
Sipatrigine
Strychnine
Sulfamidbenzamidoindane
Tedisamil
Terfenadine Tetraethylammonium chloride (TEA)
Tetrapentylammonium (TPA)
Tetraphenylporphyrin
trans-N-propyl-carbamoyloxy-PAC
UK78282
Verapamil
  Methoxyverapamil (D600)
  WIN173117-3

XE-991

Kaliotoxin-1 (KTX) / [α-KTx3.1]
Kaliotoxin-2 (KTX2) / [α-KTx3.5]
Kaliotoxin-3 (KTX3)
Limbatustoxin (LbTX)
Margatoxin (MgTx) / [α-KTx2.2]
Maurotoxin (MTX) / [α-KTx6.2]
Noxiustoxin (NTx or NxTX) / [α-KTx2.1]
OsK1 [α-KTx3.7]:
  $[K_{17},D_{26}]$-OSK1 (synthetic derivative)
  $[K_{16}]$-OSK1 (synthetic derivative)
  $[D_{26}]$-OSK1 (synthetic derivative)
  $[P_{12}K_{16},D_{26}]$-OSK1 (synthetic derivative)
  $[K_{17},D_{26}Y_{36}]$-OSK1 (synthetic derivative)
OsK2 [α-KTx3.2]
Pandinotoxins:
  Pandinotoxin-1 (Pi1 or PiTx-Kγ)
  Pandinotoxin-2 (Pi2 or PiTx-Kα) / [α-KTx7.1]
  Pandinotoxin-3 (Pi3 or PiTx-Kβ) / [α-KTx7.2]
  Pandinotoxin-4 (Pi4) / [α-KTx6.4]
  Pandinotoxin-7 (Pi7) / [α-KTx6.5]
Tamulustoxin
Tityustoxins:
  Tityustoxin-Kα (TsTX-Kα, TyKα, TsK4, TsII-9) / [α-KTx4.1]
  Tityustoxin-Kβ (TsTX-Kβ)
  Tityustoxin-IV (TsTX-IV) / [α-KTx12.1]
  Tityustoxin-V (TsTX-V or TsV)

SNAKE:
  Dendrotoxins:
    α-Dendrotoxin (α-DTX)
    β-Dendrotoxin (β-DTX)
    γ-Dendrotoxin (γ-DTX)
    δ-Dendrotoxin (δ-DTX)
    Dendrotoxin I (DTX-I or DTX$_1$)
    Dendrotoxin K (DTX$_k$ or DTX-K)

SEA ANEMONE:
  BDS-I
  BDS-II
  BgK
  Stichodactyla toxin (ShK):
    ShK-Dap22 (synthetic derivative)
    ShK(L5) (synthetic derivative)

SPIDER:
  Hanatoxin 1
  Heteropodatoxins:
    Heteropodatoxin1 (HpTx1)
    Heteropodatoxin2 (HpTx2)
    Heteropodatoxin3 (HpTx3)
  HmTx1
  HmTx2
  Phrixotoxins:
    Phrixotoxin 1 (PaTx1)
    Phrixotoxin 2 (PaTx2)
  Stromatoxin-1 (ScTx1)
  TLTx (T. leblondi) toxins:
    TlTx1
    TlTx2
    TlTx3
  VSTX1
  VSTX2
  VSTX3

FIG. 32 (cont.)

BEE VENOM:
- Mast cell degranulating peptide (MCDP)

MARINE CONE-SNAIL.
- BtMT
- Conotoxins.
  - κPVIIA
  - κSVIA
  - κM-RIIIK
  - Conkunitzin-S1 (Conk-S1)

FIG. 32 (cont.)

| geneSymbol | Cat | log2FoldChange | pvalue | padj | Gene name | yellow=interesting / blue=deleted in WS / green=myelin-related / framed=downregulated in NexKOs |
|---|---|---|---|---|---|---|
| FOLH1 | coding | -2.432173237 | 1.03254E-10 | 2.68812E-06 | Folate Hydrolase | This gene encodes a type II transmembrane glycoprotein belonging to the M28 peptidase family. Expression of this protein in the brain may be involved in a number of pathological conditions associated with glutamate excitotoxicity |
| BC071797 | coding | -2.276190323 | 2.81496E-09 | 1.83212E-05 | N/A | |
| NPY | coding | -1.961983434 | 4.52206E-08 | 0.000235455 | Neuropeptide Y | widely expressed in the central nervous system and influences many physiological processes, including cortical excitability, stress response, food intake, circadian |

FIG. 33

|  |  |  |  |  |  | rhythms, and cardiovascular function. The neuropeptide functions through G protein-coupled receptors to inhibit adenylyl cyclase, activate mitogen-activated protein kinase (MAPK), regulate intracellular calcium levels, and activate potassium channels. |
|---|---|---|---|---|---|---|
| GJB1 | coding | -1.934171214 | 2.49887E-07 | 0.000703071 | Gap Junction Protein Beta 1 | The gap junction proteins are membrane-spanning proteins that assemble to form gap junction channels that facilitate the transfer of ions and small molecules between cells. |
| TF | coding | -1.923611459 | 3.2407E-07 | 0.000703071 | Transferrin | Essential in regulation of myelin formation and metabolism. |

FIG. 33 (Cont.)

| ERMN | coding | -1.921764571 | 2.80838E-07 | 0.000703071 | Ermin | Plays a role in cytoskeletal rearrangements during the late wrapping and/or compaction phases of myelinogenesis as well as in maintenance and stability of myelin sheath in the adult. May play an important role in late-stage oligodendroglia maturation, myelin/Ranvier node formation during CNS development, and in the maintenance and plasticity of related structures in the mature CNS.cytoskeletal molecule that is exclusively expressed by oligodendrocytes. Ermin appears at a late stage during myelination, and in the mature nerves, it is localized to the outer cytoplasmic lip of the myelin sheath and the paranodal loops. |

FIG. 33 (Cont.)

|  |  |  |  |  |  |  | In cultured oligodendrocytes, Ermin becomes visible in well differentiated MBP-positive cells, where it is concentrated at the tip of F-actin-rich processes (termed "Ermin spikes"). |
|---|---|---|---|---|---|---|---|
| PLP1 | coding | - 1.899095455 | 3.2191 8E-07 | 0.0007 03071 | Proteolipid Protein 1 | This gene encodes a transmembrane proteolipid protein that is the predominant component of myelin. The encoded protein may play a role in the compaction, stabilization, and maintenance of myelin sheaths, as well as in oligodendrocyte development and axonal survival. |
| EVI2A | coding | - 1.846543267 | 7.0289 2E-07 | 0.0012 19939 | Ecotropic Viral Integration Site 2A | May complex with itself or/and other proteins within the membrane, to function as part of a cell-surface receptor |

FIG. 33 (Cont.)

| Gene | Type | | Value | p-value | Name | Function |
|---|---|---|---|---|---|---|
| MOBP | nearCoding,coding | -1.834415526 | 8.8915 2E-07 | 0.0014 46761 | Myelin-Associated Oligodendrocyte Basic Protein | May play a role in compacting or stabilizing the myelin sheath, possibly by binding the negatively charged acidic phospholipids of the cytoplasmic membrane |
| RNASE1 | coding | -1.801940388 | 5.4472 8E-07 | 0.0010 12961 | Ribonuclease 1 | This gene encodes a member of the pancreatic-type of secretory ribonucleases, a subset of the ribonuclease A superfamily. |
| TMEM144 | nearCoding,coding | -1.796122594 | 1.4043 2E-06 | 0.0018 33487 | Transmembrane Protein 144 | N/A |
| GPIHBP1 | coding | -1.791023064 | 2.2477 2E-06 | 0.0027 61366 | Glycosylphosphatidylinositol Anchored High Density Lipoprotein Binding Protein 1 | This protein plays a major role in transporting lipoprotein lipase (LPL) from the subendothelial spaces to the capillary lumen. |
| ENPP2 | coding | -1.773860014 | 1.3760 4E-06 | 0.0018 33487 | Ectonucleotide Pyrophosphatase/Phosphodiesterase 2 or autotaxin | ENPP2 regulates oligodendrocyte differentiation in vivo in the developing zebrafish hindbrain. Controls cytoskeletal |

FIG. 33 (Cont.)

| | | | | | | organization and FAK phosphorylation during myelination The protein encoded by this gene functions as both a phosphodiesterase, which cleaves phosphodiester bonds at the 5' end of oligonucleotides, and a phospholipase, which catalyzes production of lysophosphatidic acid (LPA) in extracellular fluids. LPA evokes growth factor-like responses including stimulation of cell proliferation and chemotaxis. |
|---|---|---|---|---|---|---|
| TMEM 125 | coding | - 1.769426 898 | 2.3334 9E-06 | 0.0027 61366 | Transmembrane Protein 125 | N/A |
| CNDP 1 | coding | - 1.747909 967 | 1.4085 3E-06 | 0.0018 33487 | Carnosine Dipeptidase 1 | This gene encodes a member of the M20 metalloprotease family. The encoded protein is specifically expressed in the |

FIG. 33 (Cont.)

| | | | | | | brain, is a homodimeric dipeptidase which was identified as human carnosinase. |
|---|---|---|---|---|---|---|
| KLK6 | coding | -1.746687251 | 3.47251E-06 | 0.003430016 | Kallikrein Related Peptidase 6 | The encoded preproprotein is proteolytically processed to generate the mature protease. |
| ASPA | coding | -1.730371387 | 4.01683E-06 | 0.003641062 | Aspartoacylase | Mature oligodendrocyte marker. This enzyme has been localized to oligodendrocytes. In normal mice the pattern of ASPA expression coincides with oligodendrocyte maturation. This gene encodes an enzyme that catalyzes the conversion of N-acetyl_L-aspartic acid (NAA) to aspartate and acetate. NAA is abundant in the brain where hydrolysis by aspartoacylase is thought to help maintain white matter. This protein is an |

FIG. 33 (Cont.)

|  |  |  |  |  |  |  | NAA scavenger in other tissues. ASPA encodes aspartoacylase, which catalyzes the hydrolysis of N-acetyl l-aspartic acid, a process that helps maintain white matter. Defects in aspartoacylase cause Canavan disease which is characterized by loss of the axon's myelin sheath, spongy degeneration of the white matter. Myelin-localized ASPA for lipid synthesis within the myelin sheath |
|---|---|---|---|---|---|---|---|
| MAG | coding | -1.704477536 | 5.36327E-06 | 0.004400507 | Myelin Associated Glycoprotein | | It is thought to be involved in the process of myelination. It is a lectin that binds to sialylated glycoconjugates and mediates certain myelin-neuron cell-cell interactions. Adhesion molecule in postnatal neural development that mediates |

FIG. 33 (Cont.)

|  |  |  |  |  |  |  | sialic-acid dependent cell-cell interactions between neuronal and myelinating cells |
|---|---|---|---|---|---|---|---|
| ANLN | coding | -1.700174275 | 5.57796E-06 | 0.004400507 | Anillin Actin Binding Protein | | This gene encodes an actin-binding protein that plays a role in cell growth and migration, and in cytokinesis. |
| ELOVL1 | nearCoding,coding | -1.697360007 | 3.55729E-06 | 0.003430016 | Elongation Of Very Long Chain Fatty Acids | | Catalyzes the first and rate-limiting reaction of the four that constitute the long-chain fatty acids elongation cycle. May participate to the production of both saturated and monounsaturated VLCFAs of different chain lengths that are involved in multiple biological processes as precursors of membrane lipids and lipid mediators. |
| OPALIN | nearCoding,coding | -1.697286178 | 7.62184E-06 | 0.005221763 | Oligodendrocytic Myelin Paranodal And Inner Loop Protein | | Opalin is enriched in myelin of the central nervous system, but not |

FIG. 33 (Cont.)

|  |  |  |  |  |  | that of the peripheral nervous system of mice. In addition to the somata and processes of oligodendrocytes, Opalin immunoreactivity was observed in myelinated axons in a spiral fashion, and was concentrated in the paranodal loop region. |
|---|---|---|---|---|---|---|
| CARNS1 | coding | -1.687402329 | 8.03343E-06 | 0.005362627 | Carnosine Synthase 1 | Catalyzes the synthesis of carnosine and homocarnosine. |
| TUBB1 | coding | -1.675458117 | 7.34784E-06 | 0.005170102 | Tubulin Beta 1 Class VI | Tubulin is the major constituent of microtubules. |
| HHIP | coding | -1.67076608 | 5.97797E-06 | 0.004577369 | Hedgehog Interacting Protein | The hedgehog (HH) proteins are evolutionarily conserved protein, which are important morphogens for a wide range of developmental processes, including anteroposterior patterns of limbs and regulation of left-right asymmetry in embryonic |

FIG. 33 (Cont.)

| | | | | | | development. It interacts with all three HH family members, SHH, IHH and DHH. |
|---|---|---|---|---|---|---|
| CMTM5 | nearCoding,coding | -1.662365129 | 1.13759E-05 | 0.006547765 | CKLF Like MARVEL Transmembrane Domain Containing 5 | This gene encodes a member of the chemokine-like factor superfamily. |
| GPR37 | coding | -1.655010222 | 9.51299E-06 | 0.005896697 | G Protein-Coupled Receptor 37 | identify G protein-coupled receptor 37 (GPR37) as an inhibitor of late-stage oligodendrocyte differentiation and myelination. GPR37 is enriched in oligodendrocytes and its expression increases during their differentiation into myelin forming cells. GPR37-knockout (GPR37-KO) mice display more rapid and extensive demyelination than their wild type (WT) counterparts. primary cultures of oligodendrocyte |

FIG. 33 (Cont.)

| | | | | | | s also revealed a protective role for GPR37. From these data, we conclude that loss of GPR37 alters oligodendrocyte physiology and increases susceptibility to demyelination, independent of effects on oligodendrocyte proliferation or differentiation. The present work identifies GPR37 as a potential drug target for the treatment of demyelinating diseases such as multiple sclerosis. |
|---|---|---|---|---|---|---|
| TYMS | coding | -1.652462682 | 1.07182E-05 | 0.006409037 | Thymidylate Synthetase | Contributes to the de novo mitochondrial thymidylate biosynthesis pathway. |
| MOG | nearCoding,coding | -1.647587228 | 1.15694E-05 | 0.006547765 | Myelin Oligodendrocyte Glycoprotein | The product of this gene is a membrane protein expressed on the oligodendrocyte cell surface and the outermost surface of myelin sheaths. |

FIG. 33 (Cont.)

| | | | | | | | Due to this localization, it is a primary target antigen involved in immune-mediated demyelination. This protein may be involved in completion and maintenance of the myelin sheath and in cell-cell communication. May be involved in completion and/or maintenance of the myelin sheath and in cell-cell communication. |
|---|---|---|---|---|---|---|---|
| GLDN | coding | -1.643612282 | 1.08319E-05 | 0.006409037 | | Gliomedin | Ligand for NRCAM and NFASC/neurofascin that plays a role in the formation and maintenance of the nodes of Ranvier on myelinated axons. Mediates interaction between Schwann cell microvilli and axons via its interactions with NRCAM and NFASC.Required for normal clustering of |

FIG. 33 (Cont.)

| | | | | | | sodium channels at heminodes; not required for the formation of mature nodes with normal sodium channel clusters. Required, together with NRCAM, for maintaining NFASC and sodium channel clusters at mature nodes of Ranvier. |
|---|---|---|---|---|---|---|
| NKX6-2 | coding | -1.64081922 | 1.34177E-05 | 0.007128882 | NK6 Homeobox 2 | Nkx6.2 is specifically expressed in the APC+ (CC1+) mature oligodendrocytes. Nkx6-2 promoter is active embryonically in neuroblasts and postnatally in oligodendrocytes. Nkx6-2 directly or indirectly regulates axon-glial interactions at myelin paranodes. Sox10, Olig2 and Nkx6.2 are sufficient to reprogram fibroblasts to iOPCs |

FIG. 33 (Cont.)

| NIPAL4 | coding | -1.635572105 | 1.74845E-05 | 0.00818315 | NIPA Like Domain Containing 4 | Acts as a Mg(2+) transporter |
|---|---|---|---|---|---|---|
| TRIM59 | coding | -1.630114423 | 1.82698E-05 | 0.00818315 | Tripartite Motif Containing 59 | May serve as a multifunctional regulator for innate immune signaling pathways. |
| FA2H | nearCoding,coding | -1.625366931 | 1.51151E-05 | 0.007715816 | Fatty Acid 2-Hydroxylase | Required for alpha-hydroxylation of free fatty acids and the formation of alpha-hydroxylated sphingolipids. Mutations in this gene have been associated with leukodystrophy dysmyelinating with spastic paraparesis with or without dystonia.catalyzes the 2-hydroxylation of myelin galactolipids, galactosylceramide, and its sulfated form, sulfatide. To our knowledge, this is the first identified deficiency of a lipid component of myelin and the clinical phenotype |

FIG. 33 (Cont.)

|  |  |  |  |  |  | underscores the importance of the 2-hydroxylation of galactolipids for myelin maturation.HFA-sphingolipids in CNS and PNS myelin are synthesized from 2-hydroxylated fatty acids, formed by the fatty acid 2-hydroxylase (encoded by the Fa2h gene) |
|---|---|---|---|---|---|---|
| DEPDC7 | coding | -1.61559511 | 1.32398E-05 | 0.007128882 | DEP Domain Containing 7 | Among its related pathways are Signaling by GPCR and Signaling by Rho GTPases |
| SGK2 | nearCoding,coding | -1.605954503 | 2.07748E-05 | 0.008584928 | Serine/Threonine Kinase 2 | Serine/threonine-protein kinase which is involved in the regulation of a wide variety of ion channels, membrane transporters, cell growth, survival and proliferation. |
| COL4A5 | coding | -1.601030282 | 2.61521E-05 | 0.009407174 | Collagen Type IV Alpha 5 | This gene encodes one of the six subunits of type IV collagen, the major structural component of |

FIG. 33 (Cont.)

| | | | | | | basement membranes. |
|---|---|---|---|---|---|---|
| TMEM98 | coding | -1.595146546 | 7.1176E-06 | 0.00514 7209 | Transmembrane Protein 98 | This gene encodes a transmembrane protein. |
| PPAP2C | coding | -1.581653464 | 2.65648E-05 | 0.00940 7174 | Phospholipid Phosphatase 2 | convert phosphatidic acid to diacylglycerol, and function in de novo synthesis of glycerolipids as well as in receptor-activated signal transduction mediated by phospholipase D |
| MBP | nearCoding,coding | -1.572470332 | 1.97152E-05 | 0.00836 0473 | Myelin basic protein | The protein encoded by the classic MBP gene is a major constituent of the myelin sheath of oligodendrocytes and Schwann cells in the nervous system. The most abundant protein components of the myelin membrane in the CNS. They have a role in both its formation and stabilization. |

FIG. 33 (Cont.)

| | | | | | | |
|---|---|---|---|---|---|---|
| TSPAN15 | coding | -1.571270682 | 1.62495E-05 | 0.008135384 | Tetraspanin 15 | <u>Enriched in oligodendrocytes. The proteins mediate signal transduction events that play a role in the regulation of cell development, activation, growth and motility</u> |
| NINJ2 | coding | -1.570184002 | 3.31991E-05 | 0.011080836 | Ninjurin 2 | It is a cell surface adhesion protein that is upregulated in Schwann cells surrounding the distal segment of injured nerve, and promotes neurite outgrowth, thus may have a role in nerve regeneration after nerve injury |
| PLLP | coding | -1.566390217 | 1.99105E-05 | 0.008360473 | Plasmolipin | Appears to be involved in myelination. PLLP functions in myelin biogenesis through organization of myelin liquid-ordered membranes in the Golgi complex. Could also participate in ion transport |

FIG. 33 (Cont.)

| | | | | | | events as addition of plasmolipin to lipid bilayers induces the formation of ion channels, which are voltage-dependent and K(+)-selective |
|---|---|---|---|---|---|---|
| TTYH2 | coding | -1.563327618 | 1.73328E-05 | 0.00818315 | Tweety Family Member 2 | Probable large-conductance Ca(2+)-activated chloride channel. May play a role in Ca(2+) signal transduction. May be involved in cell proliferation and cell aggregation. |
| ABCA8 | coding | -1.561397032 | 4.16696E-05 | 0.01329 5049 | ATP Binding Cassette Subfamily A Member 8 | The membrane-associated protein encoded by this gene is a member of the superfamily of ATP-binding cassette (ABC) transporters |
| TMEM63A | coding | -1.559285262 | 2.23073E-05 | 0.00900 0829 | Transmembrane Protein 63A | Acts as an osmosensitive calcium-permeable cation channel |

FIG. 33 (Cont.)

| MYRF | nearCoding,coding | -1.558955843 | 1.92165E-05 | 0.008338058 | Myelin Regulatory Factor | This gene encodes a transcription factor that is required for central nervous system myelination and may regulate oligodendrocyte differentiation. It is thought to act by increasing the expression of genes that effect myelin production but may also directly promote myelin gene expression. Loss of a similar gene in mouse models results in severe demyelination. Transcription factor that specifically activates expression of myelin genes such as MBP, MOG, MAG and PLP1 during oligodendrocyte (OL) maturation, thereby playing a central role in oligodendrocyte maturation and CNS myelination. |

FIG. 33 (Cont.)

| | | | | | | |
|---|---|---|---|---|---|---|
| PRR5L | coding | -1.547509449 | 2.9131 7E-05 | 0.0099 99634 | Proline Rich 5 Like | Associates with the mTORC2 complex that regulates cellular processes including survival and organization of the cytoskeleton |
| ACY3 | coding | -1.546340783 | 5.4253 3E-05 | 0.0155 212 | Aminoacylase 3 | Diseases associated with ACY3 include hepatitis c virus. |
| PIEZO2 | nearCoding,coding | -1.544318871 | 3.0867 5E-05 | 0.0104 36416 | Piezo Type Mechanosensitive Ion Channel Component 2 | The protein encoded by this gene contains more than thirty transmembrane domains and likely functions as part of mechanically-activated (MA) cation channels. |
| TMEM88B | coding | -1.523739493 | 6.7000 7E-05 | 0.0172 70248 | Transmembrane Protein 88B | |
| CX3CR1 | coding | -1.519268734 | 1.8545 2E-05 | 0.0081 8315 | C-X3-C Motif Chemokine Receptor 1 | Fractalkine is a transmembrane protein and chemokine involved in the adhesion and migration of leukocytes |
| ST18 | nearCoding,coding | -1.513374293 | 5.3368 5E-05 | 0.0154 37716 | Suppression Of Tumorigenicity 18, Zinc Finger | Diseases associated with ST18 include breast cancer. |

FIG. 33 (Cont.)

| | | | | | | |
|---|---|---|---|---|---|---|
| C21orf91 | nearCoding,coding | -1.513018471 | 7.07738E-05 | 0.017888583 | Chromosome 21 Open Reading Frame 91 | N/A |
| TMEM235 | coding | -1.496718155 | 4.50635E-05 | 0.013802168 | Transmembrane Protein 235 | N/A |
| RASSF2 | nearCoding,coding | -1.494013343 | 2.62731E-05 | 0.009407174 | Ras Association Domain Family Member 2 | Potential tumor suppressor. Acts as a KRAS-specific effector protein. May promote apoptosis and cell cycle arrest. |
| TNC | coding | -1.490647031 | 9.5697E-05 | 0.021664129 | Tenascin C | It is implicated in guidance of migrating neurons as well as axons during development, synaptic plasticity, and neuronal regeneration. |
| CLDN11 | nearCoding,coding | -1.487293217 | 6.87641E-05 | 0.017551027 | Claudin 11 | Oligodendrocyte Transmembrane Protein. Claudins are integral membrane proteins and components of tight junction strands. The protein encoded by this gene is a major component of central nervous system (CNS) myelin and plays an important |

FIG. 33 (Cont.)

| | | | | | | role in regulating proliferation and migration of oligodendrocytes. |
|---|---|---|---|---|---|---|
| FAM107B | nearCoding,coding | -1.483760369 | 7.28673E-05 | 0.018066921 | Family With Sequence Similarity 107 Member B | N/A |
| HSPA2 | coding | -1.478222706 | 9.48781E-05 | 0.021664129 | Heat Shock Protein Family A (Hsp70) Member 2 | Hsp70s stabilize preexistent proteins against aggregation and mediate the folding of newly translated polypeptides in the cytosol as well as within organelles. |
| GJC2 | coding | -1.466995548 | 4.79745E-05 | 0.01433218 | Gap Junction Protein Gamma 2 | This gene plays a key role in central myelination and is involved in peripheral myelination in humans |
| SMIM5 | coding | -1.466938475 | 0.000102195 | 0.022547076 | Small Integral Membrane Protein 5 | N/A |
| PPP1R14A | coding | -1.464490819 | 0.000112986 | 0.024512206 | Protein Phosphatase 1 Regulatory Inhibitor Subunit 14A | This protein is an inhibitor of smooth muscle myosin phosphatase, and has higher inhibitory activity when phosphorylated. |

FIG. 33 (Cont.)

| ERBB3 | nearCoding,coding | -1.458466467 | 5.96926E-05 | 0.016301161 | Erb-B2 Receptor Tyrosine Kinase 3 | erbB3 during late embryogenesis and postnatally express in different areas and cell types of the central nervous system, including oligodendrocytes. Results show that erbB3 is not required for normal oligodendrocyte development and myelination. Other study show erbb3 is essential for development of Schwann cells |
|---|---|---|---|---|---|---|
| LGR5 | nearCoding,coding | -1.452809796 | 7.84542E-05 | 0.018738317 | Leucine-Rich Repeat Containing G Protein-Coupled Receptor 5 | involved in the canonical Wnt signaling pathway. |
| CCNE2 | coding | -1.452784977 | 9.21205E-05 | 0.021413071 | Cyclin E2 | plays a role in cell cycle G1/S transition |
| TGFA | coding | -1.45174991 | 4.89961E-05 | 0.01433218 | Transforming Growth Factor Alpha | This gene encodes a growth factor that is a ligand for the epidermal growth factor receptor, which activates a signaling pathway for cell proliferation, |

FIG. 33 (Cont.)

| | | | | | | differentiation and development. TGF alpha is a mitogenic polypeptide that is able to bind to the EGF receptor/EGFR and to act synergistically with TGF beta to promote anchorage-independent cell proliferation in soft agar. |
|---|---|---|---|---|---|---|
| AIF1L | nearCoding,coding | -1.451604769 | 2.30137E-05 | 0.009077865 | Allograft Inflammatory Factor 1 Like | Actin-binding protein that promotes actin bundling. May neither bind calcium nor depend on calcium for function. |
| SLCO1A2 | coding | -1.449546511 | 8.1854E-05 | 0.019372615 | Solute Carrier Organic Anion Transporter Family Member 1A2 | Mediates the Na(+)-independent transport of organic anions such as sulfobromophthalein (BSP) and conjugated (taurocholate) and unconjugated (cholate) bile acids |
| SYS1-DBNDD2 | coding | -1.448548837 | 4.79954E-05 | 0.01433218 | SYS1-DBNDD2 Readthrough | RNA Gene, and is affiliated with the ncRNA class |

FIG. 33 (Cont.)

| | | | | | | |
|---|---|---|---|---|---|---|
| CNP | nearCoding,coding | -1.44634046 | 5.57377E-05 | 0.015772548 | 2',3'-Cyclic Nucleotide 3' Phosphodiesterase | May participate in RNA metabolism in the myelinating cell, CNP is the third most abundant protein in central nervous system myelin. |
| IFI44L | coding | -1.440359858 | 0.00016374 | 0.031576376 | Interferon Induced Protein 44 Like | Exhibits a low antiviral activity against hepatitis C virus. |
| VRK2 | coding | -1.435936423 | 0.000131104 | 0.027305353 | Vaccinia Related Kinase 2 | serine/threonine protein kinases. The encoded protein acts as an effector of signaling pathways that regulate apoptosis and tumor cell growth. Serine/threonine kinase that regulates several signal transduction pathways. Isoform 2 phosphorylates Thr-18 of p53/TP53, as well as histone H3. |
| SCD | coding | -1.435497053 | 4.32844E-05 | 0.013576712 | Stearoyl-CoA Desaturase (Delta-9-Desaturase) | This gene encodes an enzyme involved in fatty acid biosynthesis, primarily the |

FIG. 33 (Cont.)

| | | | | | | synthesis of oleic acid. |
|---|---|---|---|---|---|---|
| SLC5A11 | coding | -1.427100527 | 0.000150154 | 0.029172528 | Solute Carrier Family 5 Member 11 | represent a major class of proteins that make use of ion gradients to drive active transport for the cellular accumulation of nutrients, neurotransmitters, osmolytes, and ions |
| CTNNA3 | coding | -1.419162757 | 0.000139124 | 0.028519333 | Catenin Alpha 3 | May be involved in formation of stretch-resistant cell-cell adhesion complexes. |
| HAPLN2 | coding | -1.417642596 | 5.82336E-05 | 0.016128237 | Hyaluronan And Proteoglycan Link Protein 2 | May play a pivotal role in the formation of the hyaluronan-associated matrix in the central nervous system (CNS) which facilitates neuronal conduction and general structural stabilization. |
| UGT8 | nearCoding,coding | -1.410907596 | 7.22543E-05 | 0.018066921 | UDP Glycosyltransferase 8 | It catalyzes the transfer of galactose to ceramide, a key enzymatic step in the biosynthesis of |

FIG. 33 (Cont.)

| | | | | | | galactocerebrosides, which are abundant sphingolipids of the myelin membrane of the central and peripheral nervous systems. |
|---|---|---|---|---|---|---|
| CAPN3 | coding | -1.406839098 | 8.32402E-05 | 0.019523208 | Calpain 3 | Calpains are a group of calcium-sensitive cysteine proteases that are ubiquitously expressed in mammals |
| SLC31A2 | coding | -1.40550132 | 0.000127248 | 0.026933166 | Solute Carrier Family 31 Member 2 | Involved in low-affinity copper uptake. |
| DNAH17 | nearCoding,coding | -1.396168052 | 0.000119876 | 0.025792185 | Dynein Axonemal Heavy Chain 17 | Dyneins are microtubule-associated motor protein complexes composed of several heavy, light, and intermediate chains. |
| PLEKHH1 | coding | -1.39100081 | 0.000142063 | 0.028670236 | Pleckstrin Homology, MyTH4 And FERM Domain Containing H1 | N/A |
| SEPP1 | nearCoding,coding | -1.382627002 | 0.000215637 | 0.038451287 | Selenoprotein P, Plasma, 1 | Might be responsible for some of the extracellular antioxidant defense properties of |

FIG. 33 (Cont.)

| | | | | | | | selenium or might be involved in the transport of selenium. |
|---|---|---|---|---|---|---|---|
| WIPF1 | coding | -1.379389493 | 0.000246159 | 0.043300647 | WAS/WASL Interacting Protein Family Member 1 | | This gene encodes a protein that plays an important role in the organization of the actin cytoskeleton. |
| CA14 | coding | -1.377350517 | 0.000135071 | 0.027908339 | Carbonic Anhydrase 14 | | zinc metalloenzymes that catalyze the reversible hydration of carbon dioxide. They participate in a variety of biological processes, including respiration, calcification, acid-base balance, bone resorption, and the formation of aqueous humor, cerebrospinal fluid, saliva, and gastric acid. |
| SHROOM4 | nearCoding,coding | -1.370371835 | 0.000129516 | 0.027192059 | Shroom Family Member 4 | | Probable regulator of cytoskeletal architecture that plays an important role in development. May regulate cellular and |

FIG. 33 (Cont.)

| | | | | | | cytoskeletal architecture by modulating the spatial distribution of myosin II |
|---|---|---|---|---|---|---|
| GPR62 | coding | -1.356153089 | 0.000219351 | 0.03884755 | G Protein-Coupled Receptor 62 | Orphan receptor. |
| USH1C | nearCoding,coding | -1.352383331 | 0.000328314 | 0.050589002 | USH1 Protein Network Component Harmonin | This gene encodes a scaffold protein that functions in the assembly of Usher protein complexes. |
| MAL | coding | -1.35210473 | 0.000296409 | 0.047984469 | Mal T-Cell Differentiation Protein | This proteolipid is localized in compact myelin of cells in the nervous system and has been implicated in myelin biogenesis and/or function. Could be involved in myelin biogenesis and/or myelin function. |
| SEPT4 | coding | -1.347869932 | 9.46483E-05 | 0.021664129 | Septin 4 | This gene is a member of the septin family of nucleotide binding proteins, originally described in yeast as cell division cycle |

FIG. 33 (Cont.)

| | | | | | | regulatory proteins. |
|---|---|---|---|---|---|---|
| TPPP3 | coding | -1.330852168 | 0.000296747 | 0.047984469 | Tubulin Polymerization Promoting Protein Family Member 3 | Binds tubulin and has microtubule bundling activity. May play a role in cell proliferation and mitosis. |
| SELPLG | coding | -1.324367453 | 6.19207E-05 | 0.016388656 | Selectin P Ligand | This gene encodes a glycoprotein that functions as a high affinity counter-receptor for the cell adhesion molecules |
| SEMA3B | nearCoding,coding | -1.322557112 | 0.000277738 | 0.046390742 | Semaphorin 3B | members function in growth cone guidance during neuronal development. This family member inhibits axonal extension and has been shown to act as a tumor suppressor by inducing apoptosis. |
| PCSK6 | nearCoding,coding | -1.318784708 | 0.000267187 | 0.045463646 | Proprotein Convertase Subtilisin/Kexin Type 6 | proteases that process protein and peptide precursors trafficking through regulated or constitutive |

FIG. 33 (Cont.)

| | | | | | | branches of the secretory pathway. This gene is thought to play a role in tumor progression and left-right patterning. Alternatively spliced transcript variants encoding different isoforms have been identified. |
|---|---|---|---|---|---|---|
| CDC42 EP1 | coding | -1.313431413 | 0.000203921 | 0.036713258 | CDC42 Effector Protein 1 | CDC42 is a member of the Rho GTPase family that regulates multiple cellular activities, including actin polymerization.Probably involved in the organization of the actin cytoskeleton. |
| TMCC3 | coding | -1.308964502 | 0.000263364 | 0.045463646 | Transmembrane And Coiled-Coil Domain Family 3 | N/A |
| RTKN | coding | -1.30866227 | 0.000300239 | 0.048249488 | Rhotekin | Mediates Rho signaling to activate NF-kappa-B and may confer increased resistance to apoptosis to cells in gastric tumorigenesis. |

FIG. 33 (Cont.)

| ELN | nearCoding,coding | -1.308125945 | 4.18758E-05 | 0.013295049 | Elastin | This gene encodes a protein that is one of the two components of elastic fibers. |
|---|---|---|---|---|---|---|
| COL9A3 | coding | -1.295806194 | 0.00020448 | 0.036713258 | Collagen Type IX Alpha 3 | This gene encodes one of the three alpha chains of type IX collagen, the major collagen component of hyaline cartilage. |
| FGF1 | coding | -1.273193569 | 0.00029497 | 0.047984469 | Fibroblast Growth Factor 1 | FGF family members possess broad mitogenic and cell survival activities, and are involved in a variety of biological processes, including embryonic development, cell growth, morphogenesis, tissue repair, tumor growth and invasion. Plays an important role in the regulation of cell survival, cell division, angiogenesis, cell differentiation |

FIG. 33 (Cont.)

| | | | | | | and cell migration. |
|---|---|---|---|---|---|---|
| DAAM2 | coding | -1.263062931 | 0.000317797 | 0.049867681 | Dishevelled Associated Activator Of Morphogenesis 2 | Among its related pathways are Wnt signaling pathway (KEGG) and WNT Signaling. |
| LPPR1 | coding | -1.235810821 | 0.000279763 | 0.046390742 | Lipid Phosphate Phosphatase-Related Protein Type 1 | Members of the PRG family mediate lipid phosphate phosphatase activity in neurons and are known to be involved in neuronal plasticity. The protein encoded by this gene does not perform its function through enzymatic phospholipid degradation. This gene is strongly expressed in brain. It shows dynamic expression regulation during brain development and neuronal excitation. |

FIG. 33 (Cont.)

| | | | | | | |
|---|---|---|---|---|---|---|
| TMTC4 | coding | -1.204603072 | 0.000328399 | 0.050589002 | Transmembrane And Tetratricopeptide Repeat Containing 4 | N/A |
| RAMP3 | coding | -1.186023244 | 2.44915E-06 | 0.002772229 | Receptor (G Protein-Coupled) Activity Modifying Protein 3 | The protein encoded by this gene is a member of the RAMP family of single-transmembrane-domain proteins, called receptor (calcitonin) activity modifying proteins (RAMPs). |
| PRKCQ | coding | -1.183880824 | 0.000196078 | 0.035697209 | Protein Kinase C Theta | Protein kinase C (PKC) is a family of serine- and threonine-specific protein kinases that can be activated by calcium and the second messenger diacylglycerol. PKC family members phosphorylate a wide variety of protein targets and are known to be involved in diverse cellular signaling pathways. It is a calcium-independent and phospholipid-dependent protein kinase. |

FIG. 33 (Cont.)

| | | | | | | This kinase is important for T-cell activation. It is required for the activation of the transcription factors NF-kappaB and AP-1, and may link the T cell receptor (TCR) signaling complex to the activation of the transcription factors. |
|---|---|---|---|---|---|---|
| CCND1 | coding | -1.180970956 | 1.7746 1E-05 | 0.0081 8315 | Cyclin D1 | This cyclin forms a complex with and functions as a regulatory subunit of CDK4 or CDK6, whose activity is required for cell cycle G1/S transition. Also substrate for SMAD3 |
| ZDHHC9 | coding | -1.17093804 | 0.0002 73763 | 0.0462 80142 | Zinc Finger DHHC-Type Containing 9 | The ZDHHC9-GOLGA7 complex is a palmitoyltransferase specific for HRAS and NRAS |
| CABP7 | coding | -1.148663859 | 1.2528 5E-05 | 0.0069 39746 | Calcium Binding Protein 7 | Negatively regulates Golgi-to-plasma membrane trafficking by interacting with PI4KB and |

FIG. 33 (Cont.)

| | | | | | | inhibiting its activity. |
|---|---|---|---|---|---|---|
| CDH24 | coding | -1.135580754 | 6.07364E-05 | 0.016301161 | Cadherin 24 | Among its related pathways are ERK Signaling and Cell junction organization. |
| SEMA3E | coding | -1.131447951 | 7.64153E-05 | 0.018592474 | Semaphorin 3E | Plays an important role in signaling via the cell surface receptor PLXND1. Mediates reorganization of the actin cytoskeleton, leading to the retraction of cell projections. Promotes focal adhesion disassembly and inhibits adhesion of endothelial cells to the extracellular matrix. |
| C2orf82 | coding | -1.116032103 | 0.000141997 | 0.028670236 | Chromosome 2 Open Reading Frame 82 | N/A |
| THEMIS | coding | -1.087266082 | 0.000195192 | 0.035697209 | Thymocyte Selection Associated | The protein functions through T-cell antigen receptor signaling, and is necessary for proper lineage commitment and maturation of T-cells. |

FIG. 33 (Cont.)

| | | | | | | |
|---|---|---|---|---|---|---|
| FZD9 | coding | -1.084413207 | 0.000293193 | 0.047984469 | Frizzled Class Receptor 9 | receptors for Wnt proteins. |
| TBL2 | coding | -1.06420255 | 4.07981E-06 | 0.003641062 | Transducin (Beta)-Like 2 | Most proteins of the beta-transducin family are involved in regulatory functions. This protein is possibly involved in some intracellular signaling pathway. |
| DBX2 | coding | -1.059046145 | 0.000173701 | 0.033092303 | Developing Brain Homeobox 2 | GO annotations related to this gene include *sequence-specific DNA binding*. |
| EIF4H | coding | -1.041757444 | 8.64142E-06 | 0.005602172 | Eukaryotic Translation Initiation Factor 4H | This gene encodes one of the translation initiation factors, which functions to stimulate the initiation of protein synthesis at the level of mRNA utilization. |
| CCDC 109B | coding | -1.035328979 | 0.000302536 | 0.048320446 | Coiled-Coil Domain Containing 109B | Negatively regulates the activity of MCU, the mitochondrial inner membrane calcium uniporter, and |

FIG. 33 (Cont.)

|  |  |  |  |  |  | thereby modulates calcium uptake into the mitochondrion. Does not form functional calcium channels by itself. Mitochondrial calcium homeostasis plays key roles in cellular physiology and regulates cell bioenergetics, cytoplasmic calcium signals and activation of cell death pathways. |
|---|---|---|---|---|---|---|
| CLIP2 | coding | -1.023942423 | 1.16737E-07 | 0.000434163 |  | This gene is hemizygously deleted in Williams syndrome, a multisystem developmental disorder caused by the deletion of contiguous genes at 7q11.23 |
| NSUN5 | coding | -1.018572109 | 0.000100141 | 0.022282751 | NOP2/Sun RNA Methyltransferase Family Member 5 | This gene encodes a member of an evolutionarily conserved family of proteins that may function as |

FIG. 33 (Cont.)

| | | | | | | methyltransferases |
|---|---|---|---|---|---|---|
| BAZ1B | nearCoding,coding | -0.95972674 | 3.08414E-06 | 0.003211699 | Bromodomain Adjacent To Zinc Finger Domain 1B | The bromodomain is a structural motif characteristic of proteins involved in chromatin-dependent regulation of transcription. |
| WBSCR22 | nearCoding,coding | -0.936289655 | 1.8479E-05 | 0.00818315 | Williams-Beuren Syndrome Chromosome Region 22 | This gene encodes a protein containing a nuclear localization signal and an S-adenosyl-L-methionine binding motif typical of methyltransferases, suggesting that the encoded protein may act on DNA methylation. |
| GTF2I | coding | -0.924727788 | 4.19574E-06 | 0.003641062 | Generall transcription factor 2i | |
| HEXIM1 | coding | 0.778497519 | 0.000305011 | 0.048418582 | Hexamethylene Bis-Acetamide Inducible 1 | Transcriptional regulator which functions as a general RNA polymerase II transcription inhibitor. May also regulate NF-kappa-B, |

FIG. 33 (Cont.)

| | | | | | | ESR1, NR3C1 and CIITA-dependent transcriptional activity. |
|---|---|---|---|---|---|---|
| ANKRD18B | coding | 0.905209812 | 0.000265742 | 0.045463646 | Ankyrin Repeat Domain 18B | GO annotations related to this gene include *nucleotide binding*. |
| CDKN1A | coding | 1.379999562 | 0.000148246 | 0.02901831 | Cyclin-Dependent Kinase Inhibitor 1A | cyclin-dependent kinase inhibitor. The encoded protein binds to and inhibits the activity of cyclin-cyclin-dependent kinase2 or -cyclin-dependent kinase4 complexes, and thus functions as a regulator of cell cycle progression at G1. This protein was reported to be specifically cleaved by CASP3-like caspases, which thus leads to a dramatic activation of cyclin-dependent kinase2, and may be instrumental in the execution of |

FIG. 33 (Cont.)

| | | | | | | apoptosis following caspase activation. |
|---|---|---|---|---|---|---|
| MT1A | nearCoding,coding | 1.397663964 | 0.000178768 | 0.033725018 | Metallothionein 1A | Metallothioneins have a high content of cysteine residues that bind various heavy metals; these proteins are transcriptionally regulated by both heavy metals and glucocorticoids. |
| PLAUR | coding | 1.4289102 | 5.70063E-05 | 0.015958079 | Plasminogen Activator, Urokinase Receptor | Acts as a receptor for urokinase plasminogen activator. |
| HEATR7A | coding | 1.453682895 | 0.000146578 | 0.02890916 | Maestro Heat Like Repeat Family Member 1 | N/A |
| THBS1 | coding | 1.453896765 | 1.43159E-05 | 0.007454021 | Thrombospondin 1 | This protein is an adhesive glycoprotein that mediates cell-to-cell and cell-to-matrix interactions |
| CCL2 | coding | 1.537600852 | 6.05856E-05 | 0.016301161 | C-C Motif Chemokine Ligand 2 | Chemokines are a superfamily of secreted proteins involved in immunoregulatory and inflammatory processes. |

FIG. 33 (Cont.)

| EMP1 | coding | 1.669465 06 | 8.8226 6E-06 | 0.0056 02172 | Epithelial Membrane Protein 1 | N/A |
| ZFP36 | coding | 1.694362 527 | 6.1904 3E-06 | 0.0046 04617 | ZFP36 Ring Finger Protein | Among its related pathways are Gene Expression and ErbB1 downstream signaling. |

FIG. 33 (Cont.)

COMPOSITIONS AND METHODS FOR WILLIAMS SYNDROME (WS) THERAPY

CROSS-REFERENCE TO RELATED APPLICATIONS

The present application is a national stage application, filed under 35 U.S.C. § 371, of International Application No. PCT/US2018/067092, filed Dec. 21, 2018, which is related to and claims priority under 35 U.S.C. § 119(e) to U.S. provisional patent application No. 62/610,063, entitled "Compositions and Methods for Williams Syndrome (WS) Therapy," filed Dec. 22, 2017. The entire content of the aforementioned patent applications are incorporated herein by this reference.

FIELD OF THE INVENTION

The invention relates generally to methods and compositions for the treatment of Williams Syndrome (WS).

BACKGROUND OF THE INVENTION

To date, limited treatment options have been available for Williams Syndrome (WS). A need exists for improved compositions and methods for treating WS.

BRIEF SUMMARY OF THE INVENTION

The current disclosure relates, at least in part, to the discovery that Gtf2i, a gene deleted in WS, is critical for myelination mediated by neuron-oligodendrocyte interaction, and that the phenotypic defects discovered in Gtf2i-deleted mice (specifically, mice harboring a localized homozygous deletion of Gtf2i in forebrain excitatory neurons) were remarkably and robustly treatable via administration of a potassium channel blocker drug, 4-Aminopyridine (4-AP), to Gtf2i-deleted mice, or via administration of clemastine (an antihistamine and anticholinergic), to Gtf2i-deleted mice. Treatment of Gtf2i-hemizygous subjects (e.g., mice or humans) via administration of a potassium channel blocker, e.g., 4-AP, via administration of clemastine, or via administration of other compounds as described herein and/or as known in the art, is therefore also contemplated. The instant disclosure has therefore identified improved compositions and methods for treating WS, and optionally for treating other diseases or disorders characterized by neurodevelopmental myelination abnormalities, e.g., neurodevelopmental myelination deficits (as contrasted with demyelination-associated diseases, in which myelin degrades/has degraded).

In one aspect the instant disclosure provides a method of treating or preventing one or more neurological symptoms of a neurodevelopmental myelination abnormality disease or disorder in a subject by administering a potassium channel blocker or other agent capable of improving conductance through an aberrantly myelinated axon and/or provoking myelination of an aberrantly myelinated neuron to the subject in an amount sufficient to treat or prevent the one or more neurological symptoms of the neurodevelopmental myelination abnormality disease or disorder in the subject.

In another aspect, the instant disclosure provides a method for treating or preventing one or more neurological symptoms of a neurodevelopmental myelination abnormality disease or disorder in a subject, the method involving administering a potassium channel blocker or other drug for treatment of a neurodevelopmental myelination abnormality disease or disorder, or a pharmaceutically acceptable salt thereof to the subject in need of such therapy in an amount sufficient to treat or prevent the one or more neurological symptoms of the neurodevelopmental myelination abnormality disease or disorder in the subject.

In one embodiment, the potassium channel blocker is 4-Aminopyridine (4-AP), a derivative thereof, or a combination thereof; 3,4 diaminopyridine (3,4-DAP), a derivative thereof, or a combination thereof; tetraethylammonium (TEA); bretylium; other quaternary ammonium ion agent; and/or an agent of FIG. 32. Optionally, the potassium channel blocker is a presynaptic potassium channel blocker.

In one embodiment, the other drug for treatment of a neurodevelopmental myelination abnormality disease or disorder is opicinumab and/or clemastine.

In another embodiment, the potassium channel blocker or other drug for treatment of a neurodevelopmental myelination abnormality disease or disorder is a calcium channel agonist, optionally the calcium channel agonist is 4-AP, Bay K8644; (S)-(−)-Bay K8644; FPL 64176; GV-58; ML-SA1; MSP-3; Ambroxol; Amiodarone; and/or AC-265347, optionally the calcium channel agonist is a voltage-activated calcium channel (VACC) stimulatory agent.

In certain embodiments, the neurodevelopmental myelination abnormality disease or disorder is Williams Syndrome (WS), Rett Syndrome, an autism spectrum disorder and/or other neurodevelopmental disorder; optionally, the autism spectrum disorder is an autism-associated CHD8 mutation disorder or fragile X syndrome.

In some embodiments, the one or more neurological symptoms of the neurodevelopmental myelination abnormality disease or disorder include abnormal fine motor skills, optionally including tremors or limb weakness, and abnormal social skills.

In one embodiment, the potassium channel blocker or other drug for treatment of a neurodevelopmental myelination abnormality disease or disorder is administered orally, optionally as an approximately 1-30 mg tablet, optionally as an approximately 10 mg tablet, optionally administered daily.

In another embodiment, the subject exhibits a normalization of fine motor skills and/or a normalization of social preference or behavior, as compared to an appropriate control subject, after administering the potassium channel blocker or other drug for treatment of a neurodevelopmental myelination abnormality disease or disorder, or pharmaceutically acceptable salt thereof.

Another aspect of the instant disclosure provides a pharmaceutical composition for treatment of one or more neurological symptoms of a neurodevelopmental myelination abnormality disease or disorder in a subject that includes a potassium channel blocker or other drug for treatment of a neurodevelopmental myelination abnormality disease or disorder, or a pharmaceutically acceptable salt thereof, and a pharmaceutically acceptable carrier.

In one embodiment, the pharmaceutical composition is effective at normalizing fine motor skills and/or a normalizing social preference or behavior in a subject to whom the pharmaceutical composition is administered.

Another aspect of the instant disclosure provides a method for treating or preventing one or more neurological symptoms of Williams Syndrome (WS) in a subject, the method involving administering an effective amount of a pharmaceutical composition including a potassium channel blocker, opicinumab and/or clemastine, or a pharmaceutically acceptable salt thereof to the subject in need of such therapy, thereby treating or preventing the one or more neurological symptoms of WS in the subject.

In certain embodiments, the potassium channel blocker is a selective potassium channel blocker, optionally the selective potassium channel blocker is 4-Aminopyridine (4-AP), a derivative thereof, or a combination thereof; 3,4 diaminopyridine (3,4-DAP), a derivative thereof, or a combination thereof; tetraethylammonium (TEA); bretylium; other quaternary ammonium ion agent; and/or an agent of FIG. 32, optionally wherein the potassium channel blocker is 4-AP.

In one embodiment, the one or more neurological symptoms of WS include abnormal fine motor skills, optionally including tremors or limb weakness, and/or abnormal social skills.

Another aspect of the instant disclosure provides a method for treating or preventing one or more neurological symptoms of Williams Syndrome (WS) in a subject, the method involving obtaining a neuronal stem cell from the subject; repairing the Gtf2i gene in the neuronal stem cell of the subject; and administering an effective amount of the repaired neuronal stem cell to the subject in need of such therapy, thereby treating or preventing the one or more neurological symptoms of WS in the subject.

In certain embodiments, the step of repairing involves use of CRISPR/Cas 9 to repair one or more genomic copies of the Gtf2i gene in the subject.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

By "agent" is meant any small compound (e.g., small molecule), antibody, nucleic acid molecule, or polypeptide, or fragments thereof.

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoietic stem cells (HSC); bone marrow derived cells, neural progenitor cells, etc.).

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

By "marker" is meant any protein or polynucleotide having an alteration in expression level or activity that is associated with a disease or disorder.

As used herein, the term "neurodevelopmental myelination abnormality disease or disorder" refers to a disease or disorder characterized by abnormal myelination of neurons to an extent that produces an observable phenotype in a subject having such "neurodevelopmental myelination abnormality disease or disorder." In certain embodiments, a "neurodevelopmental myelination abnormality disease or disorder" is a disease or disorder for which no association between aberrant myelination and phenotype has been previously identified. Examples of a "neurodevelopmental myelination abnormality disease or disorder" include Williams Syndrome, Rett Syndrome, and autism (including autism-associated CHD8 mutation disorder and Fragile X syndrome)—where certain forms of autism spectrum disorder (ASD) likely exhibit developmental hypomyelination or hypermyelination, yet treatment of other diseases or disorders characterized by neurodevelopmental myelination abnormalities are also contemplated. Such neurodevelopmental myelination abnormality diseases or disorders are distinguishable from demyelination diseases or disorders, in which myelin degrades/has degraded, which include, e.g., multiple sclerosis (MS), spinal cord injury (SCI), Alzheimer's disease (AD), Parkinson's disease (PD), amyotrophic lateral sclerosis (ALS), CNS demyelinating autoimmune diseases, adrenoleukodystrophy, Alexander disease, Balo concentric sclerosis, CAMFAK syndrome, Canavan disease, central pontine myelinolysis, experimental autoimmune encephalomyelitis, hereditary CNS demyelinating disease, Krabbe disease, leukoencephalopathy with vanishing white matter, Marchiafava-Bignami disease, megalencephalic leukoencephalopathy with subcortical cysts, metachromatic leukodystrophy, neuromyelitis optica, Pelizaeus-Merzbacher disease and diffuse myelinoclastic sclerosis, among others. In certain aspects of the instant disclosure, a "neurodevelopmental myelination abnormality disease or disorder" is one for which developmentally aberrant neuronal myelination (e.g., hypomyelination or hypermyelination) occurs within brain neurons, optionally within a specific class of neurons in the brain of a subject, e.g., excitatory neurons and/or oligodendrocytes, optionally at the exclusion of other classes of neurons. In certain embodiments, the developmentally aberrant myelination reflects a reduction and/or absence of myelination of oligodendrocytes attributable to a reduction and/or absence of myelination mediated by neuron-oligodendrocyte interaction. Optionally, in certain respective embodiments, a "neurodevelopmental myelination abnormality disease or disorder" of the instant disclosure can be referred to, e.g., as a "neurodevelopmental oligodendrocyte myelination abnormality disease or disorder" or as a "neurodevelopmental myelination abnormality disease or disorder induced by absence of neuron-oligodendrocyte-mediated myelination." In certain embodiments, a "neurodevelopmental myelination abnormality disease or disorder" is a congenital disease or disorder. In some aspects, a "neurodevelopmental myelination abnormality disease or disorder" is characterized as distinguished from an environmentally imparted myelination defect, thus, the neurodevelopmental myelination abnormality disease or disorder reflects an etiological developmental origin.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "pharmaceutically acceptable salts, esters, amides, and prodrugs" as used herein refers to those carboxylate salts, amino acid addition salts, esters, amides, and prodrugs of the compounds of the present disclosure which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "prodrug" refers to compounds that are rapidly transformed in vivo to yield the parent compounds of the agents of the instant disclosure, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

The term "salts" refers to the relatively non-toxic, inorganic and organic acid addition salts of compounds of the present disclosure. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methlyamine, dimethlyamine, trimethlyamine, triethlyamine, ethylamine, and the like. (See, for example, S. M. Barge et al., "Pharmaceutical Salts," J. Pharm. Sci., 1977, 66:1-19 which is incorporated herein by reference).

"Slow or sustained release formulation" refers to a formulation designed to release a therapeutically effective amount of drug or other active agent such as a polypeptide or a synthetic compound over an extended period of time, with the result being a reduction in the number of treatments necessary to achieve the desired therapeutic effect. In the matter of the present disclosure, a slow release formulation would decrease the number of treatments necessary to achieve the desired effect in terms of reduction in spasticity, normalization of social behavior and/or an improvement in motor or sensory function in patients in need of such therapy, for example, in subjects having Williams Syndrome, autism spectrum disorder, or other neurodevelopmental myelination abnormality disease or disorder. The slow or sustained release formulations of the present disclosure achieve a desired pharmacokinetic profile in a subject.

"Sublingual delivery" refers to the system delivery of drugs or other agents through the mucosal membranes lining the floor of the mouth.

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A shows a western-blot of TFII-I and tubulin expression in whole cortex samples from month-old control and Gtf2i cKO mice. FIG. 1B is a histogram of TFII-I in the whole cortex, showing significantly reduced expression of TFII-I in whole cortex of 1 month-old cKO compared to controls, as measured by Western-blot. FIG. 1C is a line plot of body weight, depicting that cKO mice exhibited similar body weight compared to controls.

FIG. 1D and FIG. 1E are histograms that show one month-old cKO mice exhibited significantly reduced brain weight (FIG. 1D) and cortical thickness (FIG. 1E), as compared to controls. FIG. 1F and FIG. 1G are histograms of dyadic interaction time and dyadic social events, respectively, and show increased levels of social behavior in cKO mice, as compared to controls, as demonstrated by significantly longer duration (FIG. 1F) and higher frequency of close social interaction events (FIG. 1G) during the dyadic social interaction test. FIG. 1H is a histogram of social preference duration and shows that, in the three-chamber social interaction test, cKO mice exhibited significantly higher social preference, as compared to controls, with cKO mice observed to interact significantly longer with a stranger mouse, as compared to controls. FIG. 1I is a histogram of tube test wins and shows decreased levels of social dominance in cKO mice, demonstrated by significantly lower percentage of wins in the tube test, as compared to controls. FIG. 1J to FIG. 1L show, respectively, a line plot of open field total distance, a line plot of open field time in margins, and a histogram of zero maze time in open arms, which demonstrated that cKO mice showed significantly increased levels of anxiety-like behaviors, as compared to controls, as demonstrated by significantly shorter total exploration distance in the open field test (FIG. 1J), significantly longer duration in the margins of the open arena (FIG. 1K), and significantly less time in the open arms of an elevated zero maze (FIG. 1L), as compared to controls. *$p<0.05$, $p<0.01$, *$p<0.005$, ****$p<0.001$, N.S.=Not significant, two-tailed t-test (FIG. 1A, FIG. 1B, FIG. 1D, FIG. 1I, FIG. 1L, two-way repeated measures ANOVA with Bonferonni post-hoc test (FIG. 1C, FIG. 1J and FIG. 1K). Data are mean±s.e.m. (FIG. 1A to FIG. 1E: n=8 Control, n=10 cKO; E-G: n=8 Control pairs, n=8 cKO pairs; FIG. 1I to FIG. 1L: n=10 Control, n=10 cKO).

FIG. 2A to FIG. 2H show a series of charts, heatmaps, graphs, and images, which depict myelination-related transcriptomic and cellular alterations observed in Gtf2i cKO mice. FIG. 2A is a gene expression heatmap table including all the genes that showed significantly decreased mRNA level in the cortex of cKO mice compared to controls. Myelination-related genes are labeled by a "#" symbol. FIG. 2B is a histogram of biological pathways significantly affected in the cortex of 1 month-old cKO mice, showing significantly downregulated cellular pathways in cKO mice cortex, as compared to controls. Myelination-related pathways are labeled by a "#" symbol. FIG. 2C is a histogram of myelination-related genes assessed by qPCR, showing reduced mRNA level of myelin-related genes in the cortex of cKO mice as validated by quantitative PCR. FIG. 2D is a histogram of oligodendrocyte markers in development, which showed no significant difference in the number of oligodendrocytes precursor cells (OPC) in embryonic day 15.5 cKO embryos, as compared to controls. In the cortex and CC midline of 1 month-old cKO mice, the number of myelinating oligodendrocytes (mOLs) was significantly reduced, while OPC number was not altered. FIG. 2E depicts a series of representative images of myelinating oligodendrocytes in the cortex and CC midline. Representative images with immunofluorescence labeling demonstrated a reduced number of mOLs in the cortex and CC midline of 1 month-old cKO mice, as compared to controls. FIG. 2F shows a histogram of oligodendrocyte nuclear heterochromatin percentages, which demonstrated significantly reduced oligodendrocyte nuclear heterochromatin percentage in the CC midline of 1 month-old cKO mice, as compared to controls. FIG. 2G presents a line graph of H3ac intensity in myelinating oligodendrocytes in the cortex, which showed H3ac intensity in mOLs in the cortex of cKO mice was significantly lower than in controls. FIG. 2H shows a line graph of H3K9me3 intensity in myelinating oligodendrocytes in the cortex, which demonstrated that H3K9me3 intensity in mOLs in cKO mice cortex was significantly higher than in controls. *$p<0.05$, $p<0.01$, *$p<0.005$, N. S.=Not significant, two-tailed t-test (C-D, F, Kolmogorov-Smirnov test (G-H)). Data are mean±s.e.m. (A-B: n=3 Control, n=3 cKO; C: n=11 Control, n=11 cKO; D: n=7 Control, n=7 cKO, for both E15.5 and 1 month-old mice; F: n=30 nuclei from Control mice, n=37 nuclei from cKO mice; G: n=90 nuclei from Control mice, n=90 nuclei from cKO mice; H: n=104 nuclei from Control mice, n=93 nuclei from cKO mice).

FIG. 3A shows representative images of myelin ultrastructural abnormalities in the CC midline of cKO mice, as compared to controls (Scale bar: Left=1,500 nm; Middle=300 nm; Right=100 nm).

FIG. 3Q is a histogram of social preference index. Social preference index, as measured in the three chambers social interaction test, was decreased and normalized to control levels in cKO following 4-AP acute administration. *$p<0.05$, $p<0.01$, *$p<0.005$, ****$p<0.0001$. N.S.=Not significant, two-tailed t-test (FIG. 3B to FIG. 3Q), two-way repeated measures ANOVA with Bonferonni post-hoc test (FIG. 3J). Data are mean±s.e.m. (FIG. 3B and FIG. 3C: n=3 control, n=3 cKO; FIG. 3D to FIG. 3F: n=7 Control, n=7 cKO; FIG. 3G to FIG. 3I: n=7 Control, n=9 cKO; FIG. 3J: n=4 Control, n=9 cKO; FIG. 3L to FIG. 3O: n=6 Control, n=6 cKO; FIG. 3P: n=8 Control, n=8 cKO; FIG. 3Q: n=12 Control, n=9 cKO).

FIG. 4A shows that following 2 weeks of clemastine administration, the number of myelinating oligodendrocytes (mOLs) in the cortex and CC midline of cKO mice was significantly increased and normalized to control levels. FIG. 4B shows that significantly increased myelin thickness was observed in the CC midline of cKO mice following 2 weeks of clemastine administration, as measured by significantly decreased g ratio compared to cKO mice administered with vehicle only. FIG. 4C shows that social preference index, as measured in the three chambers social interaction test, was decreased and normalized to control levels in cKO following 2 weeks of clemastine administration. *$p<0.05$, $p<0.01$, *$p<0.005$, two-tailed t-test (FIG. 4A and FIG. 4C), one-way ANOVA with Dunnett's post-hoc test (FIG. 4B). Data are mean±s.e.m. FIG. 4A: n=10 Control, n=7 cKO-Vehicle, n=7 cKO-Clemastine; FIG. 4B: n=3 Control, n=3 cKO-Vehicle, n=4 cKO-Clemastine; FIG. 4C: n=16 Control, n=10 cKO-Vehicle, n=11 cKO-Clemastine.

FIG. 5A is a diagram of a frontal cortical region (BA9) of human brain (top panel) and an illustration of the WS chromosomal region (bottom panel). FIG. 5A also provides a visual reference for the location of frontal cortex human tissue samples. FIG. 5B is a gene expression heatmap table showing all the myelination-related genes that exhibited significantly decreased mRNA level in the cortex of WS human subjects, as compared to typically-developed controls. In bold are genes that also exhibited significantly decreased mRNA level in Gtf2i cKO mice, as compared to controls. FIG. 4C is a graph of significantly downregulated biological/cellular pathways in the cortex of WS human subjects, as compared to typically-developed controls, including myelination-related pathways (labeled by a "#" symbol). FIG. 5D is a histogram of oligodendrocyte precursor cell counts in the human cortex. No significant difference was observed in the number of oligodendrocyte precursor cells (OPC) in the cortex of WS subjects, as compared to controls. FIG. 5E shows representative images of fluorescence in Situ hybridization labeling demonstrating similar number of OPCs in the cortex of WS subjects compared to controls. FIG. 5F is a histogram of myelinating oligodendrocyte counts in the human cortex. The number of myelinating oligodendrocytes (mOLs) was reduced in the cortex of WS subjects, as compared to controls. FIG. 5G shows images of myelinating oligodendrocytes in the human cortex. Representative images of immunofluorescence labeling demonstrated a reduced number of mOLs in the cortex of WS subjects, as compared to controls. FIG. 5H is a histogram of MBP intensity in the human cortex, showing reduced intensity of myelin basic protein (MBP) in the cortex of WS subjects, as compared to controls. FIG. 5I shows images of MBP in the human cortex. Representative images of immunofluorescent labeling demonstrated a reduced intensity of MBP in the cortex of WS subjects, as compared to controls. FIG. 5J and FIG. 5K are a plot of g ratio and an image of myelin thickness, which show that significantly reduced myelin thickness was observed in the frontal cortex of WS subjects, as measured by increased g ratio in WS subjects, as compared to controls. FIG. 5L is a histogram that shows a trend of lower percentage of myelinated axons in the frontal cortex of WS subjects compared to controls. *p<0.05, p<0.01, **p<0.0001, two-tailed t-test (FIG. 5D, FIG. 5F, FIG. 5H, FIG. 5L). Data are mean±s.e.m. (FIG. 5D, FIG. 5F, FIG. 5H: n=3 Control subjects, n=3 Williams syndrome subjects. FIG. 5DJ, FIG. 5L: n=4 Control subjects, n=3 Williams syndrome subjects).

FIG. 9A is a histogram displaying cortical thickness, which shows that the cortex of cKO mice was significantly thinner than that of control mice, with the most drastic differences observed in anterior regions of the cortex. FIG. 9B is a line graph depicting the percentage of reduced cortical thickness along the anterior-posterior axis of cKO mice, as compared to control littermates. *p<0.05, **p<0.01, two-tailed t-test (FIG. 9A), two-way repeated measures ANOVA with Bonferonni post-hoc test (FIG. 9A). Data are mean±s.e.m. (FIG. 9A-FIG. 9B: n=8 Control, n=10 cKO).

In FIG. 10A and FIG. 10B, 23 day-old cKO mice showed hypersociability, as compared to controls, as was demonstrated by significantly longer duration (FIG. 10A) and higher frequency (FIG. 10B) in social interaction within the dyadic social interaction test. *p<0.05, **p<0.01, two-tailed t-test, two-way repeated measures ANOVA with Bonferonni post-hoc test. Data are mean±s.e.m. (n=8 Control, n=8 cKO).

In FIG. 11A, 1 month-old cKO mice showed increased levels of anxiety-like behavior in the open field exploration test as demonstrated by significantly shorter movement duration as compared to controls. Additionally, cKO mice explored for a significantly shorter distance (FIG. 11B) and for shorter duration in the center of the arena (FIG. 11C). *p<0.05, p<0.01, *p<0.005, two-way repeated measures ANOVA with Bonferonni post-hoc test (FIG. 11A to FIG. 11C). Data are mean±s.e.m. (FIG. 11A to FIG. 11C: n=10 Control, n=10 cKO).

(FIG. 12A to FIG. 12C: n=10 Control, n=10 cKO mice).

FIG. 13A shows a gene expression heatmap table including genes that were significantly decreased in their expression in cKO mice compared to controls. FIG. 13B shows biological pathways that were significantly downregulated in cKO mice compared to controls. Presented are −Log 10(p-value) and fold enrichment in cKO compared to controls. FIG. 13C shows a gene expression heat map table including genes that were significantly increased in their expression in cKO mice compared to controls. FIG. 13D shows biological pathways that were significantly upregulated in cKO mice compared to controls. Presented are −Log 10(p-value) and fold enrichment in cKO compared to controls. FIG. 13A to FIG. 13D: n=3 Control, n=3 cKO.

FIG. 14A shows a gene expression heat map table including genes for which expression was observed to be significantly higher in the cortex of cKO mice as compared to controls. FIG. 14B shows biological pathways that were significantly upregulated in 1 month-old cKO mouse cortex samples as compared to controls. Presented are −Log 10(p-value) and fold enrichment in cKO compared to controls. Labeled with "#" is a pathway related to myelin. FIG. 14A and FIG. 14B: n=3 Control, n=3 cKO.

FIG. 15A shows a gene set enrichment analysis of significantly downregulated genes in the cortex of 1 month-old cKO mice as compared to controls and displays the highest normalized enrichment score (NES) in myelinating oligodendrocytes. FIG. 15B shows a gene set enrichment analysis of significantly downregulated genes in the frontal cortex of WS subjects as compared to controls and displays the highest NES in myelinating oligodendrocytes.

FIG. 22A shows myelination-related gene expression results (assessed via qPCR) that revealed that reduced expression of myelin-related genes was observed in the cortex of two-weeks-old cKO mice, as compared to controls (n=12 control; n=7 cKO). FIG. 22B shows oligodendrocytes precursor cells (OPC) number results observed in the cortex of two-weeks-old cKO mice, which demonstrated that no significant difference in the number of OPC was observed in the cortex of two-weeks-old cKO mice compared to controls (n=9 control; n=6 cKO). FIG. 22C shows that the number of myelinating oligodendrocytes (mOLs) was reduced as compared to controls, but not significantly (n=9 control; n=6 cKO). *p<0.05, N.S.=not significant. Two-tailed t-test in all panels. Data shown are mean±s.e.m.

FIG. 23A shows reduced expression of myelin-related genes in the cortex of 6 month-old cKO mice, as compared to controls.

FIG. 23B shows that no significant difference was observed in the number of oligodendrocyte precursor cells (OPC) in the cortex of 6 month-old cKO mice, as compared to controls. FIG. 23C shows that in the cortex of 6 month-old cKO mice, the number of myelinating oligodendrocytes (mOLs) was significantly reduced as compared to controls. FIG. 23D and FIG. 23E show that significantly reduced myelin thickness was observed in the CC midline of 6 month-old cKO mice, as measured by increased g ratio in cKO mice compared to controls. FIG. 23F shows that a significantly lower percentage of myelinated axons were observed in the CC midline of 6 month-old cKO mice compared to controls. FIG. 23G shows representative images of myelin ultrastructural abnormalities in the CC midline of 6 month-old cKO mice compared to controls. *p<0.05, p<0.01, *p<0.005. Two-tailed t-test (FIG. 23A to FIG. 23D, FIG. 23F). Data are mean±s.e.m. (FIG. 23A to FIG. 23C: n=14 Control, n=14 cKO, FIG. 23D to FIG. 23E23F: n=3 Control, n=3 cKO).

FIG. 25A demonstrates that there were no significant differences in resting membrane properties between control and Gtf2i-KO cells obtained from 1 month-old cKO mice as measured by membrane capacitance. FIG. 25B demonstrates that no differences in access resistance were observed. FIG. 25C demonstrates that no differences in membrane resistance were observed. FIG. 25D shows that resting potential was also unaltered. Likewise, FIG. 25E to FIG. 25I show that there were no significant differences observed in intrinsic action potential properties between control and Gtf2i-KO cells from 1 month-old cKO mice as measured by rheobase (FIG. 25E), action potential half-width (FIG. 25F), action potential peak (FIG. 25G), instantaneous interspike interval after 500 pA current injection (FIG. 23H), or FI curve (FIG. 25I). Data are mean±s.e.m. (FIG. 25A to FIG. 25I: Each point is a single neuron. n=4 Control mice, n=4 cKO mice, 3-5 neurons per mouse).

FIG. 26A shows representative immunofluorescence images, and FIG. 26B shows quantification of immunofluorescence intensities of the ipsilateral side of the corticospinal axons in the cervical and lumbar spinal cord. Two-tailed t-test (FIG. 26B). Data are mean±s.e.m. (FIG. 26B: n=3 Control, n=3 cKO). N. S., not significant.

FIG. 27A shows baseline results in the three-chamber social preference test. FIG. 27B shows results in the three-chamber social preference test following 4-AP acute administration. FIG. 27B shows results in the three-chamber social preference test following the clemastine study. * indicates $p<0.05$. N.S.=not significant. A two-tailed t-test was performed in all panels. Data are mean±s.e.m. (FIG. 27A and FIG. 27B: n=12 Control, n=9 cKO, FIG. 27C: n=16 Control, n=10 cKO-Vehicle, n=11 cKO-Clemastine)

FIG. 28A shows significantly reduced expression of TFII-I was observed in whole cortex of 1 month-old Gtf2i-Het mice compared to controls, as measured by western blot. FIG. 28B FIG. 28B shows that Gtf2i-Het mice exhibited significantly increased levels of anxiety-like behaviors compared to controls, as demonstrated by significantly longer distance traveled in the margins of the open arena. FIG. 28C and FIG. 28D show that in the three-chamber social interaction test, Gtf2i-Het mice exhibited significantly higher social preference compared to controls, interacting significantly longer with a stranger mouse compared to controls. FIG. 28E shows that reduced expression of myelin-related genes was observed in the cortex of 1 month-old Gtf2i-Het mice compared to controls. FIG. 28F and FIG. 28G show significantly reduced myelin thickness was observed in the CC midline of 1 month-old Gtf2i-Het mice compared to controls, as measured by increased g ratio in Gtf2i-Het mice compared to controls. $*p<0.05$, $p<0.01$, $**p<0.001$. N.S.=Not significant. Two-tailed t-test was used evaluate FIG. 28A to FIG. 28F. Data are mean±s.e.m. (FIG. 28A: n=7 WT, n=7 Gtf2i-Het, FIG. 28B to FIG. 28D: n=13 WT, n=12 Gtf2i-Het, FIG. 28E: n=12 WT, n=9 Gtf2i-Het, FIG. 28F and FIG. 28G: n=3 WT, n=3 Gtf2i-Het).

FIG. 29A to FIG. 29D specifically show that there were no significant differences in resting membrane properties between control and Gtf2i-Het cells from 1 month-old Gtf2i-Het mice, as measured by membrane capacitance (FIG. 29A), access resistance (FIG. 29B), membrane resistance (FIG. 29C), or resting potential (FIG. 29D). Likewise, FIG. 29E to FIG. 29I show that there were no significant differences in intrinsic action potential properties observed between control and Gtf2i-Het cells from 1 month-old Gtf2i-Het mice as measured by rheobase (FIG. 29E), action potential half-width (FIG. 29F), action potential peak (FIG. 29G), instantaneous interspike interval after 500 pA current injection (FIG. 29H), or FI curve (FIG. 29I). Data are mean±s.e.m. (FIG. 29A to FIG. 29I: Each point is a single neuron. n=3 Control mice, n=3 Gtf2i-Het mice, 3-4 neurons per mouse).

FIG. 31 shows a chart of human subjects' information, specifically presenting information on the human subjects from whom the cortical tissue was acquired for the RNAseq and the myelination property assays. PMI=Postmortem interval, PM=Postmortem, WS=Williams syndrome.

FIG. 32 shows a table of blocking agents for various Kv1-Kv12 voltage-gated K+ channels, reproduced from Judge and Bevar (Pharmacology & Therapeutics 111: 224-259), where organic compounds are presented in the left column, venom-derived peptide toxins are presented in the middle column and charged elements are presented in the right column.

FIG. 33 shows a table of significantly affected human genes in WS subjects, based upon human frontal cortex bulk RNAseq results, following pathways analysis of raw data.

DETAILED DESCRIPTION OF THE INVENTION

Figure 1A:
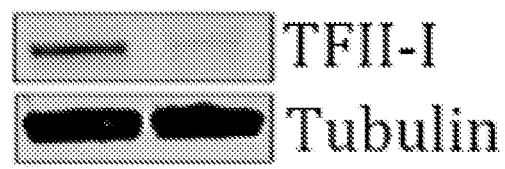
FIG. 1A to FIG. 1L present a series of graphs and images, depicting neuroanatomical and behavioral deficits observed in Gtf2i cKO mice.
Figure 1B:
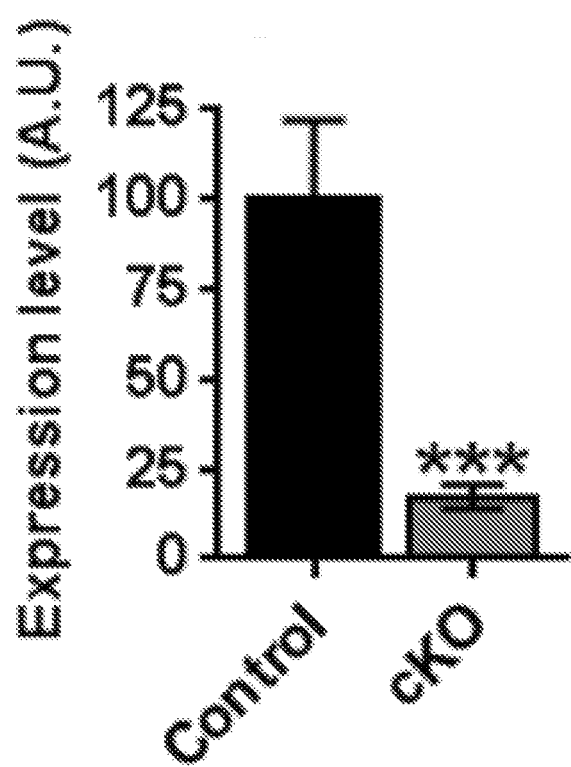

The present disclosure is directed, at least in part, to the discovery that localized Gtf2i-deleted mice exhibited myelination deficits (i.e., a developmental hypomyelination) of oligodendrocytes (including myelination deficits potentially attributable to a reduced number of oligodendrocytes and associated oligodendrocyte function deficits) that produced phenotypic effects in mice that paralleled phenotypes observed in human subjects having Williams Syndrome (WS) (human WS being a disease in which heterozygous genetic deletions that encompass Gtf2i have been described as causing such phenotypes). The instant disclosure has thereby specifically identified that Gtf2i, deleted in WS, is critical for myelination mediated by neuron-oligodendrocyte interaction. Moreover, the phenotypic defects discovered in Gtf2i-deleted mice were remarkably and robustly treatable via administration of a potassium channel blocker drug, 4-Aminopyridine (4-AP), to Gtf2i-deleted mice, or via administration of clemastine to Gtf2i-deleted mice. Treatment of Gtf2i-hemizygous mice (and/or other mammalian subjects, including humans) via administration of a potassium channel blocker drug (e.g., 4-AP), via administration of clemastine, or via administration of other compounds as described herein and/or as known in the art, was therefore also implicated. Further details of the instant disclosure are described below.

To dissect the neural function of Gtf2i and its relevance to WS, Gtf2i was selectively deleted in forebrain excitatory neurons and WS-relevant abnormalities were identified, including neuroanatomical defects, fine motor deficits, increased sociability and anxiety. Unexpectedly, 70% of the genes that exhibited significantly decreased mRNA level in mutant mouse cortex were involved in myelination. Furthermore, reduced mature oligodendrocyte cell numbers, reduced myelin thickness and impaired axonal conductivity were all observed in such mice. Strikingly, normalization of impaired myelination properties or axonal conductivity was identified to rescue behavioral deficits. Transcriptome analysis of human frontal cortex from WS patients similarly revealed significantly lower mRNA level of myelination-related genes, along with reduced myelin thickness and decreased mature oligodendrocyte cell numbers. Thus, the initial disclosure has provided molecular and cellular evidence for myelination deficits occurring in WS linked to the deletion of Gtf2i in neurons. Together, these data have provided enhanced understanding of the neurobiological etiology of WS and have identified therapeutic targets for WS-associated social and cognitive abnormalities.

Williams Syndrome

Williams syndrome (WS) is a multisystemic neurodevelopmental disorder caused by a heterozygous microdeletion of about 26 genes from chromosomal region 7q11.23, characterized by hypersociability and unique neurocognitive abnormalities and personality profiles (1, 2). Of the deleted genes, general transcription factor II-i (Gtf2i) has been linked to hypersociability in WS, though the molecular and cellular mechanisms affected by Gtf2i deletion have previously been poorly understood.

The unique cognitive and personality profiles of WS include intellectual disability, distinct overfriendliness, increased empathy, and elevated anxiety derived from fear and specific phobias (2). WS is caused by haploinsufficiency of about 26 genes from the WS chromosome region (WSCR) at 7q11.23. While ~95% of WS subjects have a hemizygous deletion of the entire WSCR, the other ~5% of subjects have atypical microdeletions that may only affect a few genes of the WSCR (3-6) and thus are helpful in defining genetic links to certain symptoms (7). In particular, atypical microdeletions that overlap with GTF2I and GTF2IRD1, which are members of the general transcription factor 2I gene family, affect the cognitive phenotype in WS subjects (3, 4, 6, 8, 9). Rare cases of individuals with microdeletions that affect either gene, but not both, has strongly indicated that GTF2IRD1 disruption is associated with WS craniofacial dysmorphism and cognitive deficits, whereas GTF2I deletion may contribute to WS social behaviors and mental impairment (4, 5, 10, 11).

GTF2I encodes the TFII-I protein, a highly conserved and ubiquitously expressed multifunctional transcription factor (TF) that regulates gene expression through interactions with tissue-specific TFs and complexes related to chromatin-remodeling (12). Previous work upon mouse models for WS (13) studied the role of Gtf2i-deletion by using either heterozygous mice with the majority of the WSCR (14) deleted, partial WSCR deletions (15), or single-gene deletion models (16-18). These studies showed correlations between Gtf2i-haploinsufficieny and certain WS-relevant behavioral phenotypes, including hypersociability and social dishabituation. However, homozygous Gtf2i knockout (KO) mice were previously described as embryonically lethal, mainly due to failed neural tube closure (17-19). Thus, prior to the instant disclosure, the neuronal function of the Gtf2i gene and its role in the molecular and cellular mechanisms underlying WS behavioral and neurodevelopmental phenotypes have not been identified.

Other Non-Canonical Developmentally Aberrant Myelination Associated Diseases

Additional neurodevelopmental myelination abnormality diseases or disorders for which treatment with potassium channel blockers and other agents of the instant disclosure are now contemplated include autism spectrum disorder, such as autism-associated CHD8 mutation disorder and fragile X syndrome, Rett Syndrome, and other neurodevelopmental disorders.

Autism Spectrum Disorder

Autism spectrum disorder (ASD) is a pervasive developmental disorder that causes severe and pervasive impairment in thinking, feeling, language, and the ability to relate to others. The onset is generally before the age of 3 years, and is usually first diagnosed in early childhood. The disorder can range from a severe form, called autistic disorder, through pervasive development disorder not otherwise specified (PDD-NOS), to a much milder form, Asperger syndrome. They also include two rare disorders, Rett syndrome and childhood disintegrative disorder. The disorder has a prevalence of 0.6% in the population, affecting many more boys than girls.

Currently there is no single best treatment package for all children with ASD nor is there a simple diagnosis method for the disorder. One point that expert professionals agree on is that early intervention is important; another is that most individuals with ASD respond well to highly structured, specialized programs. As soon as a child's disability has been identified, it is recommended that instructions should begin. Effective programs will teach early communication and social interaction skills. In children younger than 3 years, appropriate interventions usually take place in the home or a child care center. These early interventions target specific deficits in learning, language, imitation, attention, motivation, compliance, and initiative of interaction. Included are behavioral methods, communication, occupational and physical therapy along with social play interventions.

Although early intervention has been shown to have a dramatic impact on reducing symptoms and increasing a child's ability to grow and learn new skills, it is estimated that only 50 percent of children are diagnosed before kindergarten. Currently there is no method of early diagnosis and/or predictive method for autism. Parents are usually the first to notice unusual behaviors in their child. In some cases, the baby seemed "different" from birth, unresponsive to people or focusing intently on one item for long periods of time. The first signs of an autism spectrum disorder can also appear in children who had been developing normally. When an affectionate, babbling toddler suddenly becomes silent, withdrawn, self-abusive, or indifferent to social overtures, something is wrong.

Twin and family studies have estimated the heritability of autism as being up to 90%, making it one of the most heritable complex disorders. Rare genetic syndromes and known chromosomal anomalies explain roughly 10% of cases of autism, including Fragile X, tuberous sclerosis, Smith-Lemli-Opitz syndrome, and maternally-inherited duplications of the Prader-Willi/Angelman syndrome region (15q11-13). However, despite high heritability, genetic studies to date have not provided substantial insight into the 90% of autism with idiopathic etiology.

Autism-Associated CHD8 Mutation

The gene CHD8 encodes the protein chromodomain helicase DNA binding protein 8 (Nishiyama et al. Nature Cell Biology. 11: 172-82), which is a chromatin regulator enzyme that is essential during fetal development (Ronan et al. Nature Reviews Genetics. 14: 347-59). CHD8 is an ATP dependent enzyme (Thompson et al. Molecular and Cellular Biology. 28: 3894-904).

The protein contains a Snf2 helicase domain that is responsible for the hydrolysis of ATP to ADP (Thompson et al.). CHD8 encodes for a DNA helicase that function as a transcription repressor by remodeling chromatin structure by altering the position of nucleosomes (Ronan et al.). CHD8 negatively regulates Wnt signaling (Nishiyama et al. Molecular and Cellular Biology. 32: 501-12). Wnt signaling is important in the vertebrate early development and morphogenesis. It is believed that CHD8 also recruits the linker histone H1 and causes the repression of β-catenin and p53 target genes (Nishiyama et al. Nature Cell Biology. 11: 172-82). The importance of CHD8 can be observed in studies where CHD8-knockout mice died after 5.5 embryonic days because of widespread p53 induced apoptosis (Nishiyama et al. Nature Cell Biology. 11: 172-82).

Mutations in the CHD8 gene have been linked to a subset of autism (Bernier et al. Cell. 158: 263-76) cases.

Mutations in CHD8 could lead to upregulation of β-catenin-regulated genes, in some part of the brain this upregulation can cause brain overgrowth also known as macrocephaly, which occurs in 15-35% of autistic children (Ronan et al.).

Some studies have determined the role of CHD8 in autism spectrum disorder (ASD) (Ronan et al.). CDH8 expression significantly increases during human mid-fetal development (Nishiyama et al. Nature Cell Biology. 11: 172-82). The chromatin remodeling activity and its interaction with transcriptional regulators have shown to play an important role in ASD aetiology (Sugathan et al. Proceedings of the National Academy of Sciences of the United States of America. 111: E4468-77). The developing mammalian brain has a conserved CHD8 target regions that are associated with ASD risk genes (Ronan et al.). The knockdown of CHD8 in human neural stem cells results in dysregulation of ASD risk genes that are targeted by CHD8 (Cotney et al. Nature Communications. 6: 6404).

Fragile X Syndrome

The fragile X syndrome is a common form of inherited neurological disorders characterized by mental retardation and developmental disability. This condition afflicts approximately 1 in 1250 males and 1 in 2000 females. As the name implies, fragile X is an X chromosome-linked condition. The fragile X phenotype is characterized by a visible constriction near the end of the X chromosome, at locus q27.3, and there is a tendency for the tip of the X-chromosome to break off under certain conditions in tissue culture. These tissue culture procedures form the basis of the assay most commonly used for fragile X at present.

The pattern of inheritance of this condition is atypical of that associated with X-linked conditions. Typically, there is a 50% probability that the son of a woman who carries an X-linked genetic defect will be afflicted by the defect. Additionally, all males who carry the abnormal gene are afflicted by the X-linked condition in the typical pattern. Furthermore, since females have two X chromosomes, they normally do not suffer the effects of a single damaged X chromosome.

In fragile X, however, some carrier males are phenotypically normal. Moreover, about one third of the females who inherit the fragile X chromosome are afflicted. The incidence of carrier males in different generations of a family varies. Daughters of carrier males are generally non-expressing carriers, but may have afflicted sons. Furthermore, afflicted daughters occur more frequently among the offspring of carrier mothers than among the offspring of carrier fathers. See Brown, The Fragile X: Progress toward Solving the Puzzle, Am. J. Human Genet. 47 175-80, 1990. This and all other references, patents and patent applications are incorporated herein by reference for all purposes.

Researchers have identified the genomic region associated with this condition. (Oberle, et al., "Instability of a 550-Base Pair DNA Segment and Abnormal Methylation in Fragile X Syndrome", Science 252 1097-1102, 1991; Kremer, et al., "Mapping of DNA Instability at the Fragile X to a Trinucleotide Repeat Sequence p(CCG)n", Science 252 1711-14, 1991; and Bell, et al., "Physical Mapping across the Fragile X Hypermethylation and Clinical Expression of the Fragile X Syndrome", Cell 64 861-66, 1991). Additionally, researchers have sequenced a partial cDNA clone derived from this region, called FMR-1. (Verkerk, et al., "Identification of a Gene (FMR-1) Containing a CGG Repeat Coincident with a Breakpoint Cluster Region Exhibiting Length Variation in Fragile X Syndrome", Cell 65 905-14, 1991). These studies provide an explanation for the atypical pattern of inheritance of fragile X. The mutation that ultimately results in the fragile X phenotype occurs in stages. In the early stages, the gene is not fully defective, rather there is a "pre-mutation" of the gene. Carriers of the premutation have a normal phenotype. A further mutation occurs in carrier females that produce the phenotype in their offspring.

The coding sequence for FMR-1 contains a variable number of CGG repeats. Individuals who are not carriers have approximately 30 CGG repeats in their FMR-1. Carriers, however, have between 50 and 200 CGG repeats. This amplification of the FMR-1 CGG sequence is the pre-mutation. Afflicted individuals have even more CGG repeats. As many as several thousand CGG repeats have been observed in afflicted individuals. (Oberle, et al., 1991, supra).

However, most affected individuals do not express the FMR-1 mRNA (Pieretti, et al., Absence of Expression of the FMR-1 Gene in Fragile X Syndrome, Cell 66 1-201991). A CpG island, located upstream of the CGG repeat region, is methylated when the number of CGG repeats is above a threshold of about 200 copies (Oberle, et al., 1991; Kremer, et al., 1991, Bell, et al., 1991, supra). This methylation inactivates the gene.

It has been recognized that fragile X syndrome is caused by loss of expression of FMRP, a protein proposed to act as a regulator of mRNA translation which promotes synaptic maturation and function. FMRP has been found to associate with the RNP complex that mediates post-transcriptional silencing by RNA. See review by Carthew R W. "RNA interference: the fragile X syndrome connection" Curr. Biol. 2002 Dec. 23; 12(24):R852-4.

Current trends in treating the disorder include medications for symptom-based treatments that aim to minimize the secondary characteristics associated with the disorder. If an individual is diagnosed with FXS, genetic counseling for testing family members at risk for carrying the full mutation or premutation is a critical first-step. Due to a higher prevalence of FXS in boys, the most commonly used medications are stimulants that target hyperactivity, impulsivity, and attentional problems (Garber et al. European Journal of Human Genetics. 16: 666-72). For co-morbid disorders with FXS, antidepressants such as selective serotonin reuptake inhibitors (SSRIs) are utilized to treat the underlying anxiety, obsessive-compulsive behaviors, and mood disorders. Following antidepressants, antipsychotics such as Risperdal and Seroquel are used to treat high rates of self-injurious, aggressive and aberrant behaviors in this population (Bailey Jr et al., 2012). Anticonvulsants are another set of pharmacological treatments used to control seizures as well as mood swings in 13%-18% of individuals suffering from FXS. Drugs targeting the mGluR5 (metabotropic glutamate receptors) that are linked with synaptic plasticity are especially beneficial for targeted symptoms of FXS (Garber et al. European Journal of Human Genetics. 16: 666-72). Lithium is also currently being used in clinical trials with humans, showing significant improvements in behavioral functioning, adaptive behavior, and verbal memory. Alongside pharmacological treatments, environmental influences such as home environment and parental abilities as well as behavioral interventions such as speech therapy, sensory integration, etc. all factor in together to promote adaptive functioning for individuals with FXS (Hagerman et al. Pediatrics. 123: 378-90).

Current pharmacological treatment centers on managing problem behaviors and psychiatric symptoms associated with FXS. However, as there has been very little research done in this specific population, the evidence to support the use of these medications in individuals with FXS is poor (Rueda et al. BMC Neurol. 9: 53).

Rett Syndrome

Rett Syndrome is a genetic brain disorder which typically becomes apparent after six months of age in females ("Rett syndrome". Genetics Home Reference. December 2013). Symptoms include problems with language, coordination, and repetitive movements ("Rett syndrome". Genetics Home Reference. December 2013). Often there is slower growth, problems walking, and a smaller head size ("Rett syndrome". Genetics Home Reference. December 2013; "Rett Syndrome Fact Sheet". National Institute of Neurological Disorders and Stroke. Archived from the original on 14 Oct. 2017). Complications can include seizures, scoliosis, and sleeping problems ("Rett syndrome". Genetics Home Reference. December 2013). Those affected, however, may be affected to different degrees ("Rett Syndrome Fact Sheet". National Institute of Neurological Disorders and Stroke. Archived from the original on 14 Oct. 2017).

Rett syndrome occurs due to a genetic mutation of the MECP2 gene ("Rett syndrome". Genetics Home Reference. December 2013). This gene occurs on the X chromosome ("Rett Syndrome Fact Sheet". National Institute of Neurological Disorders and Stroke. Archived from the original on 14 Oct. 2017). Typically it develops as a new mutation, with less than one percent of cases being inherited from a person's parents ("Rett syndrome". Genetics Home Reference. December 2013; "Rett Syndrome Fact Sheet". National Institute of Neurological Disorders and Stroke. Archived from the original on 14 Oct. 2017). Boys who have a similar mutation typically die shortly after birth ("Rett Syndrome Fact Sheet". National Institute of Neurological Disorders and Stroke. Archived from the original on 14 Oct. 2017). Diagnosis is based on symptoms and can be confirmed with genetic testing ("Rett Syndrome Fact Sheet". National Institute of Neurological Disorders and Stroke. Archived from the original on 14 Oct. 2017).

There is no cure for Rett syndrome ("Rett Syndrome Fact Sheet". National Institute of Neurological Disorders and Stroke. Archived from the original on 14 Oct. 2017). Treatment is directed at improving symptoms ("Rett Syndrome Fact Sheet". National Institute of Neurological Disorders and Stroke. Archived from the original on 14 Oct. 2017). Anticonvulsants may be used to help with seizures ("Rett Syndrome Fact Sheet". National Institute of Neurological Disorders and Stroke. Archived from the original on 14 Oct. 2017). Special education, physiotherapy, and braces may also be useful ("Rett Syndrome Fact Sheet". National Institute of Neurological Disorders and Stroke. Archived from the original on 14 Oct. 2017). Many people with the condition live into middle age ("Rett Syndrome Fact Sheet". National Institute of Neurological Disorders and Stroke. Archived from the original on 14 Oct. 2017).

It affects about 1 in 8,500 females ("Rett syndrome". Genetics Home Reference. December 2013). Andreas Rett, a pediatrician in Vienna, first described the condition in 1966 ("Rett Syndrome Fact Sheet". National Institute of Neurological Disorders and Stroke. Archived from the original on 14 Oct. 2017; Rett A (September 1966). "[On a unusual brain atrophy syndrome in hyperammonemia in childhood]". Wien Med Wochenschr (in German). 116 (37): 723-6). As his writings were in German they did not become widely known (Percy, Alan (2013-2015). "The American History of Rett Syndrome". Pediatric neurology. 50 (1)). Bengt Hagberg, a Swedish pediatrician, published an English article in 1983 and named the condition after Rett (Percy, Alan (2013-2015). "The American History of Rett Syndrome". Pediatric neurology. 50 (1)). In 1999 Huda Zoghbi discovered the mutation that causes the condition (Percy, Alan (2013-2015). "The American History of Rett Syndrome". Pediatric neurology. 50 (1); Amir, Ruthie; Van den Veyver, Ignatia; Wan, Mimi; Tran, Charles; Francke, Uta; Zoghbi, Huda (1999). "Rett syndrome is caused by mutations in X-linked MECP2, encoding methyl-CpG-binding protein 2". Nature Genetics. 23 (2): 185-8).

In addition to the classical form of Rett syndrome (classified as Stages I to IV), several "atypical forms" have been described over the years (Jeffrey 1. Neul, J L; Kaufmann, Walter E.; Glaze, Daniel G.; Christodoulou, John; Clarke, Angus J.; Bahi-Buisson, Nadia; Leonard, Helen; Bailey, Mark E. S.; Schanen, N. Carolyn; Zappella, Michele; Renieri, Alessandra; Huppke, Peter; Percy, Alan K.; Rettsearch, Consortium (2010). "Rett syndrome: Revised diagnostic criteria and nomenclature". Annals of Neurology. 68 (6): 944-50), the main groups are:

Congenital variant (Rolando variant): in this severe subtype of Rett syndrome, the development of the patients and their head circumference are abnormal from birth (Ariani, Francesca; Hayek, Giuseppe; Rondinella, Dalila; Artuso, Rosangela; Mencarelli, Maria Antonietta; Spanhol-Rosseto, Ariele; Pollazzon, Marzia; Buoni, Sabrina; Spiga, Ottavia; Ricciardi, Sara; Meloni, Ilaria; Longo, Ilaria; Mari, Francesca; Broccoli, Vania; Zappella, Michele; Renieri, Alessandra (2008). "FOXG1 is Responsible for the Congenital Variant of Rett Syndrome". The American Journal of Human Genetics. 83 (1): 89-93). The typical gaze of Rett syndrome patients is usually absent;

Zappella variant of Rett Syndrome or preserved speech variant: in this subtype of Rett syndrome the patients acquire some manual skills and language is partially recovered around the age of 5 years (that is after the regression phase). Height, weight and head circumference are often in the normal range, and a good gross motor function can be observed (Zappella, Michele (1992). Brain and Development. 14 (2): 98-101; Skjeldal et al. Neuropediatrics. 26 (2): 87; Sørensen, E; Viken, B. Tidsskrift for den Norske laegeforening. 115 (5): 588-90; Zappella, M. European child & adolescent psychiatry. 6 Suppl 1: 23-5; Renieri et al. Brain and Development. 31 (3): 208-16; Buoni et al. Clinical Neurophysiology. 121 (5): 652-7). The Zappella variant is a milder form of Rett syndrome;

Hanefeld variant or early epilepsy variant. In this form of Rett syndrome, the patients suffer from epilepsy before 5 months of age (Huppke et al. Brain and Development. 25 (5): 346-51).

The definition itself of the Rett syndrome has been refined over the years: as the atypical forms subsist near to the classical form (Hagberg & Gillberg, 1993), the "Rett Complex" terminology has been introduced (Gillberg, C. European child & adolescent psychiatry. 6 Suppl 1: 21-2; Zappella et al. Journal of Autism and Developmental Disorders. 28 (6): 519-26).

Genetically, Rett syndrome (RTT) is caused by mutations in the gene MECP2 located on the X chromosome (which is involved in transcriptional silencing and epigenetic regulation of methylated DNA), and can arise sporadically or from germline mutations. In less than 10% of RTT cases, mutations in the genes CDKL5 or FOXG1 have also been found to resemble it. Rett syndrome is initially diagnosed by clinical observation, but the diagnosis is definitive when there is a genetic defect in the MECP2 gene. In some very rare cases, no known mutated gene can be found; possibly due to changes in MECP2 that are not identified by presently used techniques or mutations in other genes that may result in clinical similarities.

It has been argued that Rett syndrome is in fact a neurodevelopmental condition as opposed to a neurodegenerative condition. One piece of evidence for this is that mice with induced Rett Syndrome show no neuronal death, and some studies have suggested that their phenotypes can be partially rescued by adding functional MECP2 gene back when they are adults. This information has also helped lead to further studies aiming to treat the disorder (Guy et al. Science. 315 (5815): 1143-7).

In at least 95% of Rett syndrome cases, the cause is a de novo mutation in the child. That is, it is not inherited from either parent. Parents are generally genotypically normal, without a MECP2 mutation.

In cases of the sporadic form of RTT, the mutated MECP2 is thought to derive almost exclusively from a de novo mutation on the male copy of the X chromosome (Trappe et al. The American Journal of Human Genetics. 68 (5): 1093-101). It is not yet known what causes the sperm to mutate, and such mutations are rare.

It can also be inherited from phenotypically normal mothers who have a germline mutation in the gene encoding methyl-CpG-binding protein-2, MeCP2 (Zoghbi et al. Nature Genetics. 23 (2): 185-8). In these cases, inheritance follows an X-linked dominant pattern and is seen almost exclusively in females, as most males die in utero or shortly after birth ("Rett syndrome". Genetics Home Reference. Archived from the original on 2016-07-27). MECP2 is found near the end of the long arm of the X chromosome at Xq28. An atypical form of RTT, characterized by infantile spasms or early onset epilepsy, can also be caused by a mutation to the gene encoding cyclin-dependent kinase-like 5 (CDKL5). Rett syndrome affects one in every 12,500 female live births by age 12 years.

Current treatments for Rett syndrome include:
management of gastrointestinal (reflux, constipation) and nutritional (poor weight gain) issues
surveillance of scoliosis
surveillance of long QT syndrome by annual EKG
increasing the patient's communication skills, especially with augmentative communication strategies
parental counseling
modifying social medications
sleep aids
selective serotonin reuptake inhibitors (SSRIs)
anti-psychotics (for self-harming behaviors)
beta-blockers for long QT syndrome
occupational therapy, speech therapy and physical therapy Because of the increased risk of sudden cardiac death, when long QT syndrome is found on an annual screening EKG it is treated with an anti-arrhythmic such as a beta-blocker. There is some evidence that phenytoin may be more effective than a beta-blocker (McCauley et al. Science Translational Medicine. 3 (113): 113ra125).

Additional Neurodevelopmental and/or Other Disorders

Additional neurodevelopmental and/or other disorders now contemplated for treatment with the potassium channel blockers and/or other agents of the instant disclosure include, for example, Aarskog syndrome, aphasia, Bell's Palsy, Creutzfeldt-Jakob disease, cerebrovascular disease, charcot-Marie-Tooth Disease, Comelia de Lange syndrome, dementia, dentatorubral-pallidoluysian atrophy, encephalitis, epilepsy and other severe seizure disorders, essential tremor, fibromylagia, headache, hypomelanosis of Ito, Joubert syndrome, Kennedy's disease, Machado-Joseph's diseases, migraines, Moebius syndrome, myotonic dystrophy, neuromuscular disorders (e.g., Guillain-Barre and muscular dystrophy), neuro-oncology disorders (e.g., neurofibromatosis), pain, pediatric neurology (e.g., autism and dyslexia), prion disease, neuro-otology disorders (e.g., Meniere's disease), Phenylketonuria, Pick's disease, progressive supranuclear palsy, Rubinstein-Taybi syndrome, sleep disorders, spinocerebellar ataxia I (SCA1), Smith-Lemli-Opitz syndrome, Sotos syndrome, spinal bulbar atrophy, type 1 dominant cerebellar ataxia, Tourette syndrome and tuberous sclerosis complex.

4-AP (4-aminopyridine)

4-aminopyridine has the following structure:

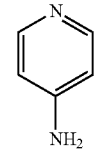

USAN: dalfampridine; CAS registry number: 504-24-5; Molecular Formula: $C_5H_6N_2$.

In the laboratory, 4-AP is a useful pharmacological tool in studying various potassium conductances in physiology and biophysics. It is a relatively selective blocker of members of Kv1 (Shaker, KCNA) family of voltage-activated K+ channels. At concentration of 1 mM it selectively and reversibly inhibits Shaker channels without significant effect on other sodium, calcium, and potassium conductances.

4-Aminopyridine is a potent convulsant and is used to generate seizures in animal models for the evaluation of antiseizure agents (Yamaguchi and Rogawski. Epilepsy Res. 11: 9-16).

Fampridine has been used clinically in Lambert-Eaton myasthenic syndrome and multiple sclerosis. It acts by blocking potassium channels, prolonging action potentials and thereby increasing neurotransmitter release at the neuromuscular junction (Judge and Bever. "Potassium channel blockers in multiple sclerosis: neuronal Kv channels and effects of symptomatic treatment". Pharmacol. Ther. 111: 224-59). The drug has been shown to reverse saxitoxin and tetrodotoxin toxicity in tissue and animal experiments (Benton et al. Toxicon. 36: 571-588; Chang et al. Fundamental and Applied Toxicology. 38: 75-88; Chen et al. Toxicology and Applied Pharmacology. 141: 44-48; Octopus Envenomations at eMedicine.com).

Fampridine has been shown to improve visual function and motor skills and relieve fatigue in patients with multiple sclerosis (MS). 4-AP is most effective in patients with the chronic progressive form of MS, in patients who are temperature sensitive, and in patients who have had MS for longer than three years. Common side effects include dizziness, nervousness and nausea, and the incidence of adverse effects was shown to be less than 5% in all studies.

Pharmacologically, the K+ channel blocking properties of 4-aminopyridine and its effects on action potential conduction in demyelinated nerve fiber preparations have been extensively characterized. At low concentrations that are relevant to clinical experience, in the range of 0.2 to 2 µM (18 to 180 ng/mL), 4-aminopyridine is able to block certain voltage-dependent K+ channels in neurons. It is this characteristic that appears to explain the ability of the drug to restore conduction of action potentials in demyelinated nerve fibers. At higher (millimolar) concentrations, 4-aminopyridine affects other types of K+ channels in both neural and non-neural tissues. Blockade of repolarizing K+ currents can increase synaptic transmission throughout the nervous system by increasing the duration of the presynaptic action potential. A range of neurological effects consistent with increased excitability of presynaptic nerve terminals occurs with clinically relevant doses of 4-aminopyridine.

Electrophysiologic studies of demyelinated axons show that augmented potassium currents increase extracellular potassium ion concentration which decreases action potential duration and amplitude which may cause conduction failure. Potassium channel blockade reverses this effect. Certain studies have also shown that 4-AP is a potent calcium channel activator and can improve synaptic and neuromuscular function by directly acting on the calcium channel beta subunit (Wu et al. The Journal of Biological Chemistry. 284: 36453-61; Li et al. Mol. Pharmacol. 86: 760-772)). Without wishing to be bound by theory, in view of the potent calcium channel activation that has also been observed for 4-AP, the instant disclosure additionally contemplates inclusion, use and/or administration of calcium channel agonists (e.g., VACC agonists) in the compositions and methods of the instant disclosure.

Further without wishing to be bound by theory, the K+ channels blocked by low concentrations of 4-aminopyridine are partially responsible for repolarization of neuronal action potentials. These appear to include those found under the myelin sheath in myelinated nerve fibers of adult mammals. These channels are located primarily in the paranodal and internodal membrane of the axon (Waxman and Ritchie, 1993) where they are not significantly activated by the passage of an action potential because the myelin sheath acts as an electrical shield. Therefore, the action potential of normal adult myelinated axons shows little or no sensitivity to 4-aminopyridine at concentrations below 100 µM (9.4 µg/mL) (Shi and Blight, 1997). Concentrations above 1 mM (94.1 µg/mL) tend to cause gradual depolarization of the axon resting potential, perhaps by interacting with leakage channels (Shi and Blight, 1997).

However, when the axon is demyelinated, the internodal membrane and its ion channels become exposed to larger electrical transients during the action potential. Leakage of ionic current through the K+ channel, under these conditions, can contribute to the phenomenon of action potential conduction block (Waxman and Ritchie, 1993). Without being bound by theory, it is understood that 4-Aminopyridine may prolong nerve action potentials by blocking these exposed channels and inhibiting repolarization (Sherratt et al., 1980). This is consistent with the ability of the drug to overcome conduction block and increase the safety factor for conduction in some critically demyelinated axons (Bostock et al., 1981; Targ and Kocsis, 1985) including those in chronically injured and partially demyelinated mammalian spinal cord (Blight, 1989; Shi and Blight, 1997). An additional study (Shi et al., 1997) showed that this effect of 4-aminopyridine in the chronically injured spinal cord of guinea pigs occurs at a concentration threshold between 0.2 to 1 µM (19.1 to 94.1 ng/mL), though in this tissue it is most effective at about 10 µM (941 ng/mL).

A range of neurological effects have been described to occur with increasing concentrations of 4-aminopyridine in the central nervous system (CNS), up to and including the initiation of seizures. Seizure activity in animals has been seen following large doses of 4-aminopyridine, and seizure activity is part of the toxicological profile of the drug. Synchronous bursting activity in the spinal cord of decerebrate cats has been recorded following administration of very large doses of 4-aminopyridine (5 to 20 mg/kg), which would be expected to produce plasma levels in the region of several hundred ng/mL (Dubuc et al., 1986).

Repetitive impulse activity, either spontaneous or in response to single stimuli, occurs in some demyelinated axons exposed to higher levels [0.1 to 1 mM (9.4 to 94.1 µg/mL)] of 4-aminopyridine in vitro (Blight, 1989; Bowe et al., 1987; Targ and Kocsis, 1985). A similar effect at lower concentrations (on susceptible neurons or nerve endings) may explain the paresthesias and pain in the area of intravenous infusion reported as side effects of clinical exposure to 4-aminopyridine in human subjects.

4-Aminopyridine is rapidly absorbed following oral administration. In an in situ study, 4-aminopyridine was more rapidly absorbed from the small intestine than from the stomach. The absorption half-life was 108.8 minutes and 40.2 minutes for the stomach and small intestine, respectively.

Following oral administration of (non-sustained release) 4-aminopyridine in animals, peak plasma concentrations occur within one hour of dosing.

When administered orally, 4-aminopyridine is completely absorbed from the gastrointestinal tract. The absolute bioavailability of two formulations of IR tablets was reported to be 95% (Uges et al., 1982). Absolute bioavailability of Fampridine-SR tablets has not been assessed, but relative bioavailability (as compared to an aqueous oral solution) is 95%. Absorption is rapid unless administered in the context of some feature that achieves delayed release. Such feature may include in a modified matrix containing the 4-AP (e.g., Fampridine-SR), or a capsule around any form of 4-AP (sustained or immediate release) that achieves delayed release of the ingredient therein.

When a single Fampridine-SR tablet 10 mg dose is administered to healthy volunteers while in a fasted state, mean peak concentrations ranging in different studies from 17.3 ng/mL to 21.6 ng/mL occurred 3 to 4 hours post-administration ($T_{max}$). In comparison, the $C_{max}$ achieved with the same 10 mg dose of a 4-aminopyridine oral solution was 42.7 ng/mL, which occurred approximately 1.1 hours after dose administration. Exposure increases proportionally with dose (linear kinetics), and steady state maximum concentrations are approximately 29-37% higher than for single doses.

4-aminopyridine is largely unbound to plasma proteins (97 to 99%). Administration of a single 20 mg intravenous dose, mean Vd is 2.6 L/kg, greatly exceeding total body water (Uges et al., 1982), this is similar to values calculated in healthy volunteers and in patients with SCI who received Fampridine-SR tablets. The plasma concentration-time profile is one of two or three compartments with a rapid initial distribution phase. Measurable levels are present in the saliva.

In single- and repeated-dose toxicity studies, the dosing regimen greatly affected the rate of side effects. Clinical signs evident after large single doses or repeated lower doses were similar in all species studied and included tremors, convulsions, ataxia, dyspnea, dilated pupils, prostration, abnormal vocalization, increased respiration, excess salivation, gait abnormalities, and hyper- and hypo-excitability. These clinical signs were not unexpected and represent exaggerated pharmacology of 4-aminopyridine.

In controlled clinical studies involving the use of 4-aminopyridine, the most frequent adverse events by body system occurred in the nervous system, "body as a whole", and digestive system. Dizziness, insomnia, paresthesia, pain, headache and asthenia are the most common nervous system adverse events, and nausea is the most frequently reported event in the digestive system category.

The most frequent treatment-related adverse events that have been reported with Fampridine-SR, in MS patients as well as other populations including spinal cord injury, may be broadly categorized as excitatory effects in the nervous system, consistent with the potassium channel blocking activity of the compound. These adverse events include dizziness, paresthesias, insomnia, balance disorders, anxiety, confusion and seizure. While an increased incidence of such events appears to be moderately dose-related, the susceptibility of individuals is quite variable. As a result of disease pathology, there appears to be potential for more lowering of seizure threshold in people with MS than for people with spinal cord injury; this may result from interaction of the channel-blocking properties of the drug with MS brain pathology in certain individuals.

4-AP derivatives are known in the art and have been described, e.g., in WO 2017/120298, US 2017/0174629, and elsewhere. Certain embodiments of the instant disclosure contemplate inclusion/use of 4-AP derivatives, which can optionally be represented by the following structure:

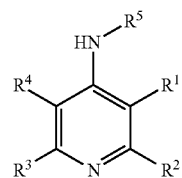

wherein $R^1$, $R^2$, $R^3$, $R^4$, and $R^5$ are each independently selected from hydrogen, halogen, amine, hydroxyl, alkoxy, carboxyl, or $C_1$-$C_6$ alkyl. Inclusion/use of pharmaceutically acceptable salts is also expressly contemplated for 4-AP and derivatives thereof, and for all agents recited herein.

Formulations of parenteral compositions (e.g., 4-AP parenteral compositions) in dosage unit form are primarily contemplated for ease of administration and uniformity of dosage. Dosage unit form as used herein refers to physically discrete units suited for administration to the subjects to be treated; each unit containing a predetermined quantity of therapeutic compound calculated to produce the desired therapeutic effect in association with any pharmaceutical carrier. Administration can be of a single dosage unit form, or administration can be of multiples of dosage unit forms, including concurrent administration of unit doses of various amounts.

In general, dosage unit forms of the instant disclosure are dictated by and directly dependent on the unique characteristics of the therapeutic compound and the particular therapeutic effect to be achieved in a given patient or patient population. Unit dosage forms can be tablets, capsule, aliquots; unit does forms can be provided as blister packs containing one or more dose. In certain administration protocols a patient may utilize more than a single unit dose at a time, e.g., consume two capsules, or two tablets contained in separate blisters of a blister pack.

The actual dosage amount of the 4-AP or derivative thereof administered to a subject may be determined by physical and physiological factors such as age, sex, body weight, severity of condition, the type of disease being treated, previous or concurrent therapeutic interventions, idiopathy of the subject and on the route of administration. Alternatively, a standard amount can be provided to essentially all patients, often the standard is derived from studies in normative population such as from data on human subjects in clinical trials. These factors may be determined by a skilled artisan, such as a health care provider, medicine prescriber, physician, pharmacist, etc. (collectively "practitioner"). In certain embodiments, the practitioner responsible for administration may determine the concentration of active ingredient(s) in a composition and appropriate dose(s) for an individual subject. In certain embodiments, the dosage may be adjusted by the individual physician in the event of any complication; in certain embodiments, a dose is administered to all patients (regardless of WS classification, temperature sensitivity, duration of disease, progressive status, etc.) at an amount that is found to be safe and effective in a nonnative reference population.

Sustained release formulations and compositions of the present disclosure exhibit a desired release profile that may be described in terms of the maximum plasma concentration of the drug or active agent at steady state ($C_{maxSS}$) and the minimum plasma concentration of the drug or active agent at steady state ($C_{minSS}$). Steady state is observed when the rate of administration (absorption) is equal to the rate of elimination of the drug or active agent. A ratio of $C_{maxSS}$ to $C_{minSS}$ ($C_{maxSS}$:$C_{minSS}$) may be calculated from the observed $C_{maxSS}$ and $C_{minSS}$. In addition, the formulations and compositions of the present disclosure exhibit a desired release profile that may be described in terms of the average maximum plasma concentration of the drug or active agent at steady state ($C_{avSS}$).

Certain sustained release 4-aminopyridine composition exhibit a $C_{maxSS}$: $C_{minSS}$ ratio from about 1.0 to 3.5 for either twice daily (BID) or once daily (QD) administration. Optionally, a sustained release formulation can comprise a $C_{maxSS}$: $C_{minSS}$ ratio of about 1.5 to about 3.0 for either twice daily (BID) or once daily (QD) administration. In another embodiment, the $C_{maxSS}$: $C_{minSS}$ ratio is about 2.0 to about 3.0 for either twice daily (BID) or once daily (QD) administration. As is readily understood by those of ordinary skill in the art, when redosing occurs at a time when plasma levels are decreasing, $C_{minSS}$ occurs at the time of redosing.

A further aspect is a sustained release composition comprising a sustained release matrix and an aminopyridine, wherein said composition provides a $C_{avSS}$ of about 15 ng/ml to about 35 ng/ml. In a further aspect, a sustained release tablet comprising a sustained release matrix and an aminopyridine, said tablet exhibiting a $C_{maxSS}$ of about 20 ng/ml to about 35 ng/ml is provided. The pharmacokinetic characteristics of sustained release aminopyridine compositions and methods of treating various neurological disorders are described in U.S. Pat. Nos. 8,440,703 and 8,007,826, the contents of which are incorporated herein by reference in their entireties.

The amount of a pharmaceutically acceptable quality aminopyridine, salt, solvated, or prodrug thereof included in the pharmaceutical composition of the present disclosure will vary, depending upon a variety of factors, including, for example, the specific potassium channel blocker and/or other agent used, the desired dosage level, the type and amount of rate-controlling polymer matrix used, and the presence, types and amounts of additional materials included in the composition. Optionally, the agent (e.g., aminopyridine) comprises from about 0.1 to about 13% w/w, in certain embodiments from about 0.5 to about 6.25% w/w. In certain embodiments of the present disclosure the agent (e.g., aminopyridine) is present from about 0.5 to 4.75% w/w of the pharmaceutical composition. It has been found that for many indications a weight (wt/wt %) above about 5% can result in undesirable side effects. Accordingly, a weight percentage less than about 4.75% can be desired. The amount of agent (e.g., aminopyridine), or a derivative thereof, in the formulation varies depending on the desired dose for efficient drug delivery, the molecular weight, and the activity of the compound. The actual amount of the used drug can depend on the patient's age, weight, sex, medical condition, disease or any other medical criteria. The actual drug amount is determined according to intended medical use by techniques known in the art. The pharmaceutical dosage formulated according to the disclosure may be administered once or more times per day, optionally two or fewer times per day as determined by the attending physician.

Typically, the agent (e.g., aminopyridine) is formulated in tablets or other pharmaceutical composition in amounts of about 0.5 mg to about 80 mg, optionally from about 5 to about 50 mg of 4-aminopyridine. Optionally, the amount of an aminopyridine in the composition is formulated to maintain therapeutic levels of the aminopyridine in patient's blood up to about 80 ng/ml.

As used herein, the term "sustained-release" includes the release of a aminopyridine from the dosage formulation at a sustained rate such that a therapeutically beneficial blood level below toxic levels of the aminopyridine is maintained over a period of at least about 12 hours, optionally about 24 hours or more. Optionally, the amount of the aminopyridine in the oral dosage formulations according to embodiments of the present disclosure establish a therapeutically useful plasma concentration through BID administration of the pharmaceutical composition.

The compositions of the present disclosure may be used for the treatment of neurological diseases characterized by aberrant nerve impulse transmission (e.g., neurodevelopmental myelination abnormality diseases or disorders) by administering to a patient the oral dosage formulation of the present disclosure. Optionally, the administration is twice daily dosage of a therapeutically effective amount of an aminopyridine, optionally, 4-AP or a derivative thereof dispersed in HPMC. The administration can also include scheduling administration of doses of the pharmaceutical so that the concentration of the aminopyridine in the patient is at about the minimum therapeutically effective level to ameliorate the neurological condition, yet relatively lower compared to the maximum concentration in order to enhance restful periods for the patient during the day. The compositions may be administered to a subject at a dose and for a period sufficient to allow said subject to tolerate said dose without showing any adverse effects and thereafter increasing the dose of said active agent in the tablets at selected intervals of time until a therapeutic dose is achieved in the subject. For example, at the commencement of treatment the active agent is optionally administered at a dose less than 15 mg/day until a tolerable state is reached. The dose administered may then be increased by amounts of at least 5-15 mg/day until a therapeutic dose is reached. For other diseases the amount of the aminopyridine required to reach a therapeutically effective amount for treatment is described in U.S. Pat. No. 5,952,357 the contents of which are incorporated herein by reference in their entirety.

Compositions of the present disclosure where the potassium channel blocker (and/or the calcium channel stimulatory agent) is a mono- or di-aminopyridine active agent are particularly suitable for use in the treatment of a neurological disease which is characterized by developmentally aberrant myelination of the central nervous system, more especially Williams syndrome. The mono- or di-aminopyridine active agent in accordance with the disclosure is also suitable for the treatment of autism and optionally other neurodevelopmental disorders, such as Fragile X syndrome and Rett Syndrome.

Durable Treatment

Certain embodiments of the present disclosure comprise methods of effectively treating WS or other neurodevelopmental myelination abnormality disease or disorder in a patient over a chronic or extended or prolonged or protracted or sustained time period; this is also referred to as a "durable" treatment or a "durable" method of treatment; this is also referred to as a "sustained" treatment or a "sustained" method of treatment. Another embodiment of the present disclosure is directed to methods of maintaining improvement of a symptom of neurodevelopmental myelination abnormality disease or disorder in a patient comprising administering a therapeutically effective amount of 4-aminopyridine or a derivative thereof to said patient after previously achieving an improvement of a symptom of the neurodevelopmental myelination abnormality disease or disorder in said patient during contiguous or continuing or prior administration of 4-aminopyridine or a derivative thereof. Any of such methods comprise administering a therapeutically effective amount of 4-aminopyridine or a derivative thereof to said patient for an extended, prolonged, protracted, sustained or chronic period of time (as used herein, extended, prolonged, protracted, sustained, chronic are synonyms unless the context clearly indicates otherwise).

In certain embodiments, the extended, prolonged, protracted, sustained or chronic period is at least or more than: 8, 9, 10, 11, 12, 13, 14, 15, 16, 17, 18, 19, 20, 21 or 22 weeks; 3, 4, 5, 6, 7, 8, 9, 10, 11, 12, 13, 14, 15, 16, 17, or 18 months; or 1, 2, 3, 4, 5, 6, or greater than 5 years. In certain embodiments, the extended, prolonged, protracted, chronic or sustained period is for the lifetime of the patient. These methods can also comprise administering the 4-aminopyridine at or to a therapeutic level (such as Cminss or an average Cminss) or range (such as a Cminss range or a reference range of average Cminss values) in accordance with the present disclosure.

In certain embodiments, the improved symptom is tremors, cognition, social traits, strength, etc. In certain embodiments one or more of these parameters may or may not be specifically included or excluded.

In certain embodiments, the therapeutically effective amount of 4-aminopyridine or a derivative thereof is 10 milligrams in a sustained release composition administered twice daily. In certain embodiments, the sustained release composition may be administered twice daily. In certain embodiments, the sustained release composition may be administered once daily. These methods can also comprise administering the 4-aminopyridine or derivative thereof at or to a therapeutic level (such as Cminss) or range (such as a Cminss range) in accordance with the present disclosure. Certain embodiments are directed to the use of 4-aminopyridine or derivative thereof for treatment of a neurodevelopmental aberrant myelination condition for at least 8, 9, 10, 11, 12, 13, 14, 15, 16, 17, 18, 19, 20, 21 or 22 weeks; 3, 4, 5, 6, 7, 8, 9, 10, 11, 12, 13, 14, 15, 16, 17, or 18 months; or 1, 2, 3, 4, 5, 6, or greater than 5 years. Still further embodiments are directed to the use of 4-aminopyridine of a derivative thereof in preparing a medicament or therapeutic or formulation for chronic or durable treatment of a neurodevelopmental myelination abnormality disease or disorder.

Further embodiments of the present disclosure are directed to methods of achieving sustained or relatively sustained improvement in a symptom of a neurodevelopmental myelination abnormality disease or disorder in a patient with a neurodevelopmental myelination abnormality disease or disorder, comprising continuing administration of a therapeutically effective amount of 4-aminopyridine or a derivative thereof to said patient over an extended period of time. Improvement is generally defined with regard to a control or standard amount or value; it is understood that there is often progressive decline in patients with a disease such as a neurodevelopmental myelination abnormality disease or disorder so that an increase or relative increase can properly be considered in regard to the decline in function attendant to the inherent progress of the neurodevelopmental myelination abnormality disease or disorder pathology.

In certain embodiments, the therapeutically effective amount of 4-aminopyridine or a derivative thereof is 10 milligrams in a sustained release composition. In certain embodiments, the sustained release composition can be administered twice daily. In certain embodiments, the sustained release composition may be administered once daily. These methods can also comprise administering the 4-aminopyridine at or to a therapeutic level (such as not going below $C_{minSS}$) or range (such as staying within a $C_{minSS}$-$C_{maxSS}$ range) in accordance with the present disclosure.

Methods of the disclosure also comprise achieving sustained improvement in a symptom of MS in a patient comprising continuing administration a therapeutically effective amount of 4-aminopyridine or a derivative thereof to said patient over an extended period of time. This sustained improvement can be relatively growing in that there is an ongoing growth in a percentage improvement relative to a reference or normative population, or this improvement can be relatively varied in that there is a fluctuating percentage improvement relative to a reference or normative population such that there is a tendency to do better than the reference group; when the improvement is relatively varied this can include periods when the subject patient may do worse relative to a reference or normative population.

Combination Treatments

The compositions and methods of the present disclosure may be used in the context of a number of therapeutic or prophylactic applications. In order to increase the effectiveness of a treatment with the compositions of the present disclosure, e.g., aminopyridines, or to augment the protection of another therapy (second therapy), it may be desirable to combine these compositions and methods with other agents and methods effective in the treatment, amelioration, or prevention of diseases and pathologic conditions, for example, dysfunctions or impairments produced by developmentally aberrant myelination of nerve cells.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

Other Potassium Channel Blockers

Other potassium channel blockers explicitly contemplated for use in the compositions and methods of the current disclosure include: 3,4 diaminopyridine (3,4-DAP) and/or derivatives thereof, additional aminopyridines 2-AP, 3-AP, 4-AMP, 4-MAP, 4-A-2MP and 4-DAMP, tetraethylammonium (TEA), bretylium, other quaternary ammonium ions, and the blocking agents for various Kv1-Kv12 voltage-gated K+ channels presented in FIG. 32, which have been reproduced from Judge and Bevar (Pharmacology & Therapeutics 111: 224-259).

3,4 diaminopyridine (3,4-DAP; Amifampridine; pyridine-3,4-diamine)

3,4 diaminopyridine has the following structure:

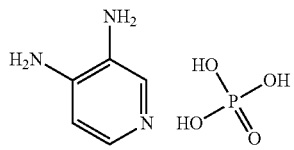

Amifampridine (pyridine-3,4-diamine, 3,4-diaminopyridine, 3,4-DAP) is used as a drug, predominantly in the treatment of a number of rare muscle diseases. The free base form of the drug has been used to treat congenital myasthenic syndromes and Lambert-Eaton myasthenic syndrome (LEMS) through compassionate use programs since the 1990s and was recommended as a first line treatment for LEMS in 2006, using ad hoc forms of the drug, since there was no marketed form.

Amifampridine phosphate has orphan drug status in the EU for Lambert-Eaton myasthenic syndrome and Catalyst holds both an orphan designation and a breakthrough therapy designation in the US.

Amifampridine is used to treat many of the congenital myasthenic syndromes, particularly those with defects in choline acetyltransferase, downstream kinase 7, and those where any kind of defect causes "fast channel" behaviour of the acetylcholine receptor (Argov Z. Current Opinion in Neurology. 22: 493-7; Abicht et al. (Jul. 14, 2016). "Congenital Myasthenic Syndromes". GeneReviews. University of Washington, Seattle).

It is also used to treat symptoms of Lambert-Eaton myasthenic syndrome ("Firdapse Summary of Product Characteristics" (PDF). EMA. Feb. 11, 2010. See EMA Index page, product tab; Keogh et al. The Cochrane Database of Systematic Reviews (2): CD003279. doi:10.1002/14651858.CD003279.pub3. PMID 21328260).

In Lambert-Eaton myasthenic syndrome, acetylcholine release is inhibited as antibodies involved in the host response against certain cancers cross-react with Ca2+ channels on the prejunctional membrane. Amifampridine works by blocking potassium channel efflux in nerve terminals so that action potential duration is increased (Kirsch and Narahashi. Biophys J. 22: 507-12). Ca2+ channels can then be open for a longer time and allow greater acetylcholine release to stimulate muscle at the end plate (Tarr et al. Molecular neurobiology. 52: 456-63).

Amifampridine is quickly and almost completely (93-100%) absorbed from the gut. In a study with 91 healthy subjects, maximum amifampridine concentrations in blood plasma were reached after 0.6 (±0.25) hours when taken without food, or after 1.3 (±0.9) hours after a fatty meal, meaning that the speed of absorption varies widely. Biological half-life (2.5±0.7 hrs) and the area under the curve (AUC=117±77 ng·h/ml) also vary widely between subjects, but are nearly independent of food intake ("Firdapse Summary of Product Characteristics" (PDF). EMA. Feb. 11, 2010. See EMA Index page, product tab).

The substance is deactivated by acetylation via N-acetyltransferases to the single metabolite 3-N-acetylamifampridine. Activity of these enzymes (primarily N-acetyltransferase 2) in different individuals seems to be primarily responsible for the mentioned differences in half-life and AUC: the latter is increased up to 9-fold in slow metabolizers as compared to fast metabolizers ("Firdapse Summary of Product Characteristics" (PDF). EMA. Feb. 11, 2010. See EMA Index page, product tab).

Amifampridine is eliminated via the kidneys and urine to 74-81% as N-acetylamifampridine and to 19% in unchanged form ("Firdapse Summary of Product Characteristics" (PDF). EMA. Feb. 11, 2010. See EMA Index page, product tab).

3,4-Diaminopyridine is a pale yellow to pale brown crystalline powder that melts at about 218-220° C. (424-428° F.) under decomposition. It is readily soluble in methanol, ethanol and hot water, but only slightly in diethyl ether ("Diaminopyridine (3,4-)" (PDF). FDA. Retrieved 28 Nov. 2015. Index page: FDA Docket 98N-0812: Bulk Drug Substances to be Used in Pharmacy Compounding; Dinnendahl, V; Fricke, U, eds. (2015). Arzneistoff-Profile (in German). 1 (28th ed.). Eschborn, Germany: Govi Pharmazeutischer Verlag. ISBN 978-3-7741-9846-3). Solubility in water at 20° C. (68° F.) is 25 g/L.

The drug formulation amifampridine phosphate contains the phosphate salt, more specifically 4-aminopyridine-3-ylammonium dihydrogen phosphate (Dinnendahl, V; Fricke, U, eds. (2015). Arzneistoff-Profile (in German). 1 (28th ed.). Eschborn, Germany: Govi Pharmazeutischer Verlag. ISBN 978-3-7741-9846-3). This salt forms prismatic, monoclinic crystals (space group C2/c) ("Crystal Structure and Solid-State Properties of 3,4-Diaminopyridine Dihydrogen Phosphate and Their Comparison with Other Diaminopyridine Salts". Cryst Growth Des. 13: 708-715) and is readily soluble in water (A. Klement (9 Nov. 2015). "Firdapse". Österreichische Apothekerzeitung (in German) (23/2015): 10f). The phosphate salt is stable, and does not require refrigeration ("Evidence Review: Amifampridine phosphate for the treatment of Lambert-Easton Myasthenic Syndrome" (PDF). NHS England. December 2015).

Amifampridine derivatives are known in the art and have been described, e.g., in U.S. Pat. No. 7,994,169 and elsewhere. Certain embodiments of the instant disclosure contemplate inclusion/use of amifampridine derivatives, which can optionally be represented by the following structure:

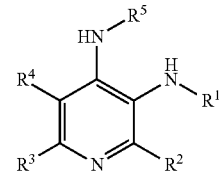

wherein R¹, R², R³, R⁴, and R⁵ are each independently selected from hydrogen, halogen, amine, hydroxyl, alkoxy, carboxyl, or C1-C6 alkyl.

Some embodiments of the instant disclosure contemplate amifampridine derivatives of the following structure:

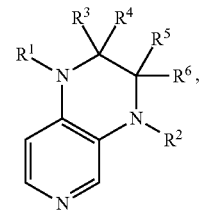

where $R^1$ and $R^2$ each represent, independently of one another, electron donors, with $R^2$ also being able to represent H; and $R^3$, $R^4$, $R^5$ and $R^6$ are each selected independently from among H, substituted or unsubstituted, straight-chain or branched alkyl, alkenyl, alkynyl, alkoxy and substituted or unsubstituted aryl, with the radicals $R^3$ and/or $R^4$ together with the radicals $R^5$ and/or $R^6$ being able to form a ring.

Additional embodiments of the instant disclosure specifically contemplate the major 3-N-acetyl metabolite of amifampridine (3-N-acetyl-3,4-diaminopyridine):

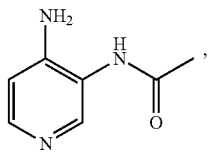

as described, e.g., in US 2014/0255380.

As noted above, inclusion/use of pharmaceutically acceptable salts is also expressly contemplated for amifampridine and derivatives thereof, and for all agents recited herein.

Additional Aminopyridines

Among the additional aminopyridines contemplated for use/inclusion in the compositions and methods of the instant disclosure include 2-AP, 3-AP, 4-AMP, 4-MAP, 4-A-2MP and 4-DAMP, which have the following structures:

2-AP
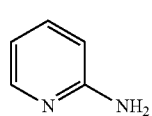

3-AP
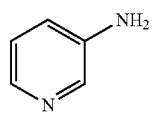

4-AMP
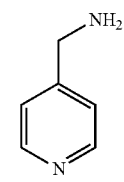

4-MAP
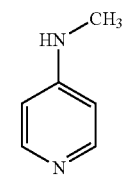

4-A-2-MP
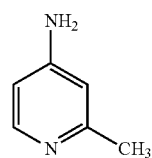

4-DAMP
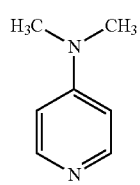

Derivatives and/or pharmaceutically acceptable salts of the above compounds are also contemplated for inclusion/use in the compositions and methods of the instant disclosure.

Tetraethylammonium (TEA)

Tetraethylammonium (TEA), (NEt4+) or (Et4N+) is a quaternary ammonium cation consisting of four ethyl groups attached to a central nitrogen atom, and is positively charged. The structure of TEA is:

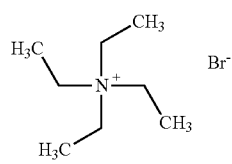

TEA is a counterion used in the research laboratory to prepare lipophilic salts of inorganic anions. It is used similarly to tetrabutylammonium, the difference being that its salts are less lipophilic and more easily crystallized.

Although TEA (sometimes under the name "Etamon" (J. P. Hendrix (1949. "Neostigmine as antidote to Etamon®." JAMA 139(11) 733-734)) was explored in a number of different clinical applications (G. K. Moe and W. A. Freyburger (1950). "Ganglionic blocking agents." Pharmacol. Rev. 2 61-95), including the treatment of hypertension (Hoobler et al. Med. Clin. N. Amer. 33 805-832), its major use seems to have been as a probe to assess the capacity for vasodilation in cases of peripheral vascular disease (A. J. P. Graham. Br. Med. J. 2: 321-322). Because of dangerous, even fatal reactions in some patients (A. J. P. Graham. Br. Med. J. 2: 321-322), as well as inconsistent cardiovascular responses, TEA was soon replaced by other drugs (Drill's Pharmacology in Medicine, 4th Ed. (1971). J. R. DiPalma (Ed.), pp. 723-724, New York: McGraw-Hill).

TEA is not orally active (Boyd et al. Lancet 251: 15-18). Typical symptoms produced in humans include the following: dry mouth, suppression of gastric secretion, drastic reduction of gastric motility, paralysis of urinary bladder, and relief of some forms of pain (G. K. Moe and W. A. Freyburger (1950). "Ganglionic blocking agents." Pharmacol. Rev. 2 61-95). Most studies with TEA seem to have been performed using either its chloride or bromide salt without comment as to any distinctions in effect, but it is noteworthy that Birchall and his co-workers preferred the use of TEA chloride in order to avoid the sedative effects of the bromide ion (Birchall et al. Am. J. Med. Sci. 213 572-578).

Bretylium

Bretylium (also bretylium tosylate) is an antiarrhythmic agent (Tiku and Nowell. British Journal of Pharmacology. 104: 895-900) having the following structure (as bretylium tosylate):

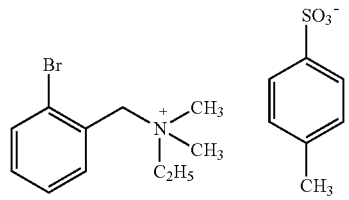

Bretylium blocks the release of noradrenaline from nerve terminals. In effect, it decreases output from the peripheral sympathetic nervous system. It also acts by blocking K+ channels and is considered a class III antiarrhythmic. The dose is 5-10 mg/kg and side effects are high blood pressure followed by low blood pressure and ventricular ectopy.

Originally introduced in 1959 for the treatment of hypertension (Harington. Proceedings of the Royal Society of Medicine. 55: 283-6), its use as an antiarrhythmic for ventricular fibrillation was discovered and patented by Marvin Bacaner in 1969 at the University of Minnesota (U.S. Pat. No. 3,441,649, which is incorporated herein in its entirety by this reference).

The American Heart Association removed bretylium from its 2000 ECC/ACC guidelines due to its unproven efficacy and ongoing supply problems. These supply problems appear to be an issue of raw materials needed in the production of Bretylium. By the release of the AHA 2005 ECC/ACC guidelines, there is no mention of Bretylium and it is virtually unavailable throughout most of the world (Khan. Encyclopedia of Heart Diseases. Academic Press. p. 221. ISBN 978-0-12-406061-6; Hypothermia~treatment at eMedicine).

As of Jun. 8, 2011 bretylium tosylate is permanently no longer available in the US after request of Hospira Inc. to withdraw its NDA from the market. Bretylium will remain on the FDA's discontinued drug list since its withdrawal was not the result of a safety or effectiveness concern (see federalregi ster.gov/articles/2011/12/19/2011-32367/determination-that-bretylium-tosylate-injection-50-milligrams-milliliter-was-not-withdrawn-from-sale).

Other Quaternary Ammonium Ions

It is contemplated that other agents having a quaternary ammonium ion structure can be employed in the compounds and methods of the instant disclosure. Quaternary ammonium ion compounds have the following, generic structure:

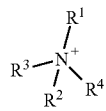

Other Drugs for Treatment of Developmentally Aberrant Myelination Disorders

Other drugs capable of treating neurodevelopmental myelination abnormality diseases or disorders are also contemplated for incorporation and use in the compositions and methods of the instant disclosure. Such drugs include, e.g., opicinumab and clemastine, among others.

Opicinumab (BIIB033), described, e.g., in WO 2009/048605 (the entire contents of which is incorporated herein by reference), is a fully human monoclonal antibody designed for the treatment of multiple sclerosis, acute optic neuritis (AON), and other associated demyelinating diseases ("Biogen Reports Top-Line Results from Phase 2 Study of Opicinumab (Anti-LINGO-1) in Multiple Sclerosis Biogen Media". media.biogen.com). A biologic drug, it is designed to function as a LINGO-1 protein antagonist, known as "Anti-Lingo-1" ("Opicinumab". drugspider.com). Phase II clinical trials are ongoing, but preliminary results released by the drug's developer, Biogen Idec Inc., indicate that primary study endpoints were not met and that opicinumab exhibits unexpected dose-response relationships. Further studies are planned by the company, as opicinumab still was deemed to show potential for clinical efficacy in the treatment of MS ("Biogen Reports Top-Line Results from Phase 2 Study of Opicinumab (Anti-LINGO-1) in Multiple Sclerosis Biogen Media". media.biogen.com).

Opicinumab has the potential to reverse nerve demyelination. LINGO-1 is described as a "human anti-Nogo receptor interacting protein-1 monoclonal antibody," LINGO-1 is considered an emerging therapy for myelin regeneration due to the fact that it ultimately has been shown to lead to "in vivo remyelination through induction of OPC differentiation and neuroprotection" in experimental immune as well as non-immune models of demyelination, where at least 10 mg/kg of the drug retained blood concentrations comparable to those previously observed in rats that showed 90% remyelination from the drug. (Tan, A. "New Multiple Sclerosis Drug May Repair Nerve Demyelination." Multiple Sclerosis News Today, Sep. 1, 2014).

Clemastine, also known as meclastin, is an antihistamine and anticholinergic (GB 942152 (1963)). Unlike loratadine or fexofenadine, clemastine is a sedating antihistamine; however, it exhibits fewer other side effects than most of the widely used antihistamines. Clemastine is also classified as an antipruritic (i.e., it stops itching). Clemastine has the following structure:

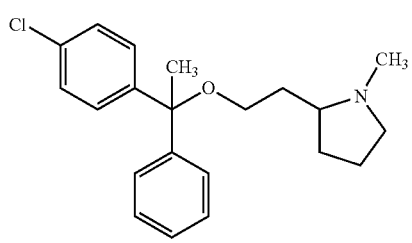 [SMILES: CN1CCCC1CCOC(C)(c1ccccc1)c1ccc(Cl)cc1]

Clemastine is an antimuscarinic compound that has previously been shown to enhance oligodendrocyte differentiation and myelination in vitro, and that has recently been described to enhance myelination in the prefrontal cortex and to rescue behavioral changes in socially isolated mice (Liu et al. J. Neurosci. 36(3): 957-62). Specifically, in such studies, clemastine was orally administered for 2 weeks to adult mice following social isolation, and such administration was observed to successfully reverse social avoidance behavior in mice undergoing prolonged social isolation. Such prolonged social isolation was observed to result in impaired myelination, which was then rescued by oral clemastine treatment, which provoked enhanced oligodendrocyte progenitor differentiation and epigenetic changes (Liu et al. J. Neurosci. 36(3): 957-62). Additional characterization of the associations between social behavior and myelination can be found in Liu et al. Nature Neuroscience 15: 1621-1623. Remyelinating agents have also been described as therapies for multiple sclerosis (Bove and Green. Neurotherapeutics 14(4): 894-904). It is believed that clemastine specifically enhances the differentiation of oligodendrocyte precursor cells into mature oligodendrocytes.

Adult dosages of clemastine tend to be 1.34 mg orally twice a day, with dosage optionally increased as required, but not to exceed 2.68 mg orally 3 times a day. Pediatric dosages of clemastine include 0.335 to 0.67 mg/day orally divided into 2 or 3 doses, where maximum daily dose is 1.34 mg, for less than six year-old subjects; 0.67 to 1.34 mg orally twice a day, where maximum daily dose is 4.02 mg, for subjects of six to twelve years of age; and the adult dosage for subjects over twelve years of age.

Clemastine has also been indicated for use in treating allergic rhinitis, such as sneezing, rhinorrhea, pruritus and lacrimation.

Overdosage symptoms are paradoxical, ranging from CNS depression to stimulation. Stimulation is most common in children, and is usually followed by excitement, hallucinations, ataxia, loss of coordination, muscle twitching, athetosis, hyperthermia, cyanosis, convulsions, tremors, and hyperreflexia. This may be followed by postictal depression and cardiovascular/respiratory arrest. Other common overdose symptoms include dry mouth, fixed dilated pupils, flushing of the face, and pyrexia. In adults, overdose usually leads to CNS depression, ranging from drowsiness to coma.

Clemastine is an antihistamine with anticholinergic and sedative effects. Antihistamines competitively bind to histamine receptor sites, thus reducing the neurotransmitter's effects. Effects of histamine (which are countered by antihistamines) include:

Increased capillary permeability

Increased capillary dilatation

Edema (i.e., swelling)

Pruritus (Itch)

Gastrointestinal/respiratory smooth muscle constriction

Clemastine inhibits both the vasoconstrictor and vasodilator effects of histamine. Depending on the dose, the drug can produce paradoxical effects, including CNS stimulation or depression.

Most antihistamines exhibit some type of anticholinergic activity. Antihistamines act by competitively binding to H1-receptor sites, thus blocking the binding endogenous histamine. Antihistamines do not chemically inactivate or prevent the normal release of histamine.

Clemastine does also act as FIASMA (functional inhibitor of acid sphingomyelinase; Kornhuber et al. PLoS ONE. 6 (8): e23852).

Clemastine is rapidly absorbed from the gastrointestinal tract and peak plasma concentrations are attained in 2-4 hours. Antihistamines are thought to be metabolized in the liver, mostly by mono-/didemethylation and glucuronide conjugation. It is an inhibitor of cytochrome P450 CYP2D6 and may interfere with other drugs metabolized by this isozyme.

Clemastine is a selective histamine H1 antagonist. It binds to the histamine H1 receptor, thus blocking the action of endogenous histamine, which leads to temporary relief of the negative symptoms caused by histamine. Clemastine is an OTC drug, and is available under many names and dosage forms worldwide.

Noting the potent calcium channel activation that has also been observed for 4-AP (Wu et al. The Journal of Biological Chemistry. 284: 36453-61; Li et al. Mol. Pharmacol. 86: 760-772), use and/or administration of calcium channel agonists (e.g., VACC agonists) within the compositions and methods of the instant disclosure is also contemplated. In addition to 4-AP, exemplary calcium channel activators include the following (among other art-recognized calcium channel stimulatory agents):

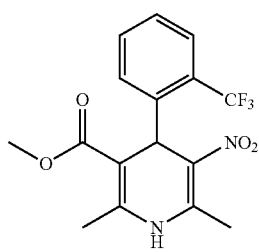 [SMILES: COC(=O)C1=C(C)NC(C)=C([N+](=O)[O-])C1c1ccccc1C(F)(F)F]

Bay K8644 (which increases influx of $Ca^{2+}$ specifically at voltage-gated calcium channels)

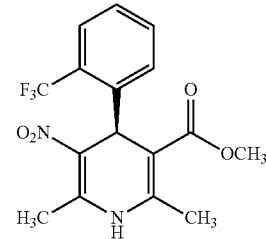 [SMILES: COC(=O)C1=C(C)NC(C)=C([N+](=O)[O-])[C@H]1c1ccccc1C(F)(F)F]

(S)-(−)-Bay K8644 ($Ca^{2+}$ channel activator; enantiomer of Bay K 8644)

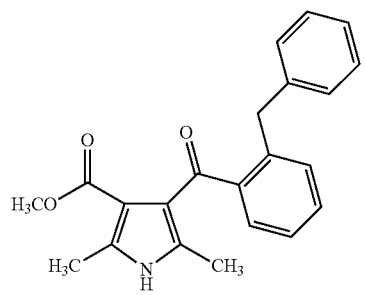 [SMILES: COC(=O)c1c(C)[nH]c(C)c1C(=O)c1ccccc1Cc1ccccc1]

FPL 64176 (a potent $Ca^{2+}$ channel (L-type) activator)

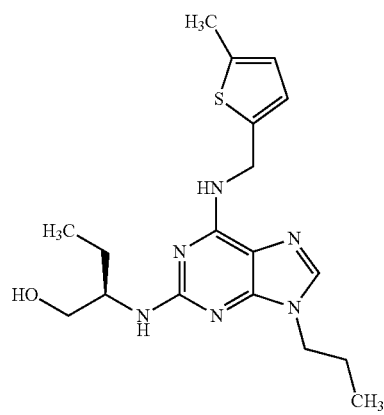 [SMILES: CCCn1cnc2c(NCc3ccc(C)s3)nc(N[C@H](CC)CO)nc21]

GV-58 (A roscovitine analog that retains the ability to prolong the open state of calcium channels, but unlike roscovitine, is inactive against Cdk activity. GV-58 is a selective agonist of N-type and P/Q type calcium channels, which are critical to the triggering of neurotransmitter release at the neuromuscular junction. GV-58 has been studied as a possible therapeutic agent in a mouse model of Lambert-Eaton myasthenic syndrome (LEMS). The EC50 values for activation of N-, P/Q- and L-type calcium channels are 6.8, 9.9 and >100 μM, respectively.)

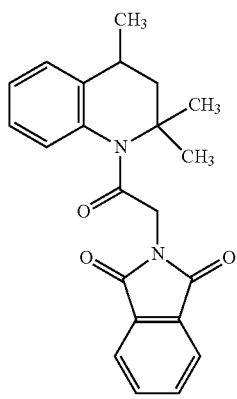 [SMILES: CC1CC(C)(C)N(C(=O)CN2C(=O)c3ccccc3C2=O)c2ccccc21]

ML-SA1 (A potent and selective cell permeable agonist of lysosomal mucolipin transient receptor potential channels (TRPML) 1, 2, 3 that significantly increases $[Ca^{2+}]$cyt in HEK293 cells stably- or transiently-expressing mutant TRPML1 channels ML1-4A)

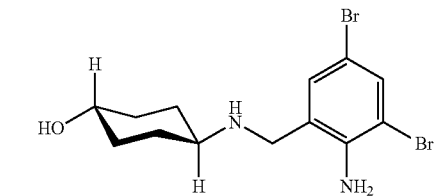

MSP-3 (A Transient Receptor Potential Vanilloid Type-1 (TRPV1) channel agonist with antioxidant and neuroprotective activity. MSP-3 activated TRPV1 channels with similar efficacy as compared to capsaicin (EC50=870 nM). It protected a keratinocyte cell line from oxidative stress damage with more efficacy than capsaicin and prevented the damage caused by H2O2 in differentiated human neuroblastoma cell lines as well as in rat cortical slices.)

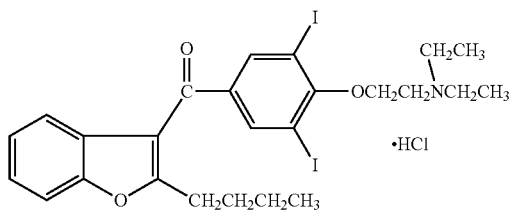

Ambroxol (a potent inhibitor of the neuronal Na+ channels, known to mobilize calcium)

Amiodarone (A non-selective ion channel blocker with broad fungicidal activity. Amiodarone induces an immediate influx of $Ca^{2+}$ in *Saccharomyces cerevisiae*, followed by mitochondrial fragmentation and cell death.)

AC-265347 (A calcimimetic that acts as agonist to calcium-sensing receptor. It reduces serum parathyroid hormone and plasma ionizable calcium. AC-265347 is a human calcium-sensing receptor (CaSR) allosteric agonist. AC-265347 activates CaSR signaling in cellular proliferation and phosphatidyl inositol (PI) hydrolysis assays.)

Stem Cell Therapies

In certain aspects of the instant disclosure, it is contemplated that stem cell-based therapies can be used to treat or prevent neurological symptoms of neurodevelopmental myelination abnormality diseases or disorders. General methods for stem cell-reliant and/or ex vivo therapeutic approaches have been documented extensively in the art.

Pharmaceutical Compositions

Agents of the present disclosure can be incorporated into a variety of formulations for therapeutic use (e.g., by administration) or in the manufacture of a medicament (e.g., for treating or preventing a neurodevelopmental myelination abnormality disease or disorder, such as WS or autism) by combining the agents with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols.

Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, non-therapeutic, nonimmunogenic stabilizers, excipients and the like. The compositions can also include additional substances to approximate physiological conditions, such as pH adjusting and buffering agents, toxicity adjusting agents, wetting agents and detergents.

Further examples of formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977):1-19, incorporated herein by reference. The salts can be prepared in situ during the final isolation and purification of the FDA-approved compounds of the application, or separately by reacting a free base or free acid function with a suitable reagent, as described generally below. For example, a free base function can be reacted with a suitable acid. Furthermore, where the FDA-approved compounds of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent FDA-approved compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the FDA-approved compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of an agent of the instant disclosure, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, (1987), both of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent, such as a potassium channel blocker, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the individual instant disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an agent of the present disclosure may be used (e.g., administered to an individual, such as a human individual, in need of treatment with a presynaptic potassium channel blocker or other agent of the disclosure) in accord with known methods, such as intravenous administration as a bolus or by continuous infusion over a period of time, by intramuscular, intraperitoneal, intracerobrospinal, intracranial, intraspinal, subcutaneous, intraarticular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the agents of the present disclosure, normal dosage amounts may vary from about 10 ng/kg up to about 100 mg/kg of an individual's and/or subject's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An effective amount of an agent of the instant disclosure may vary, e.g., from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An exemplary dosing regimen may include administering an initial dose of an agent of the disclosure of about 200 µg/kg, followed by a weekly maintenance dose of about 100 µg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the agent(s) administered, can vary over time independently of the dose used.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methyl cellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, German® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., a potassium channel blocker or other agent of the instant disclosure) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient.

Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

FDA-approved drugs provided herein are typically formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., a potassium channel blocker or other agent of the instant disclosure) described herein.

As noted elsewhere herein, a drug or, e.g., a stem cell agent of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

The FDA-approved drug or other therapy is administered to the subject in an amount sufficient to achieve a desired effect at a desired site (e.g., reduction of disease or disorder-associated neurological effects, reduction of tremors, normalization of social interactions, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Additional exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 µg/kg/day, at least 100 µg/kg/day, at least 250 µg/kg/day, at least 500 µg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and a therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 µg/kg/day, and less than 500 µg/kg/day.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., a potassium channel blocker or other agent of the instant disclosure) described herein. In certain embodiments, a dose described herein includes independently between 1 mg and 3 mg, inclusive, of an agent (e.g., a potassium channel blocker or other agent of the instant disclosure) described herein. In certain embodiments, a dose described herein includes independently between 3 mg and 10 mg, inclusive, of an agent (e.g., a potassium channel blocker or other agent of the instant disclosure) described herein. In certain embodiments, a dose described herein includes independently between 10 mg and 30 mg, inclusive, of an agent (e.g., a potassium channel blocker or other agent of the instant disclosure) described herein. In certain embodiments, a dose described herein includes independently between 30 mg and 100 mg, inclusive, of an agent (e.g., a potassium channel blocker or other agent of the instant disclosure) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., a potassium channel blocker or other agent of the instant disclosure) or composition, as described herein, can be administered in combination with one or more additional pharmaceutical agents (e.g., therapeutically and/or prophylactically active agents), which are different from the agent or composition and may be useful as, e.g., combination therapies. The agents or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk of developing a disease in a subject in need thereof, in inhibiting the replication of a virus, in killing a virus, etc. in a subject or cell. In certain embodiments, a pharmaceutical composition described herein including an agent (e.g., a potassium channel blocker or other agent of the instant disclosure) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from an agent of the disclosure is administered prior to, in combination with, at the same time, or after administration of the agent of the disclosure. In some embodiments, the second therapeutic agent is selected from the group consisting of a chemotherapeutic, an antioxidant, an antiinflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, neuron-targeting and/or axon conductivity-enhancing agents, immunomodulatory agents, anti-cancer agents, anti-proliferative agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the agents described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Dosages for a particular agent of the instant disclosure may be determined empirically in individuals who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

The present disclosure provides agents capable of reducing the observed effect(s) of developmentally aberrant neuronal myelination. These agents are useful for preventing, reducing risk, or treating neurodevelopmental myelination abnormality diseases or disorders. Accordingly, as disclosed herein, agents of the present disclosure may be used for treating, preventing, or reducing risk of neurodevelopmental myelination abnormality diseases or disorders in an individual. In some embodiments, the individual has a neurodevelopmental myelination abnormality disease or disorder, such as Williams syndrome. In some embodiments, the individual is a human.

Kits

The instant disclosure also provides kits containing agents of this disclosure for use in the methods of the present disclosure. Kits of the instant disclosure may include one or more containers comprising a purified agent (e.g., a potassium channel blocker or other agent of the instant disclosure) of this disclosure. In some embodiments, the kits further include instructions for use in accordance with the methods of this disclosure. In some embodiments, these instructions comprise a description of administration of the agent to treat or diagnose, e.g., Williams syndrome, according to any of the methods of this disclosure. In some embodiments, the instructions comprise a description of how to detect Williams syndrome, other neurodevelopmental myelination abnormality disease or disorder and/or associated phenotype(s), for example in an individual, in a tissue sample, or in a cell. The kit may further comprise a description of selecting an individual suitable for treatment based on identifying whether that subject has the disease or disorder and the stage of the disease or disorder.

The instructions generally include information as to dosage, dosing schedule, and route of administration for the intended treatment. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., Williams syndrome, autism, etc. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). In certain embodiments, at least one active agent in the composition is a potassium channel blocker. In some embodiments, at least one active agent in the composition is a calcium channel agonist, optionally a voltage-activated calcium channel (VACC) stimulatory agent. The container may further comprise a second pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

Mice

Gtf2i conditional knockout mice (21) were backcrossed to pure C57B1/6J (The Jackson Laboratory, stock #000664) for more than 15 generations. Germline deletion of a single Gtf2i allele (Gtf2i-Het mice) was achieved by breeding Gtf2i conditional knockout to Beta-actin-Cre transgenic mice, followed by another breeding to C57B1/6J, to breed out the Beta-actin-Cre. All animal-related work was performed under the guidelines of Division of Comparative Medicine (DCM), with protocol approved by the Committee for Animal Care (CAC) of Massachusetts Institute of Technology and was consistent with the Guide for Care and Use of Laboratory Animals, National Research Council 1996. Each cage contained 2-5 mice regardless of genotype, and mice were housed at a constant 23° C. in a 12-h light/dark cycle (lights on at 07:00, lights off at 19:00) with ad libitum food and water. Nex-Cre mice are in a C57B1/6 background (22). Nex-Cre mice were previously shown to behave and develop normally, and to have Cre activity starting from around embryonic day 11.5, specifically restricted to forebrain excitatory neurons located mainly in the cortex and hippocampus (22). Rosa26-flox-stop-tdTomat$^{+/-}$ mice were used to assess Cre recombinase activity in the brain of 1 month-old male Nex-Cre mice.

Western Blot

Whole cortex of 1-month-old mice was dissected and separated via SDS-PAGE. Western blotting was performed and quantified using a Licor Odyssey CLx imaging system. Commercial antibodies used included TFII-I (Cell Signaling, 4562) and Tubulin (Sigma, T5168), employed as a loading control.

Behavioral Studies

All behavioral studies were carried out and analyzed with the experimenter blinded to genotypes. All test mice were males and were habituated in the test room for 1 h prior to all tests. Each cohort of test mice was used for a maximum of three behavioral tests with a minimum of 3 days break between tests. In all behavioral tests, except from the juvenile dyadic social interaction test, mice were 1-month-old.

Juvenile Dyadic Social Interaction Test

The juvenile play apparatus was made of a non-transparent Plexiglas box (32 cm (L)×32 cm (W)×32 cm (H)) and indirectly illuminated with 10 lux inside. Test mice were weaned at P21 and individually habituated inside the test chamber with a thin layer of bedding for two consecutive days, two 30-minute sessions per day. A pair of P23 test mice unfamiliar with each other and of the same genotype was gently placed into the test chamber and was videotaped for 10 min. Dyadic social interaction was scored using Observer XT (Noldus) by trained observers blinded to genotypes. The following behaviors were coded: direct contact, following, nose-to-nose, nose-to-anogenital, crawling under or over, and allogrooming.

Social Preference Test

Stranger mice were wildtype S129 Sv males (Jackson Laboratory) with matched age and body weight to test mice. Stranger mice were habituated by placing them inside an inverted wire cup for 30 min, two sessions per day for three consecutive days before tests. Each stranger mouse was used a maximum of two times per day. The social test apparatus was made of a clear Plexiglas box (65 cm (L)×44 cm (W)×30 cm (H)) with a removable floor and partitions dividing the box into left, center, and right chambers. The center chamber (21 cm×22 cm) was half the width of the left and right chambers (each is 21 cm×44 cm). These three chambers were interconnected with 5 cm openings between each chamber that could be closed or opened manually with a lever-operated door. The inverted wire cups containing the stranger mice were cylindrical, 10 cm in height, with a bottom diameter of 10 cm and with metal bars spaced 0.8 cm apart. A weighted cup was placed on top of the inverted wire cups to prevent the test mice from climbing onto the wire cup. Each wire cup was used only one time per day, followed by extensive cleaning with 75% ethanol and water at the end of the test day. During the habituation phase, an empty wire cup was placed into left and right chamber, and the test mouse was placed into the middle chamber and allowed to explore for 15 minutes, with the doors into both side chambers open. To test for social preference, the test mouse was gently introduced to the middle chamber with the doors to both side chambers closed, and a stranger mouse was placed under the inverted wire cup in one of the side-chambers. An inanimate object was placed under the inverted wire cup placed in the opposite side chamber. The location of the stranger mouse and object was counterbalanced between test trials to exclude side preference. The experimenter then lifted up the doorways to both side chambers simultaneously, and the test mouse was allowed to explore all three chambers for 15 minutes. Then, experimenter blinded to genotypes analyzed for timespent in close proximity to the stranger mouse or object was analyzed using the Noldus Ethovison XT software. Social preference index was calculated as follows: (time in close interaction with stranger)/(time in close interaction with object).

Tube-Test

Transparent Plexiglas tubes with a 30 cm length and 3 cm inner diameter were used, so that a 1-month-old mouse was able to walk through without being able to reverse its body direction. Before testing, mice were habituated to walk through the tube two sessions per day for four consecutive days. On test day, two unfamiliar mice with different genotypes were inserted to the tube and released simultaneously by an experimenter blinded to genotypes. The first mouse to completely retreat from the tube within the first 6 min of the test was defined as the loser, and the other as the winner. When no mice retreated within 6 min, tests were repeated with entry sides reversed. The tubes were cleaned with 75% ethanol between trials. A chi-square analysis was applied to determine the significance of test score between mice when compared with an outcome expected by chance (i.e. a 50:50 win-lose outcome).

Open-Field Exploration Test

Spontaneous locomotion was measured by placing a mouse in a Plexiglas box (40 cm (L)×40 cm (W)×30 cm (H)) for 1 h. Motor activity was detected by infrared photobeam sensors in an automated Omnitech Digiscan apparatus (AccuScan Instruments) and analyzed by VersaMax animal activity monitoring system (AccuScan Instruments). Experimenter was blinded to genotypes. Elevated zero maze: The zero maze was indirectly illuminated at 60 lux on the open arms and 10 lux on the closed arms. Testing started with an animal being placed into a closed arm of the maze. Behavior was video-recorded for 5 min. Experimenter was blinded to genotypes.

Hot Plate

Mice were placed onto a heating block set to 55° C. surface temperature (Columbus Instruments). Latency to lick a forepaw or hindpaw was measured. The average of three trials with an inter-trial interval of 5 min was recorded. Experimenter was blinded to genotypes.

Acoustic Startle Response and Prepulse Inhibition Test

Experiments were performed using two identical sound attenuating test chambers (65 cm (L)×35 cm (W)×25 cm (H)). Each test chamber was equipped with a loudspeaker mounted 25 cm above the holding cylinder and a commercial startle reflex system (SR Lab, San Diego Instruments, CA). An individual mouse was placed inside the Plexiglas holding cylinder mounted on a Plexiglas platform. A piezoelectric accelerometer located beneath the platform was used to transform startle responses into units based on force and latency of startle. Data were collected at 250 samples/sec and the maximum voltage attained on each trial was used as the dependent variable. Each test session started with a 5 min acclimation period in the presence of 65 dB acoustic background noise followed by five 120 dB startle pulses. Pre-pulse trials followed the initial 120 dB startle acclimation. Each pre-pulse stimulation was 20 ms in duration, followed by a 40 ms startle stimulus of 120 dB. PPI was recorded for pre-pulse intensities of 70, 75, 80, 85 and 90 dB, and no stimulus. Each prepulse trial was administered ten times in a random order. Trials of 120 dB alone were randomly interspersed within the pre-pulse trials and used for comparison with the prepulse trials. The percent PPI was calculated using the formula [100−(response to pre-pulse+ 120 dB)/(response for 120 dB alone)×100]. Acoustic startle trials followed the PPI trials. Startle trials consisted of 40 ms pulses at 0 (no stimulus), 70, 75, 80, 85, 90, 95, 100, 105, 110, 115, and 120 dB. Each trial was presented five times in a randomized order. Experimenter was blinded to genotypes.

Horizontal Ladder Walking

Mice were tested for their ability to walk on a horizontal ladder with irregularly spaced rungs, following the procedure described previously (44). Animals were trained to cross the ladder until their performance achieved the plateau (with a forelimb error of 20% or less). The irregular pattern was changed from trial to trial during training. All trials were video recorded with Hotshot e64 and paw placement was analyzed. The paw placement on rungs were categorized as Hit (platar contact and digits closure), Miss (paw falls between rungs) and Slip (imprecise contact with one or few digits). Experimenter was blinded to genotypes.

Grip Strength

Mice forelimb and hindlimb grip strength was measured using a grip strength meter (TSE Systems) according to manufacturer's instructions. Each mouse was tested on 3 consecutive trials to obtain the average force (g). Experimenter was blinded to genotypes.

Single-Pellet Food Retrieval Task

The single-pellet food retrieval task was carried out following previously established procedures with minor modification (67). Mice were inserted into the training chamber built with clear Plexiglas (1 mm thickness, dimensions 20 cm×15 cm×8.5 cm) having a narrow vertical slit (0.5 cm wide; 13 cm high) located on the front wall of the box. A single sugar pellet (dustless precision pellet, 20 mg, Bioserv) was placed on an exterior shelf with 1.5 cm height affixed to the wall in front of the slit. Mice were food-restricted for 1 night before training and were maintained above 90% of free feeding weight throughout the training session. Twenty pellets were used for daily training until the performance plateaued. The success rate was calculated as: number of successful retrievals/total attempts per trail *100. Experimenter was blinded to genotypes.

RNA Isolation and Quantitative PCR

For human tissue samples, frozen tissue was used directly from −80° C. For mouse tissue, mice were decapitated after an isofluorane overdose and the whole cortex was dissected and snap-frozen on dry ice. Total RNA was extracted using the RNeasy Mini kit (QIAGEN) following the standard user manual. Equivalent amounts of mouse total mRNAs were reverse-transcribed to cDNA with the iScript cDNA Synthesis Kit (Bio-Rad). Quantitative real-time PCR (q-PCR) was carried out using the iQ5 real-time PCR detection system (Bio-Rad) with the iQ SYBR Green Supermix kit (Bio-Rad) following the manufacturer's protocol.

RNAseq Analysis

For QC purposes, BEDTools (version 2.17.0) was used to count the reads classified as genes, coding regions, intronic regions, 5' or 3' UTRs, flanking 3kb genic regions, and intergenic regions. Other basic statistics, including mapping rate, ratio of sense vs. anti-sense reads, and rRNA percentages were collected for each sample. RSEM (version 1.2.15) was used to estimate gene expression levels based on mm9 UCSC known gene annotations. The count table was imported into DESeq (version 1.10.1) for differential gene expression testing. The gene expression (Log 2FPKM values) table was then run through GSEA for gene set enrichment analysis. To do functional analysis with DAVID, up- and down-regulated coding genes (p-value<0.05) were compared to the expressed genes (coding genes with average FPKM>1). Networks were also generated through the use of QIAGEN's Ingenuity Pathway Analysis (IPA®, QIAGEN Redwood City, www.qiagen.com/ingenuity).

GSEA Analysis

Gene Set Enrichment Analysis (GSEA) was performed to determine whether the myelination-related down-regulated gene set from the mouse and human samples were enriched within oligodendrocyte precursor cells, newly-formed oligodendrocytes, or myelinating oligodendrocytes (http://www.broad.mit.edu/gsea/).

Immunofluorescence Staining

Basic immunofluorescence procedure was used as previously described (68). Mice were deeply anesthetized with isoflurane and transcardially perfused with 15 ml ice-cold PBS solution followed by 15 ml fresh ice-cold 4% paraformaldehyde (PFA) in PBS. Brains were dissected and kept in 4% PFA overnight at 4° C. and then sectioned at 100 μm thickness by vibratome (Leica). Floating brain slices were washed 3 times, 5 min each, with PBS and permeabilized with 1.2% Triton X-100 in PBS for 15 min at room temperature. Slices were then washed 3 times, 5 min each, followed by blocking with 5% normal goat serum, 2% BSA, 0.2% Triton X-100 in PBS for 1 h at room temperature. Primary antibodies diluted in blocking buffer were applied to sections overnight at 4° C. Slices were then washed 3 times with PBS for 15 min each and stained with secondary antibodies conjugated with Alexa488/555/647 (Invitrogen) in blocking buffer for 1 h at room temperature. Slices were washed twice in PBS for 15 min, followed by DAPI (1:10,000) staining in PBS for 5 min, and additional 5 min wash in PBS. VECTASHIELD mounting medium (Vector Laboratories) was used to mount slices on glass slides. Images were captured using an Olympus Fluoview FV1000 confocal microscope.

To quantify cellular properties in the cortex, images were taken by an experimenter blinded to genotypes with a 10× magnification at the motor cortex area at bregma 0.5 mm. For each mouse, both hemispheres were imaged. The midline of the CC was imaged at the same bregma, using a 40× magnification, and the whole depth of the CC was imaged by taking 10 images as part of a Z-stack serial imaging, and then all images were stacked together to a single image which was then analyzed for quantification. Cell numbers were quantified blindly with automation using ImageJ. For the cortex, the two values of hemispheres from each mouse were averaged. The pixel intensity of H3ac and H3K9me3 was quantified using ImageJ, as was previously described (37).

Commercial antibodies used included TFII-I (1:1,000, Cell Signaling, 4562), CaMKIIa (1:400, Millipore, 05-532), GFP (1:3,000, Invitrogen, A11122), Sox10 (1:100, Santa-Cruz 365692), PDGFRa (1:1,000, Santa-Cruz 338), Olig2 (1:1,000, Millipore AB9610), CC1 (1:500, Calbiochem OP80), NeuN (1:1,000, Millipore MAB377), S 100B (1:600, Sigma S2532) GAD67 (1:1,000, Millipore 5406).

E15.5 Immunohistochemistry

Females were checked daily for semen plugs and separated from male mice once a plug was detected. Pregnant dams were euthanized on embryonic day 15.5 and embryos were immediately dissected into ice-cold PBS. Tissue was taken for genotyping and brains were dissected and transferred to ice-cold 4% PFA. Whole brains were fixed in 4% PFA overnight, embedded in OCT, and 12 μm coronal sections were cut using a cryostat (Leica).

Electron Microscopy

Figure 30:
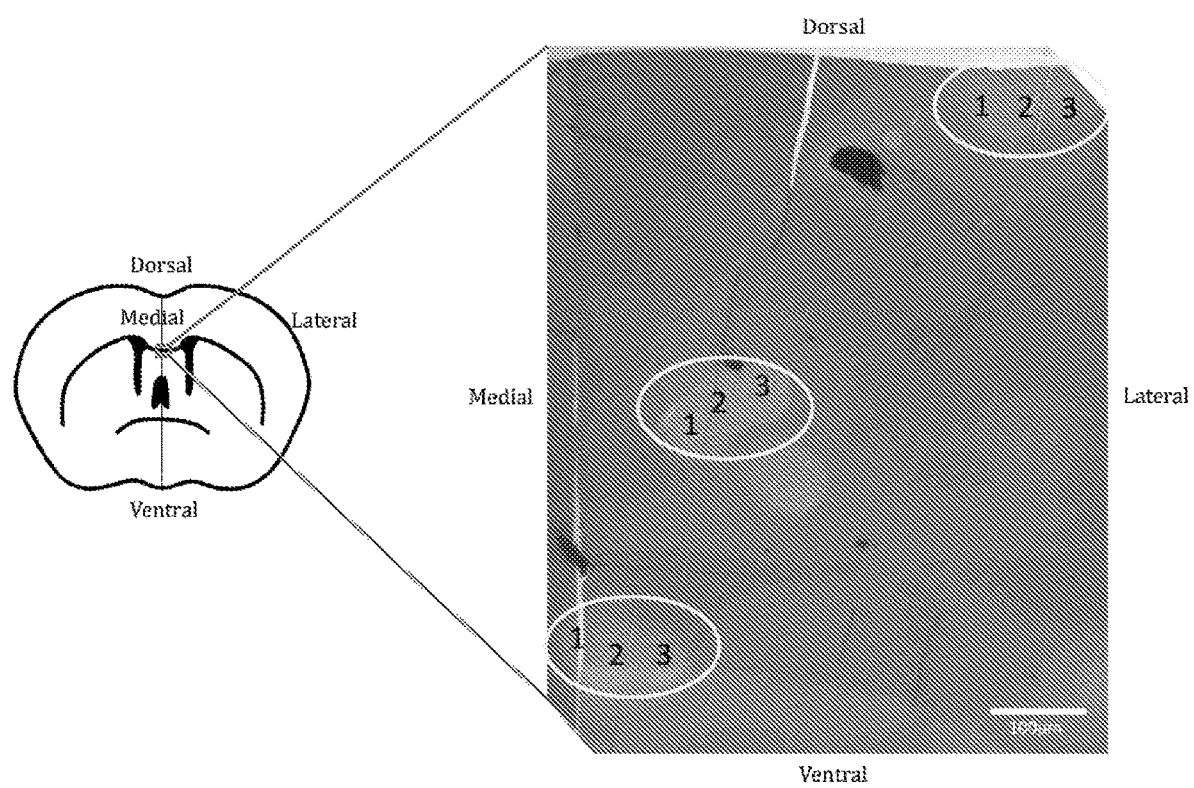
FIG. 30 shows an image of electron microscopy sampling. Three different locations along the mediolateral axis of the corpus callosum, here circled in yellow, were imaged and quantified.

One-month-old or six-month-old mice were deeply anesthetized with isoflurane, and transcardially perfused with 15 ml ice-cold PBS solution followed by 15 ml fresh ice-cold 2.5% glutaraldehyde+2% paraformaldehyde in 0.1 M sodium cacodylate buffer (pH 7.4). Brains were dissected and kept in the fixation solution overnight at 4° C. Small pieces (1-2 mm cubes) of tissue samples from corpus callosum at the level of the fornix were post-fixed for at least two hours at RT in the fixation solution, washed in 0.1M cacodylate buffer, and post-fixed with 1% Osmiumtetroxide (OsO4)/1.5% Potassium ferrocyanide(KFeCN6) for one hour, washed in water three times, and incubated in 1% aqueous uranyl acetate for one hour followed by two washes in water and subsequent dehydration in grades of alcohol (10 min each; 50%, 70%, 90%, 2×10 min 100%). The samples were then put in propyleneoxide for one hour and infiltrated overnight in a 1:1 mixture of propyleneoxide and TAAB Epon (Marivac Canada Inc. St. Laurent, Canada). The following day the samples were embedded in TAAB Epon and polymerized at 60° C. for 48 hrs. Ultrathin sections (~60 nm) were cut on a Reichert Ultracut-S microtome, picked up on copper grids stained with lead citrate and examined in a JEOL 1200EX Transmission electron microscope or a Tecnai$G^2$ Spirit BioTWIN and images were recorded with an AMT 2k CCD camera. To quantify the number of myelinated axons and to characterize g ratio, three images were taken along the dorso-ventral axis of the corpus callosum in each of 3 different locations along the medio-lateral axis of the corpus callosum, to cover multiple regions of the corpus callosum (FIG. 30). For g ratio quantification ~200 myelinated axons per mouse were analyzed by an experimenter blinded to genotypes, by manually measuring the ratio of the axon diameter and the myelinated axon diameter. For the quantification of the percentage of myelinated axons in the corpus callosum, ~1,500 axons per mouse were analyzed by an experimenter blinded to genotypes, by manually counting the myelinated and unmyelinated axons.

Nucleic heterochromatin was determined as previously described (37). Briefly, OL cells were identified by an experimenter blinded to genotypes by the presence of microtubules combined with the absence of intermediate filaments and glycogen granules. The total nuclear area was calculated by the isolation of nucleus of each cell using the 'clear outside' function of the ImageJ software. Heterochromatin, qualitatively defined as a gray scale density of 100 or greater on a 256 gray scale, was selected using the threshold tool and reported as percentage of total nuclear area.

For human samples, fixed tissue was used and processed similarly to the mouse brain tissue. To quantify g ratio ~100 myelinated axons per human subject were analyzed by an experimenter blinded to genotypes, by manually measuring the ratio of the axon diameter and the myelinated axon diameter. For the quantification of the percentage of myelinated axons in the frontal cortex of human subjects, ~300 axons per human subject were analyzed by an experimenter blinded to genotypes, by manually counting the myelinated and unmyelinated axons.

Evoked Field Potential Recordings in Corpus Callosum

In vivo evoked field potential recording in corpus callosum was referenced to that from in vitro studies (69, 70). Animals were anesthetized with urethane (1,000 mg/kg) and placed on a stereotaxic instrument. Body temperature was maintained by thermostat at 37.5-38° C. Craniotomy was performed and dura was kept intact. Stainless steel stimulation electrode (300~500 kOhm, WPI) was positioned in corpus callosum in left hemisphere (1.5 mm posterior to Bregma, 1 mm lateral from midline, 1,000~1,300 μm beneath cortical surface), and tungsten recording electrode (2~3 MOhm, FHC) was positioned in corpus callosum at same coronal plane in right hemisphere (1.5 mm posterior to Bregma, 1 mm from midline, 1,000~1,300 μm beneath cortical surface). Electrical stimulation (0~200 uA, 0.2 ms pulse width, 0.2 Hz) was delivered while both positions of stimulation and recording electrodes were slightly adjusted to optimize signal. Signals were filtered at 0.1-3,000 Hz and gained at 1,000 times (Model 1700, A-M Systems), digitized and sampled at 10,000 Hz (Digidata 1440A, Molecular Devices), and analyzed offline (Clampfit). Electrical stimulation was increased from 0 μA with 10 μA step until response latency reached minimum and response amplitude reached maximum. Peak latency was defined as time from stimulation onset to response peak. Response amplitude was determined by measuring the vertical distance from negative peak to the tangent joining preceding and following positivities. After recording, a 10 μA constant current for 10 seconds was delivered at all electrodes to burn small holes at the tips, and fluorescent Nissl staining was performed on perfused brain slice to verify the electrodes to be in desired position. Experimenter was blinded to genotypes.

4-AP Pharmacological Treatment

Mice were habituated to needle injections (i.p.) for three days before behavioral tests, by two i.p. injections of 200 μL of saline administered per day. Based on calibration experiments run, experiments found that 4-AP (Sigma (275875), 1 mg/kg) achieved its maximal effect within 1-3 hr post systemic administration (i.p.). All behavioral tests were therefore accomplished three hours post systemic administration. Saline-injected mice in each genotype (Control or cKO mice) were referred as the baseline group for the treatment group, which was injected with 4-AP. Experimenter was blinded to genotypes.

Clemastine Pharmacological Treatment

For the chronic clemastine treatment, mice were given vehicle (DMSO) or clemastine (dissolved in DMSO, 10 mg kg-1 body weight; Tocris Bioscience) daily through gastric gavaging for 14 consecutive days before tests were taken. Experimenter was blinded to genotypes.

Corticospinal Axon Projection Characterization

AAV2/8-ChR2-mCherry (titer: 1×10$^{13}$ copies/ml) was unilaterally delivered to the sensorimotor cortex by stereotaxic brain injection (46). Two weeks later, animals that had received brain injection were perfused. Transverse sections of the spinal cord were then processed for immunostaining with primary antibody against RFP [Abeam (Cat: ab34771), 1:200]. Images were taken using a Zeiss Confocal 700. ImageJ was used for quantification of fluorescence intensities. Experimenter was blinded to genotypes.

Intra-Cortical Microstimulation (ICMS) and EMG Recording

ICMS and EMG recording protocol was adopted from previous studies (71, 72). Each animal was anesthetized with ketamine-xylazine (100 mg/kg ketamine, 10 mg/kg xylazine, i.p.). Anesthesia level was maintained at a steady level to that animal was unresponsive to toe pinch while muscle tone was present. Supplemental doses of ketamine-xylazine at ⅒ of initial dose were administrated every 30 minutes or when breathing rate dramatically increased and whisker started to shake.

A digital stereotaxic frame was used to mount the animal's head and guide stimulation electrode (stainless steel, 0.5 MOhm; World Precision Instruments) over an array of motor cortical sites (0.9 mm caudal and 0.6 mm rostral to Bregma, 0.9 mm to 1.8 mm lateral to midline, with 300 μm spacing between sites). Stimulation electrode was inserted into the cortex at 500 μm depth, targeting layer V motor neurons. The exposed brain area was immersed with silicon oil to avoid dehydration. Electrical stimulation (biphasic, 0.2 ms pulse width, 333 Hz, 45 ms) was adjusted between 100 to 300 μA and located at the position that has the lowest threshold to trigger EMG signal. Stimulation intensity of two folds of threshold was then used for EMG recording and analysis. To perform EMG recording, an incision was made on hindlimb to expose the muscles while fascia remained intact. Nichrome wires (762000, A-M Systems, WA) were deinsulated at the tip for 1 mm, and customized for a small hook that secured its position within the muscle. A pair of electrodes were then inserted into the motor endplate area of tibialis anterior muscle using a 25 G needle. EMG signals were acquired using differential AC amplifier (1700, A-M Systems, WA) with 10-1000 Hz bandpass filter, sampled at 5 kHz using a digitizer (Digidata 1440A, Axon Instruments), and analyzed by pClamp Software. EMG traces were rectified and averaged among traces, and the peak amplitude in a window of 0 to 50 ms from stimulation onset was used to define EMG response. The latency was defined by measuring the time from stimulation onset to the beginning of EMG response over three times of standard deviation of baseline.

4-AP (2 mg/kg, i.p.) was administrated, and post treatment test was carried out 30 to 60 minutes after injection. Experimenter was blinded to genotypes.

Slice Physiology

Mice were deeply anesthetized with isoflurane, then perfused with ice cold, oxygenated sucrose cutting solution (in mM: 30 NaCl, 4.5 KCl, 1.2 NaH$_2$PO$_4$, 26 NaHCO$_3$, 194 sucrose, 10 glucose, 8 MgCl$_2$, 0.2 CaCl$_2$). The brain was dissected, and 300 μm thick coronal slices of M1 were sectioned on a vibratome (VT1200, Leica) in the sucrose cutting solution. Slices were recovered in oxygenated artificial cerebrospinal fluid (ACSF, in mM 119 NaCl, 11 glucose, 26.2 NaHCO$_3$, 2.3 KCl, 2.5 CaCl$_2$, 1 NaH$_2$PO$_4$ and 1.3 MgCl$_2$, pH 7.3, 310-320 mOsm) (37° C.) for 8 min and allowed to acclimate to room temperature for at least 30 min prior to recordings.

Intrinsic membrane and spiking properties were recorded from layer 5, M1 pyramidal cells in oxygenated ACSF using an internal solution that contained (in mM) 120 potassium gluconate, 10 KCl, 10 phosphocreatine, 4 Mg-ATP, 0.3 Na-GTP, 10 HEPES and 0.1% biocytin (pH 7.3, 290-300 mOsm). Resting potential and compensated input resistance was recorded within seconds of breaking into a cell. Cells with a series resistance of <25 MΩ and <25% change for the duration of the experiment were used for analysis. Analysis of current-clamp electrophysiological data was performed using pClamp10 (Molecular Devices) Single action potential parameters (peak amplitude, half-width and hyperpolarization anti-peak) were measured at threshold and spike amplitudes and after-hyperpolarization potentials were measured relative to the spike threshold. To measure pyramidal cell firing properties, the frequency-current relationship (FI curve) was calculated as the spike frequency after current steps from 0 pA (resting ∼−60 mV) to 1000 pA were applied in increments of 50 pA (0.05 Hz, 1,000 ms duration). Experimenter was blinded to genotypes.

Human Samples

Human brain samples of frontal cortex (BA9) were obtained from the NIH Neurobiobank at the University of Maryland, Baltimore. Frozen and fixed tissue from WS subjects and controls was used (FIG. 31).

Fluorescence In Situ Hybridization (FISH) on Human Tissue

Blocks of fresh frozen control and William Syndrome human Broca's Area 9 (BA9) cortical brain samples were acquired from the NIH Neurobiobank at the University of Maryland, Baltimore. Blocks were then embedded in Optimal Cutting Temperature (OCT) freezing medium and flash frozen in an isopropyl ethanol-dry ice bath. Samples were cut on a cryostat (Leica CM 850) into 16 μm sections, adhered to SuperFrost Plus microscope slides (Fisher Scientific, 12-550-15), and stored at −80° C. until use. Samples were immediately fixed in 4% paraformaldehyde for 20 min on ice, and stained on the slide according to the Advanced Cell Diagnostics RNAscope Fluorescent Multiplex Assay (ACD, 320850) protocol. Samples were stained for MBP (ACD, 411051), and PDGFRa (ACD, 604481) with antisense probes, and coverslipped with Vectashield hardset antifade mounting medium with DAPI (Vector Laboratories, H-1500). Z-stack serial images were taken through the whole depth of the field on a Nikon Ti Eclipse inverted microscope with an Andor CSU-W1 confocal spinning disc unit and an Andor DU-888 EMCCD unit using a 20×, 0.75 NA air objective and a 60×, 1.40 NA oil immersion objective. Fields of view were randomly chosen across the whole cortical sample. Experimenter was blinded to genotypes.

FISH Analysis and Quantification

Quantification of co-localization and florescence intensity was performed on 20× images using the Cell Counter FIJI ImageJ (NIH) plugin and was performed blinded to sample type. For quantification, all image Z-stacks were max projected, adjusted for brightness and contrast, and color flattened identically across samples using ImageJ. PDGFRa FISH experiments were quantified per cell, identified by DAPI, per 1024×1024 pixel field of view taken from two adjacent fields of view stitched together. MBP FISH experiments were analyzed for the corrected total cell fluorescence (CTCF) to match quantification from immunofluorescence staining procedures as previously described. 400×400 pixel random fields of view were used to calculate CTCF levels of MBP in ImageJ. Experimenter was blinded to genotypes.

Immunofluorescence on Human Tissue

Blocks of fresh frozen control and Williams Syndrome human Brodmann Area 9 (BA9) cortical brain samples were acquired from the NIH Neurobiobank at the University of Maryland, Baltimore. Blocks were then embedded in Optimal Cutting Temperature (OCT) freezing medium and flash frozen in an isopropyl ethanol-dry ice bath. Samples were cut on a cryostat (Leica CM 850) into 16 μm sections, adhered to SuperFrost Plus microscope slides (Fisher Scientific, 12-550-15), and stored at −80° C. until use. Sections were air-dried for 20 minutes at room temperature, before being fixed in 4% paraformaldehyde for 30 minutes at 4° C. Samples were washed, and then permeabilized and blocked with 1.2% Triton X-100 and 3% normal goat serum in PBS at room temperature for 1 hour, before incubation for 5 days at 4° C. with the primary antibodies, OLIG2 (1:100, Millipore, AB9610) and APC (1:2, Calbiochem, OP80-100UG). Samples were washed extensively in PBS and then stained with secondary antibodies conjugated with Alexa488 and 568 for 2 hrs at room temperature (Invitrogen, A1101, A21245). As a final step, TrueBlack Lipofusin Autofluorescence Quencher (Biotium, 23007) was incubated on the samples for 1.5 minutes at room temperature in 70% ethanol and then washed thoroughly in PBS, before staining with DAPI, and then coverslipped with Vectashield antifade mounting medium. Images were taken on an Olympus Fluoview FV1000 confocal microscope, using a 20×, 0.75 NA objective, and on an Olympus BX61 Epi microscope, using a 10×, 0.40 NA objective.

To quantify, images were taken with the same imaging constraints and corrections. Cell numbers were quantified blindly by an experimenter, by counting the number of Olig2+, CC1+ cells.

Statistical Analysis

All comparisons between groups were collected from littermate animals with experiments performed at the same time. All data sets were analyzed using D'Agostino-Pearson omnibus test and Shapiro-Wilk test for normality. Data sets with normal distributions were analyzed for significance using either unpaired Student's two-tailed t-test or one-way or two-way analysis of variance with proper post hoc test (GraphPad Prism). Data sets with non-normal distributions were analyzed using Kruskal-Wallis test with adjustments for multiple comparisons or using Wilcoxon matched-pairs signed rank test. Further details on particular statistical analyses can be found on the respective figures/results section for each data set. No statistical methods were used to predetermine sample size. Sample size used was based upon common and accepted size in the field. No animal or sample was excluded from the analysis. Experiments were randomized (mice order, items positions and samples loading were all randomized and counterbalanced) and the investigators were blinded to genotype during experiments and outcome assessment. All results were presented as mean±s.e.m. *$p<0.05$, $p<0.01$, *$p<0.001$, ****$p<0.0001$.

Figure 6:
FIG. 6 shows an image of Cre recombinase activity in the Nex-Cre line. A Nex-Cre mouse was crossed to a Rosa-tdT reporter mouse line. Labeled brain regions are those in which Cre-recombinase is active, and brain regions receiving axon projections from Cre-expressing neurons.
Figure 7:
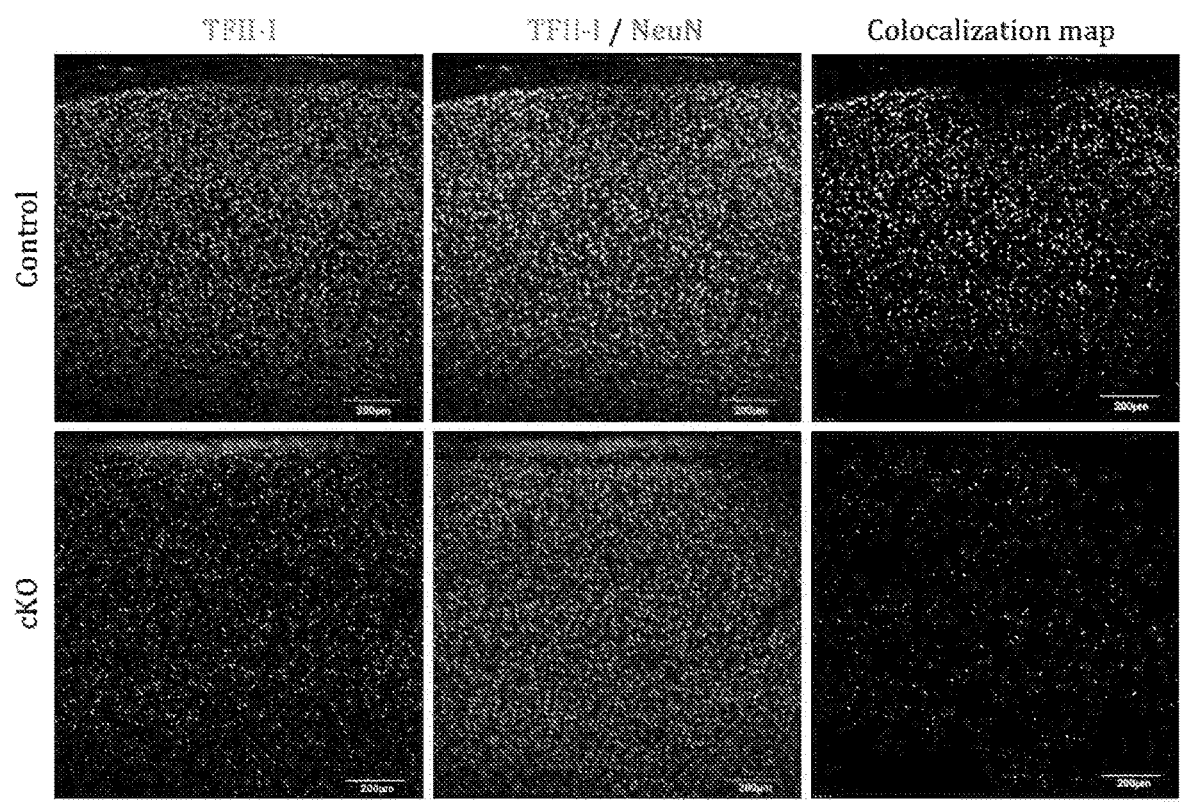
FIG. 7 shows Cre recombinase activity in the cortex of the Nex-Cre line. In the upper row, TFII-I expression in the cortex highly colocalized with the neuronal marker NeuN in the control mice. In the lower row, cKO cortex showed dramatically reduced TFII-I expression. The remaining expression colocalized with the NeuN marker (right panel) in cKO mice was presumably from non-excitatory neurons.
Figure 8:
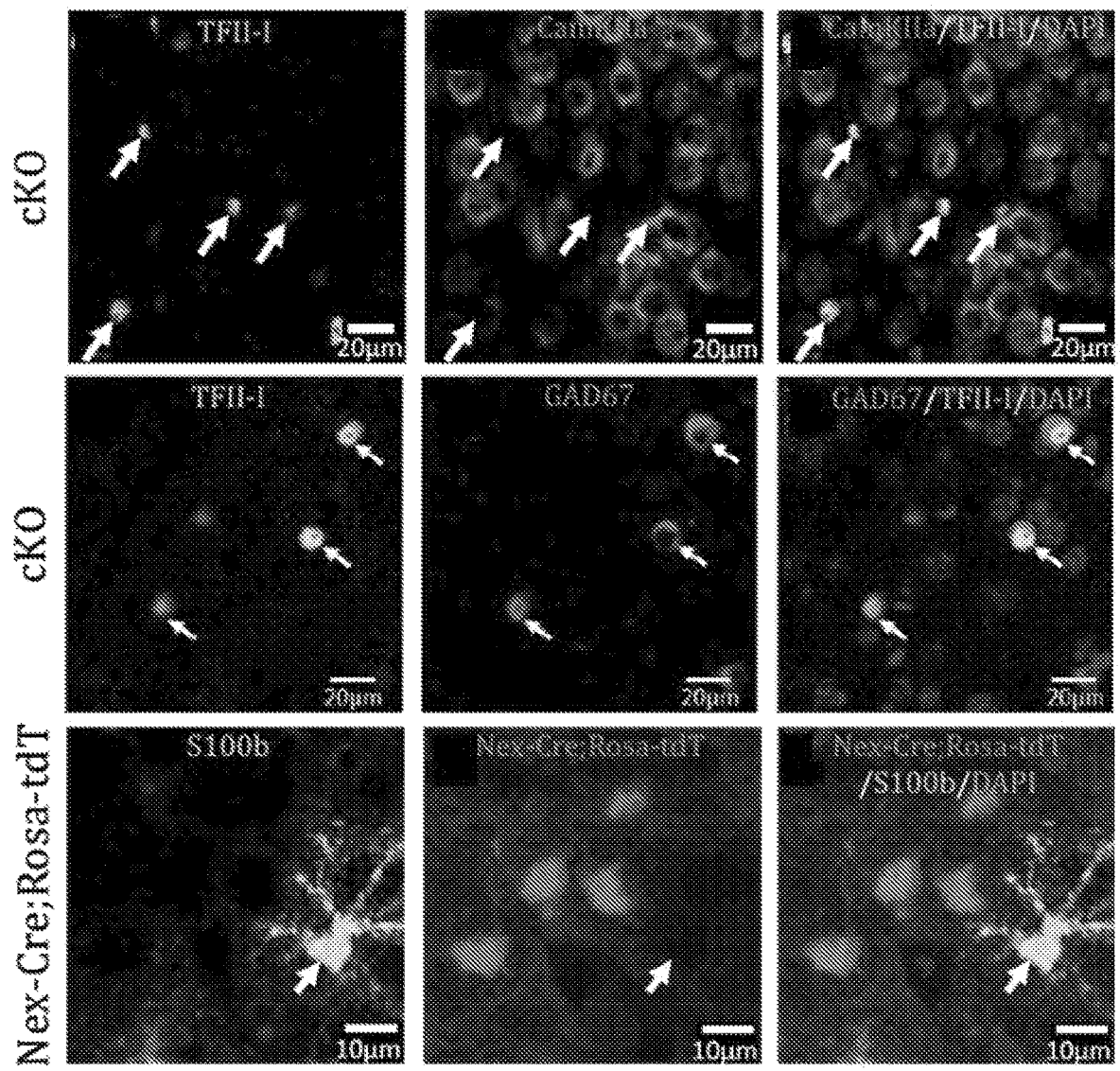
FIG. 8 shows Cre recombinase activity properties in the Nex-Cre line. The top row shows that the cortex of 1 month-old cKO mice displayed no expression of TFII-I in excitatory neurons (arrows, CamKIIa-positive cells). The middle row shows that TFII-I levels were intact and high in inhibitory neurons in cKO mice (arrows, GAD67-positive cells). The bottom row shows that Cre recombinase activity was detected by crossing Nex-Cre with the reporter line Rosa-tdT. No colocalization was detected between tdT and the astrocyte-marker S100b, which demonstrated the lack of Cre recombinase activity in astrocytes the in Nex-Cre line.

Example 2: Gtf2i Deletion in Forebrain Excitatory Neurons Caused Neuroanatomical and Behavioral Alterations To dissect the function of Gtf2i in neurons, studies were designed that crossed Gtf2i conditional knockout mice (21) with Nex-Cre mice (22), a Cre line that expresses Cre recombinase selectively in forebrain excitatory neurons (FIG. 6) starting around embryonic day 11.5 (22). The resulting mice, referred to herein as cKO (Gtf2i$^{f/f}$:Nex-Cre$^{+/-}$), exhibited a homozygous deletion of Gtf2i selectively in forebrain excitatory neurons (FIG. 1A, FIG. 1B, FIG. 7, FIG. 8).

Figure 1C:
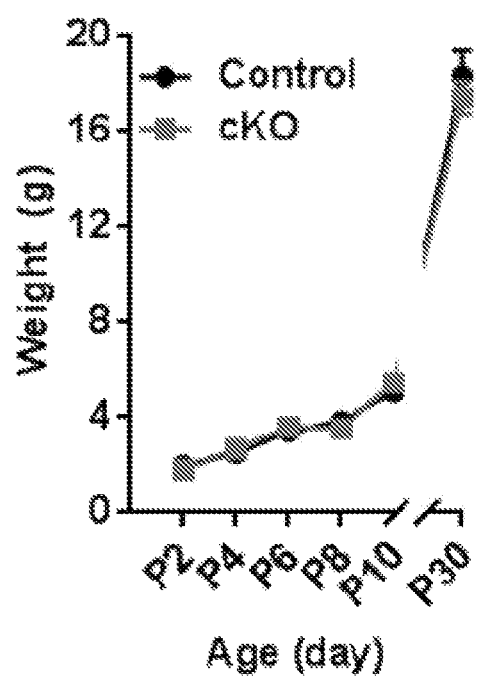
Figure 1D:
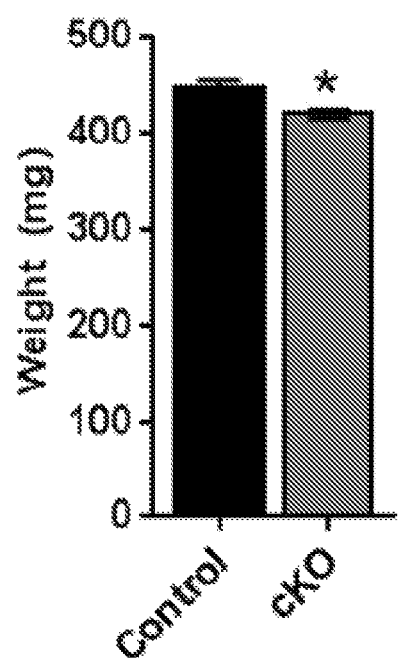
Figure 1E:
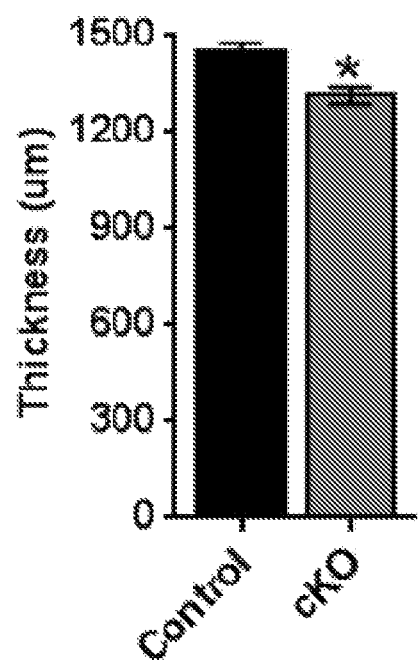
Figure 9A:
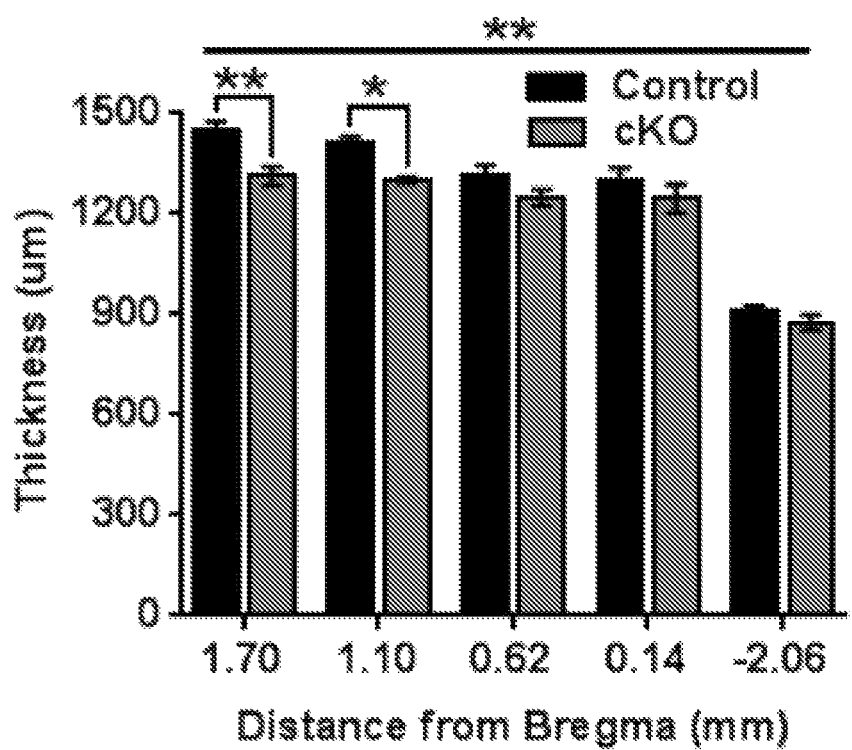
FIG. 9A and FIG. 9B show neuroanatomical properties of control and cKO mice.
Figure 9B:
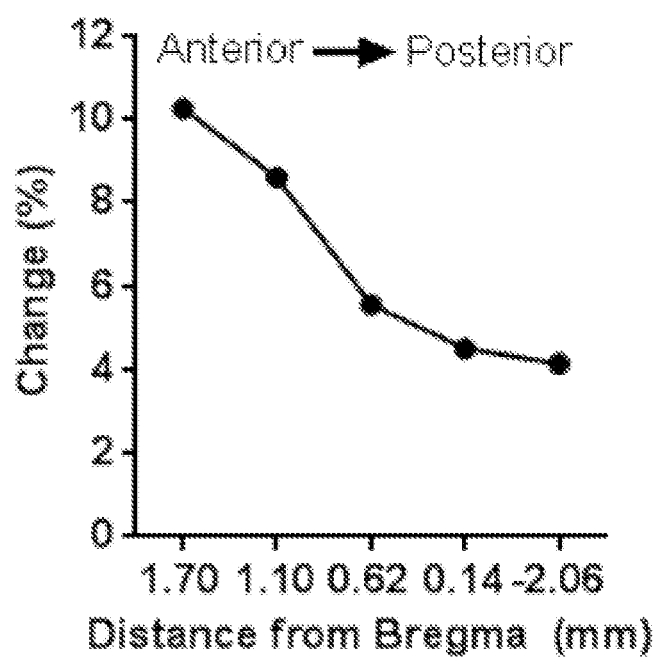

WS subjects were previously described to show altered brain volume and cortical thickness (23-25). The instant experiments examined whether deletion of Gtf2i from forebrain excitatory neurons would be sufficient to cause neuroanatomical abnormalities. While cKOs showed normal body weight as compared to control (Gtf2i$^{f/f}$:Nex-Cre$^{-/-}$) littermates (FIG. 1C), one-month-old cKO mice showed significantly reduced brain weight (FIG. 1D) and cortical thickness as compared to controls (FIG. 1E, FIG. 9A and FIG. 9B).

Figure 1F:
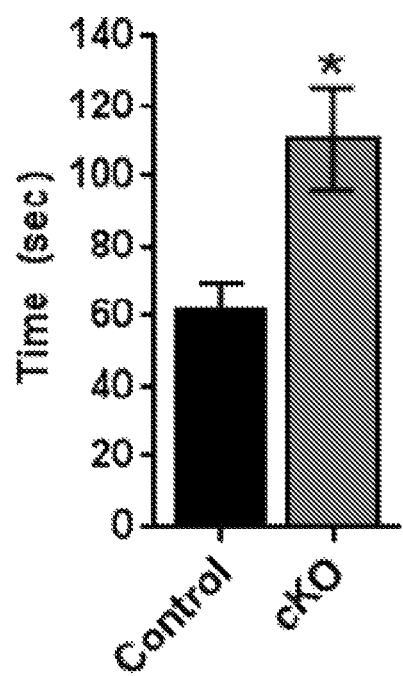
Figure 1G:
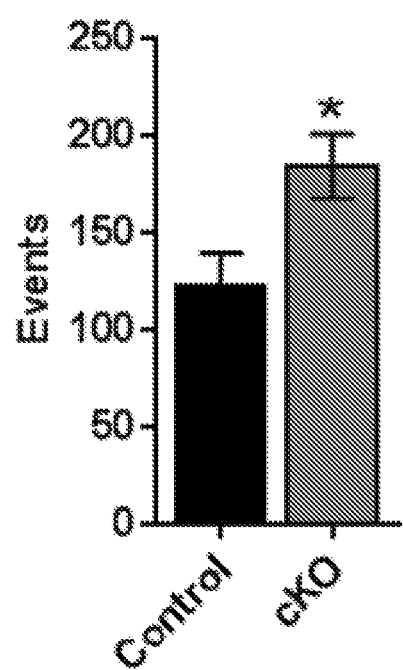
Figure 1H:
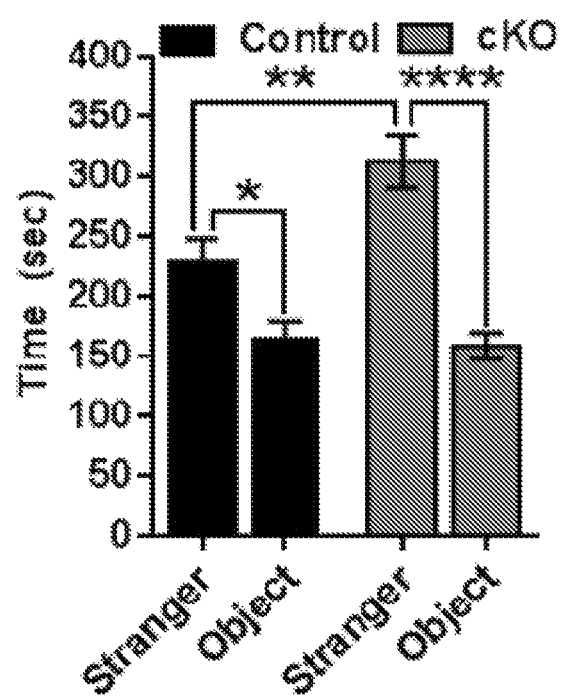
Figure 1I:
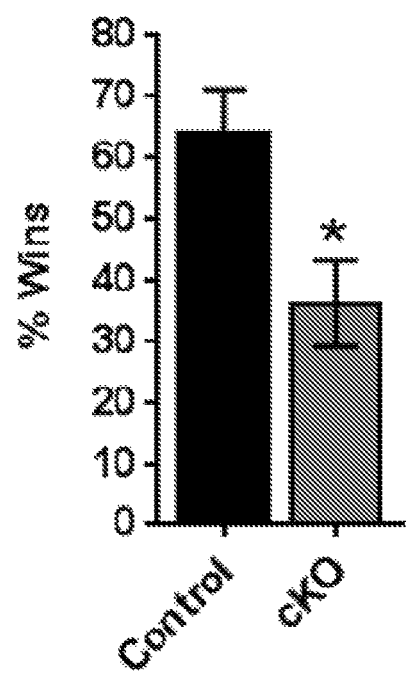
Figure 1J:
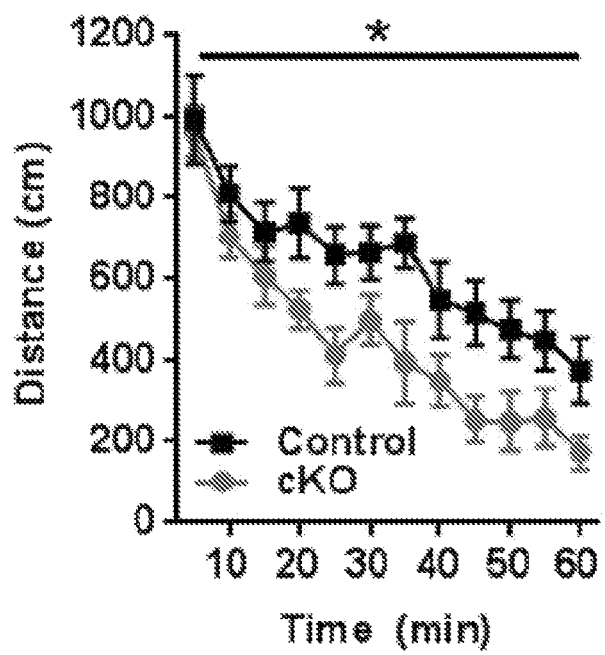
Figure 1K:
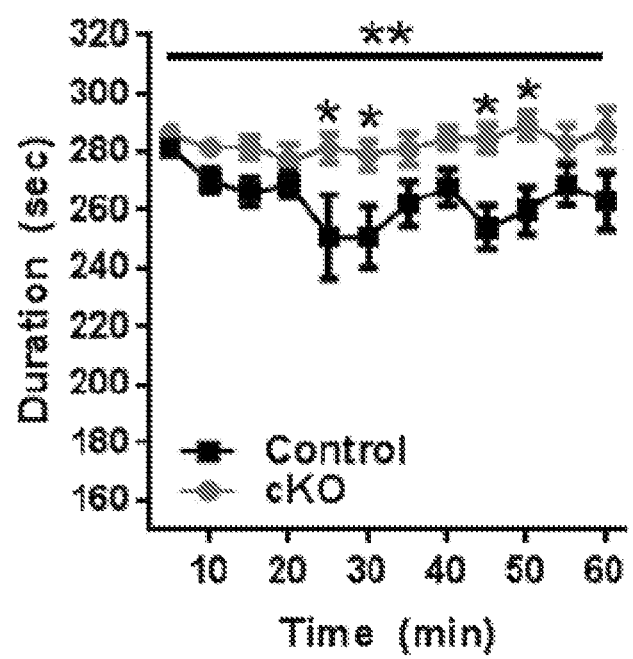
Figure 10A:
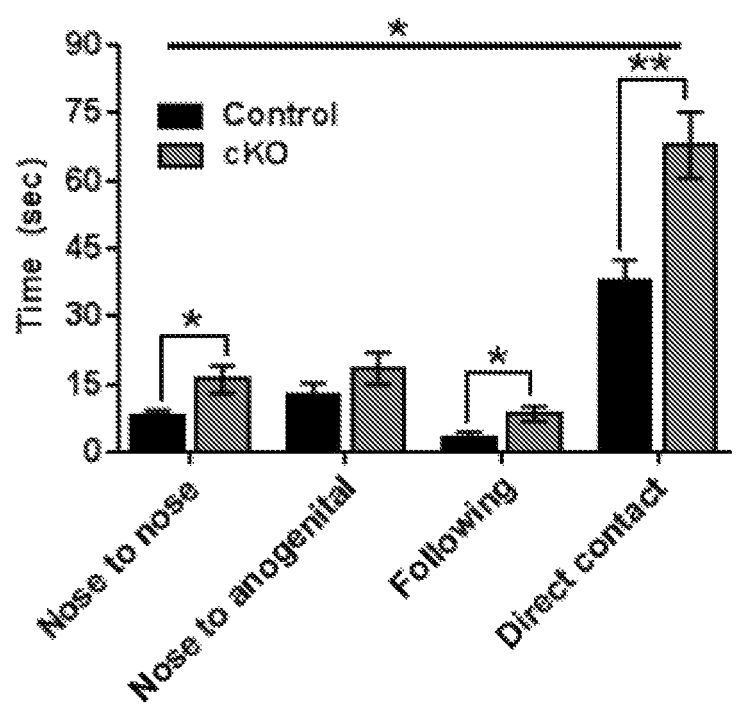
FIG. 10A and FIG. 10B are histograms of duration of social events and frequency of social interaction, respectively, which show that cKO mice demonstrated increased levels of social behavior in the dyadic social interaction test.
Figure 10B:
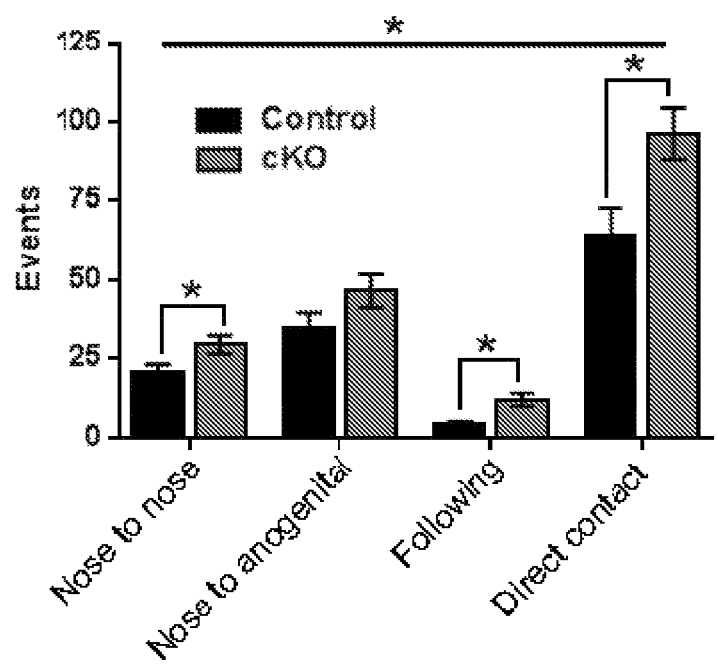
Figure 11A:
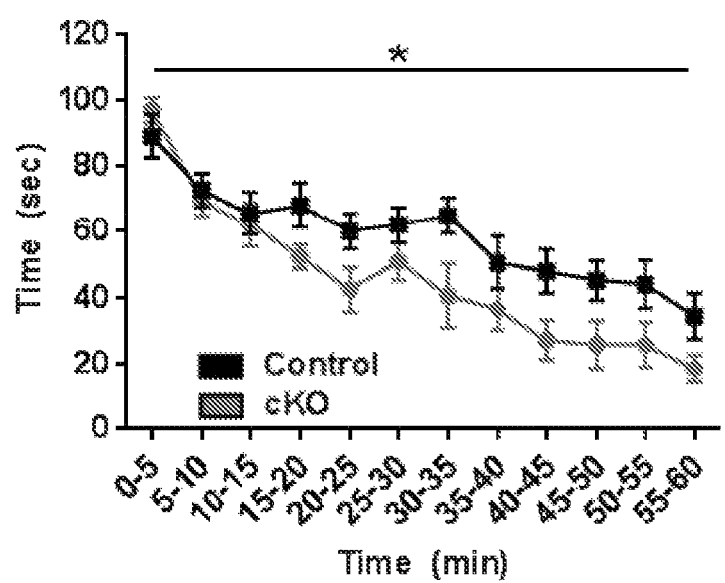
FIG. 11A to FIG. 11C are line plots of open field movement time, open field center distance, and open field center time, respectively, which revealed that cKO mice showed increased levels of anxiety-like behavior.
Figure 11B:
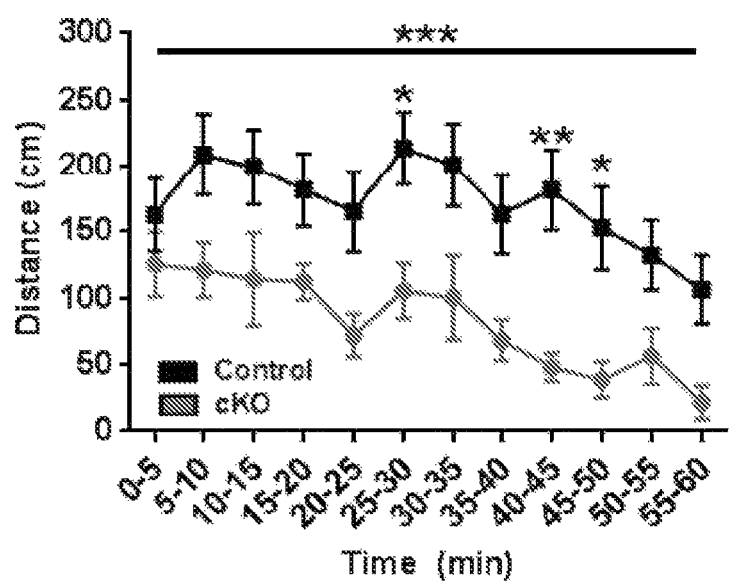
Figure 11C:
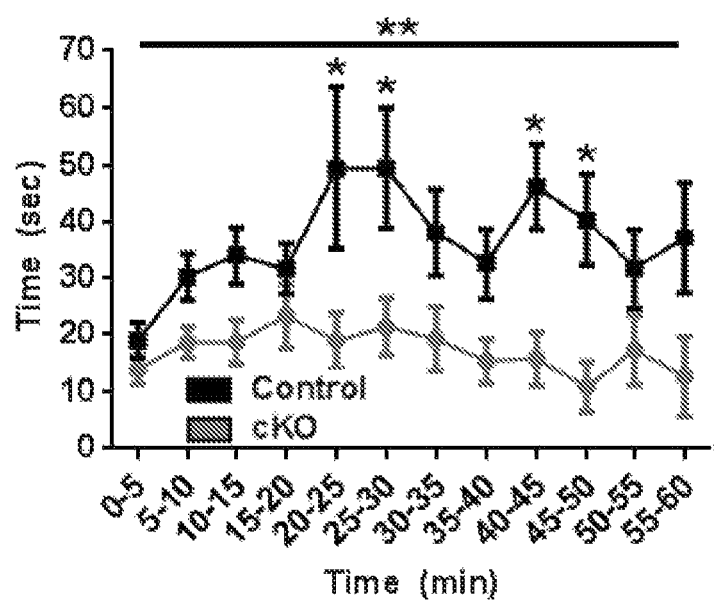

Behaviorally, cKO mice were observed to demonstrate significantly higher levels of social behavior as assessed in three different social behavior-related tests. Specifically, compared to controls, 23 day-old cKO mice showed significantly longer duration (FIG. 1F and FIG. 10A) and significantly higher frequency (FIG. 1G and FIG. 10B) of close interactions in the dyadic social interaction test. In the social preference test, one-month-old cKO mice showed significantly higher preference to interact with a stranger mouse than with an object, as compared to controls (FIG. 1H). cKO mice also exhibited significantly decreased social dominance, as demonstrated by a significantly lower win percentage than controls during matches with a stranger mouse in the tube test (FIG. 1I).

Figure 1L:
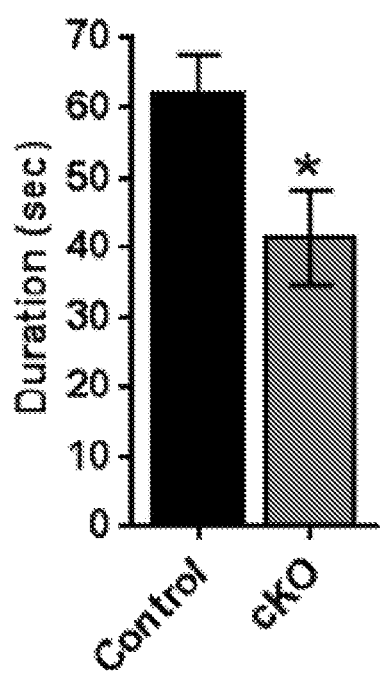
Figure 12A:
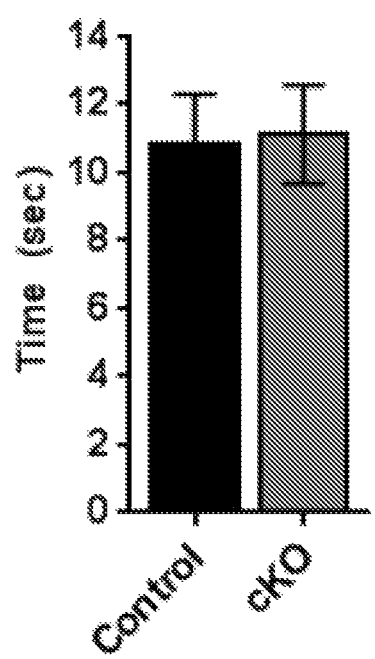
FIG. 12A to FIG. 12C show a series of graphs depicting hot plate test, startle response, and pre-pulse inhibition test, respectively, which demonstrated that cKO mice showed normal behavior in the hot plate, startle response and pre-pulse inhibition tests. No significant differences were found between 1 month-old cKO and control mice in pain sensitivity as assessed by the hot plate test (FIG. 12A), acoustic startle response (FIG. 12B) or in the pre-pulse inhibition test (FIG. 12C). Two-tailed t-test (FIG. 12A, FIG. 12C), two-way repeated measures ANOVA with Bonferonni post-hoc test (FIG. 12B). Data are mean±s.e.m.
Figure 12B:
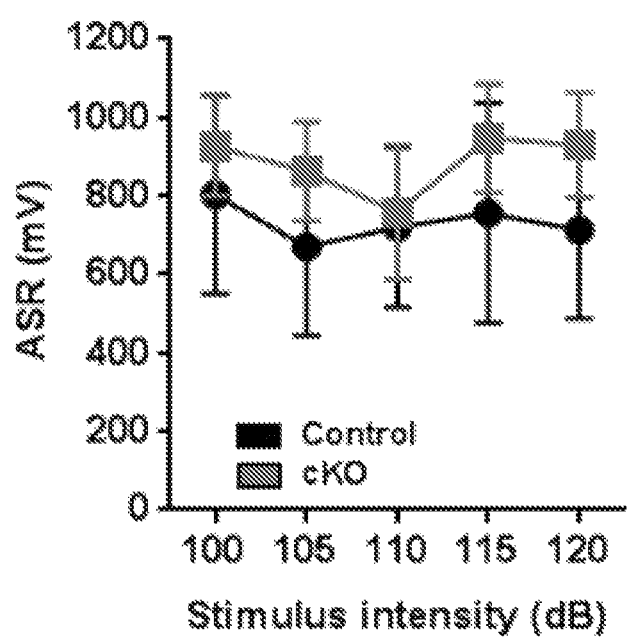
Figure 12C:
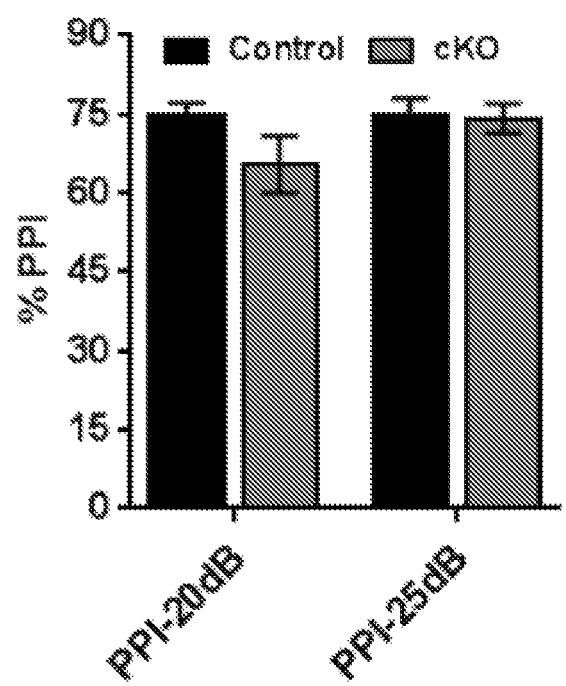
Figure 13A:
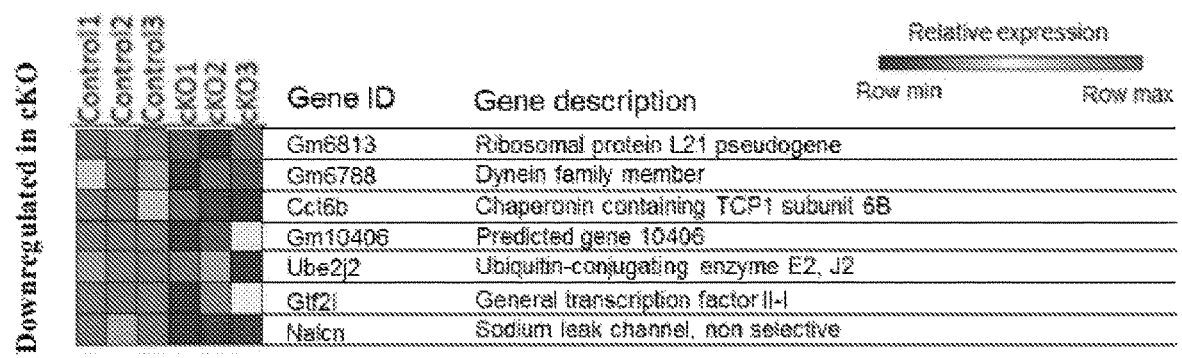
FIG. 13A to FIG. 13D depict a series of heat maps and charts of genes that exhibited significantly decreased expression in 1 day-old cKO cortex, downregulated pathways in 1 day-old cKO cortex, genes with significantly increased expression in 1 day-old cKO cortex, and upregulated pathways in 1 day-old cortex, respectively. RNAseq results are shown, observed from whole cortex of 1 day-old mice, which revealed moderate changes in the transcriptome of cKO mice. Transcriptional changes were measured using RNAseq performed upon whole cortex of 1 day-old cKO mice and controls.
Figure 13B:
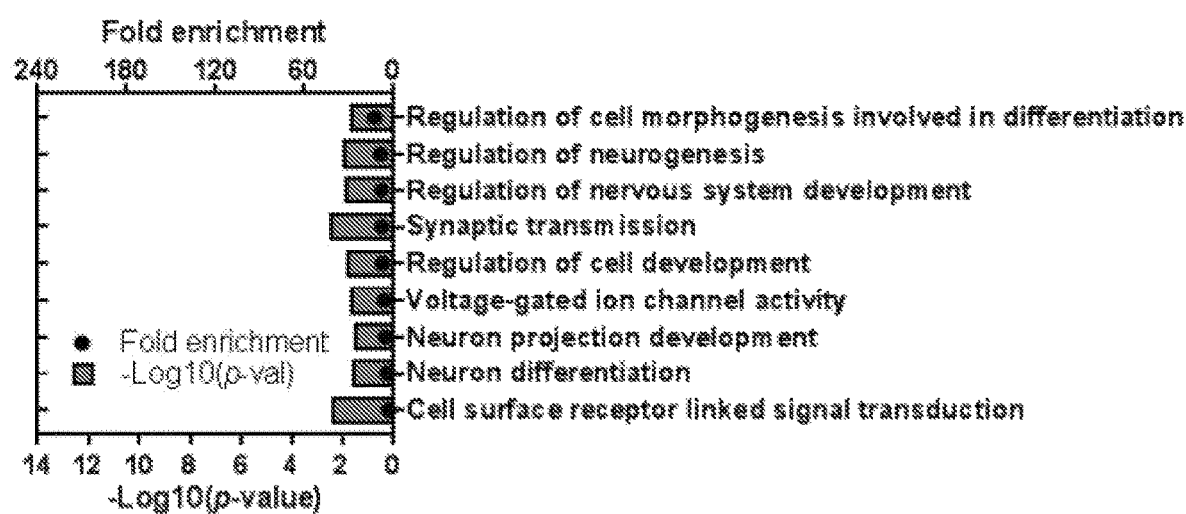
Figure 13C:
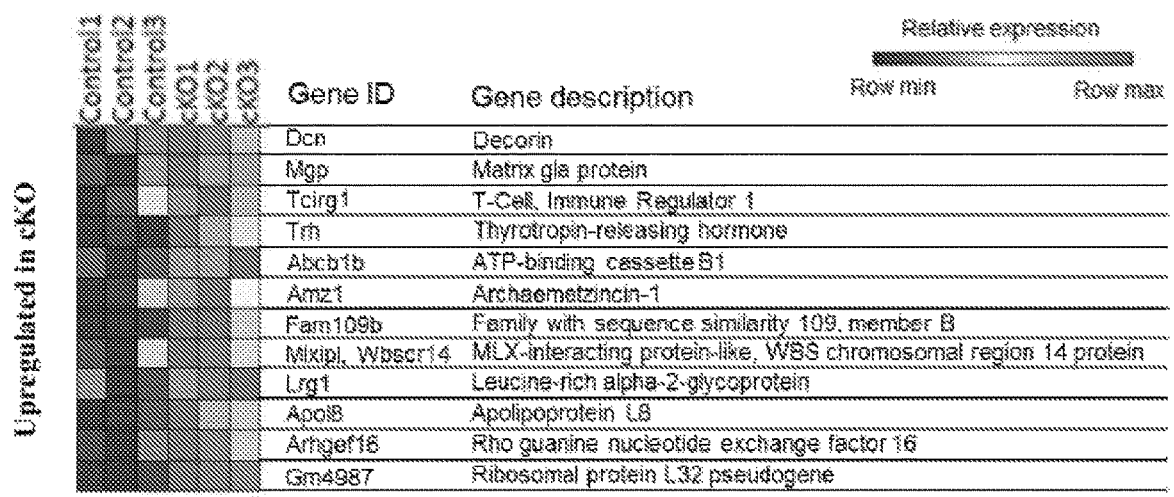
Figure 13D:
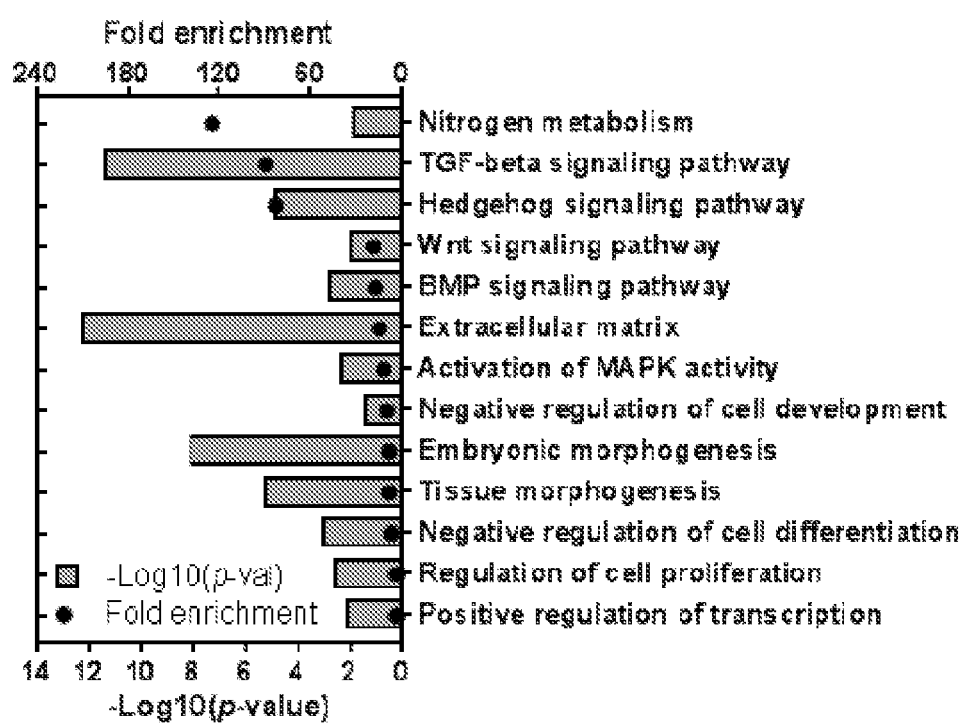
Figure 14A:
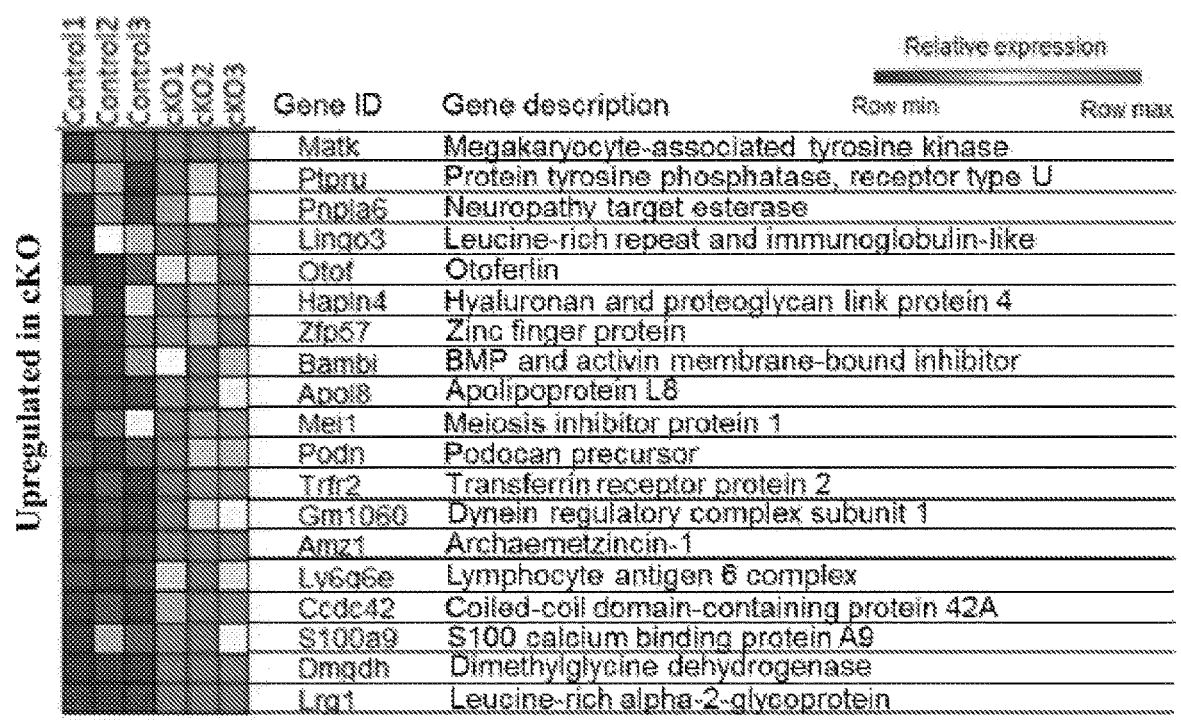
FIG. 14A and FIG. 14B present heat maps and graphs, which show genes observed to exhibit significantly increased expression in the whole cortex of 1 month-old mice. Transcriptional changes were measured using RNAseq performed upon whole cortex of 1 month-old cKO mice and controls.
Figure 14B:
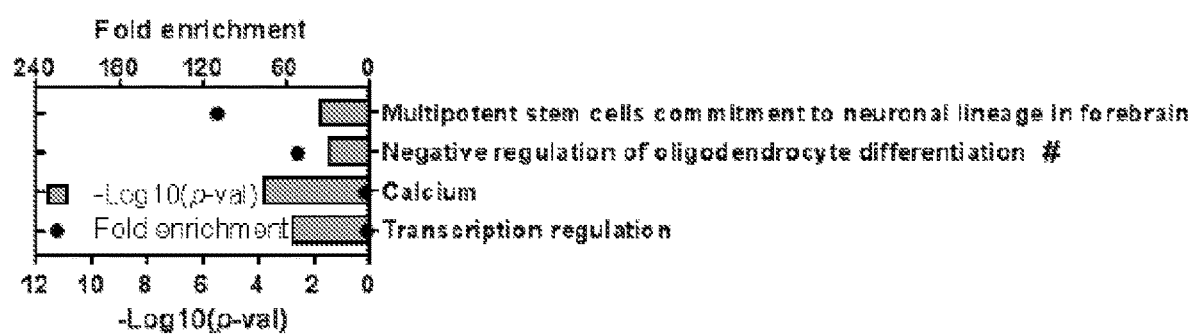

Heightened non-social-related anxiety has been described as a prominent feature of WS (1). Experiments were performed that tested mice for anxiety-like behaviors in an open-field exploration test (FIG. 1J, FIG. 1K and FIG. 11A to FIG. 11C) and elevated zero maze test (FIG. 1L). Such experiments identified significantly higher levels of non-social anxiety-like behaviors in cKO mice, as compared to controls. No other significant behavioral differences were observed in cKO mice as compared to controls (FIG. 12A to FIG. 12C). These data suggested that Gtf2i deletion in forebrain excitatory neurons was sufficient to induce hypersociability and increased levels of non-social-related anxiety, which resembled some core phenotypes found in WS subjects.

Figure 2B:
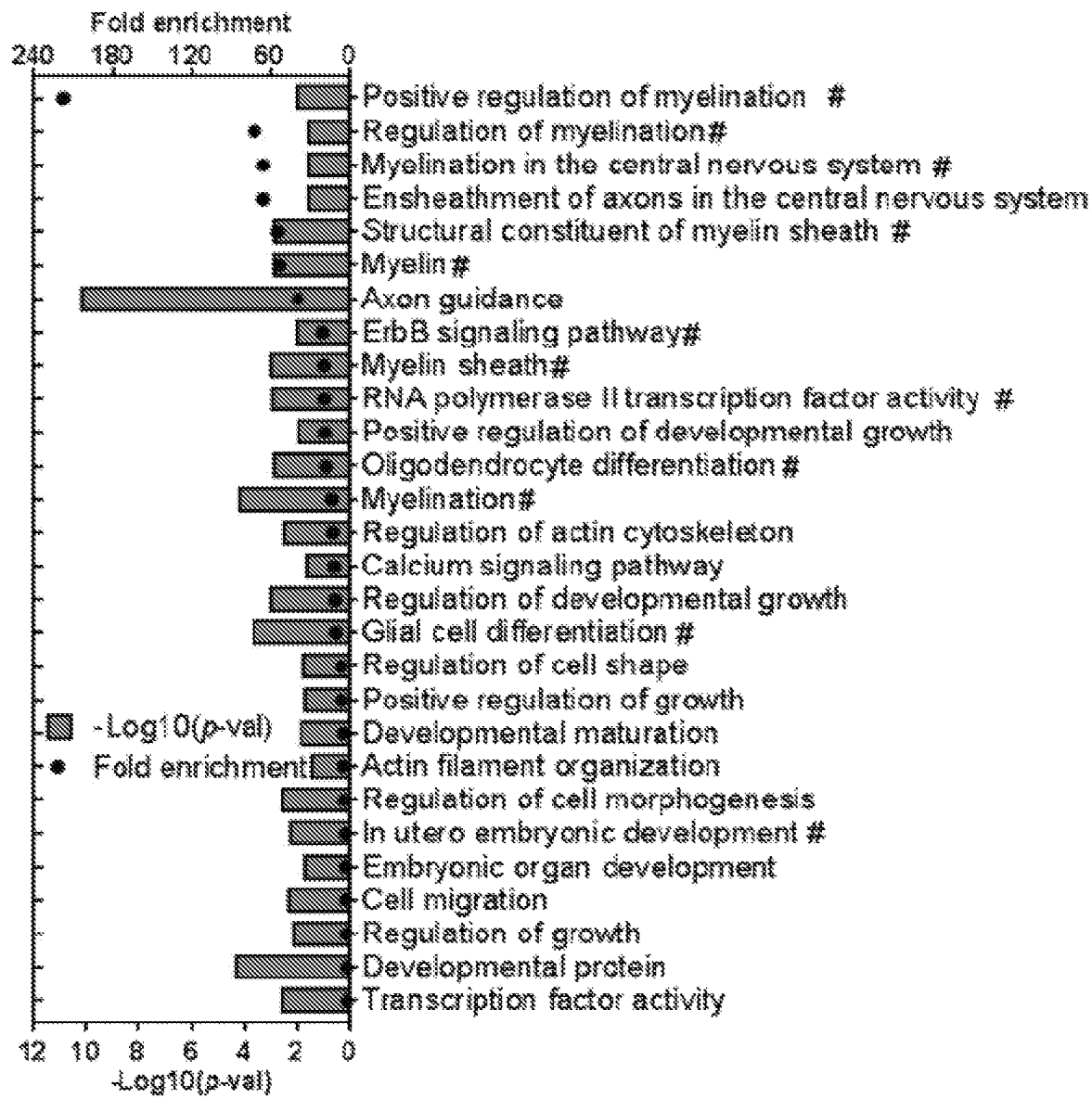
Figure 2C:
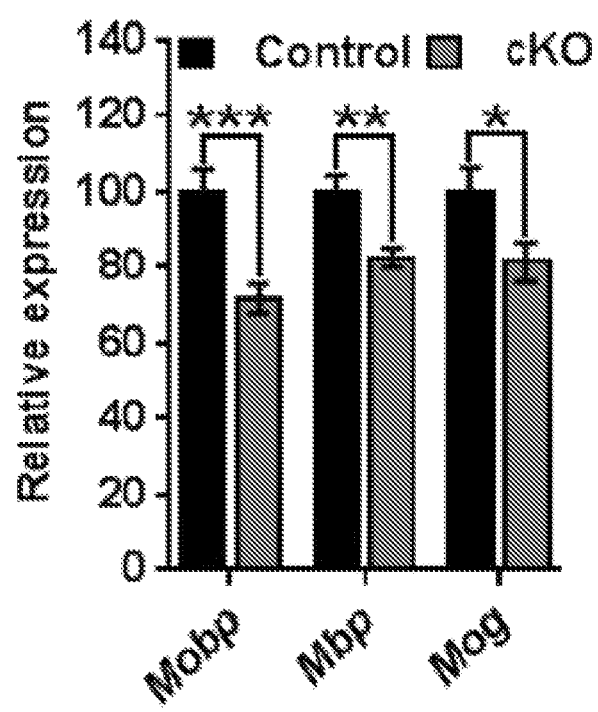
Figure 15A:
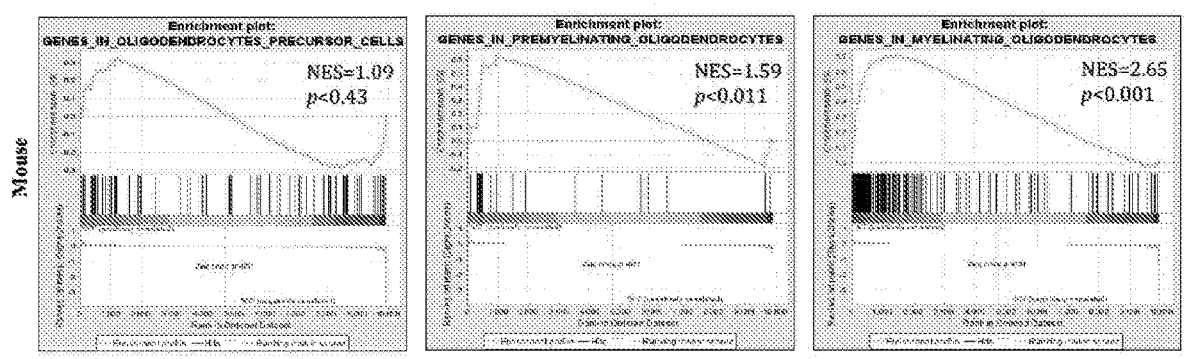
FIG. 15A and FIG. 15B show gene-set enrichment analyses for mouse and human samples, respectively, which displayed significant enrichment for genes expressed in myelinating oligodendrocytes.
Figure 15B:
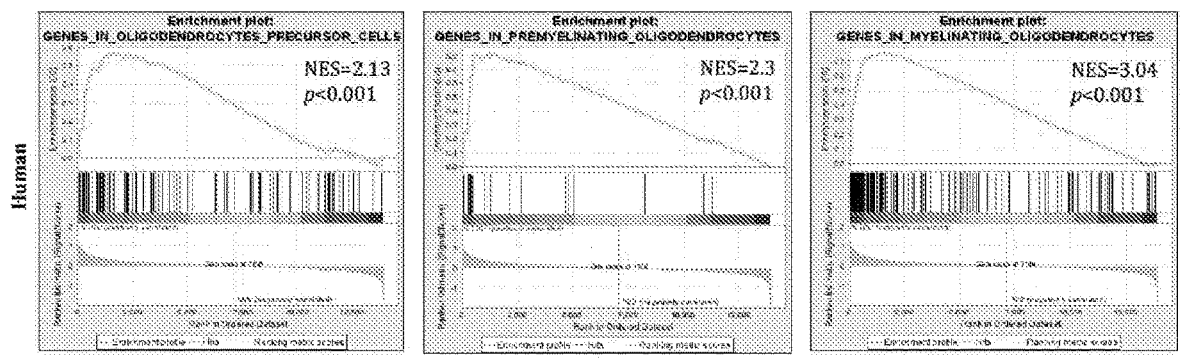

Example 3: Gtf2i Neuronal Deletion Affected Myelination-Related Transcriptomic and Cellular Properties To identify whether altered molecular processes might underlie the behavioral and anatomical abnormalities observed in cKO mice, RNAseq studies were initially performed upon whole cortex of cKO mice and their controls. To characterize the transcriptional abnormalities in a developmental manner, such experiments used one-day-old (FIG. 13A to FIG. 13D and data not shown) and one-month-old mice (FIG. 2A to FIG. 2C, FIG. 14A, FIG. 14B and data not shown). Surprisingly, although Gtf2i was selectively deleted in excitatory neurons, 70% of the genes that showed a significantly lower mRNA level in the cortex of one-month-old cKO mice were involved in myelin development and function (FIG. 2A to FIG. 2C and data not shown) (30, 31). These genes encode proteins involved in the development, differentiation and function of oligodendrocytes (OLs) (32-34), and have been described to play key roles in the formation, maintenance and functionality of myelin sheaths (35, 36). Computationally, these genes were found to be significantly enriched in myelinating OLs (mOLs), but not in OL precursor cells (OPCs) (FIG. 15A and FIG. 15B), indicating a potential non-cell autonomous effect of neuronal Gtf2i deletion on OLs.

Figure 2D:
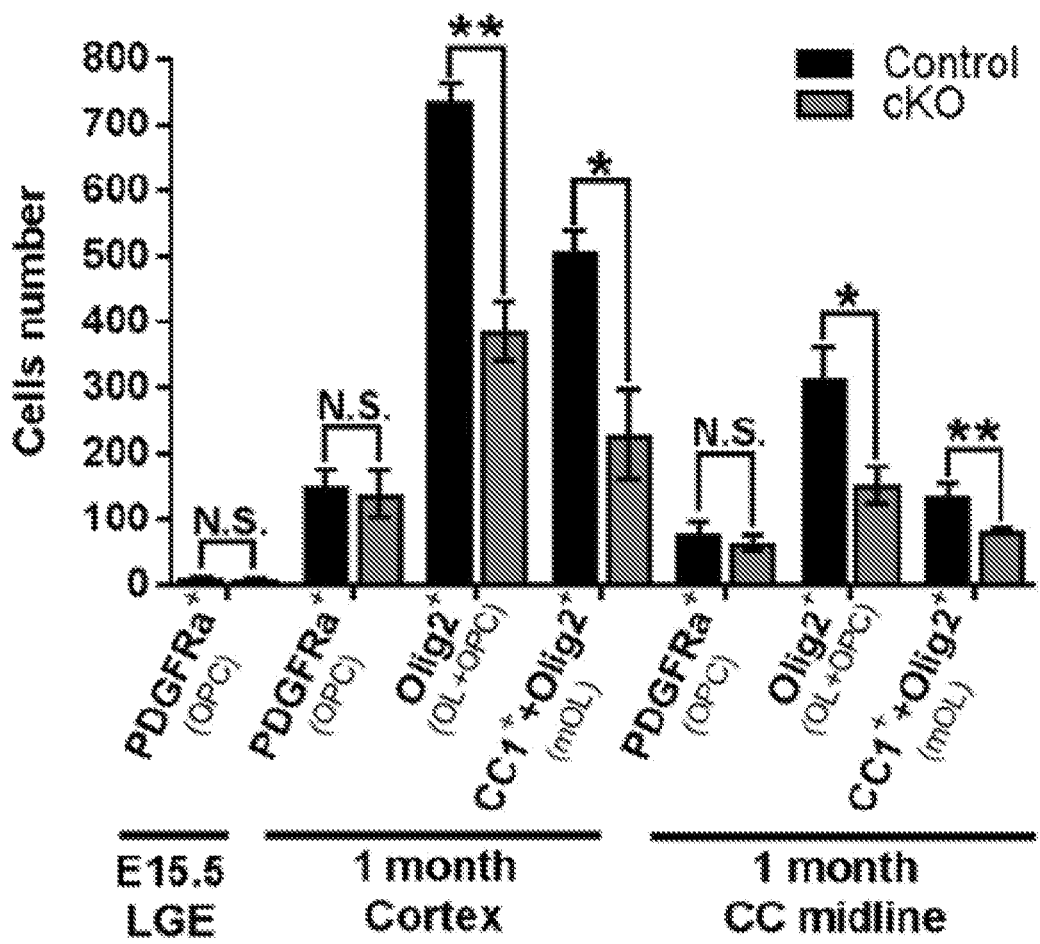
Figure 2E:
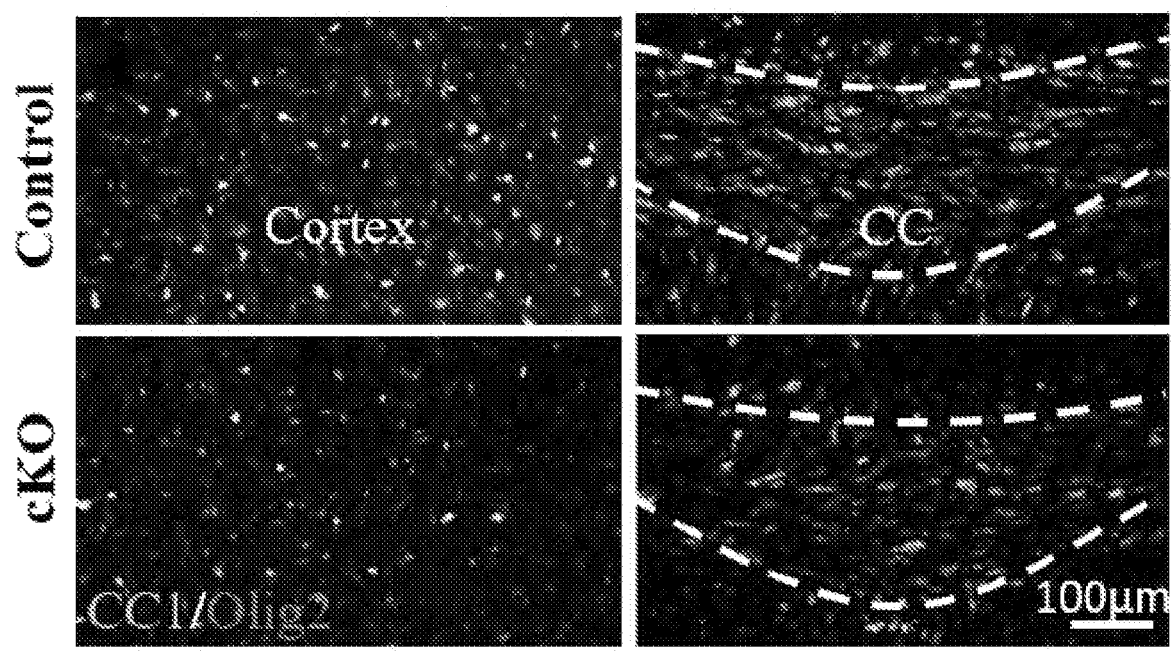
Figure 16:
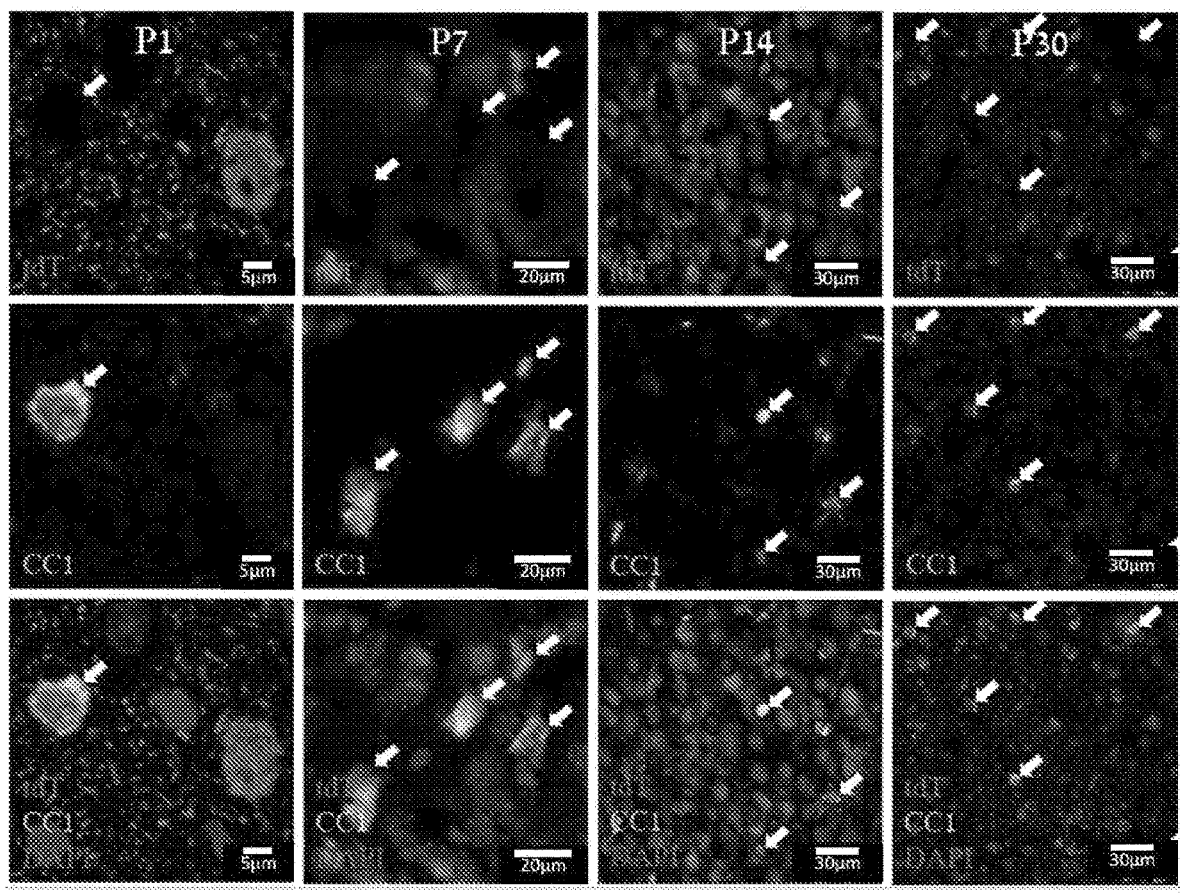
FIG. 16 shows images that demonstrated that no Cre recombinase activity was observed in myelinating oligodendrocytes during postnatal development of the Nex-Cre line, in which a Nex-Cre mouse was crossed to a Rosa-tdT reporter mouse line. Red-labeled cells are those in which Cre-recombinase was active, as well as brain regions receiving axon projections from Cre-expressing neurons. Green-labeled cells are myelinating oligodendrocytes (CC1-positive cells). No Cre recombinase activity was observed in myelinating oligodendrocytes at P1 (left column), P7 (second column from left), P14 (second column from right), or P30 (right column).
Figure 17:
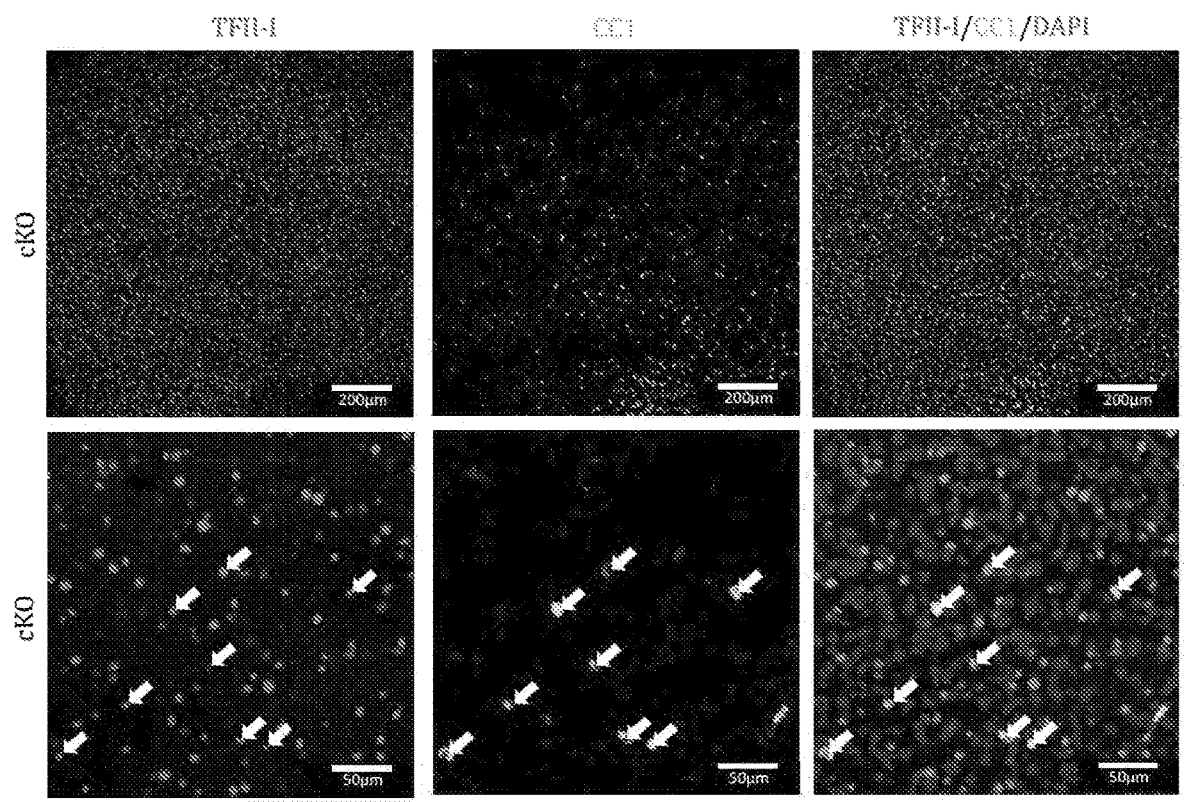
FIG. 17 shows images that demonstrated that TFII-I was expressed in myelinating oligodendrocytes in the cortex of cKO mice. TFII-I (in red) was expressed normally in myelinating oligodendrocytes (in green) in the cortex of 1 month-old cKO mice. Upper row 10× magnification, lower row 20× magnification.
Figure 18:
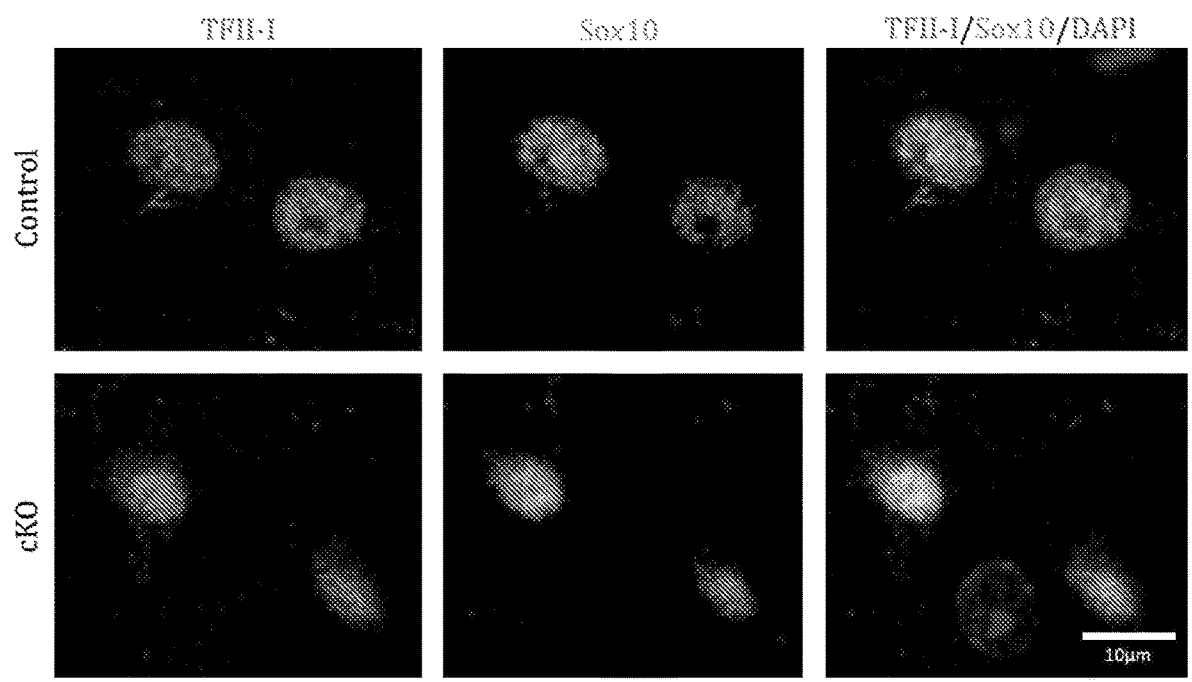
FIG. 18 shows images that demonstrated that TFII-I levels in oligodendrocytes were normal in the cortex of cKO mice. TFII-I expression levels in oligodendrocytes (Sox10-positive cells) were similar in the cortex of 1 month-old controls and cKO mice.

To examine how reduced mRNA level of these genes might be reflected in the development of OL-related cell populations, experiments were performed to quantify the number of OPCs and mOLs in cKO mice. Of special note, it was previously demonstrated that Cre recombinase was not active in OLs in Nex-Cre mice (22) and the instant studies confirmed this finding using a Cre reporter line (FIG. 16). The instant experiments further confirmed that TFII-I expression was normal in OLs of cKO mice (FIG. 17 and FIG. 18). In E15.5 cKO embryos, no significant difference was identified in OPC number in the lateral ganglionic eminence, as compared to controls (FIG. 2D). Similarly, no significant difference was observed in OPC number in the cortex and corpus callosum (CC) midline between one-month-old cKO mice and their controls (FIG. 2D). However, the number of OLs and mOLs in the cortex and CC midline of one-month-old cKO was significantly reduced as compared to that of controls (FIG. 2D and FIG. 2E).

Figure 2F:
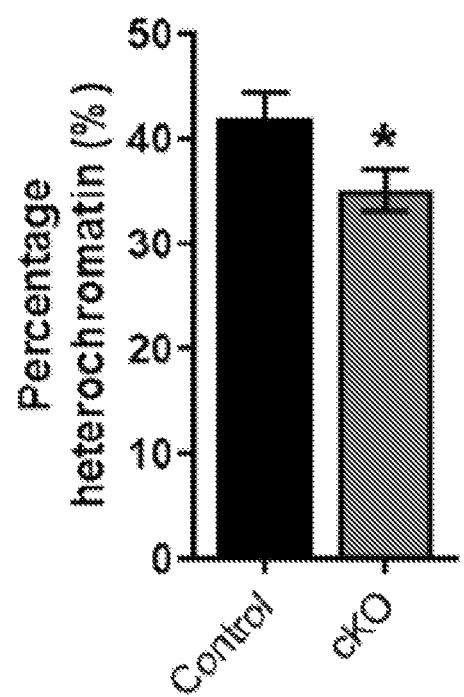
Figure 2G:
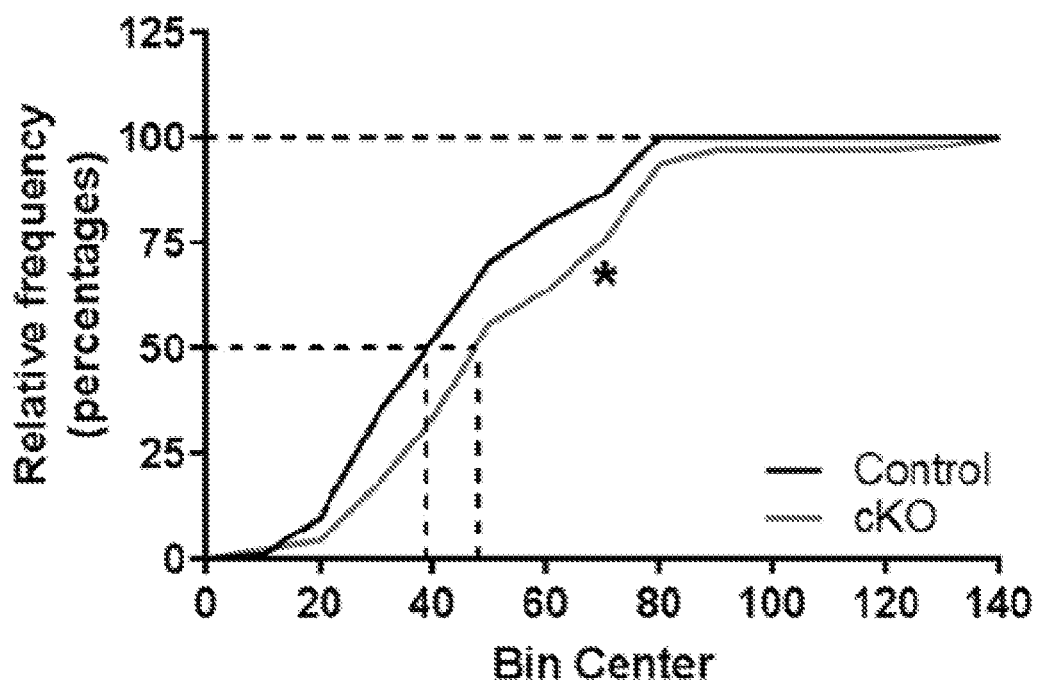
Figure 2H:
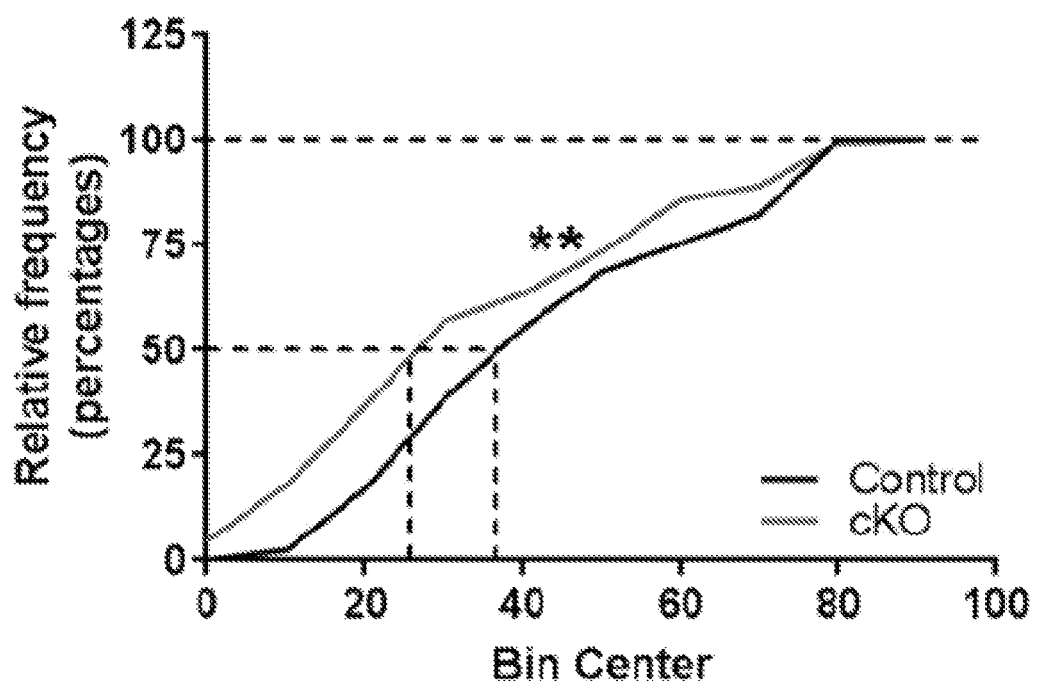
Figure 19:
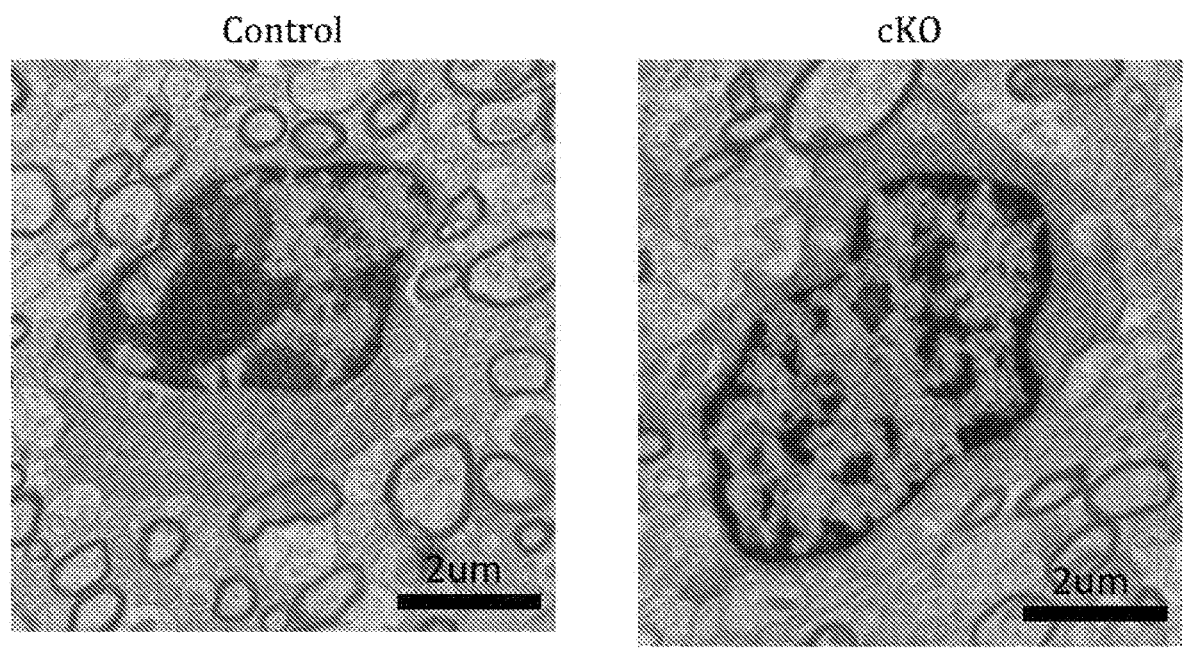
FIG. 19 shows that nuclear chromatin condensation was reduced in the CC of cKO mice. Electron micrograph images of the CC were obtained for 1 month-old mice, and revealed oligodendrocytes with less condensed nuclear chromatin in the cKO mice as compared to controls.
Figure 20:
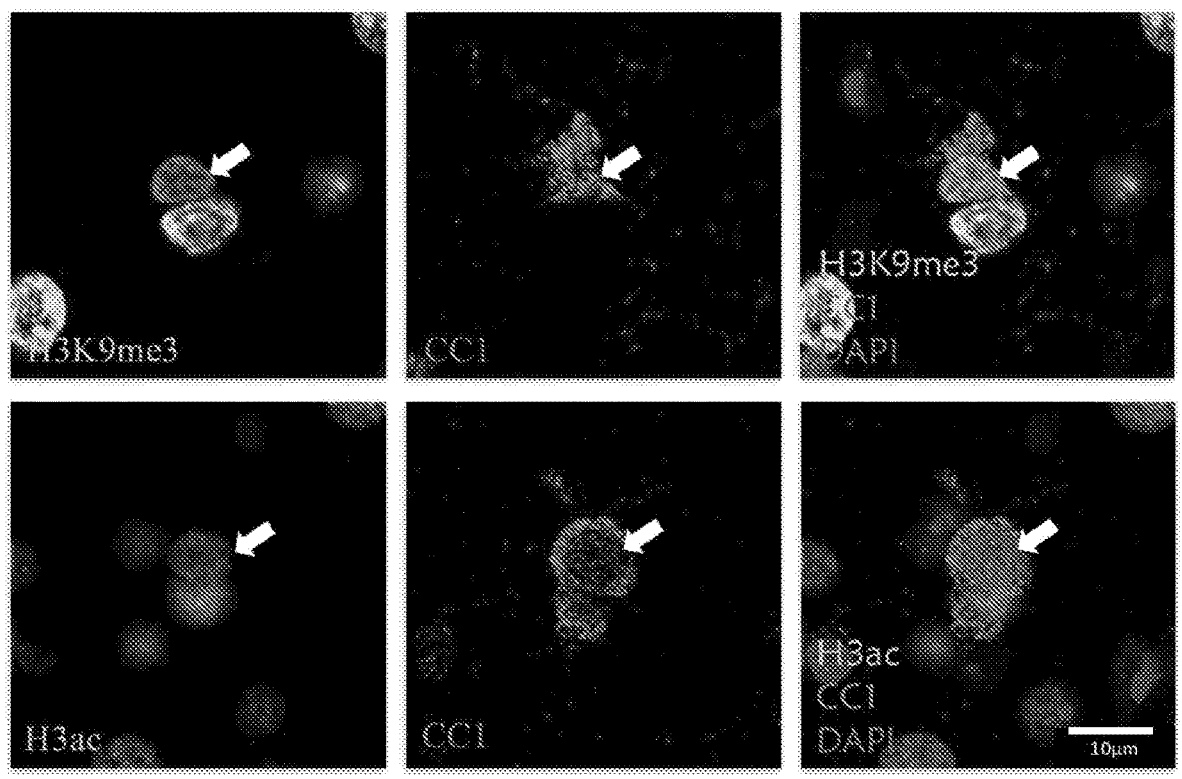
FIG. 20 shows immunofluorescence images of myelinating oligodendrocytes and nuclear markers. Confocal images were taken of 1 month-old cKO mice, which demonstrated that myelinating oligodendrocytes (CC1-positive cells, in red) co-labeled with antibodies for a repressive methylation mark (H3K9me3, upper row, in green) or acetylated histone marks (H3ac, lower row, in green).

To test whether the reduced number of observed OLs and mOLs was a result of lack of OL maturation, studies were performed to analyze the extent of nuclear chromatin condensation (37). OLs in the CC midline of one-month-old cKO were found to exhibit a significantly lower proportion of nuclear heterochromatin (FIG. 2F and FIG. 19) than control animals. There were also significantly higher levels of histone acetylation (FIG. 2G and FIG. 20) and significantly lower levels of repressive histone methylation marks (FIG. 2H and FIG. 20) detected in the cortex of cKO mice as compared to controls. Without wishing to be bound by theory, elevated levels of nuclear heterochromatin, reduced levels of histone acetylation and elevated levels of repressive histone methylation marks have all been previously described as being essential for OL differentiation and chromatin compaction (37-40).

Figure 3A:
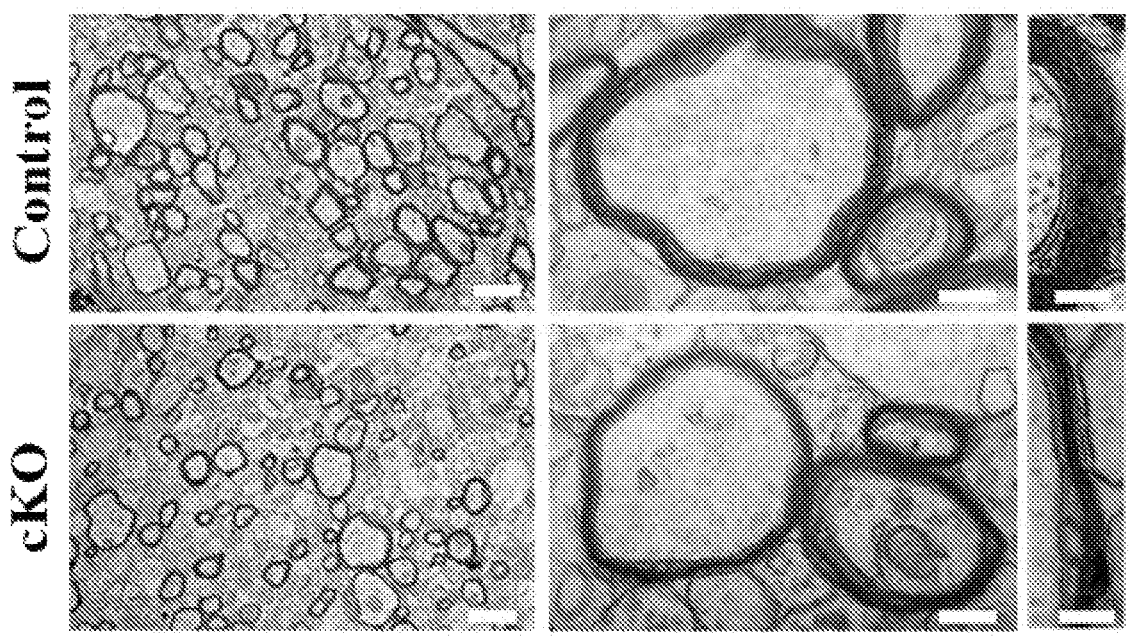
FIG. 3A to FIG. 3Q show a series of graphs and images, which demonstrated that Gtf2i cKO mice exhibited impaired myelin ultrastructure, neuronal conductivity and motor skills that were rescued following acute administration of 4-AP.
Figure 3B:
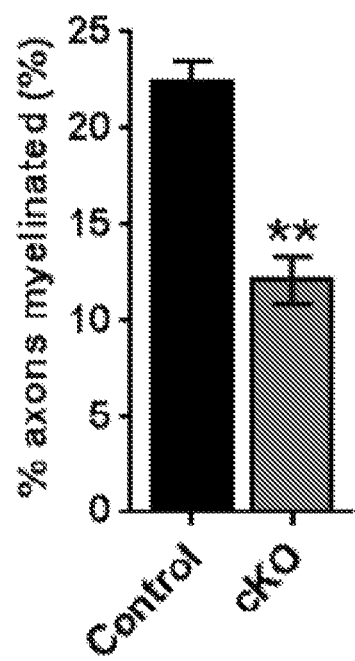
FIG. 3B is a histogram of the percentage of myelinated axons and shows that a significantly lower percentage of myelinated axons in the CC midline of cKO mice were observed, as compared to controls.
Figure 3C:
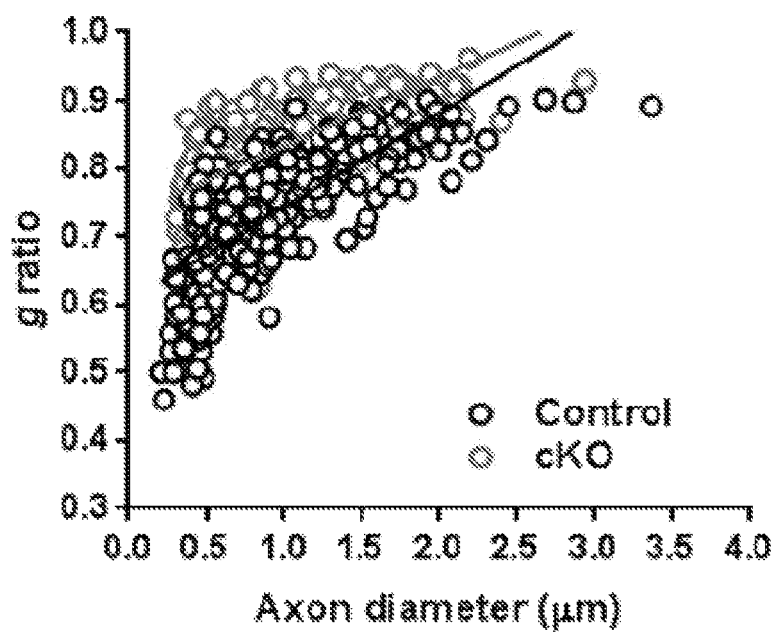
FIG. 3C is a graph of g-ratio that demonstrated that significantly reduced myelin thickness was observed in the CC midline of cKO mice, as measured by increased g ratio in cKO mice, as compared to controls.
Figure 21:
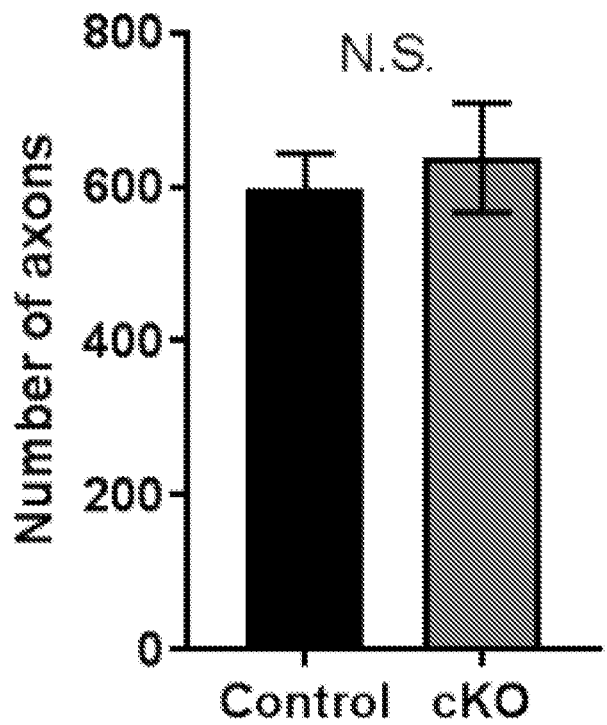
FIG. 21 shows that the total number of axons in the CC was similar in cKO and control mice. The histogram specifically shows that no significant difference was observed in the total number of axons in the CC of one-month-old cKO and control mice. A two-tailed t-test was performed, and data shown are mean±s.e.m. (n=3 control; n=3 cKO; N.S. indicates not significant).
Figure 22A:
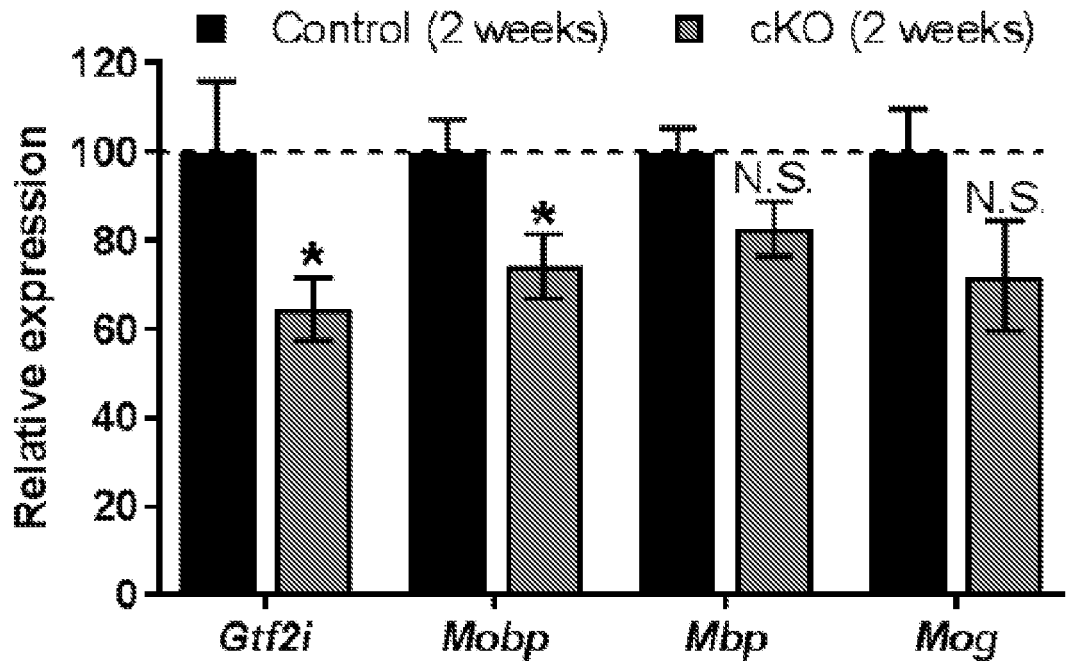
FIG. 22A to FIG. 22C present a series of histograms depicting qPCR for myelination-related genes, oligodendrocyte precursor cell number, and mylinating oligodendrocyte number for mice at 2 weeks of age, which demonstrated that moderate myelination-related deficits were observed in two-weeks-old cKO mice.
Figure 22B:
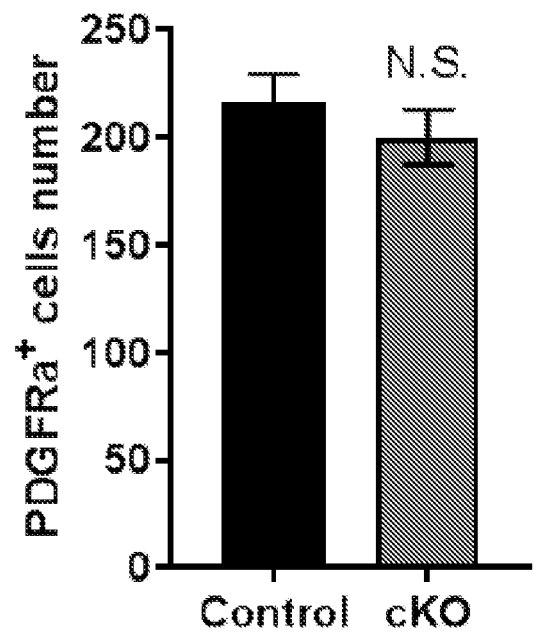
Figure 22C:
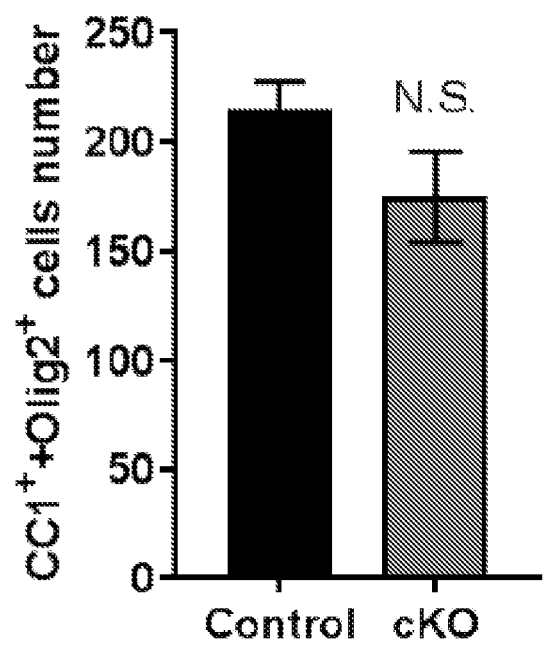
Figure 23A:
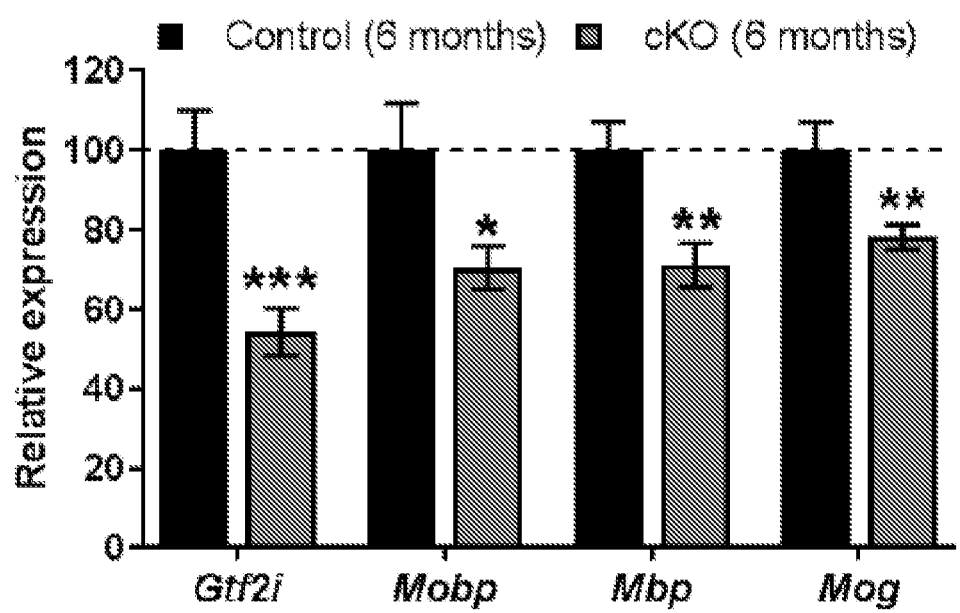
FIG. 23A to FIG. 23G present a series of graphs and images showing pPCR results for myelination-related genes, oligodendrocyte precursor cell numbers, myelinating oligodendrocyte numbers, observed g ratio, observed g ratio with axon diameter (g ratio scatter plot), percentage of axons myelinated and myelin ultrastructure in CC, respectively, which demonstrated that significant myelination-related deficits were observed in 6 month-old cKO mice.
Figure 23B:
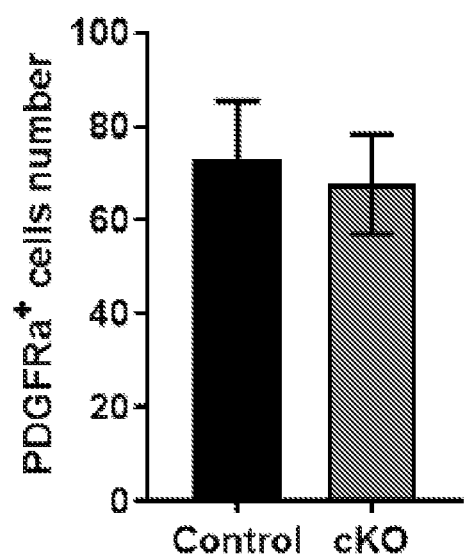
Figure 23C:
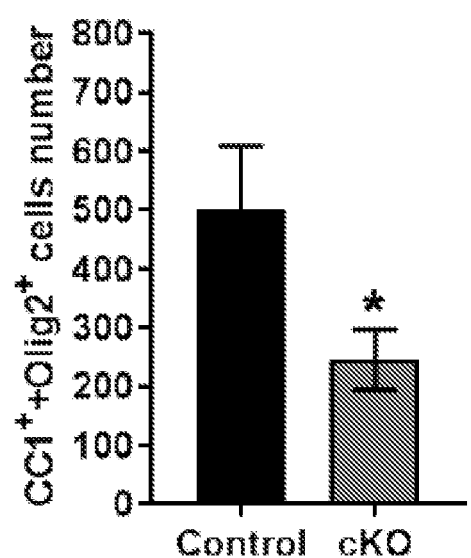
Figure 23D:
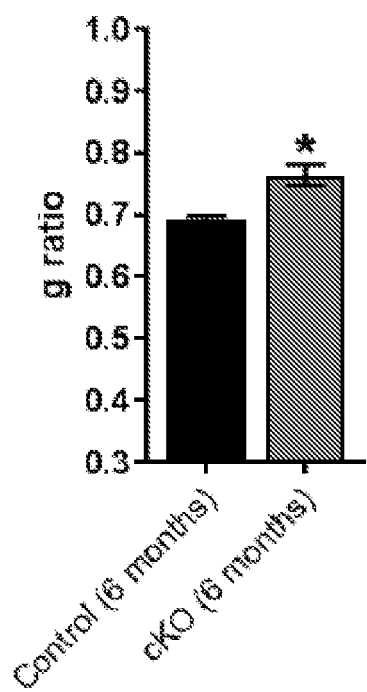
Figure 23E:
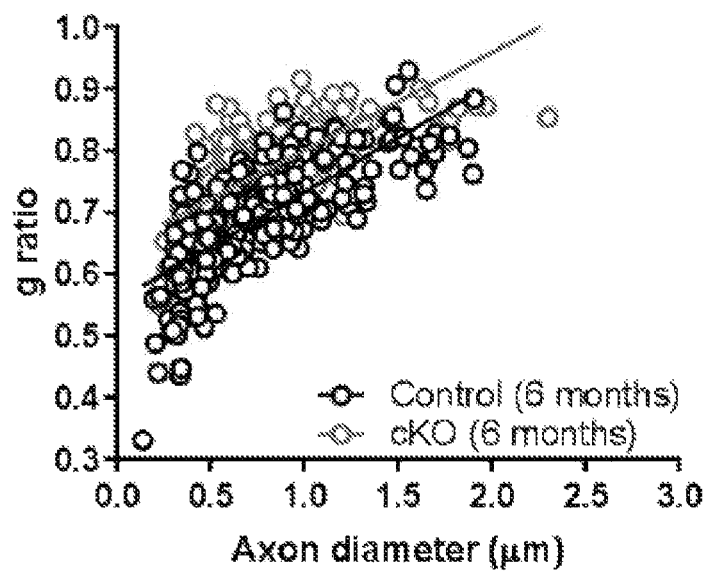
Figure 23F:
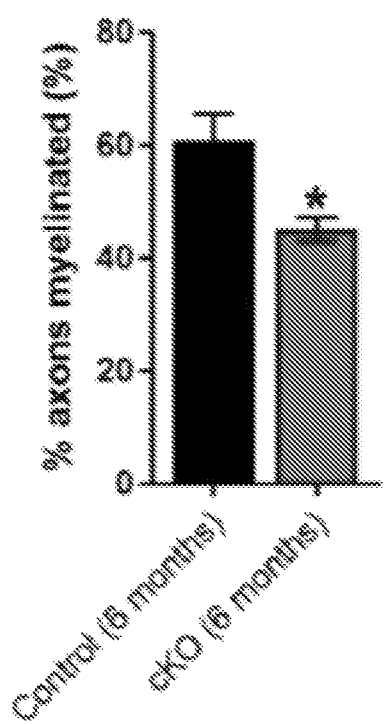
Figure 23G:
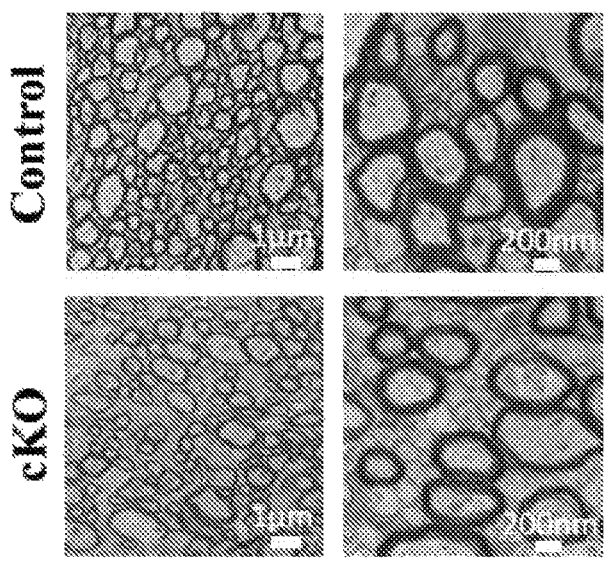
Figure 24:
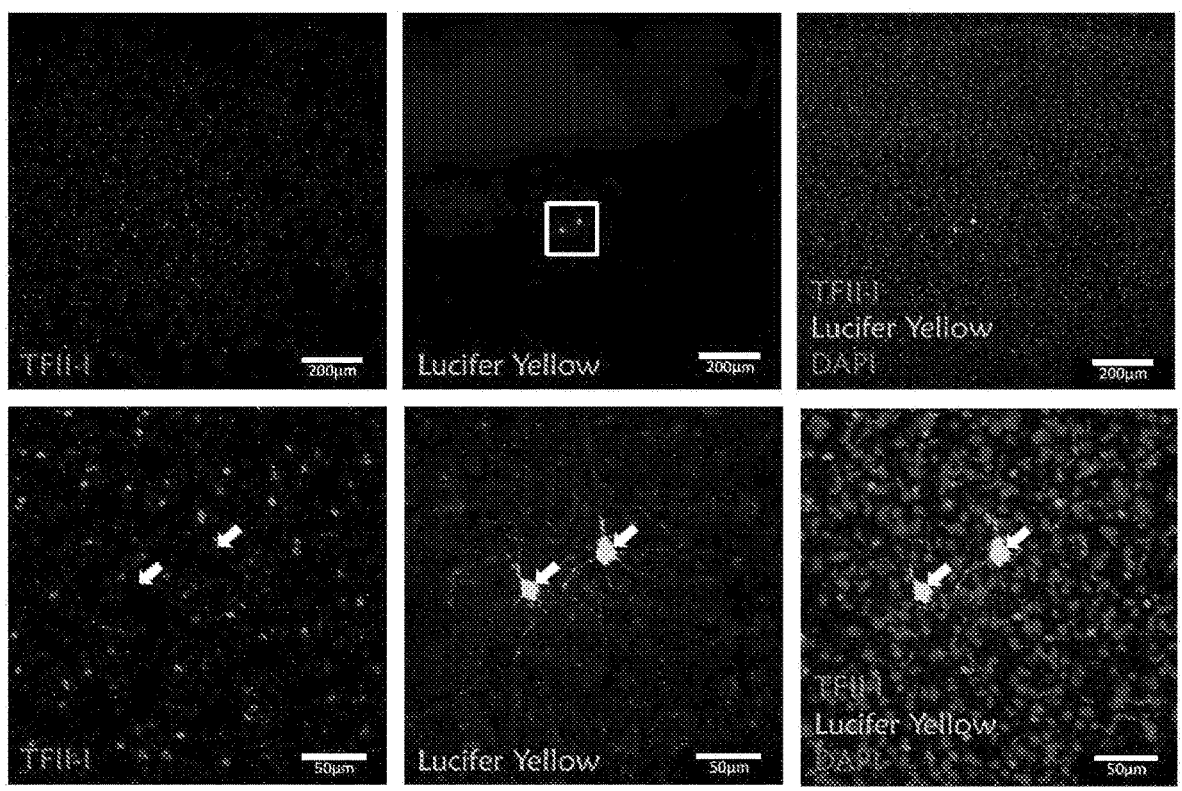
FIG. 24 shows *lucifer* yellow labeling (filling) of neurons recorded for electrophysiological properties. Confocal images of 1 month-old cKO mice show Gtf2i-KO neurons in the cortex that were recorded for electrophysiological properties and then filled up with *Lucifer* yellow. Lower row displays enlarged images of the square inset in the upper row.
Figure 25A:
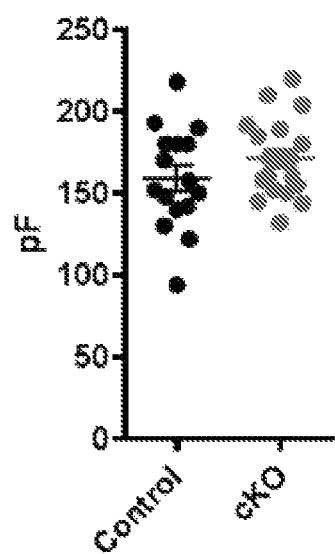
FIG. 25A to FIG. 25I present a series of graphs of Cm, Ra, Rm, resting potential, rheobase, AP half-width, AP peak, 500 pA ISI, and FI curve, respectively, which collectively demonstrate that no significant differences in passive and active membrane properties were observed for Gtf2i-KO neurons obtained from cKO mice, as compared to controls.
Figure 25B:
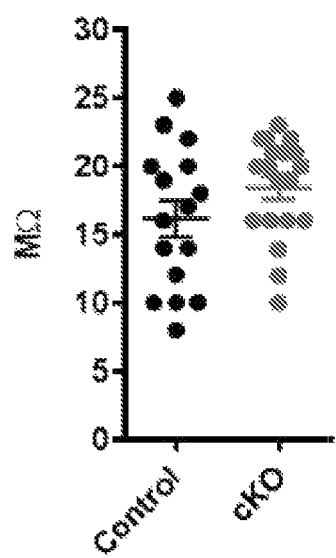
Figure 25C:
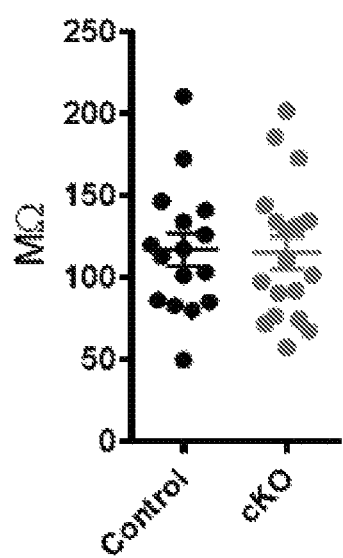
Figure 25D:
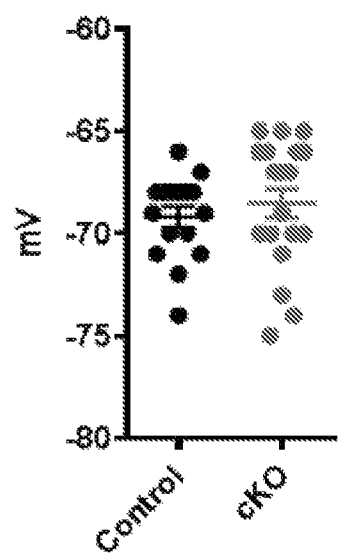
Figure 25E:
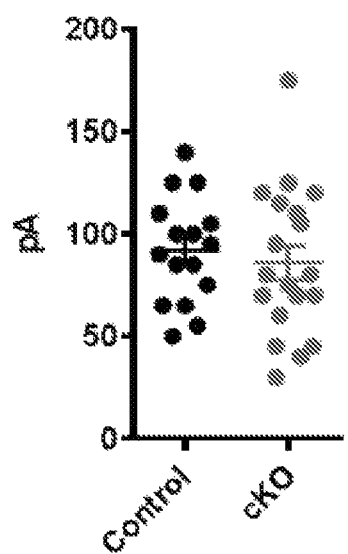
Figure 25F:
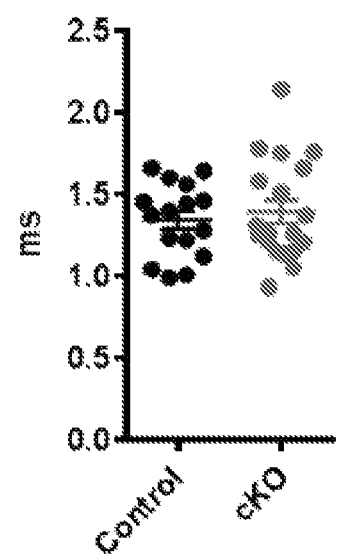
Figure 25G:
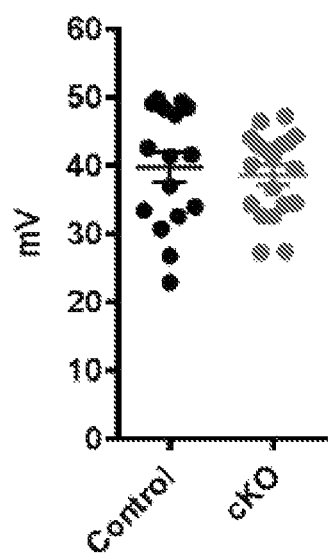
Figure 25H:
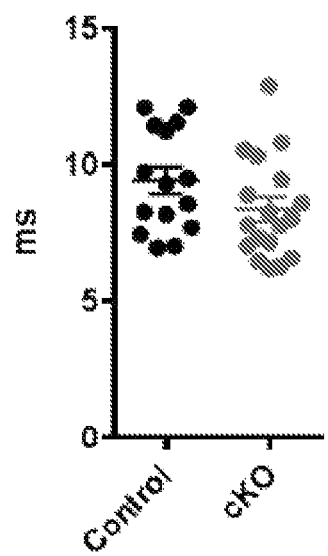
Figure 25I:
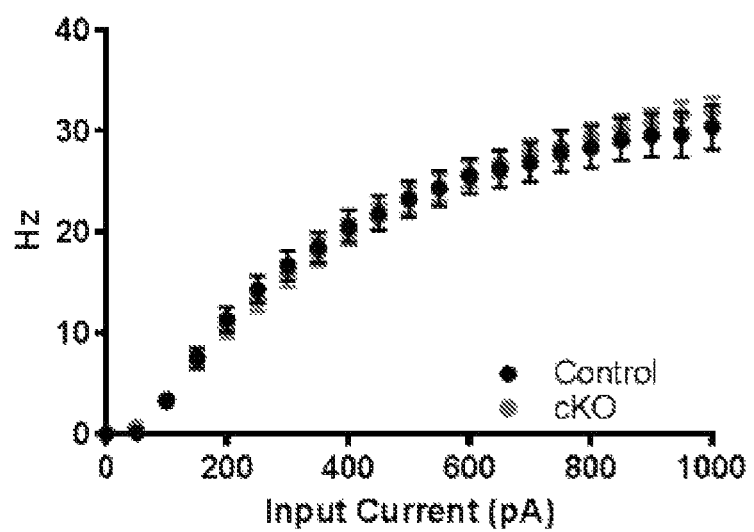

Example 4: Gtf2i Neuronal Deletion Impaired Myelin Ultrastructure, Neuronal Conductivity and Motor Skills Next, studies were performed to investigate whether the above-identified molecular and cellular deficits affected myelin structure and function. Analysis of myelin ultrastructure (FIG. 3A) revealed a significantly lower percentage of myelinated axons at the CC midline of one-month-old cKO mice as compared to controls (FIG. 3B and FIG. 21) and a significantly increased g ratio, a parameter often used for assessing axonal myelination (FIG. 3C), indicating significantly reduced myelin thickness in cKO mice as compared to controls. Similar myelination deficits were also observed in two-weeks-old cKO mice as compared to controls, although to a lesser extent (FIG. 22A to FIG. 22C). These myelination deficits persisted in six-month-old cKO mice as compared to controls (FIG. 23A to FIG. 23G), suggesting they were not simply a result of delayed myelination.

Figure 3D:
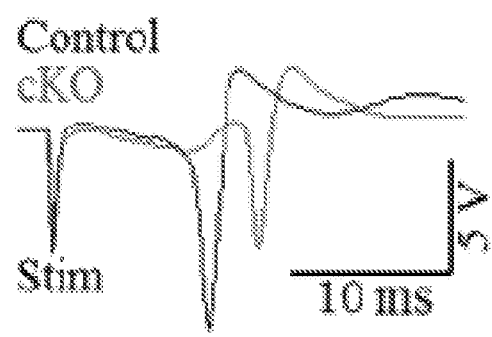
FIG. 3D is a trace of neural activity (10 ms vs. 3V) observed for control and cKO mice.
Figure 3E:
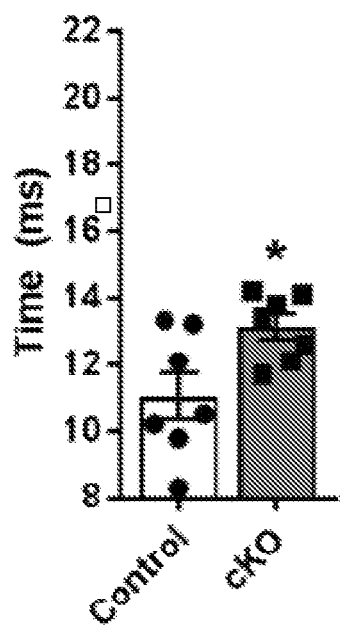
FIG. 3E and FIG. 3F are histograms showing observed peak latency and observed peak amplitude of the CC midline, respectively. Neuronal conductivity deficits were observed in the CC of cKO mice, as demonstrated by significantly longer response latency (FIG. 3D shows representative traces of evoked field potentials associated with the FIG. 3E histogram) and lower peak amplitude of evoked field potential (FIG. 3F) in cKO mice, as compared to controls.
Figure 3F:
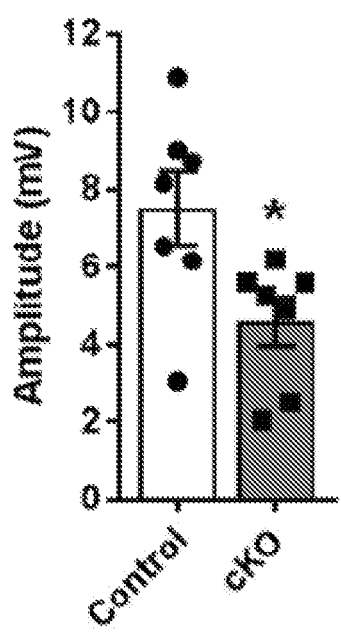

To examine whether the myelination abnormalities observed in cKO mice might have contributed to functional deficits, experiments were performed to measure axonal conductivity of the CC in one-month-old mice. Such studies involved stimulation of the axon bundle of the CC of one hemisphere and recordation and analysis of the evoked field potentials in the other hemisphere. These studies identified a significantly longer response latency (FIG. 3D) and significantly lower peak amplitude (FIG. 3E) of evoked field potentials in cKO mice as compared to that of controls. However, no significant changes were observed in intrinsic membrane or firing properties of neurons in layer 5 of primary motor cortex in Gtf2i-deleted neurons as compared to controls (FIG. 24 and FIG. 25A to FIG. 25I).

Figure 3G:
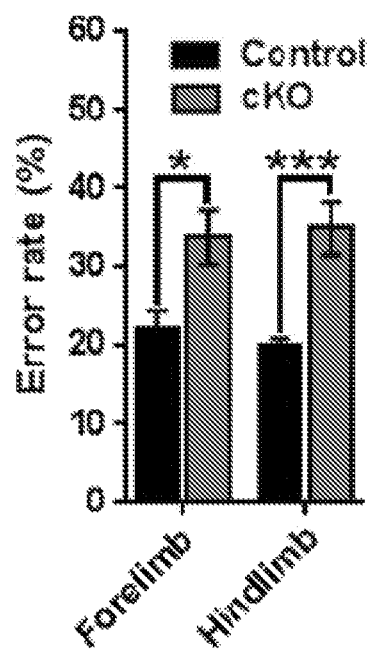
FIG. 3G and FIG. 3H are histograms of irregular ladder walking observed without and with hit, error miss, and error slip data, respectively. Fine motor deficits were observed in cKO mice as compared to controls, as demonstrated by significantly higher error rates in cKO mice for both forelimb and hindlimb in the horizontal irregular ladder walking test.
Figure 3H:
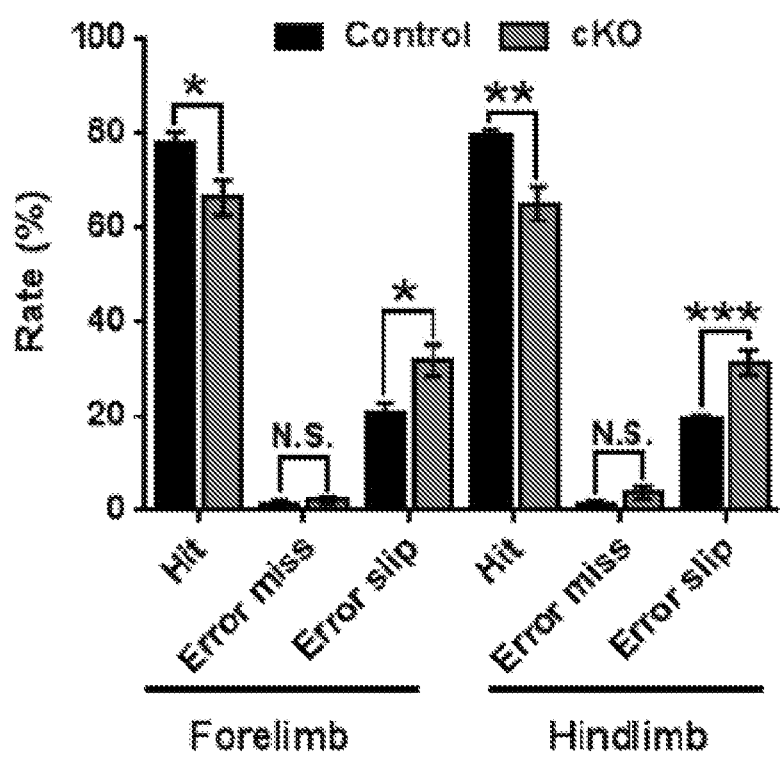
Figure 3I:
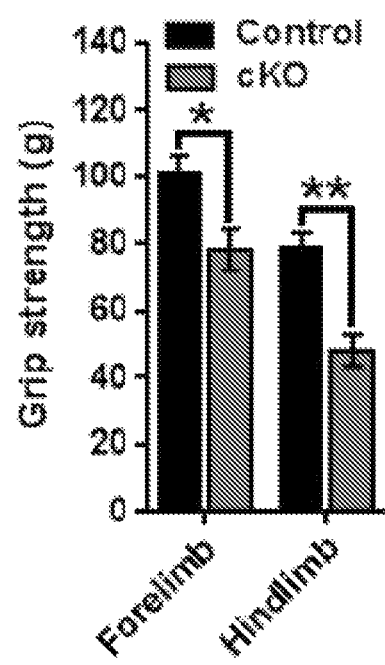
FIG. 3I is a histogram of paw grip strength. Reduced paw grip strength was observed for both forelimb and hindlimb in cKO mice, as compared to controls.
Figure 3J:
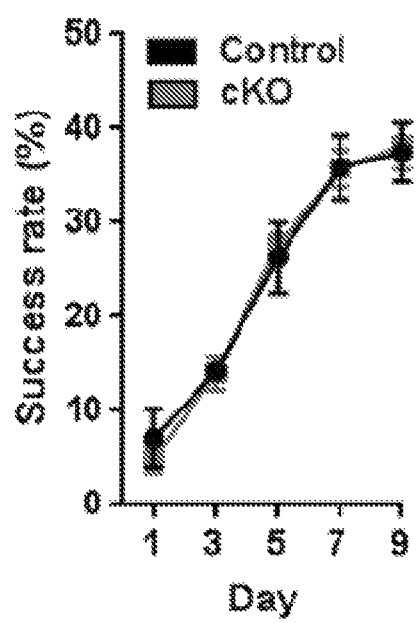
FIG. 3J is a line plot of single food pellet retrieval data. No significant difference between cKO mice and controls in the single pellet food retrieval task was observed during the learning phase.
Figure 3K:
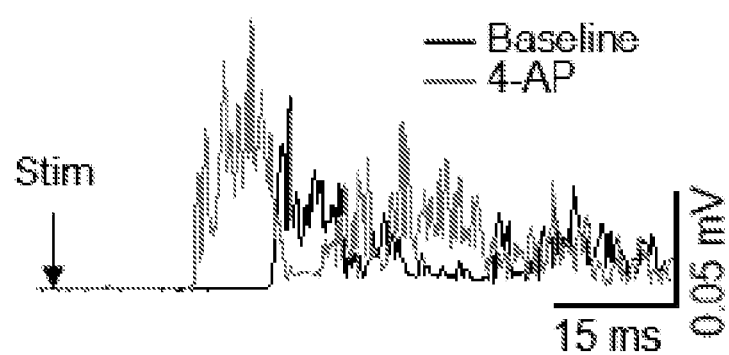
FIG. 3K is a trace of neuronal activity (15 ms vs. 0.05 mV) comparing baseline to 4-AP-treated mice.
Figure 26A:
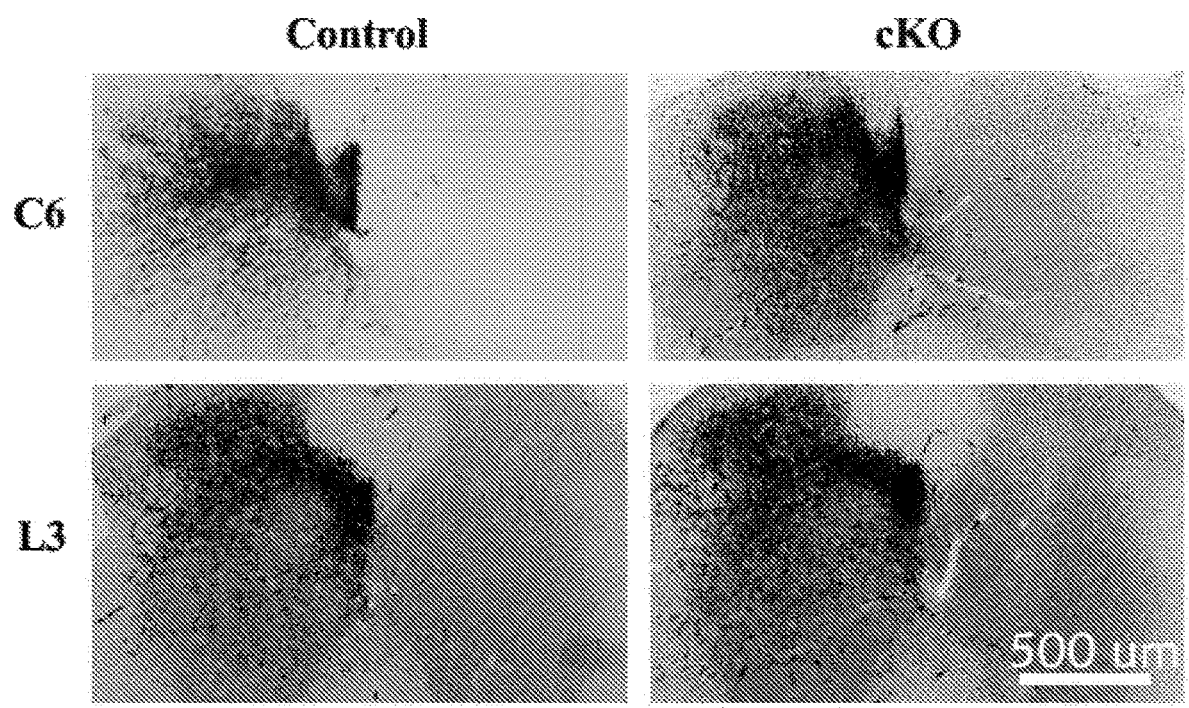
FIG. 26A and FIG. 26B present images and graphs of corticospinal axons in the spinal cord and fluorescence intensity, respectively, which demonstrate that corticospinal axon projection pattern in the spinal cord was unperturbed in cKO mice, as compared to control mice.
Figure 26B:
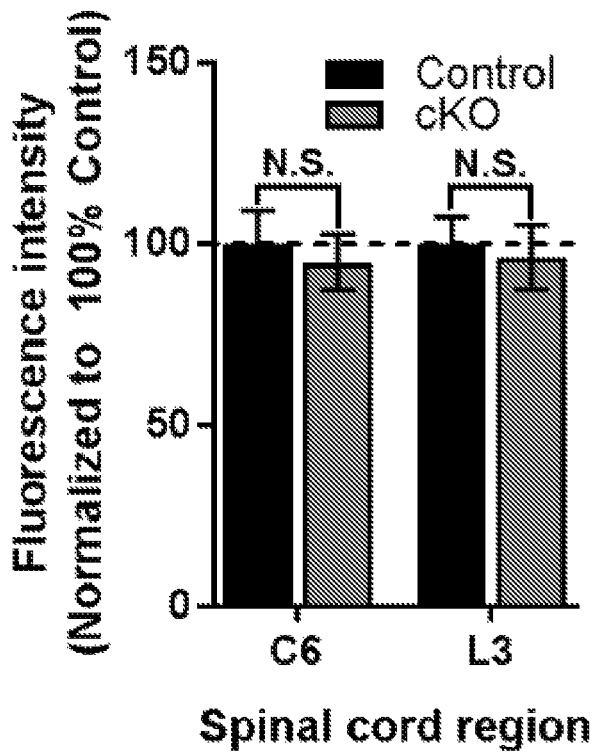

WS patients have been described to demonstrate fine motor deficits and delays in acquisition of early motor skills (2, 41, 42). To investigate how the instantly identified deficits in myelination and axonal conduction might affect fine motor skills, mice were tested in a horizontal ladder walking assay (as described in references 43 and 44). This test is known to be highly dependent on supraspinal connections composed of heavily myelinated long-distance axons (45, 46). Compared to controls, one-month-old cKO mice exhibited a significant increase in the imprecise paw placement rate in both forelimbs and hindlimbs (FIG. 3G and FIG. 3H). Additionally, the forepaw and hindpaw grip strength of cKO mice was significantly reduced as compared to that of controls (FIG. 3I), which indicated an impaired descending drive to motor neurons innervating forepaws and hindpaws. In contrast, cKO mice showed no overt abnormalities in learning and executing the single-pellet food retrieval task as compared to controls (FIG. 3J). Thus, cKO mice showed impairments in fine control of voluntary movements, along with weaker muscle tone for both forepaws and hindpaws, consistent with findings observed for WS patients (2, 42). Notably, the axonal projection pattern of the corticospinal tract was unaffected by Gtf2i-deletion, as indicated by similar corticospinal axon projection pattern and densities into the dorsal and intermediate laminae at cervical and lumbar spinal cord levels of cKO mice (FIG. 26A and FIG. 26B).

Figure 3L:
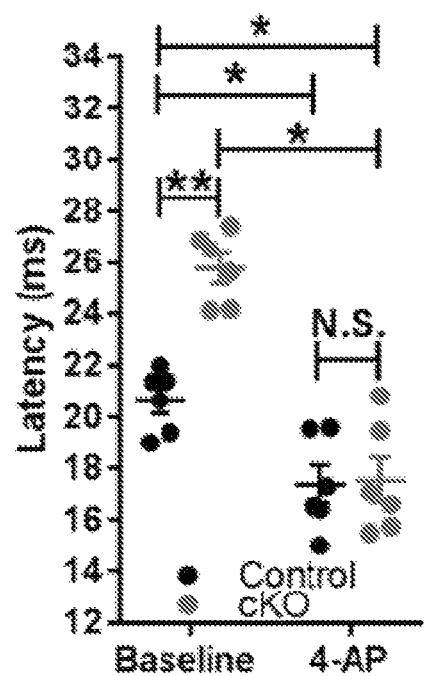
FIG. 3L is a box plot of peak latency data observed for 4-AP-treated mice, as compared to baseline for cKO and control mice in the CST. Neuronal conductivity deficits in the cortico-spinal tract (CST) of cKO mice were demonstrated by significantly longer response latency. Following 4-AP acute administration, latency deficits were significantly decreased and normalized to control levels.
Figure 3M:
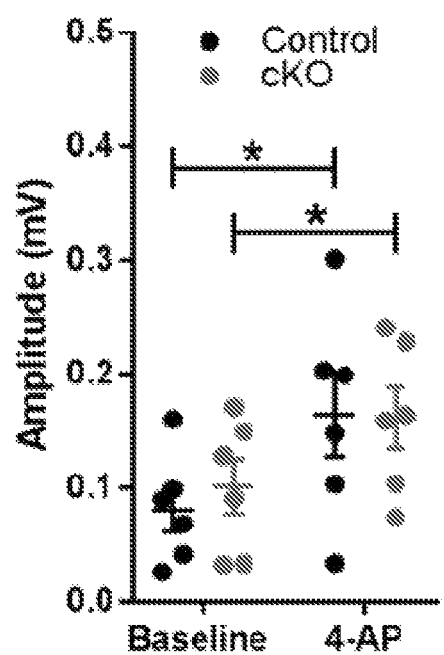
FIG. 3M is a box plot of peak amplitude data for 4-AP treatment, as compared to baseline, in cKO and Control mice in the CST. Peak amplitude in the CST of cKO was not significantly different as compared to controls, and was increased following 4-AP acute administration. (As noted above, FIG. 3K presents representative traces of evoked field potentials, relevant to such box plots.)

To further characterize physiological properties of these fine motor deficits, studies were performed to measure functional connectivity in corticospinal output, by applying electrical stimulation in primary motor cortex and recording electromyography (EMG) activity in contralateral tibialis anterior muscle of hindlimb. In cKO mice, the observed response latency of EMG was significantly longer than that of control mice (FIG. 3L, Baseline), whereas the EMG amplitude of cKO mice was similar to controls (FIG. 3M, Baseline).

Figure 3N:
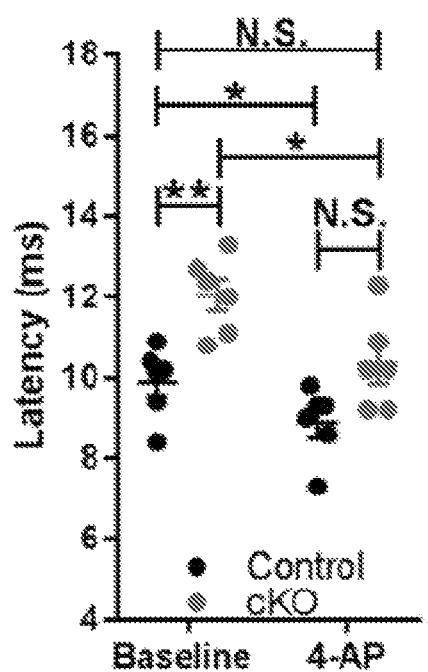
FIG. 3N is a box plot of peak latency data in the CC midline. Neuronal conductivity deficits in the corpus callosum (CC) of cKO mice were demonstrated by significantly longer response latency. Following 4-AP acute administration, latency deficits were significantly decreased and normalized to control levels.
Figure 3O:
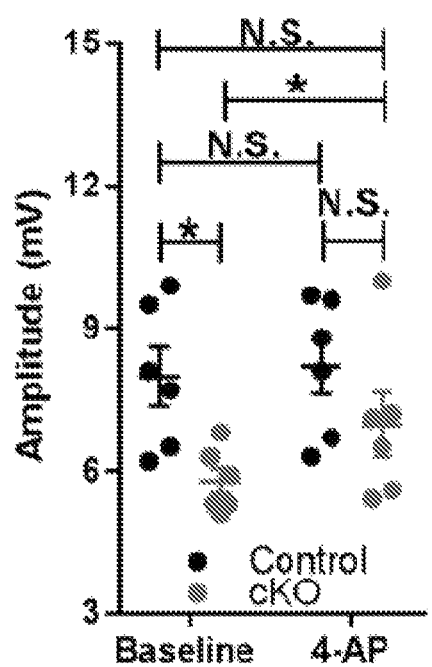
FIG. 3O is a box plot of peak amplitude data in the CC midline. Peak amplitude in the CC of cKO was significantly lower in cKO as compared to controls, and was increased following 4-AP acute administration and normalized to control levels.
Figure 4A:
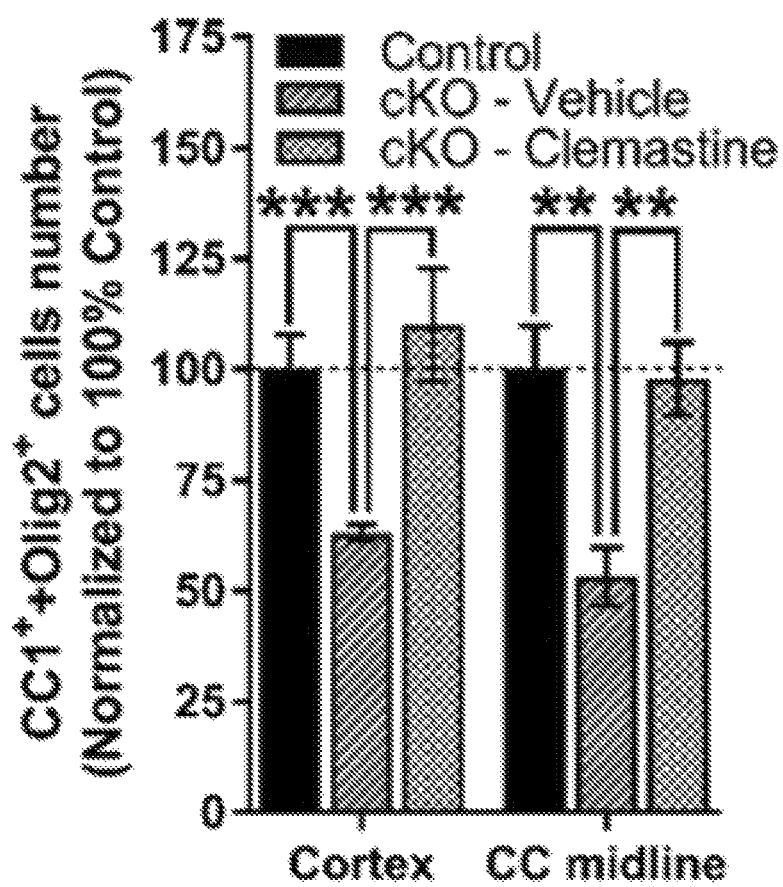
FIG. 4A to FIG. 4C show that Gtf2i cKO mice impaired myelin-related properties were rescued following chronic administration of clemastine.

Example 5: Normalization of Impaired Myelination Properties or Axonal Conductivity Rescued Behavioral Deficits To investigate whether increasing axonal conductivity could rescue behavioral defects, experiments were performed to test the effect of 4-AP (4-aminopyridine), an FDA-approved medication that has been described to improve axon conductivity by selectively blocking potassium channels (47). Strikingly, the acute administration of 4-AP significantly shortened EMG latency in cKO and control mice, resulting in similar EMG latency of cKO and control mice (FIG. 3L, 4-AP). EMG amplitudes of both control and cKO mice were also increased significantly after 4-AP treatment (FIG. 3M, 4-AP). In addition, in the CC, 4-AP treatment also normalized both the latency (FIG. 3N) and amplitude (FIG. 3O) of evoked potential in cKO mice.

Figure 3P:
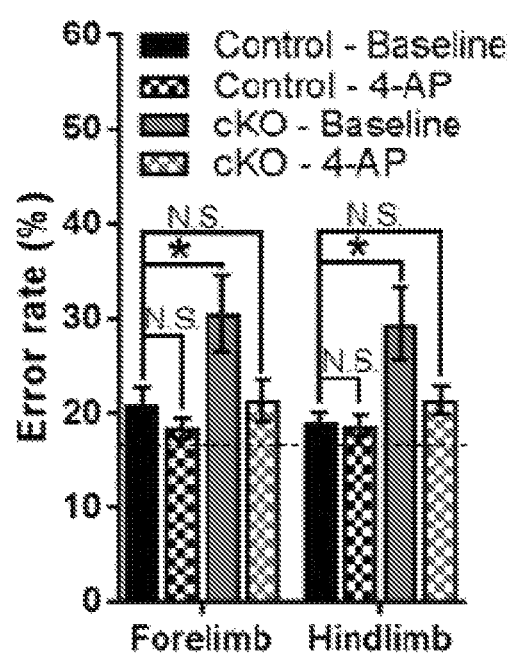
FIG. 3P is a histogram of irregular ladder walking data. The fine motor deficits in cKO were rescued following 4-AP acute administration in both forelimb and hindlimb.
Figure 3Q:
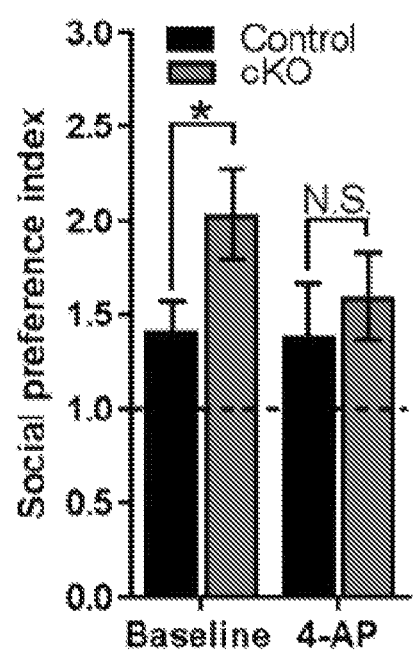
Figure 27A:
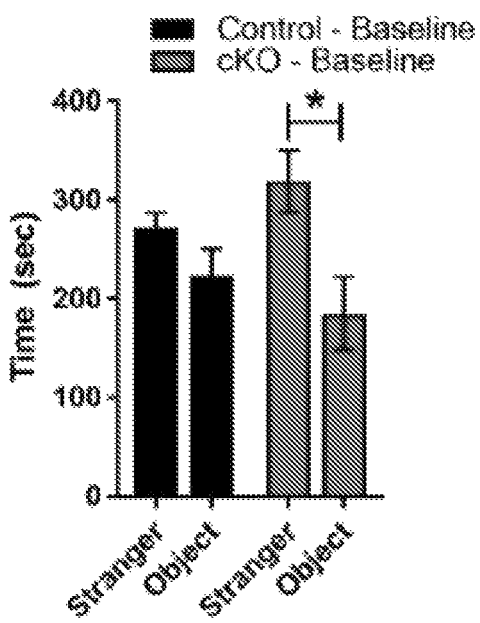
FIG. 27A to FIG. 27C show a series of histograms that assessed social preference-duration values in the three-chamber social preference test across baseline, 4-AP treatment and clemastine treatments, respectively.
Figure 27B:
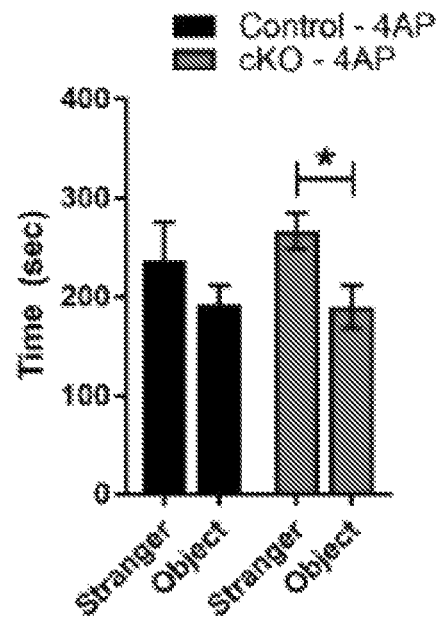

Behaviorally, acute 4-AP administration led to normalized fine motor skills in cKO mice in the horizontal ladder walking test in both forelimb and hindlimb (FIG. 3P). Additionally, cKO mice showed normalized social preference following acute administration of 4-AP in the social preference test (FIG. 3Q, FIG. 27A and FIG. 27B).

Figure 4B:
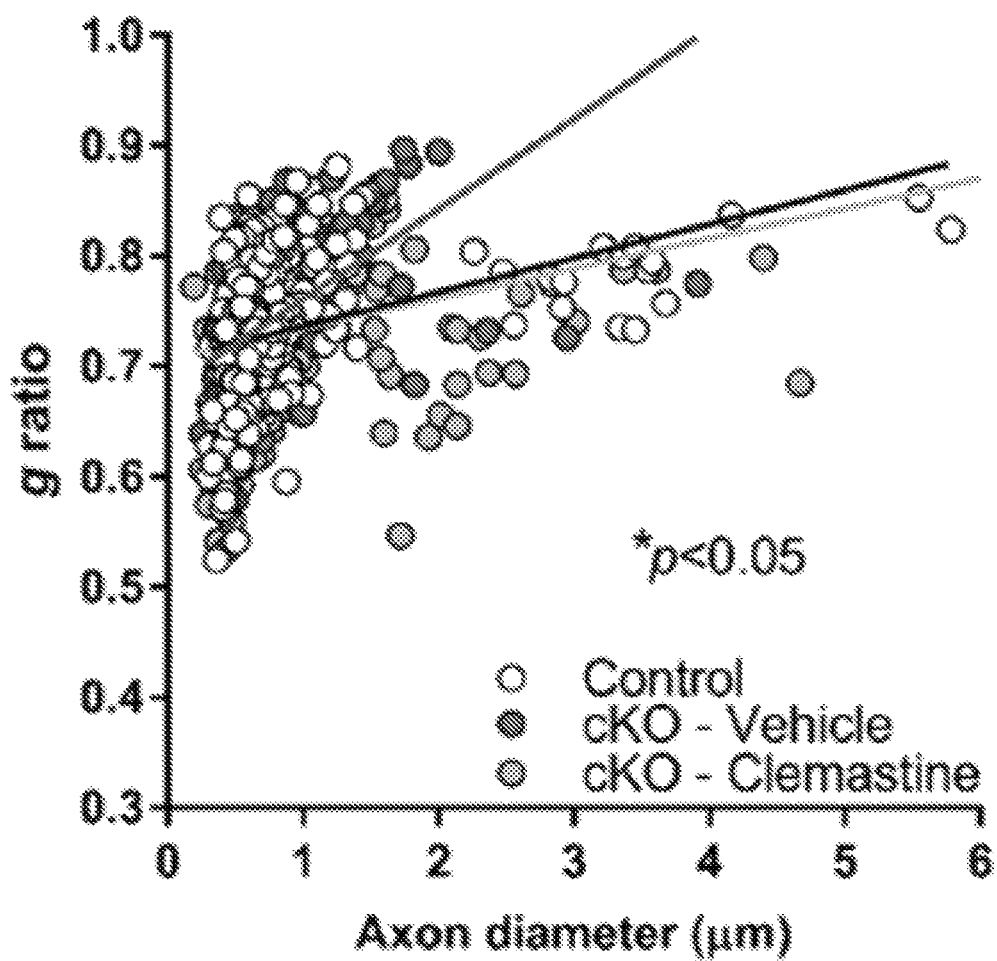
Figure 4C:
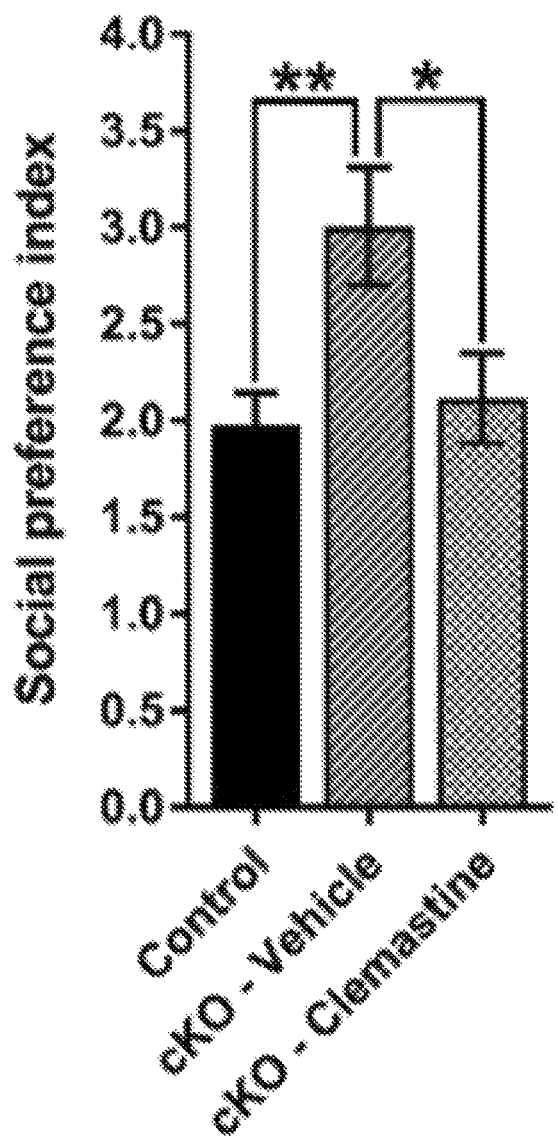
Figure 27C:
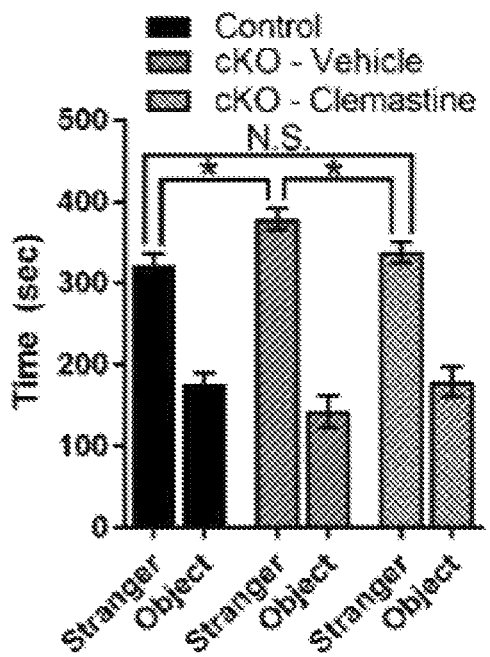

To examine whether changes in myelination led to the impaired conductivity observed in the cKO mice, myelination-related properties were rescued by chronic administration of the FDA-approved pro-differentiation compound clemastine (48-51) to 1 month-old cKO and control mice. Clemastine treatment normalized the number of mOLs in the cortex and the CC of cKO mice (FIG. 4A), and increased the myelin thickness in cKO mice, as demonstrated by significantly reduced g ratio in cKO mice treated with clemastine compared to cKO mice administered with vehicle (FIG. 4B). Rescuing the myelination deficit was sufficient to normalize social preference index in the social preference test (FIG. 4C and FIG. 27C).

Example 6: Gtf2i-Het Mice Demonstrated Myelination-Related Deficits

Figure 28A:
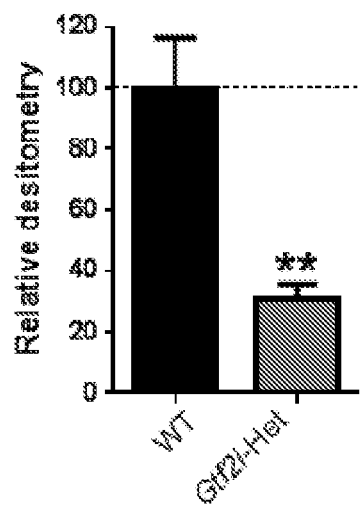
FIG. 28A to FIG. 28G present a series of graphs showing protein levels, margins distance, social preference, preference index, qPCR for myelination-related genes, g ratio, and g ratio with axon diameter (g ratio scatter plot), respectively, which demonstrate that Gtf2i-haploinsufficiency resulted in behavioral and myelination abnormalities.
Figure 28B:
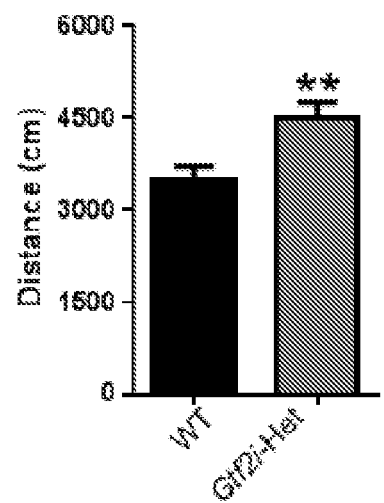
Figure 28C:
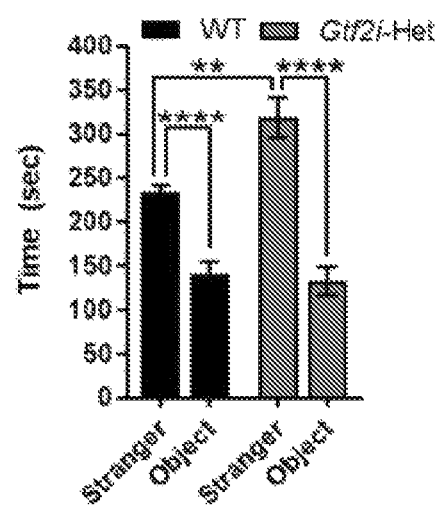
Figure 28D:
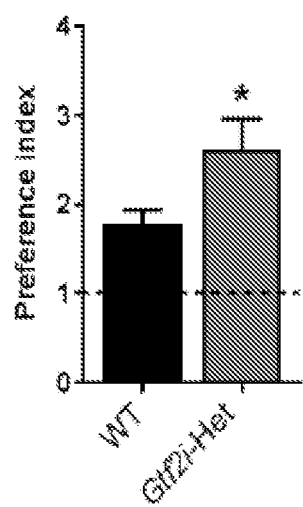
Figure 28E:
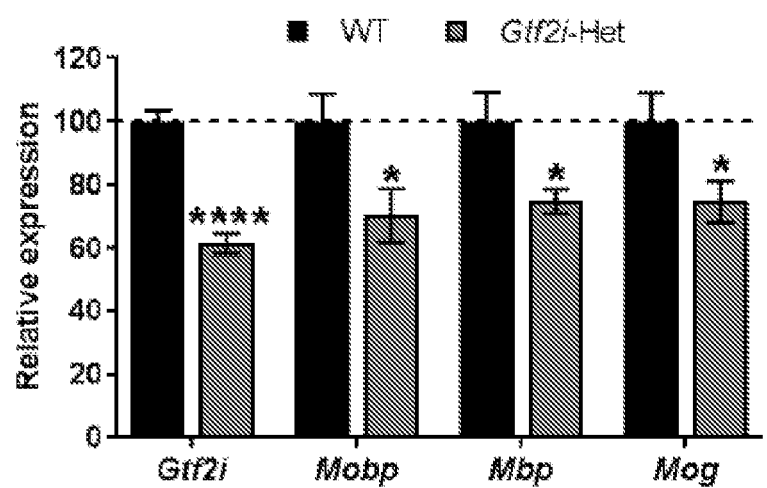
Figure 28F:
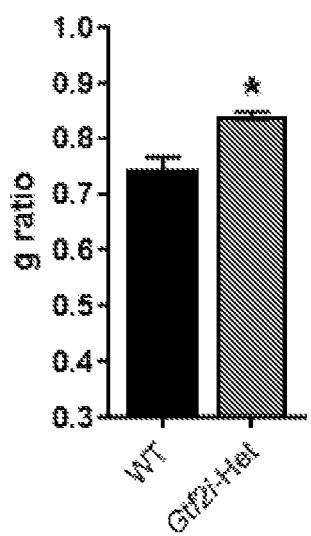
Figure 28G:
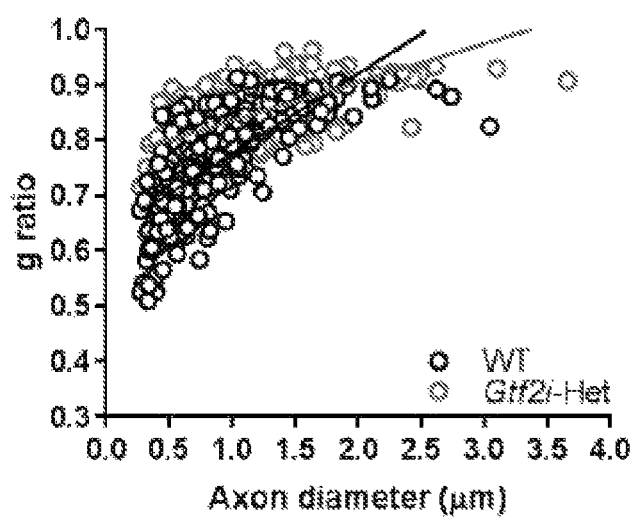
Figure 29A:
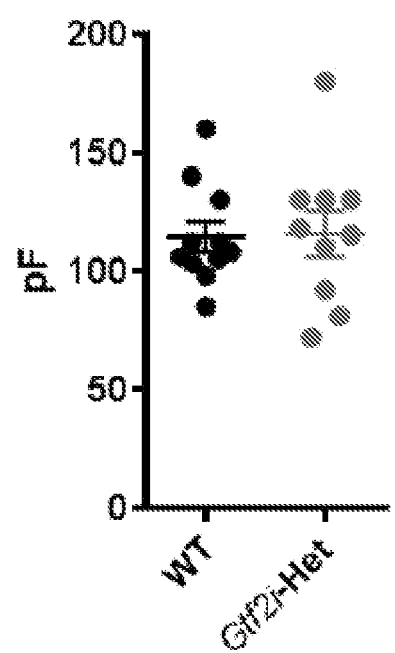
FIG. 29A to FIG. 29I present a series of graphs of Cm, Ra, Rm, resting potential, rheobase, AP half-width, AP peak, 500 pA ISI, and FI Curve, which collectively demonstrate that no significant differences were observed in passive and active membrane properties of Gtf2i-Het neurons from Gtf2i-Het mice compared to controls.
Figure 29B:
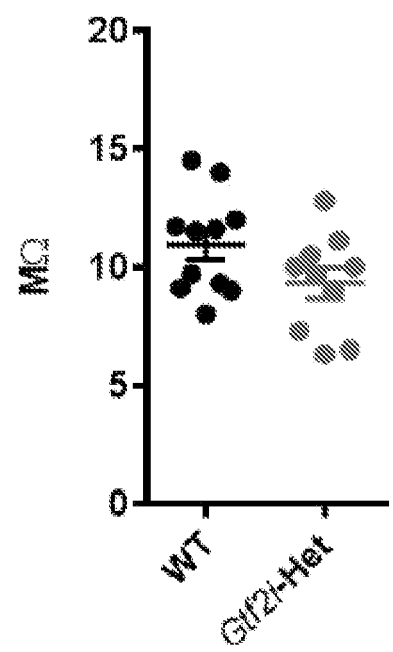
Figure 29C:
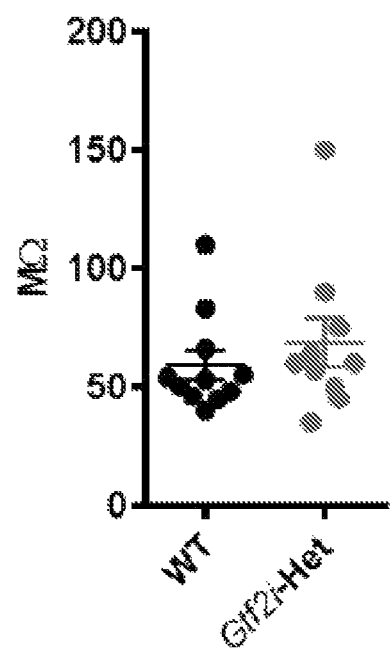
Figure 29D:
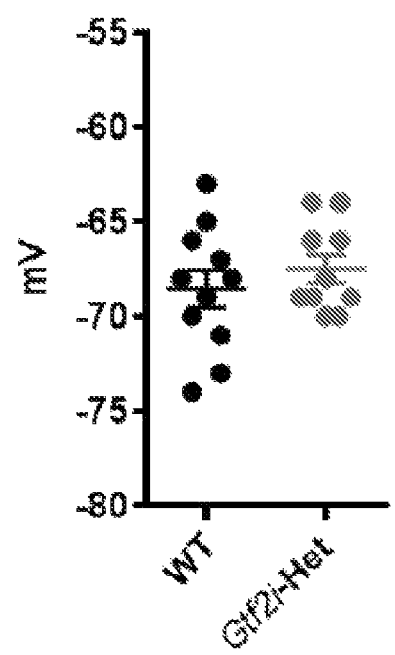
Figure 29E:
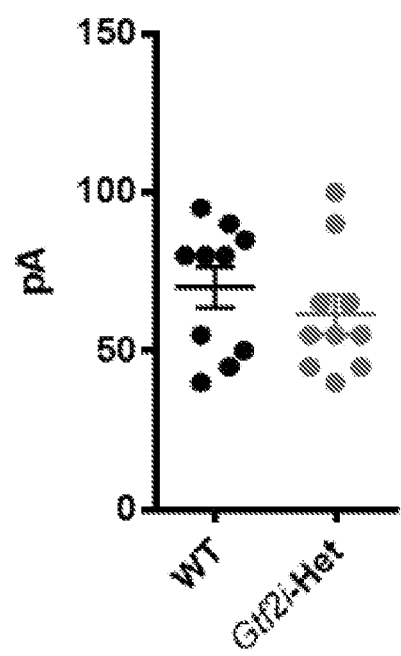
Figure 29F:
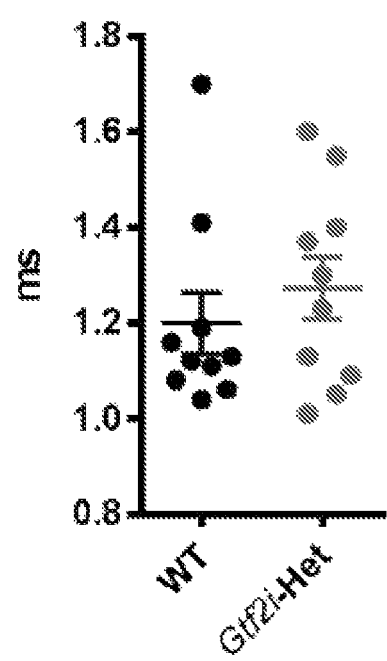
Figure 29G:
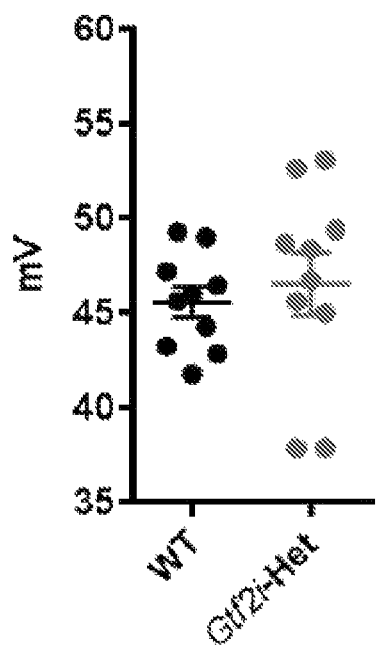
Figure 29H:
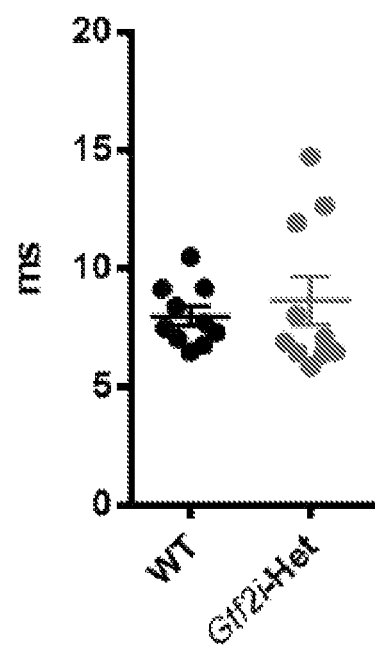
Figure 29I:
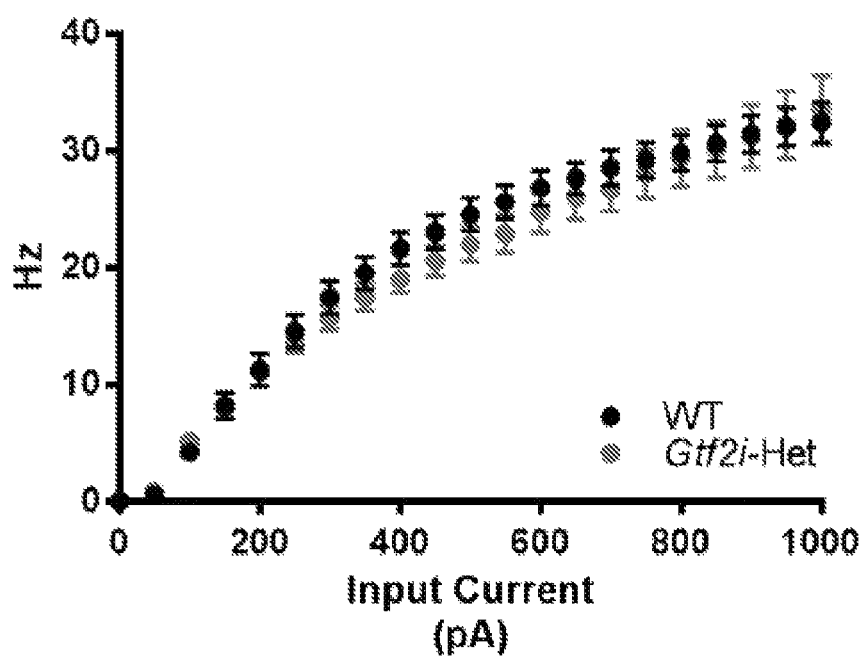

To examine whether the myelination deficits found in the cKO mice were also present in Gtf2i-Het mice (where Gtf2i-Het mice model the Gtf2i-encompassing hemizygosity observed for human WS patients), experiments were designed and performed to study one-month-old Gtf2i heterozygous mice for such deficits. As shown in FIG. 28A and FIG. 28B to FIG. 28D, Gtf2i heterozygous mice were observed to exhibit significantly increased levels of anxiety-like behavior (FIG. 28B) and social preference (FIG. 28C and FIG. 28D), similar to cKO mice. Importantly, similar to cKO mice, Gtf2i heterozygous mice also exhibited significantly lower mRNA levels of myelin-related genes (FIG. 28E) and significantly thinner myelin thickness compared to WT as demonstrated by significantly higher g ratio (FIG. 28F and FIG. 28G), as compared to wild-type control mice. Also similar to cKO mice, no significant changes in passive and active membrane properties were identified in neurons of Gtf2i-hemizygous mice, as compared to controls (FIG. 29A to FIG. 29I).

Figure 5A:
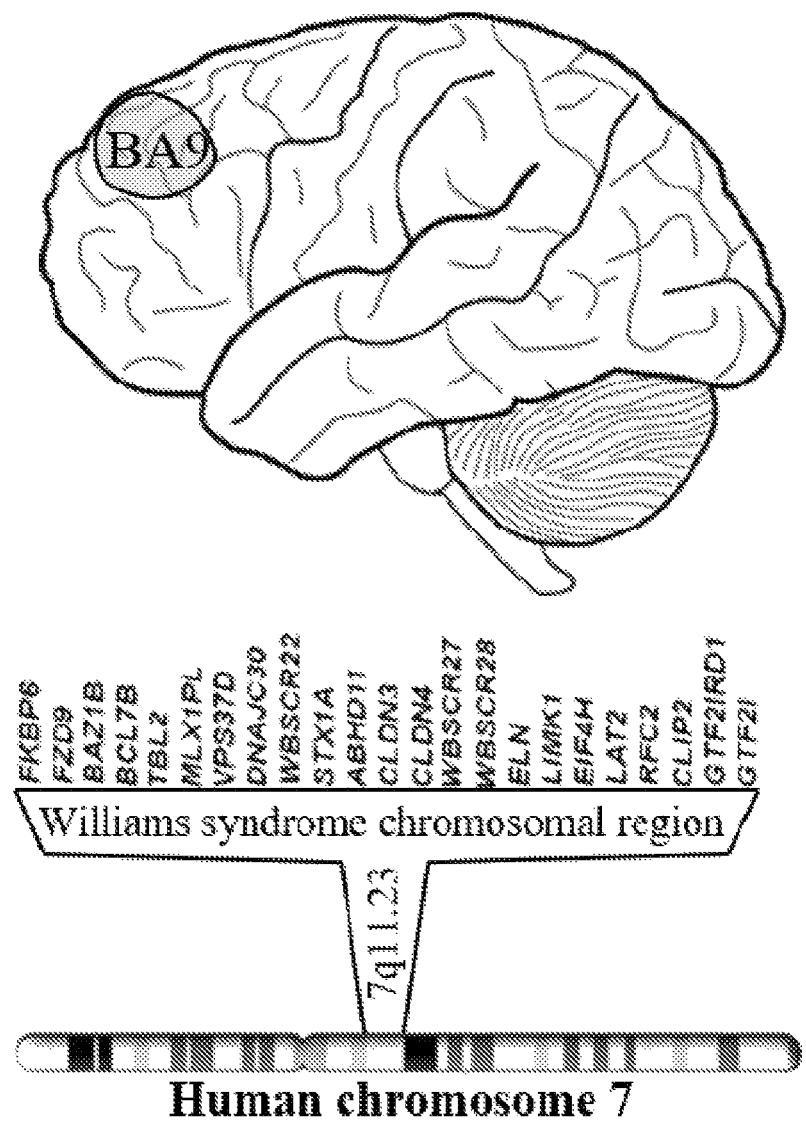
FIG. 5A to FIG. 5L present a series of images, graphs, and heat maps of myelination-related transcriptomic alterations in the frontal cortex of WS subjects.
Figure 5B:
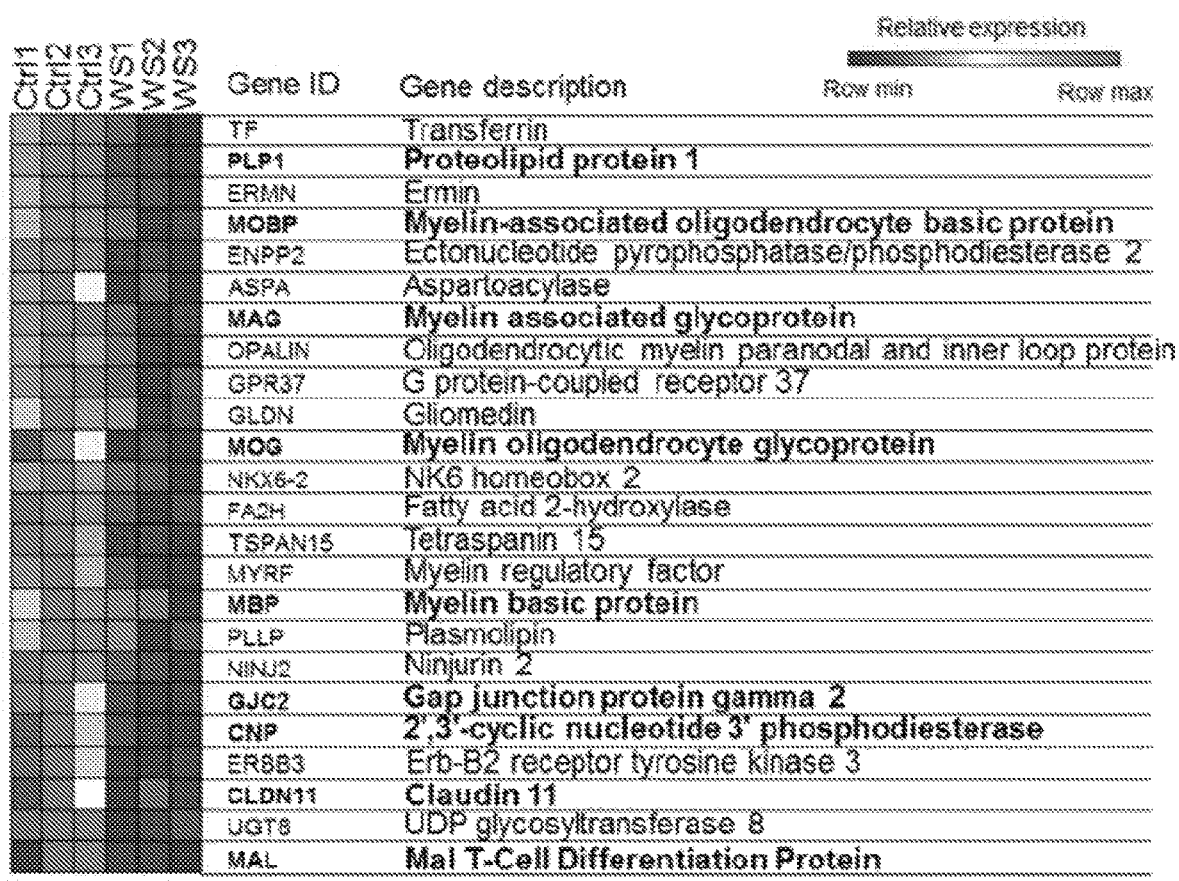
Figure 5C:
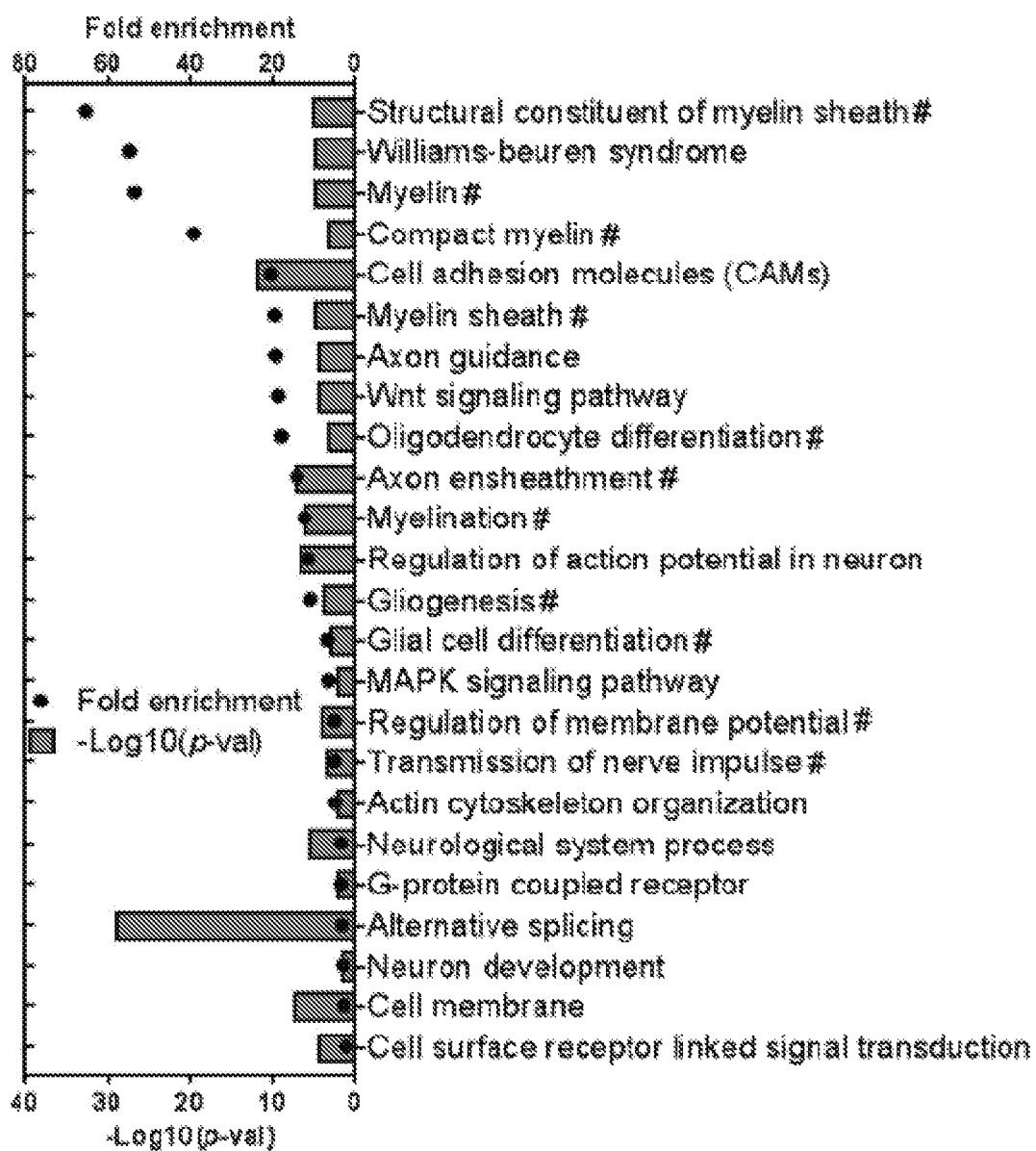
Figure 5D:
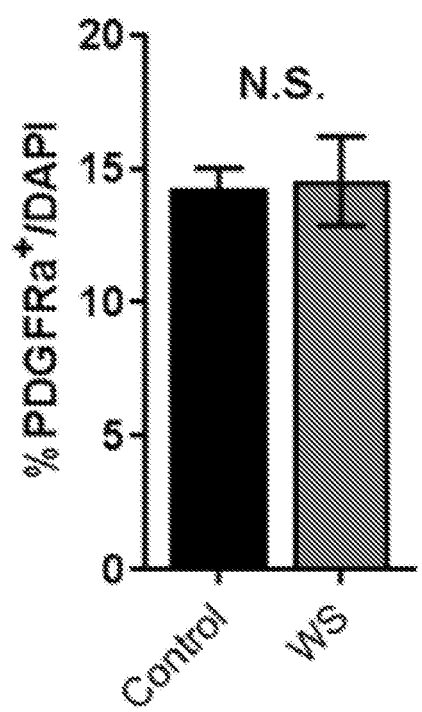
Figure 5E:
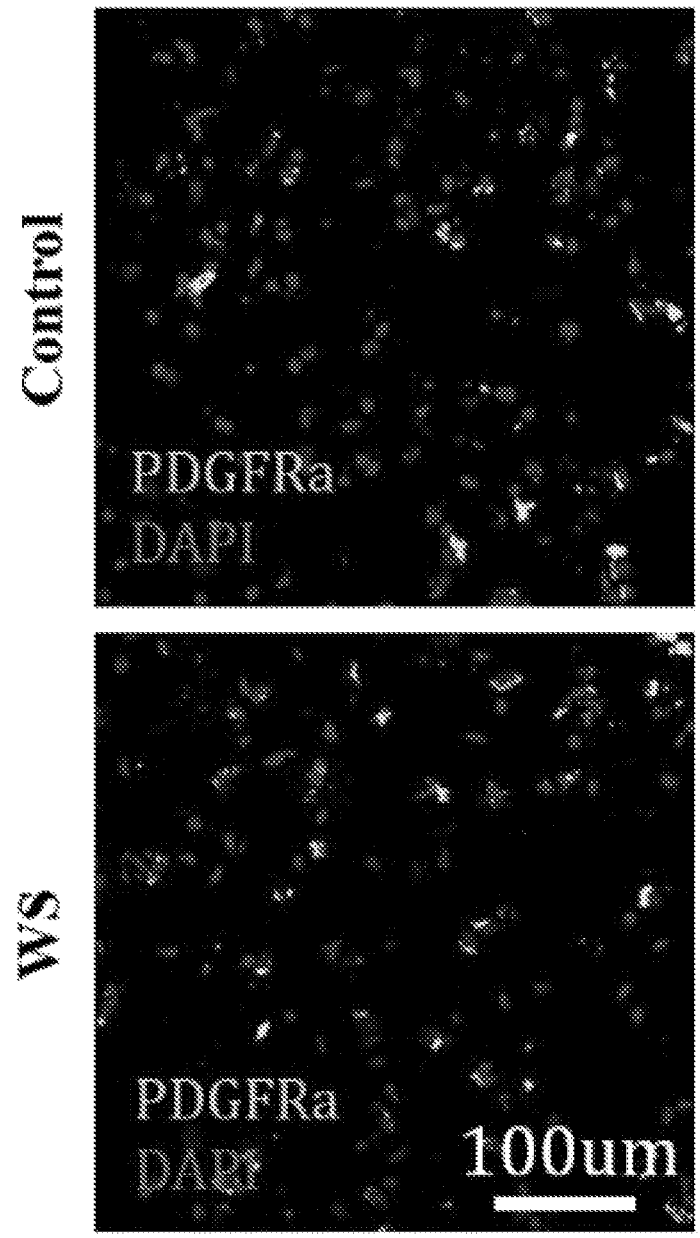
Figure 5F:
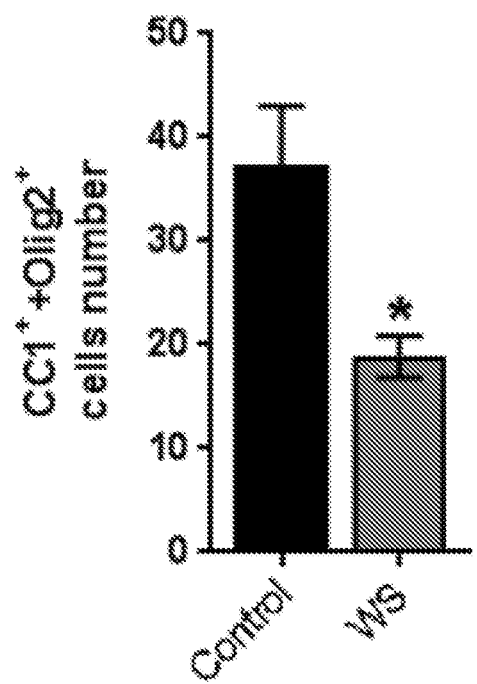
Figure 5G:
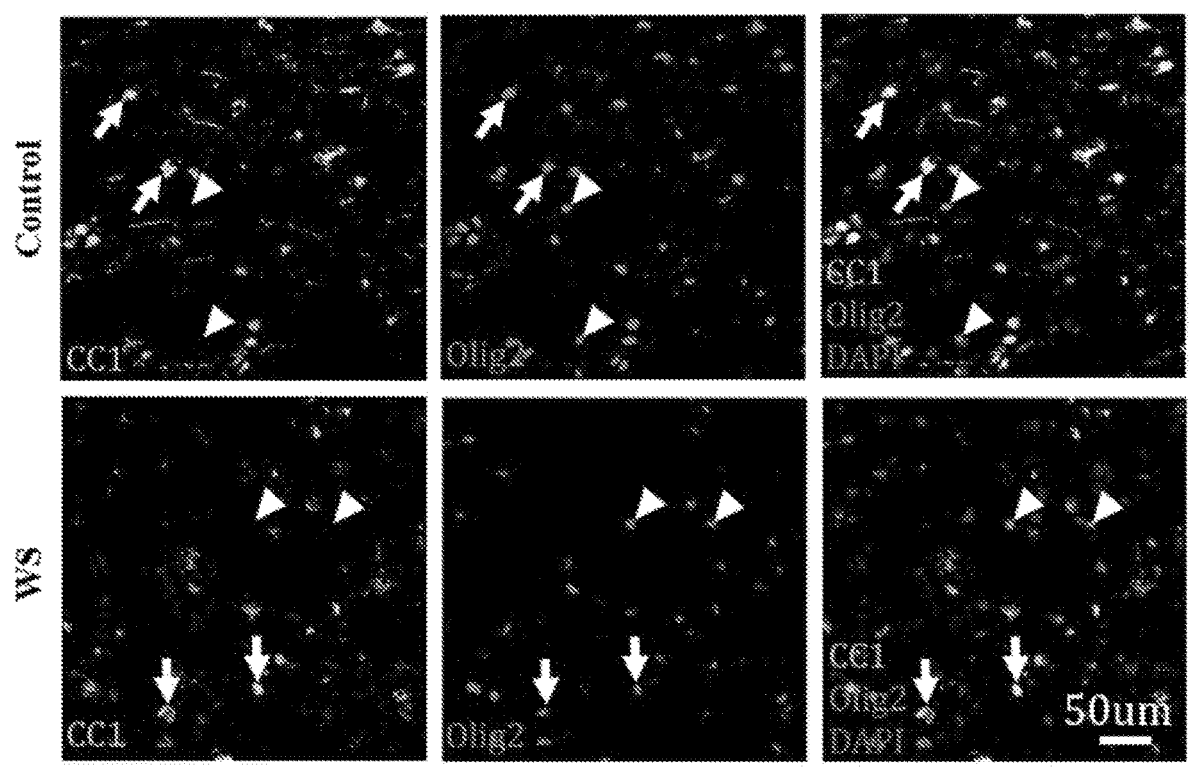
Figure 5H:
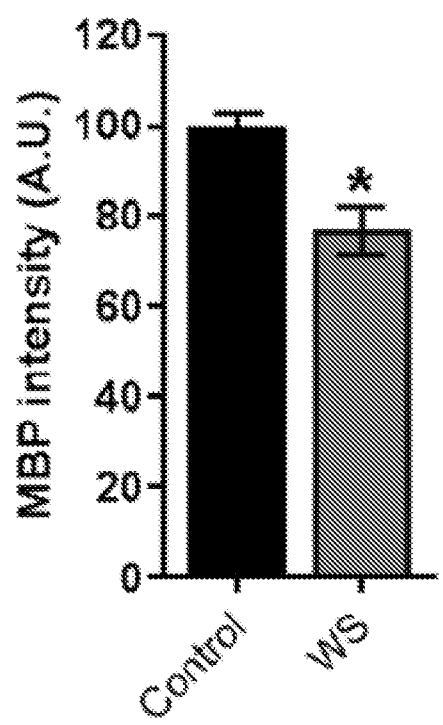
Figure 5I:
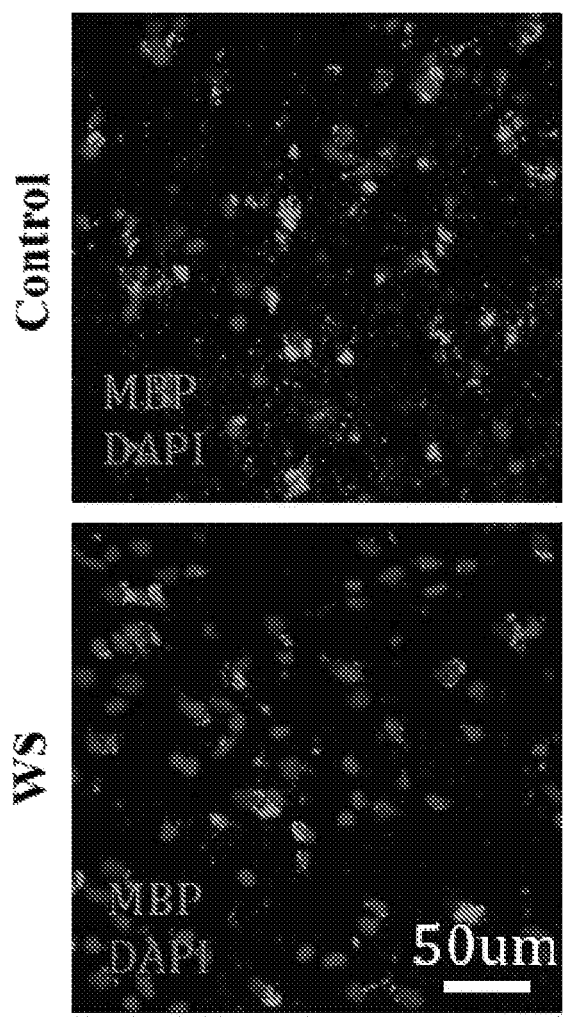
Figure 5J:
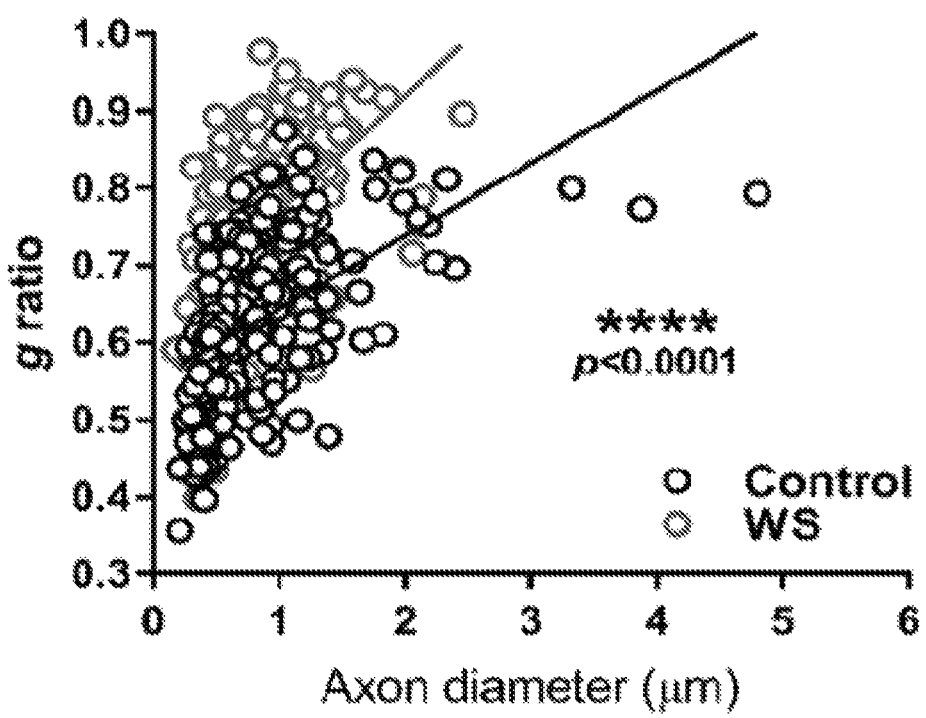
Figure 5K:
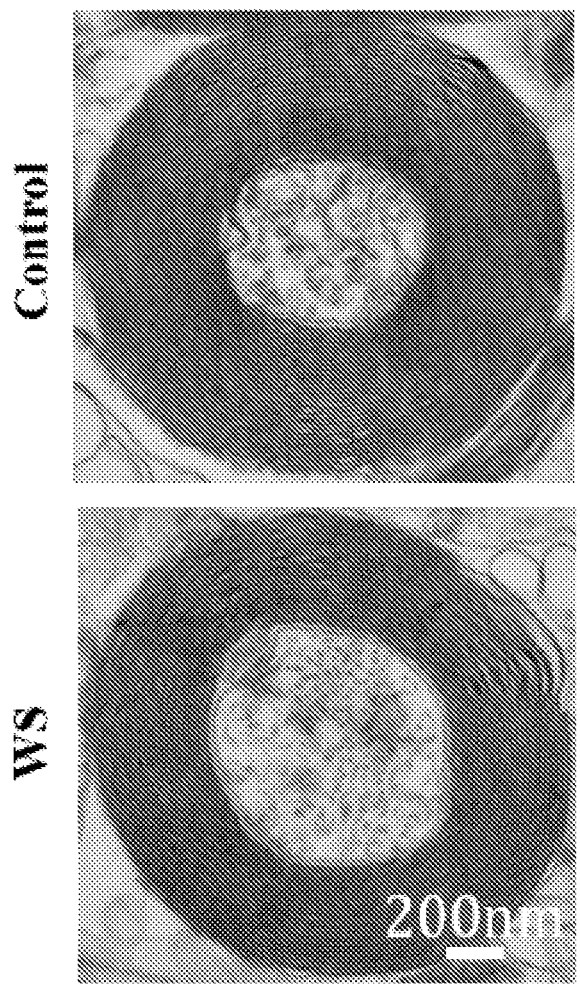
Figure 5L:
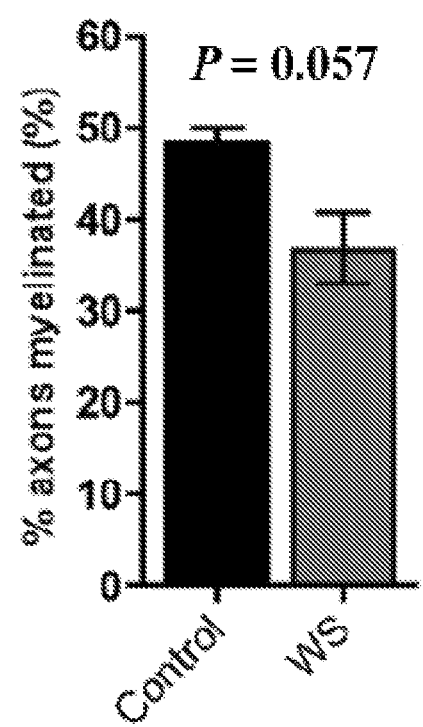

Example 7: Myelination-Related Transcriptomic, Cellular and Ultrastructural Alterations Observed in the Frontal Cortex of WS Subjects To examine whether the instant findings of myelination deficits in mouse studies corresponded to any similar deficits that might occur in WS subjects, RNAseq was performed upon frontal cortex samples obtained from adult WS subjects with typical full WSCR deletion, as compared to normal control samples (FIG. 5A and FIG. 32). Although a complete WSCR deletion encompasses deletion of 26 genes, the instant studies identified that 19% of all genes that exhibited significantly altered (increased or decreased) mRNA level in WS subjects as compared to controls were myelination-related genes (FIG. 5B, FIG. 5C and FIG. 32). These affected myelination-related genes exhibited significantly lower expression in WS subjects as compared to controls (FIG. 5B and FIG. 5C), and many of them were the same genes affected in Gtf2i cKO mice (shown in bold in FIG. 5B). As in mice, these genes were highly enriched in mOLs (FIG. 15A and FIG. 15B), and encoded proteins previously described as important for the formation, stability, compaction and maintenance of myelin (32-34). Similar to the deficits characterized in cKO mice, these studies identified no significant change in the number of OPCs between WS subjects and controls (FIG. 5D and FIG. 5E); however, significantly reduced mOL numbers were observed (FIG. 5F and FIG. 5G), as well as significantly reduced MBP intensity (FIG. 5H and FIG. 5I) in frontal cortex postmortem tissue of WS subjects as compared to controls. Additionally, as in cKO mice, significantly decreased myelination thickness was observed in WS subjects as compared to controls, as indicated by significantly increased g ratio (FIG. 5J and FIG. 5K). Lastly, a trend of reduced percentage of myelinated axons in frontal cortex postmortem tissues of WS subjects as compared to controls was identified (FIG. 5L, p=0.057, n=4 Control subjects, n=3 Williams syndrome subjects).

Thus, by deleting Gtf2i exclusively from excitatory neurons in mice, an unexpectedly dramatic reduction in myelin-related gene transcripts, mOL number, axon myelination and neuronal function was identified. These results were further corroborated by similar transcriptional changes and myelination-related deficits in Gtf2i heterozygous deletion mice and in the brain of WS subjects. Together, these data suggested that the observed myelination defect in both mice and human WS subjects represents an important pathological change that occurs in WS patients, and that the deletion of Gft2i in WSCR is a likely cause of this pathology. The instant disclosure has therefore identified an apparently novel function of Gtf2i expression in excitatory neurons for proper OL development and myelination and that this dysfunction may contribute to some of the neurological and behavioral symptoms associated with WS. These results have further supported the importance of axon-OL interaction in the development of myelination and have provided initial insight into the neurobiological mechanisms underlying signal transduction from excitatory neurons, regulated by Tfii-I, to OLs.

Previous human studies showed abnormalities in the axonal integrity and myelination status in WS subjects (53-59). These human studies showed that radial diffusivity, an indicator of axonal integrity and myelination status, was significantly reduced in WS brains as compared to controls (55). However, the cellular nature of these deficits and the molecular processes leading to them were previously unknown. These data were noted to be consistent with the clinical data and likely provide a mechanistic explanation.

Thus, in the instant studies, selective deletion of Gtf2i was performed in forebrain excitatory neurons of conditional knockout mice, and such mice were characterized for molecular, cellular and behavioral changes in the brain. It was identified that forebrain excitatory neuron-specific Gtf2i knockout mice showed WS-relevant abnormalities, including neuroanatomical defects, fine motor deficits, increased sociability and anxiety. Surprisingly, RNA-seq analysis revealed that 70% of the genes with significantly decreased mRNA level were involved in myelination. Furthermore, reduced numbers of mature oligodendrocytes, reduced myelin thickness and impaired axonal conductivity were identified. It was further demonstrated that normalization of impaired myelination properties or axonal conductivity rescued behavioral deficits. Importantly, similar myelination defects were also found in postmortem human frontal cortex of WS patients. Together, these data indicated that myelination, linked to neuronal loss of Gtf2i, was likely an important pathophysiology in WS.

Previous mouse studies showed a relationship between white matter integrity and social behavior performance (60, 61). However, experimental evidences for this have been contrasting; for example, differences in both sensorimotor coordination and social interaction correlated with CC demyelination, demonstrated by increased frequency of interactive behaviors among resident mice after acute or chronic demyelination by cuprizone (62). Oppositely, mice given cuprizone for 28 days displayed less social interactions (63), and a positive correlation was found with the CC thickness and social behavior (64). Therefore, the issue of precisely how myelination properties mediate social behavior developmentally and functionally in health or in illness (i.e. in WS), although of high interest, remains largely unknown.

The instant disclosure has therefore shed light upon how myelination and axonal conductivity properties affect social behavior in the frame of WS, and have therefore provided and facilitated the development of new treatment strategies for behavioral abnormalities. Because the efficiency and speed of conductivity relies on myelin (65), impairments in myelination properties are likely to affect proper communication and synchronization between different brain regions essential for proper execution of normal behaviors (66). Currently, the exact mechanisms underlying abnormal social behaviors in WS are not clear. However, rescue of abnormal social behavior in Gtf2i mutant mice by increasing axonal conductivity using 4-AP has herein indicated that the defect is functional rather than structural/developmental. These results are also consistent with recent studies that have demonstrated rescue of social interaction deficits in adult mouse ASD models (52). The improvement in social behavior following clemastine treatment demonstrated herein has indicated that myelination-related deficits are responsible for the behavioral alterations, and raises the likelihood that targeting of myelination deficits and their functional consequences presents a beneficial therapeutic strategy for treatment of WS and similar diseases and disorders (including, e.g., not only WS but also autism and other neurodevelopmental myelination abnormality diseases or disorders).

REFERENCES

1 Barak, B. & Feng, G. Neurobiology of social behavior abnormalities in autism and Williams syndrome. Nat Neurosci 19, 647-655, (2016).
2 Pober, B. R. Williams-Beuren syndrome. N Engl J Med 362, 239-252, (2010). Karmiloff-Smith, A., Broadbent, H., Farran, E. K., Longhi, E., D'Souza, D., Metcalfe, K., Tassabehji, M., Wu, R., Senju, A., Happe, F., Turnpenny, P. & Sansbury, F. Social cognition in williams syndrome: genotype/phenotype insights from partial deletion patients. Front Psychol 3, 168, (2012).
4 Dai, L., Bellugi, U., Chen, X. N., Pulst-Korenberg, A. M., Jarvinen-Pasley, A., Tirosh-Wagner, T., Eis, P. S., Graham, J., Mills, D., Searcy, Y. & Korenberg, J. R. Is it Williams syndrome? GTF2IRD1 implicated in visual-spatial construction and GTF2I in sociability revealed by high resolution arrays. Am J Med Genet A 149a, 302-314, (2009).
5 Morris, C. A., Mervis, C. B., Hobart, H. H., Gregg, R. G., Bertrand, J., Ensing, G. J., Sommer, A., Moore, C. A., Hopkin, R. J., Spallone, P. A., Keating, M. T., Osborne, L., Kimberley, K. W. & Stock, A. D. GTF2I hemizygosity implicated in mental retardation in Williams syndrome: genotype-phenotype analysis of five families with deletions in the Williams syndrome region. Am J Med Genet A 123a, 45-59, (2003).
6 Bayes, M., Magano, L. F., Rivera, N., Flores, R. & Perez Jurado, L. A. Mutational mechanisms of Williams-Beuren syndrome deletions. Am J Hum Genet 73, 131-151, (2003).
7 Sanders, S. J., Ercan-Sencicek, A. G., Hus, V., Luo, R., Murtha, M. T., Moreno-De-Luca, D., Chu, S. H., Moreau, M. P., Gupta, A. R., Thomson, S. A., Mason, C. E., Bilguvar, K., Celestino-Soper, P. B., Choi, M., Crawford, E. L., Davis, L., Wright, N. R., Dhodapkar, R. M., DiCola, M., DiLullo, N. M., Fernandez, T. V., Fielding-Singh, V., Fishman, D. O., Frahm, S., Garagaloyan, R., Goh, G. S., Kammela, S., Klei, L., Lowe, J. K., Lund, S. C., McGrew, A. D., Meyer, K. A., Moffat, W. J., Murdoch, J. D., O'Roak, B. J., Ober, G. T., Pottenger, R. S., Raubeson, M. J., Song, Y., Wang, Q., Yaspan, B. L., Yu, T. W., Yurkiewicz, I. R., Beaudet, A. L., Cantor, R. M., Curland, M., Grice, D. E., Gunel, M., Lifton, R. P., Mane, S. M., Martin, D. M., Shaw, C. A., Sheldon, M., Tischfield, J. A., Walsh, C. A., Morrow, E. M., Ledbetter, D. H., Fombonne, E., Lord, C., Martin, C. L., Brooks, A. I., Sutcliffe, J. S., Cook, E. H., Jr., Geschwind, D., Roeder, K., Devlin, B. & State, M. W. Multiple recurrent de novo CNVs, including duplications of the 7q11.23 Williams syndrome region, are strongly associated with autism. Neuron 70, 863-885, (2011).
8 Hong, E. J., West, A. E. & Greenberg, M. E. Transcriptional control of cognitive development. Curr Opin Neurobiol 15, 21-28, (2005).
9 Morris, C. A., Demsey, S. A., Leonard, C. O., Dilts, C. & Blackburn, B. L. Natural history of Williams syndrome: physical characteristics. J Pediatr 113, 318-326, (1988).
10 Antonell, A., Del Campo, M., Magano, L. F., Kaufmann, L., de la Iglesia, J. M., Gallastegui, F., Flores, R., Schweigmann, U., Fauth, C., Kotzot, D. & Perez-Jurado, L. A. Partial 7q11.23 deletions further implicate GTF2I and GTF2IRD1 as the main genes responsible for the Williams-Beuren syndrome neurocognitive profile. J Med Genet 47, 312-320, (2010).
11 Tassabehji, M., Hammond, P., Karmiloff-Smith, A., Thompson, P., Thorgeirsson, S. S., Durkin, M. E., Popescu, N. C., Hutton, T., Metcalfe, K., Rucka, A., Stewart, H., Read, A. P., Maconochie, M. & Donnai, D. GTF2IRD1 in craniofacial development of humans and mice. Science 310, 1184-1187, (2005).
12 Roy, A. L. Biochemistry and biology of the inducible multifunctional transcription factor TFII-I: 10 years later. Gene 492, 32-41, (2012).
13 Osborne, L. R. Animal models of Williams syndrome. Am J Med Genet C Semin Med Genet 154c, 209-219, (2010).
14 Segura-Puimedon, M., Sahun, I., Velot, E., Dubus, P., Borralleras, C., Rodrigues, A. J., Valero, M. C., Valverde, O., Sousa, N., Herault, Y., Dierssen, M., Perez-Jurado, L. A. & Campuzano, V. Heterozygous deletion of the Williams-Beuren syndrome critical interval in mice recapitulates most features of the human disorder. Hum Mol Genet 23, 6481-6494, (2014).
15 Li, H. H., Roy, M., Kuscuoglu, U., Spencer, C. M., Halm, B., Harrison, K. C., Bayle, J. H., Splendore, A., Ding, F., Meltzer, L. A., Wright, E., Paylor, R., Deisseroth, K. & Francke, U. Induced chromosome deletions cause hyper- 16 Borralleras, C., Sahun, I., Perez-Jurado, L. A. & Campuzano, V. Intracisternal Gtf2i Gene Therapy Ameliorates Deficits in Cognition and Synaptic Plasticity of a Mouse Model of Williams-Beuren Syndrome. Mol Ther 23, 1691-1699, (2015).

17 Lucena, J., Pezzi, S., Aso, E., Valero, M. C., Carreiro, C., Dubus, P., Sampaio, A., Segura, M., Barthelemy, I., Zindel, M. Y., Sousa, N., Barbero, J. L., Maldonado, R., Perez-Jurado, L. A. & Campuzano, V. Essential role of the N-terminal region of TFII-I in viability and behavior. BMC Med Genet 11, 61, (2010).

18 Sakurai, T., Dorr, N. P., Takahashi, N., McInnes, L. A., Elder, G. A. & Buxbaum, J. D. Haploinsufficiency of Gtf2i, a gene deleted in Williams Syndrome, leads to increases in social interactions. Autism Res 4, 28-39, (2011).

19 Enkhmandakh, B., Makeyev, A. V., Erdenechimeg, L., Ruddle, F. H., Chimge, N. O., Tussie-Luna, M. I., Roy, A. L. & Bayarsaihan, D. Essential functions of the Williams-Beuren syndrome-associated TFII-I genes in embryonic development. Proc Natl Acad Sci USA 106, 181-186, (2009).

20 Gandal, M. J., Leppa, V., Won, H., Parikshak, N. N. & Geschwind, D. H. The road to precision psychiatry: translating genetics into disease mechanisms. Nat Neurosci 19, 1397-1407, (2016).

21 Enkhmandakh, B., Stoddard, C., Mack, K., He, W., Kaback, D., Yee, S. P. & Bayarsaihan, D. Generation of a mouse model for a conditional inactivation of Gtf2i allele. Genesis 54, 407-412, (2016).

22 Goebbels, S., Bormuth, I., Bode, U., Hermanson, O., Schwab, M. H. & Nave, K. A. Genetic targeting of principal neurons in neocortex and hippocampus of NEX-Cre mice. Genesis 44, 611-621, (2006).

23 Chailangkarn, T., Trujillo, C. A., Freitas, B. C., Hrvoj-Mihic, B., Herai, R. H., Yu, D. X., Brown, T. T., Marchetto, M. C., Bardy, C., McHenry, L., Stefanacci, L., Jarvinen, A., Searcy, Y. M., DeWitt, M., Wong, W., Lai, P., Ard, M. C., Hanson, K. L., Romero, S., Jacobs, B., Dale, A. M., Dai, L., Korenberg, J. R., Gage, F. H., Bellugi, U., Halgren, E., Semendeferi, K. & Muotri, A. R. A human neurodevelopmental model for Williams syndrome. Nature 536, 338-343, (2016).

24 Chiang, M. C., Reiss, A. L., Lee, A. D., Bellugi, U., Galaburda, A. M., Korenberg, J. R., Mills, D. L., Toga, A. W. & Thompson, P. M. 3D pattern of brain abnormalities in Williams syndrome visualized using tensor-based morphometry. Neuroimage 36, 1096-1109, (2007).

25 Green, T., Fierro, K. C., Raman, M. M., Saggar, M., Sheau, K. E. & Reiss, A. L. Surface-based morphometry reveals distinct cortical thickness and surface area profiles in Williams syndrome. Am J Med Genet B Neuropsychiatr Genet 171b, 402-413, (2016).

26 Meda, S. A., Pryweller, J. R. & Thornton-Wells, T. A. Regional brain differences in cortical thickness, surface area and subcortical volume in individuals with Williams syndrome. PLoS One 7, e31913, (2012).

27 Reiss, A. L., Eckert, M. A., Rose, F. E., Karchemskiy, A., Kesler, S., Chang, M., Reynolds, M. F., Kwon, H. & Galaburda, A. An experiment of nature: brain anatomy parallels cognition and behavior in Williams syndrome. J Neurosci 24, 5009-5015, (2004).

28 Reiss, A. L., Eliez, S., Schmitt, J. E., Straus, E., Lai, Z., Jones, W. & Bellugi, U. IV. Neuroanatomy of Williams syndrome: a high-resolution Mill study. J Cogn Neurosci 12 Suppl 1, 65-73, (2000).

29 Thompson, P. M., Lee, A. D., Dutton, R. A., Geaga, J. A., Hayashi, K. M., Eckert, M. A., Bellugi, U., Galaburda, A. M., Korenberg, J. R., Mills, D. L., Toga, A. W. & Reiss, A. L. Abnormal cortical complexity and thickness profiles mapped in Williams syndrome. J Neurosci 25, 4146-4158, (2005).

30 Cahoy, J. D., Emery, B., Kaushal, A., Foo, L. C., Zamanian, J. L., Christopherson, K. S., Xing, Y., Lubischer, J. L., Krieg, P. A., Krupenko, S. A., Thompson, W. J. & Barres, B. A. A transcriptome database for astrocytes, neurons, and oligodendrocytes: a new resource for understanding brain development and function. J Neurosci 28, 264-278, (2008).

31 Zuchero, J. B. & Barres, B. A. Glia in mammalian development and disease. Development 142, 3805-3809, (2015).

32 Chang, K. J., Redmond, S. A. & Chan, J. R. Remodeling myelination: implications for mechanisms of neural plasticity. Nat Neurosci 19, 190-197, (2016).

33 Rosenberg, S. S. & Chan, J. R. Modulating myelination: knowing when to say Wnt. Genes Dev 23, 1487-1493, (2009).

34 Rosenberg, S. S., Powell, B. L. & Chan, J. R. Receiving mixed signals: uncoupling oligodendrocyte differentiation and myelination. Cell Mol Life Sci 64, 3059-3068, (2007).

35 Mikoshiba, K., Okano, H., Tamura, T. & Ikenaka, K. Structure and function of myelin protein genes. Annu Rev Neurosci 14, 201-217, (1991).

36 Nave, K. A. & Werner, H. B. Myelination of the nervous system: mechanisms and functions. Annu Rev Cell Dev Biol 30, 503-533, (2014).

37 Liu, J., Dietz, K., DeLoyht, J. M., Pedre, X., Kelkar, D., Kaur, J., Vialou, V., Lobo, M. K., Dietz, D. M., Nestler, E. J., Dupree, J. & Casaccia, P. Impaired adult myelination in the prefrontal cortex of socially isolated mice. Nat Neurosci 15, 1621-1623, (2012).

38 Douvaras, P., Rusielewicz, T., Kim, K. H., Haines, J. D., Casaccia, P. & Fossati, V. Epigenetic Modulation of Human Induced Pluripotent Stem Cell Differentiation to Oligodendrocytes. Int J Mol Sci 17, (2016).

39 Liu, J., Dupree, J. L., Gacias, M., Frawley, R., Sikder, T., Naik, P. & Casaccia, P. Clemastine Enhances Myelination in the Prefrontal Cortex and Rescues Behavioral Changes in Socially Isolated Mice. J Neurosci 36, 957-962, (2016).

40 Liu, J., Magri, L., Zhang, F., Marsh, N. O., Albrecht, S., Huynh, J. L., Kaur, J., Kuhlmann, T., Zhang, W., Slesinger, P. A. & Casaccia, P. Chromatin landscape defined by repressive histone methylation during oligodendrocyte differentiation. J Neurosci 35, 352-365, (2015).

41 Chapman, C. A., du Plessis, A. & Pober, B. R. Neurologic findings in children and adults with Williams syndrome. J Child Neurol 11, 63-65, (1996).

42 Trauner, D. A., Bellugi, U. & Chase, C. Neurologic features of Williams and Down syndromes. Pediatr Neurol 5, 166-168, (1989).

43 Jin, D., Liu, Y., Sun, F., Wang, X., Liu, X. & He, Z. Restoration of skilled locomotion by sprouting corticospinal axons induced by co-deletion of PTEN and SOCS3. Nat Commun 6, 8074, (2015).

44 Metz, G. A. & Whishaw, I. Q. Cortical and subcortical lesions impair skilled walking in the ladder rung walking test: a new task to evaluate fore- and hindlimb stepping, placing, and coordination. J Neurosci Methods 115, 169-179, (2002).
45. Carmel, J. B., Kimura, H. & Martin, J. H. Electrical stimulation of motor cortex in the uninjured hemisphere after chronic unilateral injury promotes recovery of skilled locomotion through ipsilateral control. J Neurosci 34, 462-466, (2014).
46. Liu, Y., Wang, X., Li, W., Zhang, Q., Li, Y., Zhang, Z., Zhu, J., Chen, B., Williams, P. R., Zhang, Y., Yu, B., Gu, X. & He, Z. A Sensitized IGF1 Treatment Restores Corticospinal Axon-Dependent Functions. Neuron 95, 817-833.e814, (2017).
47. Hayes, K. C. The use of 4-aminopyridine (fampridine) in demyelinating disorders. CNS Drug Rev 10, 295-316, (2004).
48. Green, A. J., Gelfand, J. M., Cree, B. A., Bevan, C., Boscardin, W. J., Mei, F., Inman, J., Arnow, S., Devereux, M., Abounasr, A., Nobuta, H., Zhu, A., Friessen, M., Gerona, R., von Budingen, H. C., Henry, R. G., Hauser, S. L. & Chan, J. R. Clemastine fumarate as a remyelinating therapy for multiple sclerosis (ReBUILD): a randomised, controlled, double-blind, crossover trial. Lancet 390, 2481-2489, (2017).
49. Cree, B. A. C., Niu, J., Hoi, K. K., Zhao, C., Caganap, S. D., Henry, R. G., Dao, D. Q., Zollinger, D. R., Mei, F., Shen, Y. A., Franklin, R. J. M., Ullian, E. M., Xiao, L., Chan, J. R. & Fancy, S. P. J. Clemastine rescues myelination defects and promotes functional recovery in hypoxic brain injury. Brain 141, 85-98, (2018).
50. Wang, F., Yang, Y. J., Yang, N., Chen, X. J., Huang, N. X., Zhang, J., Wu, Y., Liu, Z., Gao, X., Li, T., Pan, G. Q., Liu, S. B., Li, H. L., Fancy, S. P. J., Xiao, L., Chan, J. R. & Mei, F. Enhancing Oligodendrocyte Myelination Rescues Synaptic Loss and Improves Functional Recovery after Chronic Hypoxia. Neuron 99, 689-701.e685, (2018).
51. Mei, F., Fancy, S. P. J., Shen, Y. A., Niu, J., Zhao, C., Presley, B., Miao, E., Lee, S., Mayoral, S. R., Redmond, S. A., Etxeberria, A., Xiao, L., Franklin, R. J. M., Green, A., Hauser, S. L. & Chan, J. R. Micropillar arrays as a high-throughput screening platform for therapeutics in multiple sclerosis. Nat Med 20, 954-960, (2014).
52. Mei, Y., Monteiro, P., Zhou, Y-Kim, J-A., Gao, X., Fu Z and Feng, G. Adult Restoration of Shank3 Expression Rescues Selective Autistic-Like Phenotypes. Nature 530: 481-484, (2016).
53. Arlinghaus, L. R., Thornton-Wells, T. A., Dykens, E. M. & Anderson, A. W. Alterations in diffusion properties of white matter in Williams syndrome. Magn Reson Imaging 29, 1165-1174, (2011).
54. Avery, S. N., Thornton-Wells, T. A., Anderson, A. W. & Blackford, J. U. White matter integrity deficits in prefrontal-amygdala pathways in Williams syndrome. Neuroimage 59, 887-894, (2012).
55. Faria, A. V., Landau, B., O'Hearn, K. M., Li, X., Jiang, H., Oishi, K., Zhang, J. & Mori, S. Quantitative analysis of gray and white matter in Williams syndrome. Neuroreport 23, 283-289, (2012).
56. Hoeft, F., Barnea-Goraly, N., Haas, B. W., Golarai, G., Ng, D., Mills, D., Korenberg, J., Bellugi, U., Galaburda, A. & Reiss, A. L. More is not always better: increased fractional anisotropy of superior longitudinal fasciculus associated with poor visuospatial abilities in Williams syndrome. J Neurosci 27, 11960-11965, (2007).
57. Jabbi, M., Kippenhan, J. S., Kohn, P., Marenco, S., Mervis, C. B., Morris, J. A., Meyer-Lindenberg, A. & Berman, K. F. The Williams syndrome chromosome 7q11.23 hemideletion confers hypersocial, anxious personality coupled with altered insula structure and function. Proc Natl Acad Sci USA 109, E860-866, (2012).
58. Marenco, S., Siuta, M. A., Kippenhan, J. S., Grodofsky, S., Chang, W. L., Kohn, P., Mervis, C. B., Morris, C. A., Weinberger, D. R., Meyer-Lindenberg, A., Pierpaoli, C. & Berman, K. F. Genetic contributions to white matter architecture revealed by diffusion tensor imaging in Williams syndrome. Proc Natl Acad Sci USA 104, 15117-15122, (2007).
59. Meyer-Lindenberg, A., Hariri, A. R., Munoz, K. E., Mervis, C. B., Mattay, V. S., Morris, C. A. & Berman, K. F. Neural correlates of genetically abnormal social cognition in Williams syndrome. Nat Neurosci 8, 991-993, (2005).
60. Makinodan, M., Rosen, K. M., Ito, S. & Corfas, G. A critical period for social experience-dependent oligodendrocyte maturation and myelination. Science 337, 1357-1360, (2012).
61. Miller, V. M., Gupta, D., Neu, N., Cotroneo, A., Boulay, C. B. & Seegal, R. F. Novel inter-hemispheric white matter connectivity in the BTBR mouse model of autism. Brain Res 1513, 26-33, (2013).
62. Hibbits, N., Pannu, R., Wu, T. J. & Armstrong, R. C. Cuprizone demyelination of the corpus callosum in mice correlates with altered social interaction and impaired bilateral sensorimotor coordination. ASN Neuro 1, (2009).
63. Xu, H., Yang, H. J., McConomy, B., Browning, R. & Li, X. M. Behavioral and neurobiological changes in C57BL/6 mouse exposed to cuprizone: effects of antipsychotics. Front Behav Neurosci 4, 8, (2010).
64. Fairless, A. H., Dow, H. C., Toledo, M. M., Malkus, K. A., Edelmann, M., Li, H., Talbot, K., Arnold, S. E., Abel, T. & Brodkin, E. S. Low sociability is associated with reduced size of the corpus callosum in the BALB/cJ inbred mouse strain. Brain Res 1230, 211-217, (2008).
65. Seidl, A. H. Regulation of conduction time along axons. Neuroscience 276, 126-134, (2014).
66. Bosma, I., Douw, L., Bartolomei, F., Heimans, J. J., van Dijk, B. W., Postma, T. J., Stam, C. J., Reijneveld, J. C. & Klein, M. Synchronized brain activity and neurocognitive function in patients with low-grade glioma: a magnetoencephalography study. Neuro Oncol 10, 734-744, (2008).
67. Blanco, J. E., Anderson, K. D. & Steward, O. Recovery of forepaw gripping ability and reorganization of cortical motor control following cervical spinal cord injuries in mice. Exp Neurol 203, 333-348, (2007).
68. Barak, B., Okun, E., Ben-Simon, Y., Lavi, A., Shapira, R., Madar, R., Wang, Y., Norman, E., Sheinin, A., Pita, M. A., Yizhar, O., Mughal, M. R., Stuenkel, E., van Praag, H., Mattson, M. P. & Ashery, U. Neuron-specific expression of tomosyn in the mouse hippocampal dentate gyrus impairs spatial learning and memory. Neuromolecular Med 15, 351-363, (2013).
69. Crawford, D. K., Mangiardi, M., Song, B., Patel, R., Du, S., Sofroniew, M. V., Voskuhl, R. R. & Tiwari-Woodruff, S. K. Oestrogen receptor beta ligand: a novel treatment to enhance endogenous functional remyelination. Brain 133, 2999-3016, (2010).
70. Crawford, D. K., Mangiardi, M. & Tiwari-Woodruff, S. K. Assaying the functional effects of demyelination and remyelination: revisiting field potential recordings. J Neurosci Methods 182, 25-33, (2009).

71 Asante, C. O. & Martin, J. H. Differential joint-specific corticospinal tract projections within the cervical enlargement. PLoS One 8, e74454, (2013).

72 Wang, X., Liu, Y., Li, X., Zhang, Z., Yang, H., Zhang, Y., Williams, P. R., Alwahab, N. S. A., Kapur, K., Yu, B., Zhang, Y., Chen, M., Ding, H., Gerfen, C. R., Wang, K. H. & He, Z. Deconstruction of Corticospinal Circuits for Goal-Directed Motor Skills. Cell 171, 440-455.e414, (2017).

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The present disclosure teaches one skilled in the art to test various combinations and/or substitutions of chemical modifications described herein toward generating conjugates possessing improved contrast, diagnostic and/or imaging activity. Therefore, the specific embodiments described herein are not limiting and one skilled in the art can readily appreciate that specific combinations of the modifications described herein can be tested without undue experimentation toward identifying conjugates possessing improved contrast, diagnostic and/or imaging activity.

The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A method for treating Williams Syndrome in a subject, the method comprising:
   administering a potassium channel blocker, or a pharmaceutically acceptable salt thereof, to the subject in need of such therapy in an amount sufficient to treat Williams Syndrome in the subject.

2. The method of claim 1, wherein the potassium channel blocker is selected from the group consisting of 4-Aminopyridine (4-AP), a derivative thereof, or a combination thereof; 3,4 diaminopyridine (3,4-DAP), a derivative thereof, or a combination thereof; tetraethylammonium (TEA); bretylium; other quaternary ammonium ion agent; Bay K8644; (S)-(−)-Bay K8644; FPL 64176; GV-58; ML-SA1; MSP-3; Ambroxol; Amiodarone; AC-265347; 2,3-Diaminopyridine (2,3-DAP); 4-Aminopyridine methiodide (4-APMI); 3-Hydroxypyridine (3-HP); a voltage-activated calcium channel (VACC) stimulatory agent opicinumab and clemastine, or a pharmaceutically acceptable salt thereof; Bay K8644; (S)-(—)-Bay K8644; FPL 64176; GV-58; ML-SA1; MSP-3; Ambroxol; Amiodarone; AC-265347; 2,3-Diaminopyridine (2,3-DAP); 4-Aminopyridine methiodide (4-APMI); 3-Hydroxypyridine (3-HP); a voltage-activated calcium channel (VACC) stimulatory agent opicinumab; and clemastine, or a pharmaceutically acceptable salt thereof.

3. The method of claim 1, wherein the potassium channel blocker is a presynaptic potassium channel blocker.

4. The method of claim 1, wherein the potassium channel blocker is a calcium channel agonist, optionally the calcium channel agonist is selected from the group consisting of 4-AP, Bay K8644; (S)-(−)-Bay K8644; FPL 64176; GV-58; ML-SA1; MSP-3; Ambroxol; Amiodarone; and AC-265347, optionally the calcium channel agonist is a voltage-activated calcium channel (VACC) stimulatory agent.

5. The method of claim 1, wherein one or more neurological symptoms of Williams Syndrome are treated in the subject.

6. The method of claim 5, wherein the one or more neurological symptoms of Williams Syndrome are selected from the group consisting of abnormal fine motor skills, optionally including tremors or limb weakness, and abnormal social skills.

7. The method of claim 1, wherein the potassium channel blocker is administered orally, optionally as an approximately 1-30 mg tablet, optionally as an approximately 10 mg tablet, optionally wherein the potassium channel blocker is administered daily.

8. The method of claim 1, wherein the subject exhibits a normalization of fine motor skills and/or a normalization of social preference or behavior, as compared to an appropriate control subject, after administering the potassium channel blocker, or pharmaceutically acceptable salt thereof.

* * * * *